(12) United States Patent
Altmann et al.

(10) Patent No.: US 7,910,698 B2
(45) Date of Patent: Mar. 22, 2011

(54) NPC1L1 ORTHOLOGUES

(75) Inventors: Scott Altmann, Asbury Park, NJ (US); Xiaorui Yao, Piscataway, NJ (US); Kim Ann O'Neill, Scotch Plains, NJ (US); Brian E. Hawes, Hillsborough, NJ (US)

(73) Assignee: Schering Corporation, Kenilworth, NJ (US)

( * ) Notice: Subject to any disclaimer, the term of this patent is extended or adjusted under 35 U.S.C. 154(b) by 861 days.

(21) Appl. No.: 11/710,295

(22) Filed: Feb. 22, 2007

(65) Prior Publication Data

US 2009/0098128 A1 Apr. 16, 2009

Related U.S. Application Data

(60) Provisional application No. 60/776,394, filed on Feb. 24, 2006.

(51) Int. Cl.
*C07K 14/00* (2006.01)
*C12N 11/00* (2006.01)
*C12P 21/06* (2006.01)
*C12P 21/04* (2006.01)
*C12Q 1/00* (2006.01)
*G01N 33/567* (2006.01)
*G01N 33/53* (2006.01)
*G01N 33/00* (2006.01)
*C12Q 1/16* (2006.01)
*A01N 37/18* (2006.01)
*A61K 38/16* (2006.01)
*A61K 38/00* (2006.01)

(52) U.S. Cl. ...... 530/350; 435/174; 435/69.1; 435/69.7; 435/4; 435/7.21; 435/7.71; 435/7.8; 435/7.93; 435/35; 514/2; 514/8; 514/21

(58) Field of Classification Search .......... None
See application file for complete search history.

(56) References Cited

U.S. PATENT DOCUMENTS

| | | | |
|---|---|---|---|
| 5,306,817 | A | 4/1994 | Thiruvengadam et al. |
| 5,561,227 | A | 10/1996 | Thiruvengadam et al. |
| 5,618,707 | A | 4/1997 | Homann et al. |
| 5,624,920 | A | 4/1997 | McKittrick et al. |
| 5,627,176 | A | 5/1997 | Kirkup et al. |
| 5,631,365 | A | 5/1997 | Rosenblum et al. |
| 5,633,246 | A | 5/1997 | McKittrick et al. |
| 5,656,624 | A | 8/1997 | Vaccaro et al. |
| 5,661,145 | A | 8/1997 | Davis |
| 5,688,785 | A | 11/1997 | Vaccaro |
| 5,688,787 | A | 11/1997 | Burnett et al. |
| 5,688,990 | A | 11/1997 | Shankar |
| 5,698,548 | A | 12/1997 | Dugar et al. |
| 5,728,827 | A | 3/1998 | Thiruvengadam et al. |
| 5,739,321 | A | 4/1998 | Wu et al. |
| 5,744,467 | A | 4/1998 | McKittrick et al. |
| 5,756,470 | A | 5/1998 | Yumibe et al. |
| 5,767,115 | A | 6/1998 | Rosenblum et al. |
| 5,846,966 | A | 12/1998 | Rosenblum et al. |
| 5,856,473 | A | 1/1999 | Shankar |
| 5,886,171 | A | 3/1999 | Wu et al. |
| 5,919,672 | A | 7/1999 | Homann et al. |
| 6,093,812 | A | 7/2000 | Thiruvengadam et al. |
| 6,096,883 | A | 8/2000 | Wu et al. |
| 6,133,001 | A | 10/2000 | Homann et al. |
| 6,207,822 | B1 | 3/2001 | Thiruvengadam et al. |
| RE37,721 | E | 5/2002 | Rosenblum et al. |
| 6,426,198 | B1 | 7/2002 | Carstea et al. |
| 6,593,078 | B1 | 7/2003 | Altmann et al. |
| 6,627,757 | B2 | 9/2003 | Fu et al. |
| 6,632,933 | B2 | 10/2003 | Altmann et al. |
| 7,135,556 | B2 | 11/2006 | Altmann et al. |
| 2002/0151536 | A1 | 10/2002 | Davis et al. |
| 2003/0125253 | A1 | 7/2003 | Taniyama et al. |
| 2004/0093629 | A1 | 5/2004 | Altmann et al. |
| 2004/0132058 | A1 | 7/2004 | Altmann et al. |
| 2004/0137467 | A1 | 7/2004 | Altmann et al. |
| 2004/0161838 | A1 | 8/2004 | Altmann et al. |
| 2006/0035835 | A1 | 2/2006 | Taniyama et al. |

FOREIGN PATENT DOCUMENTS

| | | |
|---|---|---|
| WO | WO00/20623 | 4/2000 |
| WO | WO00/34240 | 6/2000 |
| WO | WO00/60107 | 10/2000 |
| WO | WO00/63703 | 10/2000 |
| WO | WO01/57190 | 8/2001 |
| WO | WO01/70974 | 9/2001 |
| WO | WO01/75067 | 10/2001 |
| WO | WO02/079174 | 10/2002 |
| WO | WO03/100094 | 12/2003 |
| WO | WO2004/009772 | 1/2004 |
| WO | WO2004/014947 | 2/2004 |
| WO | WO2004/032716 | 4/2004 |
| WO | WO2005/015988 | 2/2005 |
| WO | WO2005/069900 | 8/2005 |
| WO | WO2006/015365 | 2/2006 |

OTHER PUBLICATIONS

Passarelli et al. (Diabetes Jul. 2005 vol. 54 No. 7 2198-2205).*
Abstracts 1-79 from "The Second International Conference on Niemann-Pick Type C Disease"; May 29-31, 2003; Tuscon, Arizona.
Acton, et al., "Expression Cloning of SR-BI, a CD36-related Class B Scavenger Receptor"; The Journal of Biological Chemistry 269(33): 21003-21009 (1994).
Allayee, et al., "Biochemistry. An absorbing study of cholesterol"; Science. 290(5497):1709-1711 (2000).
Altmann, et al., "The identification of intestinal scavenger receptor class B, type I (SR-BI) by expression cloning and its role in cholesterol absorption."; Biochim. Biophys. ACTA 1580: 77-93 (2002).
Altmann, et al., "Niemann-Pick C1 Like 1 protein is critical for intestinal cholesterol absorption."; Science. Feb. 20, 2004;303(5661):1201-1204.
Amigo, et al., "Relevance of Niemann-Pick Type C1 Protein Expression in Controlling Plasma Cholesterol and Biliary Lipid Secretion in Mice"; Hepatology 36(4): 819-828 (2002).

(Continued)

*Primary Examiner* — Suzanne M Noakes
*Assistant Examiner* — Jae W Lee

(57) ABSTRACT

The present invention provides, in part, NPC1L1 from various species. Methods of using the NPC1L1 polypeptides and polynucleotide set forth herein, e.g., in screening assays, are also set forth.

35 Claims, 8 Drawing Sheets

OTHER PUBLICATIONS

Berge, et al., "Accumulation of dietary cholesterol in sitosterolemia caused by mutations in adjacent ABC transporters"; Science 290(5497):1771-1775 (2000).

Blom, et al., "Defective endocytic trafficking of NPC1 and NPC2 underlying infantile Niemann-Pick type C disease"; Hum Mol Genet. Feb. 1, 2003;12(3):257-272.

Carstea, et al., "Niemann-Pick C1 disease gene: homology to mediators of cholesterol homeostasis"; Science 277:228-231 (1997).

Davies, et al., "Evidence for a Niemann-pick C (NPC) gene family: identification and characterization of NPC1L1"; Genomics 65(2): 137-145 (2000).

Davies, et al., "Inactivation of NPC1L1 causes multiple lipid transport defects and protects against diet-induced hypercholesterolemia"; J. Biol. Chem. Apr. 1, 2005;280(13):12710-1220.

Davis, H.R., et al.; "The Synergistic Hypocholesterolemic Activity of the Potent Cholesterol Absorption Inhibitor, Ezetimibe, in combination with 3-hydroxy-3-methylglutaryl Coenzyme A Reductase Inhibitors in Dogs"; Metabolism; 50(10):1234-1241 (2001).

Dawson, et al., "Intestinal cholesterol absorption"; Curr Opin Lipidol. 10(4):315-320 (1999).

Deninno, et al., "Steroidal glycoside cholesterol absorption inhibitors"; J. Med. Chem. 40(16):2547-2554 (1997).

Detmers, et al., "A target for cholesterol absorption inhibitors in the enterocyte brush border membrane"; Biochimica et Biophysica Acta 1486: 243-252 (2000).

Erickson, et al., "Pharmacological and genetic modifications of somatic cholesterol do not substantially alter the course of CNS disease in Niemann-Pick C mice."; J. Inherit. Metab. Dis. Feb. 2000;23(1):54-62.

Erickson, et al., "Studies on neuronal death in the mouse model of Niemann-Pick C disease."; J. Neurosci. Res. Jun. 15, 2002;68(6):738-744.

Erickson, et al., "mdr1a deficiency corrects sterility in Niemann-Pick C1 protein deficient female mice."; Mol. Reprod. Dev. Jun. 2002;62(2):167-173.

Garcia-Calvo, Margarita, et al.; "The target of ezetimibe is Niemann-Pick C1-Like 1 (NPC1L1)"; Proceedings of the National Academy of Sciences of the United States of America; 102(23):8132-8137 (2005).

Hauser, et al., "Identification of a Receptor Mediating Absorption of Dietary Cholesterol in the Intestine"; Biochemistry 37(51): 17843-17850 (1998).

Hawes, Brian, et al.; "In vivo responsiveness to exetimibe correlates with Niemann-Pick C1 like-1 (NPC1L1) binding affinity: Comparison of multiple species NPC1L1 orthologs"; Molecular Pharmacology; 71(1):19-29 (2007).

Hernandez, et al., "Intestinal absorption of cholesterol is mediated by a saturable, inhibitable transporter"; Biochimica et Biophysica Acta 1486: 232-242 (2000).

Ioannou, Yiannis A., "The structure and function of the Niemann-Pick C1 protein."; Mol. Genet. Metab. 71(1-2): 175-181 (2000).

Ioannou, Yiannis A., "Multidrug permeases and subcellular cholesterol transport"; Nat Rev Mol Cell Biol. Sep. 2001;2(9):657-668.

Jourdheuil-Rahmani, et al., "Biliary anionic peptide fraction and apoA-I regulate intestinal cholesterol uptake"; Biochem Biophys Res Commun 292(2):390-395 (2002).

Kramer, et al., "Characterization and identification of the intestinal cholesterol uptake system"; Falk Symposium 129, Bile Acids: From Genomics to Disease and Therapy, 147-160 (2003).

Lipka, Leslie J.; "Ezetimibe: A first-in-class, novel cholesterol absorption inhibitor"; Cardiovascular Drug Reviews; 21(4):293-312 (2003).

Minhas, "Current Progress in Lipid Therapy"; Br. J. Cardiology 10(1): 59-68 (2003).

Reiss, P., et al.; "An enzymatic synthesis of glucuronides of azetidinone-based cholesterol absorption inhibitors"; Bioorganic & Medicinal Chemistry; 7(10):2199-2202 (1999).

Repa, et al., "Inhibition of cholesterol absorption by SCH 58053 in the mouse is not mediated via changes in the expression of mRNA for ABCA1, ABCG5, or ABCG8 in the enterocyte"; Journal of Lipid Research 43:1864-1874 (2002).

Rudel, Lawrence L.; "Preclinical and clinical pharmacology of a new class of lipid management agents"; The American Journal of Managed Care; 8(2):S33-S35 (2002).

Smart, et al., "Annexin 2-caveolin 1 complex is a target of ezetimibe and regulates intestinal cholesterol transport"; Proc. Natl. Acad. Sci. 101(10):3450-3455 (2004).

Van Der Veen, Jelske, N., et al.; "Reduced cholesterol absorption upon PPARδ activation coincides with decreased intestinal expression of NPC1L1"; Journal of Lipid Research; 46(3):526-534 (2005).

Werder, et al., "Role of scavenger receptors SR-BI and CD36 in selective sterol uptake in the small intestine"; Biochemistry 40(38):11643-11650 (2001).

Genbank Sequence Disclosure; Accession No. AF192522 (accessed online Apr. 20, 2004).

Genbank Sequence Disclosure; Accession No. AF002020 (accessed online Apr. 20, 2004).

Genbank Sequence Disclosure, Accession No. AK078947 (accessed online Apr. 20, 2004).

International Search Report for International Application No. PCT/US03/22467 (completed Nov. 4, 2005; mailed Jan. 6, 2006).

International Search Report for International Application No. PCT/US03/40113 (completed Mar. 19, 2004; mailed Jun. 7, 2004).

International Search Report for International Application No. PCT/US07/005037 (completed Jul. 12, 2007).

MGI web page "gene detail" of the NPC1L1 gene (accessed online Nov. 4, 2005).

Polypeptide Sequence ABG22693 disclosed in WO 01/75067 (published Oct. 11, 2001).

Zetia™ Prescribing Information Sheet (Zetia sold in US starting 2002).

* cited by examiner

A

B

A.

SCH 354909  SCH 610396

```
hamster RLERAKDATVSMGSAVFAGVAMTNFPGILILGFADAQLIQIFFFRLNLLITLLGLLHGLVFLPVVLSYLGPDVNPELVLEEKL-ATEAAVAPEP-SSPKY
cow     RLERAKEATISMGSAVFAGVAMTNLPGILVLQLAKAQLIQIFFFRLNLLITVLGLLHGLVFLPVILSYLGPDVNPALVQQQKQ-QEEAAAAKET SCSKH
rabbit  RLERAKEATISMGSAVFAGVAMTNLPGILILQLAKAQLIQIFFFRLNLLITLLGLLHGLVFLPVILSYLGPDVNPALVALERTRAQEAADAAAG-SCPNH human    PSRVSTADNIYVNHSFEGS-IKGAGAIS-NFLPNNGRQF
chimp    PSRVSTADNIYVNHSFEGS-IKGAGAIS-NFLPNNGRQF
monkey   PSRVSTADNIYVNHSFEGS-IKGAGAVS-NFLPNNGRQF
canine   --PTSTASSTYVNYGFQH---PANGVVGDSSLPRSGPDL
mouse    PFPADANTSDYVNYGFNPEFIPEINAAS-SSLPKSDQKF
rat      PSPADADAN--VNYGFAPELAHGANAAR-SSLPKSDQKF
hamster  PFP----DNDVVNHSFEEAT-PGAAAAS-SSLPKSGQKF
cow      PAQMSTDYGVYVNCSFEHP-AKSVGGLE-SSPSENRQKF
rabbit   PDP---TSNIYVNSGFDE-----AARDVGSSAPTRKQKF
```

NPC1L1 ORTHOLOGUES

This application claims the benefit of U.S. provisional patent application No. 60/776,394, filed Feb. 24, 2006, which is herein incorporated by reference in its entirety.

FIELD OF THE INVENTION

The present invention relates to polynucleotides and polypeptides encoding NPC1L1 from various species and uses thereof.

BACKGROUND OF THE INVENTION

A factor leading to development of vascular disease, a leading cause of death in industrialized nations, is elevated serum cholesterol. It is estimated that 19% of Americans between the ages of 20 and 74 years of age have high serum cholesterol. The most prevalent form of vascular disease is arteriosclerosis, a condition associated with the thickening and hardening of the arterial wall. Arteriosclerosis of the large vessels is referred to as atherosclerosis. Atherosclerosis is the predominant underlying factor in vascular disorders such as coronary artery disease, aortic aneurysm, arterial disease of the lower extremities and cerebrovascular disease.

Cholesteryl esters are a major component of atherosclerotic lesions and the major storage form of cholesterol in arterial wall cells. Formation of cholesteryl esters is also a step in the intestinal absorption of dietary cholesterol. Thus, inhibition of cholesteryl ester formation and reduction of serum cholesterol can inhibit the progression of atherosclerotic lesion formation, decrease the accumulation of cholesteryl esters in the arterial wall, and block the intestinal absorption of dietary cholesterol.

The regulation of whole-body cholesterol homeostasis in mammals and animals involves the regulation of intestinal cholesterol absorption, cellular cholesterol trafficking, dietary cholesterol and modulation of cholesterol biosynthesis, bile acid biosynthesis, steroid biosynthesis and the catabolism of the cholesterol-containing plasma lipoproteins. Regulation of intestinal cholesterol absorption has proven to be an effective means by which to regulate serum cholesterol levels. For example, a cholesterol absorption inhibitor, ezetimibe (

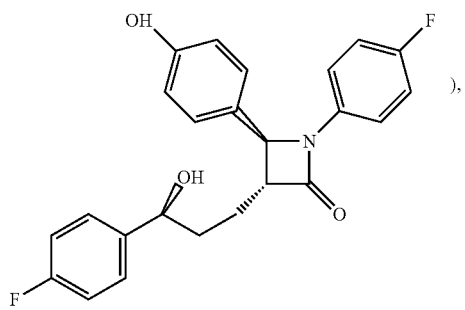

), has been shown to be effective in this regard. A pharmaceutical composition containing ezetimibe is commercially available from Merck/Schering-Plough Pharmaceuticals, Inc. under the tradename Zetia®. Identification of a gene target through which ezetimibe acts is important to understanding the process of cholesterol absorption and to the development of other, novel absorption inhibitors.

The molecular target through which ezetimibe acts, in humans, rats and mice, has been identified previously to be NPC1L1 (also known as NPC3; published U.S. patent application no. 2004/0161838; Genbank Accession No. AF192522; Davies, et al., (2000) Genomics 65(2):137-45 and Ioannou, (2000) Mol. Genet. Metab. 71(1-2):175-81).

There remains a need in the art for the identification of orthologues of NPC1L1, for example, from non-human animals such as canines, rabbits, hamsters, and monkeys. Identification of such targets would aid in the discovery and development of both human and non-human, veterinary treatments for hyperlipidemia, hypertriglyceridemia and/or hypercholesterolemia which target NPC1L1.

SUMMARY OF THE INVENTION

The present invention addressed the need in the art for veterinary and human treatments for cardiovascular disorders therein (e.g., hyperlipidemia, hypertriglyceridemia, or hypercholesterolemia), in part, by providing orthologues of NPC1L1 from rabbit, hamster, canine and monkey species.

The present invention provides, an isolated polypeptide (e.g., an antigenic polypeptide) comprising an amino acid selected from the group consisting of: 527 or more contiguous amino acids from SEQ ID NO: 2; 42 or more contiguous amino acids from SEQ ID NO: 4; 70 or more contiguous amino acids from SEQ ID NO: 6; 84 or more contiguous amino acids from SEQ ID NO: 8; and 104 or more contiguous amino acids from SEQ ID NO: 10. In an embodiment of the invention, the isolated polypeptide comprises an amino acid sequence selected from SEQ ID NOs: 2, 4, 6, 8 and 10. In an embodiment of the invention, the polypeptide is labeled with a member selected from the group consisting of $^{32}P$, $^{35}S$, $^{3}H$, $^{99m}Tc$, $^{123}I$, $^{111}In$, $^{68}Ga$, $^{18}F$, $^{125}I$, $^{131}I$, $^{113m}In$, $^{76}Br$, $^{67}Ga$, $^{99m}Tc$, $^{123}I$, $^{111}In$ and $^{68}Ga$. The present invention also provides an isolated fusion polypeptide comprising the polypeptide of claim 1 fused to a heterologous polypeptide (e.g., glutathione-S-transferase (GST), a hexahistidine (His6) tag, a maltose binding protein (MBP) tag, a haemagglutinin (HA) tag, a cellulose binding protein (CBP) tag and a myc tag). An embodiment of the invention also includes a polypeptide of the invention, complexed with a member selected from the group consisting of compounds 1-9, a sterol (e.g., cholesterol), and a 5α-stanol; or a detectably labeled (e.g., $^{3}H$ or $^{125}I$) version thereof.

The present invention further provides an isolated polynucleotide which hybridizes to a polynucleotide encoding a polypeptide of the invention (e.g., as set forth above) under high stringency hybridization conditions. An embodiment of the invention includes an isolated polynucleotide encoding a polypeptide of the invention. An embodiment of the invention includes an isolated polynucleotide comprising a nucleotide sequence selected from SEQ ID NOs: 1, 3, 5, 7 and 9. The present invention also includes a recombinant vector comprising a polynucleotide of the invention (e.g., as set forth above). The present invention also includes an isolated host cell comprising a vector of the invention.

The present invention further provides an isolated antibody (e.g., monoclonal, polyclonal, a human antibody, a canine antibody, a hamster antibody, a rabbit antibody, a rhesus monkey antibody, a cynomolgus monkey antibody, chimeric, anti-idiotypic, recombinant and/or a humanized antibody) which specifically binds to a polypeptide (e.g., an antigenic polypeptide) of the invention. The present invention also includes a complex comprising an antibody of the invention bound to a polypeptide of the invention (e.g., a complex between an isolated antibody and a polypeptide in the body of a patient, e.g., in the intestinal tract of the patient or an in vitro complex). The present invention further provides a pharmaceutical formulation comprising an antibody of the invention along with a pharmaceutically acceptable carrier.

The present invention further provides an isolated canine, hamster, rabbit, rhesus monkey or cynomolgus monkey cell (e.g., an enterocyte) which lacks a gene which encodes a functional canine, hamster, rabbit, rhesus monkey or cynomolgus monkey NPC1L1 protein (e.g., SEQ ID NO: 2, 4, 6, 8 or 10), respectively. In an embodiment of the invention, the cell is isolated from duodenum, gall bladder, liver, small intestine or stomach tissue.

The present also provides a kit comprising: a substituted azetidinone (e.g., ezetimibe) in a pharmaceutical dosage form; and information indicating that canine, hamster, rabbit, rhesus monkey or cynomolgus monkey NPC1L1 is a target of the substituted azetidinone. In an embodiment of the invention, the dosage form is a tablet comprising 10 mg ezetimibe. In an embodiment of the invention, the kit further comprises simvastatin in a pharmaceutical dosage form (e.g., wherein the pharmaceutical dosage form comprises 5 mg, 10 mg, 20 mg, 40 mg or 80 mg simvastatin). In an embodiment of the invention, the simvastatin in pharmaceutical dosage form and the ezetimibe in pharmaceutical dosage form are associated in a single pill or tablet.

The present invention also provides a mutant transgenic dog, hamster, rabbit, rhesus monkey or cynomolgus monkey comprising a homozygous mutation of endogenous, chromosomal NPC1L1 wherein said dog, hamster, rabbit, rhesus monkey or cynomolgus monkey does not produce any functional NPC1L1 protein. In an embodiment of the invention, the animal exhibits a reduced serum sterol or 5α-stanol level, a reduced liver sterol or 5α-stanol level or a reduced level of intestinal absorption of sterol or 5α-stanol. An offspring or progeny of the dog, hamster, rabbit, rhesus monkey or cynomolgus monkey which has inherited a mutated NPC1L1 allele of said dog, hamster, rabbit, rhesus monkey or cynomolgus monkey is also within the scope of the present invention.

The present invention also includes a method for making a polypeptide comprising culturing a host cell (e.g., bacterial cell, an insect cell or a mammalian cell) of the invention (e.g., comprising a vector comprising a polynucleotide that encodes a polypeptide of the invention) under conditions in which the polynucleotide is expressed. In an embodiment of the invention, the polypeptide is isolated from the culture. The present invention further provides any polypeptide produced by said method.

The present invention further provides a method for identifying (i) an antagonist of NPC1L1 (e.g., human NPC1L1) or (ii) a substance useful for the treatment or prevention of hyperlipidemia, hypertriglyceridemia, hycholesterolemia, atherosclerosis or arteriosclerosis or (iii) an inhibitor of intestinal sterol (e.g., cholesterol) or 5α-stanol absorption comprising: (a) contacting a host cell (e.g., chinese hamster ovary (CHO) cell, a J774 cell, a macrophage cell or a Caco2 cell) expressing an NPC1L1 polypeptide of the invention e.g., polypeptide comprising an amino acid sequence selected from SEQ ID NOs: 2, 4, 6, 8 and 10 or a functional fragment thereof on a cell surface, in the presence of a known amount of detectably labeled substance which is known to bind to said polypeptide (e.g., a radiolabeled (e.g., $^3$H or $^{125}$I) compound represented by structural formula 1, 2, 3, 4, 5, 6, 7, 8 or 9) with a sample to be tested for the presence of the antagonist; and (b) measuring the amount of the detectably labeled substance specifically bound to the polypeptide; wherein an NPC1L1 antagonist in the sample is identified by measuring substantially reduced binding of the detectably labeled substance to the polypeptide, compared to what would be measured in the absence of such an antagonist. The present invention also provides a method for inhibiting NPC1L1 mediated sterol or 5α-stanol uptake, in a subject, by administering, to the subject, a substance identified by such a method.

The present invention further provides a method for identifying (i) an antagonist of NPC1L1 (e.g., human NPC1L1) or (ii) a substance useful for the treatment or prevention of hyperlipidemia, hypertriglyceridemia, hycholesterolemia, atherosclerosis or arteriosclerosis or (iii) an inhibitor of intestinal sterol (e.g., cholesterol) or 5α-stanol absorption comprising: (a) placing, in an aqueous suspension, a plurality of support particles, impregnated with a fluorescer (e.g., yttrium silicate, yttrium oxide, diphenyloxazole or polyvinyltoluene), to which a host cell (e.g., chinese hamster ovary (CHO) cell, a J774 cell, a macrophage cell or a Caco2 cell) expressing a polypeptide of the invention (e.g., comprising an amino acid sequence selected from SEQ ID NOs: 2, 4, 6, 8 and 10 or a functional fragment thereof) on a cell surface is attached; (b) adding, to the suspension, a radiolabeled substance which is known to bind said polypeptide (e.g., a radiolabeled (e.g., $^3$H or $^{125}$I) compound represented by structural formula 1, 2, 3, 4, 5, 6, 7, 8 or 9) and a sample to be tested for the presence of the antagonist, wherein the radiolabel emits radiation energy capable of activating the fluorescer upon binding of the substance to the polypeptide to produce light energy, whereas radiolabeled substance that does not bind to the polypeptide is, generally, too far removed from the support particles to enable the radioactive energy to activate the fluorescer; and (c) measuring the light energy emitted by the fluorescer in the suspension; wherein an NPC1L1 antagonist in the sample is identified by measuring substantially reduced light energy emission, compared to what would be measured in the absence of such an antagonist. The present invention also provides a method for inhibiting NPC1L1 mediated sterol or 5α-stanol uptake, in a subject, by administering, to the subject, a substance identified by such a method.

The present invention also provides a method for identifying (i) an antagonist of NPC1L1 (e.g., human NPC1L1) or (ii) a substance useful for the treatment or prevention of hyperlipidemia, hypertriglyceridemia, hycholesterolemia, atherosclerosis or arteriosclerosis or (iii) an inhibitor of intestinal sterol (e.g., cholesterol) or 5α-stanol absorption comprising: (a) contacting a host cell (e.g., chinese hamster ovary (CHO) cell, a J774 cell, a macrophage cell or a Caco2 cell) expressing an NPC1L1 polypeptide of the invention (e.g., comprising an amino acid sequence selected from SEQ ID NOs: 2, 4, 6, 8 and 10 or a functional fragment thereof) on a cell surface with a detectably labeled (e.g., $^3$H, $^{14}$C and $^{125}$I) sterol (e.g., cholesterol) or 5α-stanol and with a sample to be tested for the presence of the antagonist; and (b) measuring the amount of detectably labeled sterol or 5α-stanol in the cell; wherein an NPC1L1 antagonist in the sample is identified by measuring substantially reduced detectably labeled sterol or 5α-stanol within the host cell, compared to what would be measured in the absence of such an antagonist. The present invention also provides a method for inhibiting NPC1L1 mediated sterol or 5α-stanol uptake, in a subject, by administering, to the subject, a substance identified by such a method.

The present invention further provides a method for screening a sample for (i) an antagonist of NPC1L1 (e.g., human NPC1L1) or (ii) a substance useful for the treatment or prevention of hyperlipidemia, hypertriglyceridemia, hycholesterolemia, atherosclerosis or arteriosclerosis or (iii) an inhibitor of intestinal sterol (e.g., cholesterol) or 5α-stanol absorption comprising: (a) feeding a sterol or 5α-stanol-containing substance to a first and second animal which is a canine, hamster, rabbit, rhesus monkey or cynomolgus monkey comprising a functional NPC1L1 gene and to a third, mutant animal which is a canine, hamster, rabbit, rhesus monkey or cynomolgus monkey which does not comprise a functional NPC1L1 gene; (b) administering the sample to be tested for the presence of the antagonist to the first animal but not the second animal; (c) measuring the amount of sterol or 5α-stanol absorption in the intestine of said first, second and third animals; and (d) comparing the levels of intestinal sterol or 5α-stanol absorption in said first, second and third animals; wherein the sample is determined to contain the intestinal sterol or 5α-stanol absorption antagonist when the level of intestinal sterol or 5α-stanol absorption in the first animal and third animal are less than the amount of intestinal sterol or 5α-stanol absorption in the second animal. In an embodiment of the invention, the level of sterol or 5α-stanol cholesterol absorption is determined by measuring the level of serum sterol or 5α-stanol in the canine, hamster, rabbit, rhesus monkey or cynomolgus monkey. The present invention also provides a method for inhibiting NPC1L1 mediated sterol or 5α-stanol uptake, in a subject, by administering, to the subject, a substance identified by such a method.

The present invention also provides a method for decreasing the level of intestinal sterol (e.g., cholesterol) or 5α-stanol absorption in a non-human mammalian subject (e.g., a canine such as a dog, hamster, rabbit, rhesus monkey or cynomolgus monkey) comprising reducing the level of expression of endogenous NPC1L1 in the subject. In an embodiment of the invention, the level of expression of NPC1L1 in the subject is reduced by mutating NPC1L1 in the subject.

BRIEF DESCRIPTION OF THE FIGURES

FIG. 7. Comparison of the amino acid sequences of monkey NPC1L1 (SEQ ID NO: 8), canine NPC1L1 (SEQ ID NO: 2), hamster NPC1L1 (SEQ ID NO: 6), rabbit NPC1L1 (SEQ ID NO: 4), human NPC1L1 (SEQ ID NO: 25), rat NPC1L1 (SEQ ID NO: 28), mouse NPC1L1 (SEQ ID NO: 27) (Altmann et al., Science 303:1201-1204 (2004)), chimpanzee NPC1L1 (SEQ ID NO: 26) (Genbank XM_519072) and cow NPC1L1 (SEQ ID NO: 29) (Genbank XM_588051).

DETAILED DESCRIPTION OF THE INVENTION

Figure 1:
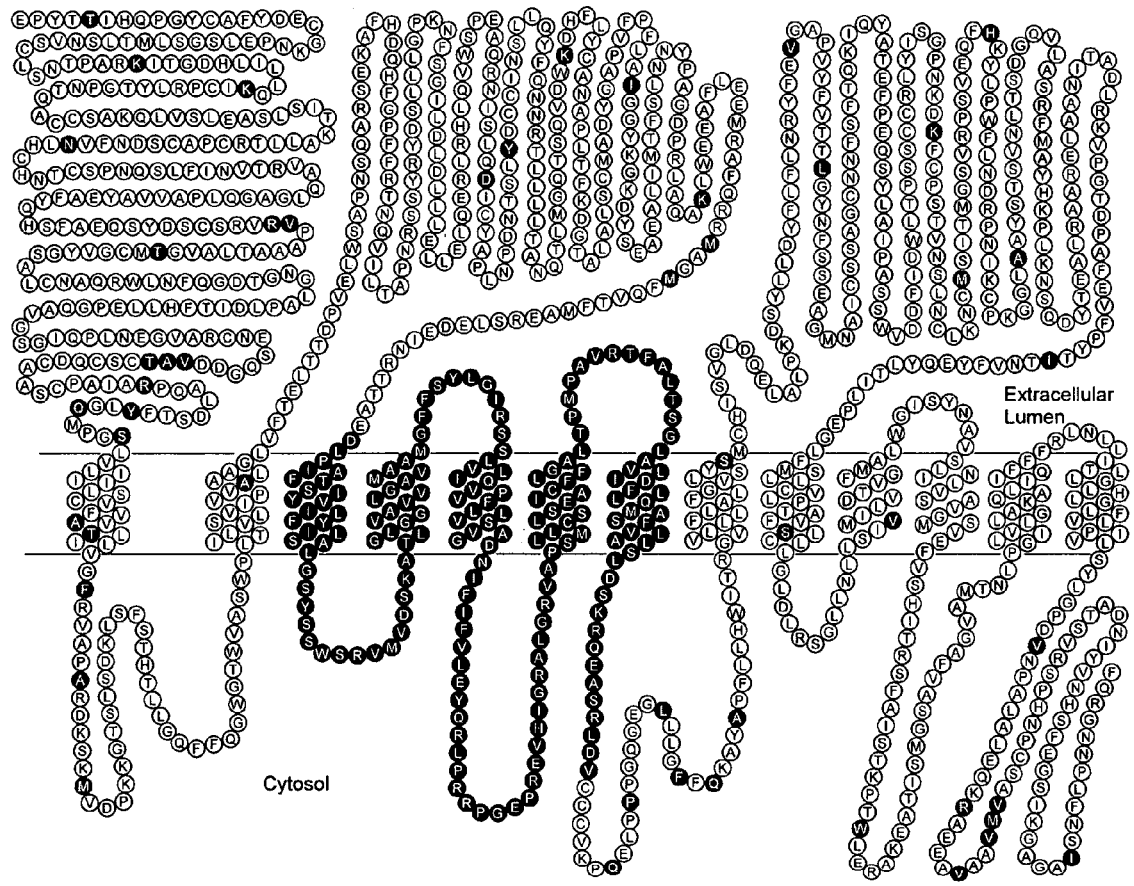
FIG. 1. Ball model of predicted membrane topology of human NPC1L1 (SEQ ID NO: 25). Residues highlighted (black) identify the predicted sterol sensing domain (Carstea et al., Science; 277:228-231 (1997)). Shaded residues (gray) identify amino acids that are not conserved between human and monkey proteins.

The present invention includes any isolated polynucleotide or isolated polypeptide (or any antigenic and/or active fragment thereof) comprising a nucleotide or amino acid sequence referred to, below, in Table 1.

TABLE 1

Polynucleotides and Polypeptides of the Invention.

| Polynucleotide or Polypeptide | Sequence Identifier |
| --- | --- |
| Canine NPC1L1 polynucleotide | SEQ ID NO: 1 |
| Canine NPC1L1 polypeptide | SEQ ID NO: 2 |
| Rabbit NPC1L1 polynucleotide | SEQ ID NO: 3 |
| Rabbit NPC1L1 polypeptide | SEQ ID NO: 4 |
| Hamster NPC1L1 polynucleotide | SEQ ID NO: 5 |
| Hamster NPC1L1 polypeptide | SEQ ID NO: 6 |
| Rhesus monkey NPC1L1 polynucleotide | SEQ ID NO: 7 |
| Rhesus monkey NPC1L1 polypeptide | SEQ ID NO: 8 |
| Cynomolgus monkey NPC1L1 polynucleotide | SEQ ID NO: 9 |
| Cynomolgus monkey NPC1L1 polypeptide | SEQ ID NO: 10 |

The term "rhesus monkey" is well known in the art and typically refers to the Rhesus Macaque or the *Macaca mulatto*.

The term "cynomolgus monkey" is also well known in the art and typically refers to the *Macaca fascicularis*.

The term "canine" includes any animal of the genus *Canis* and any species, variety or breed thereof, for example, the domestic dog-*Canis familiaris* (e.g., beagle). Structural formulas representing compounds 1-9 are as follows:

Compound 1
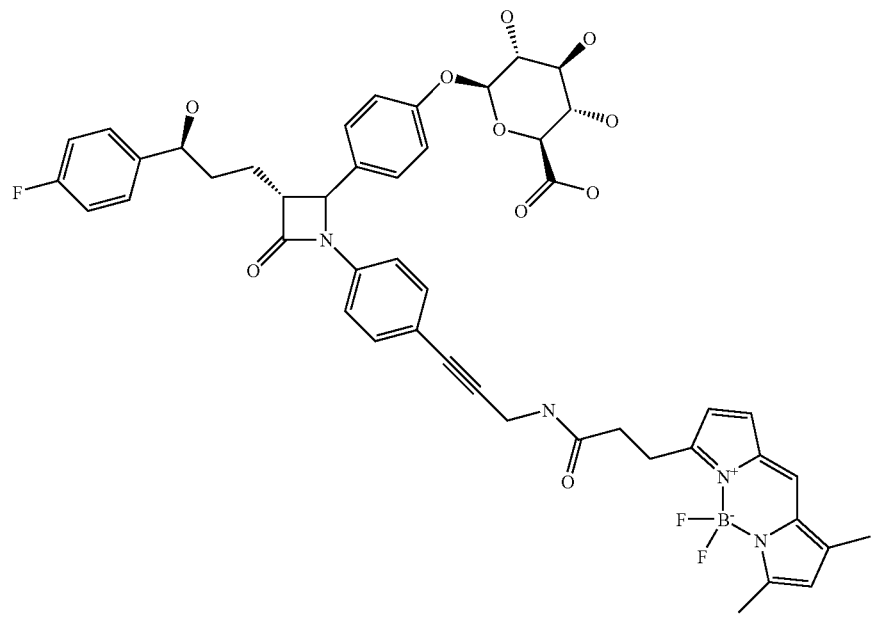
Compound 2
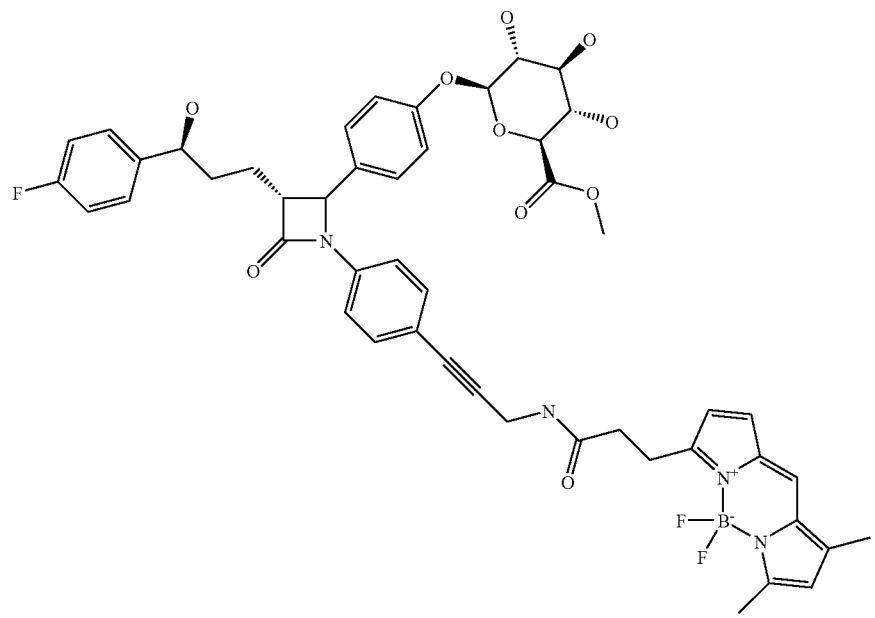
Compound 3
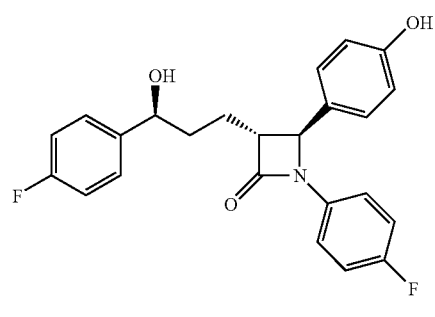
Compound 4
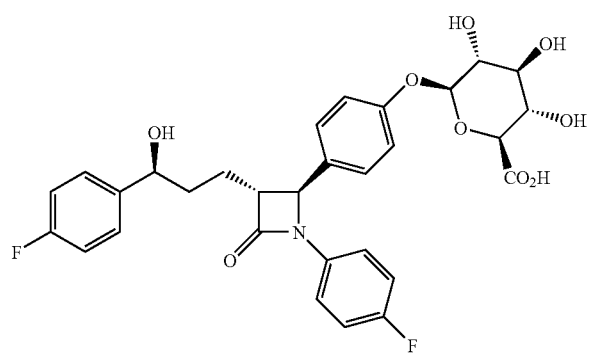

Compound 5

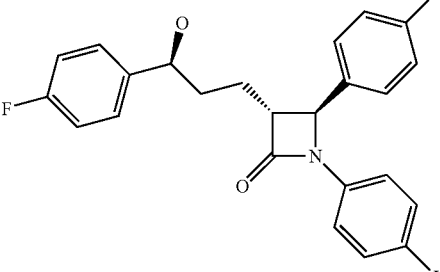

Compound 6

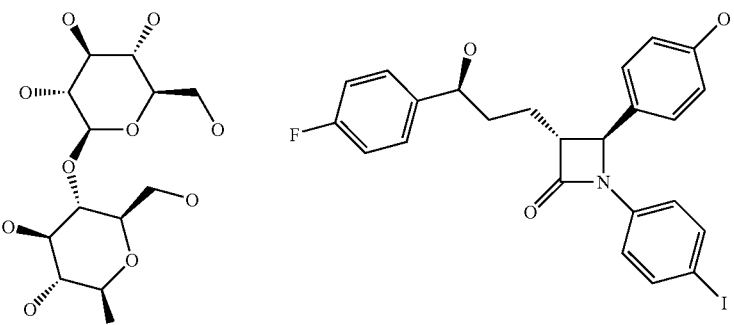

Compound 7

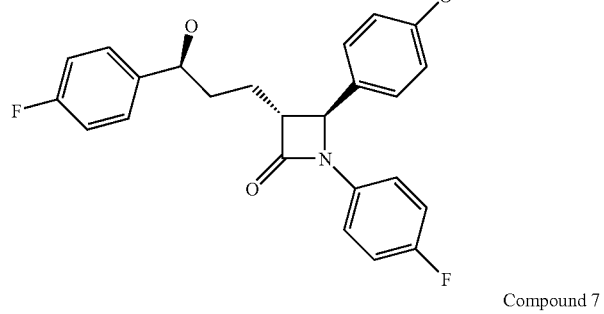

Compound 8

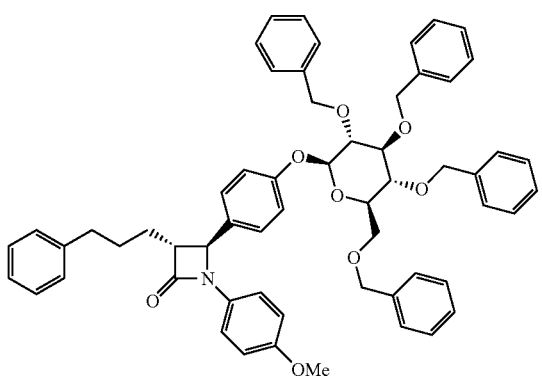

Compound 9

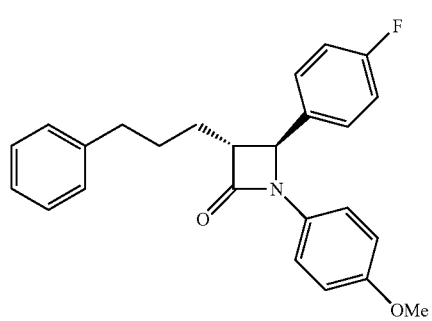

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

A "polynucleotide", "nucleic acid" or "nucleic acid molecule" includes the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine;

"DNA molecules"), or any phosphoester analogs thereof, such as phosphorothioates and thioesters, in single stranded form, double-stranded form or otherwise.

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

A "coding sequence" or a sequence "encoding" an expression product, such as a RNA, polypeptide, protein, or enzyme, is a nucleotide sequence that, when expressed, results in production of the product.

The term "gene" means a DNA sequence that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

The present invention includes nucleic acid fragments of any of SEQ ID NOs: 1, 3, 5, 7, or 9. For example, the present invention includes any polynucleotide encoding a polypeptide comprising the amino acid sequence of SEQ ID NO: 2, 4, 6, 8, or 10 as well as any polynucleotide encoding a fragment (e.g., an antigenic fragment) of a polypeptide comprising the amino acid sequence of SEQ ID NO: 2, 4, 6, 8, or 10 for example as set forth herein. In an embodiment of the invention, the polynucleotide comprises at least about 1550, 1560, 1570, 1580, 1590, 1600, 1610, 2000, 2500, 3000, 3400, 3800, 3900 or 3950 contiguous nucleotides of SEQ ID NO: 1. In an embodiment of the invention, the polynucleotide comprises at least about 100, 110, 120, 123, 124, 125, 150, 300, 600, 900, 1000, 1500, 2000, 2300, 2600, 2900, 3300, 3500, 3700, 3900 or 3950 contiguous nucleotides of SEQ ID NO: 3. In an embodiment of the invention, the polynucleotide comprises at least about 230, 235, 240, 243, 244, 245, 246, 247, 248, 249, 250, 251, 252, 300, 500, 700, 900, 1000, 1300, 1500, 1700, 1900, 2000, 2200, 2400, 2600, 2900, 3000, 3300, 3500, 3700, 3800, 3900 or 3950 contiguous nucleotides of SEQ ID NO: 7. In an embodiment of the invention, the polynucleotide comprises at least about 300, 301, 302, 303, 304, 305, 306, 307, 308, 309, 310, 311, 312, 313, 314, 315, 316, 500, 700, 900, 1000, 1300, 1500, 1700, 1900, 2000, 2200, 2400, 2600, 2900, 3000, 3300, 3500, 3700, 3800, 3900 or 3950 contiguous nucleotides of SEQ ID NO: 9.

As used herein, the term "oligonucleotide" refers to a nucleic acid, generally of no more than about 100 nucleotides (e.g., 30, 40, 50, 60, 70, 80, or 90), that may be hybridizable to a genomic DNA molecule, a cDNA molecule, or an mRNA molecule encoding a gene, mRNA, cDNA, or other nucleic acid of interest. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, preferably on a nucleic acid synthesizer.

A "protein sequence", "peptide sequence" or "polypeptide sequence" or "amino acid sequence" refers to a series of two or more amino acids in a protein, peptide or polypeptide.

"Protein", "peptide" or "polypeptide" includes a contiguous string of two or more amino acids. Preferred peptides of the invention include those set forth in any of SEQ ID NOs: 2, 4, 6, 8 or 10 as well as variants and fragments thereof. In an embodiment of the invention, the fragment is an antigenic fragment. In an embodiment, the fragment is an active fragment which is capable of binding to an azetidinone such as ezetimibe or a related compounds such as any of those set forth herein (e.g., any of compounds 1-9)-active fragments are useful, e.g., for identification of NPC1L1 antagonists, for example, in an assay as set forth herein. Such fragments (e.g., antigenic fragments) comprise, in an embodiment of the invention, at least about 10 (e.g., 11, 12, 13, 14, 15, 16, 17, 18 or 19), or at least about 20 (e.g., 21, 22, 23, 24, 25, 26, 27, 28, 29, 30, 35, 40), or at least about 42 (e.g., 43, 44, 45, 46, 47, 48, 49, 50, 60, 70, 80, 90, 100, 110, 120 or 130) or more contiguous amino acid residues from any of SEQ ID NOs: 2, 4, 6, 8, or 10. An embodiment of the invention includes any polypeptide comprising at least about 527 contiguous amino acids from SEQ ID NO: 2 (e.g., 500, 505, 510, 515, 520, 550, 600, 650, 700, 750, 800, 850, 900, 1000, 1050, 1100, 1150, 1200, 1250, 1300 or 1320 contiguous amino acids). An embodiment of the invention includes any polypeptide comprising at least about 42 contiguous amino acids from SEQ ID NO: 4 (e.g., 35, 37, 40, 41, 50, 100, 150, 200, 250, 300, 350, 400, 450, 500, 550, 600, 650, 700, 750, 800, 850, 900, 1000, 1050, 1100, 1150, 1200, 1250, 1300 or 1320 contiguous amino acids). An embodiment of the invention includes any polypeptide comprising at least about 70 or more contiguous amino acids from SEQ ID NO: 6 (e.g., 60, 65, 67, 69, 80, 90, 100, 150, 200, 250, 300, 350, 400, 450, 500, 550, 600, 650, 700, 750, 800, 850, 900, 1000, 1050, 1100, 1150, 1200, 1250, 1300 or 1320 contiguous amino acids). An embodiment of the invention includes any polypeptide comprising at least about 84 or more contiguous amino acids from SEQ ID NO: 8 (e.g., 75, 77, 79, 82, 83, 90, 100, 150, 200, 250, 300, 350, 400, 450, 500, 550, 600, 650, 700, 750, 800, 850, 900, 1000, 1050, 1100, 1150, 1200, 1250, 1300, 1320 or 1330 contiguous amino acids). An embodiment of the invention includes any polypeptide comprising at least about 104 or more contiguous amino acids from SEQ ID NO: 10 (e.g., 90, 93, 95, 97, 99, 100, 101, 102, 103, 105, 150, 200, 250, 300, 350, 400, 450, 500, 550, 600, 650, 700, 750, 800, 850, 900, 1000, 1050, 1100, 1150, 1200, 1250, 1300, 1320 or 1330 contiguous amino acids. Also included within the scope of the present invention is any polynucleotide that encodes such a polypeptide. In an embodiment of the invention, a polypeptide as set forth above is an antigenic polypeptide.

In an embodiment of the invention, a polypeptide of the invention (e.g., SEQ ID NO: 2, 4, 6, 8 or 10 or any fragment thereof, e.g., as set forth herein) exhibits the ability to bind to ezetimibe or any structurally related compound (e.g., any of compounds 1-9 herein). The scope of the invention also includes any polynucleotide encoding such a polypeptide.

The polypeptides of the invention can be produced by proteolytic cleavage of an intact peptide, by chemical synthesis or by the application of recombinant DNA technology and are not limited to polypeptides delineated by proteolytic cleavage sites. The polypeptides, either alone or cross-linked or conjugated to a carrier molecule to render them more immunogenic, are useful as antigens to elicit the production of antibodies and fragments thereof and are within the scope of the present invention. The antibodies can be used, e.g., in immunoassays for immunoaffinity purification or for inhibition of NPC1L1, etc.

The terms "isolated polynucleotide" or "isolated polypeptide" include a polynucleotide (e.g., RNA or DNA molecule, or a mixed polymer) or a polypeptide, respectively, which are partially (to any degree) or fully separated from other components that are normally found in cells or in recombinant DNA expression systems. These components include, but are not limited to, cell membranes, cell walls, ribosomes, polymerases, serum components and extraneous genomic sequences.

An isolated polynucleotide or polypeptide will, in an embodiment of the invention, be an essentially homogeneous composition.

"Amplification" of DNA as used herein includes the use of polymerase chain reaction (PCR) to increase the concentration of a particular DNA sequence within a mixture of DNA sequences. For a description of PCR see Saiki, et al., Science (1988) 239:487.

A practitioner or ordinary skill in the art could easily isolate and express any of the NPC1L1 genes (e.g., SEQ ID NO: 1, 3, 5, 7 or 9) and proteins (e.g., SEQ ID NO: 2, 4, 6, 8 or 10) set forth herein. For example, a convenient method for obtaining an NPC1L1 gene of the invention is to simply amplify the gene, using standard PCR methods from a cDNA library that was generated from canine, rabbit, hamster, rhesus monkey or cynomolgus monkey tissue or cells. Such a cDNA library can be generated using any of several well known methods in the art. In such an embodiment of the invention, oligonucleotide PCR primers, to be used in PCR amplification of an NPC1L1 of the invention, anneal to the extreme 5' and 3' ends of a gene of the invention (e.g., SEQ ID NO: 1, 3, 5, 7, or 9).

The term "host cell" includes any cell of any organism that is selected, modified, transfected, transformed, grown, or used or manipulated in any way, for the production of a substance by the cell, for example the expression or replication, by the cell, of a gene, a DNA or RNA sequence or a protein. Suitable host cells include bacterial cells (e.g., E. coli) and mammalian cells such as chinese hamster ovary (CHO) cells, murine macrophage J774 cells or any other macrophage cell line and human intestinal epithelial Caco2 cells.

The nucleotide sequence of a nucleic acid may be determined by any method known in the art (e.g., chemical sequencing or enzymatic sequencing). "Chemical sequencing" of DNA includes methods such as that of Maxam and Gilbert (1977) (Proc. Natl. Acad. Sci. USA 74:560), in which DNA is randomly cleaved using individual base-specific reactions. "Enzymatic sequencing" of DNA includes methods such as that of Sanger (Sanger, et al., (1977) Proc. Natl. Acad. Sci. USA 74:5463).

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the β-lactamase promoter (Villa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

The present invention comprises a nucleotide encoding NPC1L1 or a fragment thereof (e.g., a functional or antigenic fragment) operably associated with a control sequence such as a promoter. A coding sequence is "under the control of", "functionally associated with" or "operably associated with" transcriptional and translational control sequences in a cell when the sequences direct RNA polymerase mediated transcription of the coding sequence into RNA, preferably mRNA, which then may be RNA spliced (if it contains introns) and, optionally, translated into a protein encoded by the coding sequence.

The terms "express" and "expression" mean allowing or causing the information in a gene, RNA or DNA sequence to become manifest; for example, producing a protein by activating the cellular functions involved in transcription and translation of a corresponding gene. A DNA sequence is expressed in or by a cell to form an "expression product" such as an RNA (e.g., mRNA) or a protein. The expression product itself may also be said to be "expressed" by the cell.

The term "transformation" means the introduction of a nucleic acid into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species.

The term "vector" includes a vehicle (e.g., a plasmid) by which a DNA or RNA sequence can be introduced into a host cell, so as to transform the host and, optionally, promote expression and/or replication of the introduced sequence.

The present invention includes any polynucleotide (e.g., comprising a nucleotide sequence of SEQ ID NO: 1, 3, 5, 7 or 9) encoding an NPC1L1 polypeptide (e.g., comprising an amino acid sequence of SEQ ID NO: 2, 4, 6, 8 or 10) in a vector. Vectors that can be used in this invention include plasmids, viruses, bacteriophage, integratable DNA fragments, and other vehicles that may facilitate introduction of the nucleic acids into the genome of the host. Plasmids are the most commonly used form of vector but all other forms of vectors which serve a similar function and which are, or become, known in the art are suitable for use herein. See, e.g., Pouwels, et al., *Cloning Vectors: A Laboratory Manual*, 1985 and Supplements, Elsevier, N.Y., and Rodriguez et al. (eds.), *Vectors: A Survey of Molecular Cloning Vectors and Their Uses*, 1988, Buttersworth, Boston, Mass.

The term "expression system" means a host cell and compatible vector which, under suitable conditions, can express a protein or nucleic acid which is carried by the vector and introduced to the host cell. Common expression systems include *E. coli* host cells and plasmid vectors, insect host cells and Baculovirus vectors, and mammalian host cells and vectors.

Expression of nucleic acids encoding the NPC1L1 polypeptides of this invention can be carried out by conventional methods in either prokaryotic or eukaryotic cells. Although *E. coli* host cells are employed most frequently in prokaryotic systems, many other bacteria, such as various strains of *Pseudomonas* and *Bacillus*, are known in the art and can be used as well. Suitable host cells for expressing nucleic acids encoding the NPC1L1 polypeptides include prokaryotes and higher eukaryotes. Prokaryotes include both gram-negative and gram-positive organisms, e.g., *E. coli* and *B. subtilis*. Higher eukaryotes include established tissue culture cell lines from animal cells, both of non-mammalian origin, e.g., insect cells, and birds, and of mammalian origin, e.g., human, primates, and rodents. The present invention comprise any host cell comprising an NPC1L1 polynucleotide of the invention and/or expressing an NPC1L1 polypeptide of the invention, for example, on the cell surface.

Prokaryotic host-vector systems include a wide variety of vectors for many different species. A representative vector for amplifying DNA is pBR322 or many of its derivatives (e.g., pUC18 or 19). Vectors that can be used to express the NPC1L1 polypeptides include, but are not limited to, those containing the lac promoter (pUC-series); trp promoter (pBR322-trp); lpp promoter (the plN-series); lambda-pP or pR promoters (pOTS); or hybrid promoters such as ptac (pDR540). See Brosius et al., "Expression Vectors Employing Lambda-, trp-, lac-, and lpp-derived Promoters", in Rodriguez and Denhardt (eds.) *Vectors: A Survey of Molecular Cloning Vectors and Their Uses*, 1988, Buttersworth, Boston, pp. 205-236. Many polypeptides can be expressed, at high levels, in an *E. coli*/T7 expression system as disclosed in U.S. Pat. Nos. 4,952,496, 5,693,489 and 5,869,320 and in Davanloo, P., et al., (1984) Proc. Natl. Acad. Sci. USA 81: 2035-2039; Studier, F. W., et al., (1986) J. Mol. Biol. 189: 113-130; Roseonberg, A. H., et al., (1987) Gene 56: 125-135; and Dunn, J. J., et al., (1988) Gene 68: 259.

Higher eukaryotic tissue culture cells may also be used for the recombinant production of the NPC1L1 polypeptides of the invention. Although any higher eukaryotic tissue culture cell line might be used, including insect baculovirus expression systems, mammalian cells are preferred. Transformation or transfection and propagation of such cells have become a routine procedure. Examples of useful cell lines include HeLa cells, chinese hamster ovary (CHO) cell lines, J774 cells, Caco2 cells, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also, usually, contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Examples of expression vectors include pCR®3.1, pCDNA1, pCD (Okayama, et al., (1985) Mol. Cell Biol. 5:1136), pMC1neo Poly-A (Thomas, et al., (1987) Cell 51:503), pREP8, pSVSPORT and derivatives thereof, and baculovirus vectors such as pAC373 or pAC610. One embodiment of the invention includes membrane bound NPC1L1. In this embodiment, NPC1L1 can be expressed in the cell membrane of a eukaryotic cell and the membrane bound protein can be isolated from the cell by conventional methods which are known in the art.

The present invention also includes fusions which include the NPC1L1 polypeptides and NPC1L1 polynucleotides of the present invention and a second, heterologous polypeptide or polynucleotide moiety (different from the NPC1L1 moiety in the fusion), which may be referred to as a "tag". The fusions of the present invention include any of the polynucleotides or polypeptides set forth in Table 1 or any subsequence or fragment thereof (discussed above). The fused polypeptides of the invention may be conveniently constructed, for example, by insertion of a polynucleotide of the invention or fragment thereof into an expression vector. The fusions of the invention include tags which facilitate purification or detection. Such tags include green fluorescent protein (GFP) or any mutant thereof (e.g., S65T mutant; see Heim et al., Nature 373: 663-664 (1995)), glutathione-S-transferase (GST), hexahistidine (His6) tags, maltose binding protein (MBP) tags, haemagglutinin (HA) tags, cellulose binding protein (CBP) tags and myc tags. Detectable tags such as $^{32}P$, $^{35}S$, $^{3}H$, $^{99m}Tc$, $^{123}I$, $^{111}In$, $^{68}Ga$, $^{18}F$, $^{125}I$, $^{131}I$, $^{113m}In$, $^{76}Br$, $^{67}Ga$, $^{99m}Tc$, $^{123}I$, $^{111}In$ and $^{68}Ga$ may also be used to label the polypeptides and polynucleotides of the invention. Methods for constructing and using such fusions are very conventional and well known in the art.

Modifications (e.g., post-translational modifications) that occur in a polypeptide often will be a function of how it is made. For polypeptides made by expressing a cloned gene in a host, for instance, the nature and extent of the modifications, in large part, will be determined by the host cell's post-translational modification capacity and the modification signals present in the polypeptide amino acid sequence. For instance, as is well known, glycosylation often does not occur in bacterial hosts such as *E. coli*. Accordingly, when glycosylation is desired, a polypeptide can be expressed in a glycosylating host, generally a eukaryotic cell. Insect cells often carry out post-translational glycosylations which are similar to those of mammalian cells. For this reason, insect cell expression systems have been developed to express, efficiently, mammalian proteins having native patterns of glycosylation. An insect cell which may be used in this invention is any cell derived from an organism of the class Insecta. In an embodiment of the invention, the insect is *Spodoptera fruigiperda* (Sf9 or Sf21) or *Trichoplusia ni* (High 5). Examples of insect expression systems that can be used with the present invention, for example to produce NPC1L1 polypeptide, include Bac-To-Bac (Invitrogen Corporation, Carlsbad, Calif.) or Gateway (Invitrogen Corporation, Carlsbad, Calif.). If desired, deglycosylation enzymes can be used to remove carbohydrates attached during production in eukaryotic expression systems. The present invention includes both glycosylated and un-glycosylated canine, rabbit, hamster, cynomolgus monkey and rhesus monkey NPC1L1.

Other modifications may also include addition of aliphatic esters or amides to the polypeptide carboxyl terminus. The present invention also includes analogs of the NPC1L1 polypeptides which contain modifications, such as incorporation of unnatural amino acid residues, or phosphorylated amino acid residues such as phosphotyrosine, phosphoserine or phosphothreonine residues. Other potential modifications include sulfonation, biotinylation, or the addition of other moieties. For example, the NPC1L1 polypeptides of the invention may be appended with a polymer which increases the half-life of the peptide in the body of a subject. Subitable polymers include polyethylene glycol (PEG) (e.g., PEG with a molecular weight of 2 kDa, 5 kDa, 10 kDa, 12 kDa, 20 kDa, 30 kDa and 40 kDa), dextran and monomethoxypolyethylene glycol (mPEG).

The peptides of the invention may also be cyclized. Specifically, the amino- and carboxy-terminal residues of an NPC1L1 polypeptide or two internal residues of an NPC1L1 polypeptide of the invention can be fused to create a cyclized peptide. Methods for cyclizing peptides are conventional and very well known in the art; for example see Gurrath, et al., (1992) Eur. J. Biochem. 210:911-921.

The present invention contemplates any superficial or slight modification to the amino acid or nucleotide sequences which correspond to the NPC1L1 polypeptides of the invention. In particular, the present invention contemplates sequence conservative variants of the nucleic acids which encode the polypeptides of the invention. "Sequence-conservative variants" of a polynucleotide sequence are those in which a change of one or more nucleotides in a given codon results in no alteration in the amino acid encoded at that position. Function-conservative variants of the polypeptides of the invention are also contemplated by the present invention. "Function-conservative variants" are those in which one or more amino acid residues in a protein or enzyme have been changed without altering the overall conformation and function of the polypeptide, including, but, by no means, limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids which may be interchangeable include aspartic acid and glutamic acid and basic amino acids which may be interchangeable include histidine, lysine and arginine.

The present invention includes polynucleotides encoding canine, hamster, rabbit, rhesus monkey and cynomolgus monkey NPC1L1 and fragments thereof as well as nucleic acids which hybridize to the polynucleotides. Preferably, the nucleic acids hybridize under low stringency conditions, more preferably under moderate stringency conditions and most preferably under high stringency conditions. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. In an embodiment of the invention, low stringency hybridization conditions are 55° C., 5×SSC, 0.1% SDS, 0.25% milk, and no formamide at 42° C.; or 30% formamide, 5×SSC, 0.5% SDS at 42° C. In an embodiment of the invention, moderate stringency hybridization conditions are similar to the low stringency conditions except the hybridization is carried out in 40% formamide, with 5× or 6×SSC at 42° C. In an embodiment of the invention, high stringency hybridization conditions are similar to low stringency conditions except the hybridization conditions are carried out in 50% formamide, 5× or 6×SSC and, optionally, at a higher temperature (e.g., higher than 42° C.: 57° C., 59° C., 60° C., 62° C., 63° C., 65° C. or 68° C.). In general, SSC is 0.15M NaCl and 0.015M Na-citrate.

In an embodiment of the invention, low stringency hybridization conditions comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5×Denhardt's reagent (50×Denhardt's contains per 500 ml:05 g Ficoll (Type 400, Pharmacia):05 g BSA (Fraction V; Sigma)) and 100 µg/ml denatured salmon sperm DNA followed by washing in a solution comprising 1×SSPE, 0.1% SDS at 42° C. when a probe of about 500 nucleotides in length is employed.

In an embodiment of the invention, medium stringency conditions comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 5.0×SSPE, 1.0% SDS at 42° C. when a probe of about 500 nucleotides in length is employed.

In an embodiment of the invention, high stringency conditions comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 5-10×SSPE, 1.0% SDS at 42° C. when a probe of about 500 nucleotides in length is employed.

Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, i.e., oligonucleotides, the position of mismatches becomes more important, and the length of the oligonucleotide determines its specificity (see Sambrook, et al., supra).

In an embodiment of the invention, a polynucleotide of the invention (e.g., SEQ ID NO: 1, 3, 5, 7, or 9 or any polynucleotide that hybridizes thereto under any condition, for example, high stringency conditions e.g., as set forth herein) encodes a polypeptide that exhibits the ability to bind to ezetimibe or any structurally related compound (e.g., any of compounds 1-9 herein). The scope of the invention also includes any such polypeptide.

Also included in the present invention are polynucleotides comprising nucleotide sequences and polypeptides comprising amino acid sequences which are at least about 70% identical, preferably at least about 80% identical, more preferably at least about 90% identical and most preferably at least about 95% identical (e.g., 95%, 96%, 97%, 98%, 99%, 100%) to the reference canine, hamster, rabbit, rhesus monkey, or cynomolgus monkey NPC1L1 nucleotide (e.g., any of SEQ ID NOs: 1, 3, 5, 7, or 9) or amino acid sequences (e.g., SEQ ID NOs: 2, 4, 6, 8, or 10) when the comparison is performed by a BLAST algorithm wherein the parameters of the algorithm are selected to give the largest match between the respective sequences over the entire length of the respective reference sequences. Polypeptides comprising amino acid sequences which are at least about 70% similar or homologous, preferably at least about 80% similar or homologous, more preferably at least about 90% similar or homologous and most preferably at least about 95% similar or homologous (e.g., 95%, 96%, 97%, 98%, 99%, 100%) to the reference canine, hamster, rabbit, rhesus monkey, or cynomolgus monkey NPC1L1 (e.g., SEQ ID NOs: 2, 4, 6, 8 or 10), when the comparison is performed with a BLAST algorithm wherein the parameters of the algorithm are selected to give the largest match between the respective sequences over the entire length of the respective reference sequences, are also included in the present invention.

Sequence identity refers to exact matches between the nucleotides or amino acids of two sequences which are being compared. Sequence similarity or homology refers to both exact matches between the amino acids of two polypeptides which are being compared in addition to matches between nonidentical, biochemically related amino acids. Biochemically related amino acids which share similar properties and may be interchangeable are discussed above.

In an embodiment of the invention, a polypeptide of the invention (e.g., SEQ ID NO: 2, 4, 6, 8 or 10 or any polypeptide bearing similarity or identity thereto e.g., 95% or more, including 97% or 99%) exhibits the ability to bind to ezetimibe or any structurally related compound (e.g., any of compounds 1-9 herein). The scope of the invention also includes any polynucleotide encoding such a polypeptide.

The following references regarding the BLAST algorithm are herein incorporated by reference: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M., et al., (1994) Comput. Appl. Biosci. 10:67-70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in *Atlas of Protein Sequence and Structure*, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, New York.

Protein Purification

The proteins, polypeptides and antigenic fragments of this invention can be purified by standard methods, including, but not limited to, salt or alcohol precipitation, affinity chromatography (e.g., used in conjunction with a purification tagged NPC1L1 polypeptide as discussed above), preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in "*Guide to Protein Purification*", Methods in Enzymology, Vol. 182, M. Deutscher, Ed., 1990, Academic Press, New York, N.Y.

Purification steps can be followed by performance of assays for receptor binding activity as described below. Particularly where an NPC1L1 polypeptide is being isolated from a cellular or tissue source, it is preferable to include one or more inhibitors of proteolytic enzymes in the assay system, such as phenylmethanesulfonyl fluoride (PMSF), Pefabloc SC, pepstatin, leupeptin, chymostatin and EDTA.

In an embodiment of the invention, canine, hamster, rabbit, cynomolgus monkey or rhesus monkey NPC1L1 is purified by isolating a cell membrane comprising the polypeptide from other contents of a host cell. For example, the cell carrying the NPC1L1 polypeptide can be lysed and the membranes from the cell can be pelleted by centrifugation.

NPC1L1

The present invention includes canine, hamster, rabbit, cynomolgus monkey or rhesus monkey NPC1L1 polypeptides and polynucleotides as set forth below along with allelic variants and fragments thereof (e.g., antigenic fragments thereof).

```
Canine NPC1L1 ORF
                                                             (SEQ ID NO: 1)
atggcggaca ctggcctgag gggctggctg ctatgggcac tgctcctgca tgtggcccag    60
agtgagctgt acacacccat ccaccagcct ggctactgcg ctttctacga cgagtgtggg   120
aagaacccag agctgtctgg gggactggcg cctctgtcta atgtgtcctg cctgtccaac   180
acgcccgccc tccgtgtcac tggtgagcac ctgaccctcc tacagcgcat ctgcccccgc   240
ctctacacgg gcaccaccac ctatgcctgc tgctccccca agcagctgct gtccctggag   300
acgagcctgg cggtcaccaa ggccctcctc acccgctgcc ccacctgctc cgacaacttt   360
gtgaacctgc actgccaaaa cacctgcagc cccaaccaaa gtctcttcat caacgtgacc   420
cgcgtggctg ggggcggggg tggccggccc caggctgtgg tggcctatga ggccttctac   480
caggacacct ttgcccagca gacctacgac tcttgcagcc gggtgcgcat ccctgcggct   540
gccacgctgg ccgtgggcac catgtgtggc gtttatggct ccaccctctg caatgctcag   600
cgctggctca atttccaggg ggacacttcg aatggcctgg ctcccctaga catcaccttc   660
cacctgatgg agcccggcca ggccctaggg agtgggatgc aggctctgac cggggagatc   720
```

-continued

```
aggccctgca acgagtccca gggcaatggc acggtggcct gctcctgcca ggactgtgct    780
gcgtcctgcc ccaccatccc ccagcccag gcactggact ccaccttcta cctgggcggg    840
ctggaaggtg ggctggccct tgtcatcatc ctctgctctg cttttgccct gcttaccacc    900
ttcctggtgg gtacccgcct ggcctcctcc tgtggcaagg acaagacgcc agaccccaag    960
gcaggcatga gcctgtctga caaactcagc ctctccacca acgtcatcct tagccagtgc   1020
ttccagaact ggggcacatg ggtggcctca tggccgctga ccatcctgtt ggtgtccatc   1080
gccgtggtat tggccttgtc aggaggcctg gcctttgtgg aactgaccac ggacccagtg   1140
gagctgtggt cggcccccag cagccaagcc cggagtgaga aggcttttcca cgaccagcat   1200 tttggcccct tcctccgaac caaccaggtg atcttgacgg ctcccaaccg gcccagctac   1260
cactacgact ccctgctcct ggggcccaag aacttcagtg gggtcctggc ctctgacctc   1320
ctgctggagc tgctggagct acaggagacG ctgcggcacc tccaggtgtg gtcgcccgag   1380
gagcagcgcc acatctcgct gcaggacatc tgcttcgcgc ccctcaaccc tcacaatgcc   1440
agcctctccg actgctgcat caacagcctc ctgcagtatt ccagagcaa ccgcacgcac   1500 ctgctgctca cggccaacca gacgctgacg ggccagacct cccaggtgga ctggagggac   1560
cactttctct actgtgctaa cgccccactc accttcaagg atggcacagc cctagccctg   1620
agctgcatgg ctgactatgg gggccctgtc ttcccctccc ttgccgtggg tggctacaaa   1680
gggaaggact actctgaggc ggaggccctg attatgacct tctccctcaa caactatgcc   1740
cctggggacc cccggctggc ccaggctaag ctctgggagg cagccttctt ggaggagatg   1800
aaagccttcc agcggcggac agctggcact ttccaggtca cattcatggc tgagcgctcc   1860
ctggaggacg agattaaccg cacgacggcg gaggacctcc ccatcttcgg agtcagctac   1920
atcatcatct tcctgtacat ctccctggcg ctgggcagct actccagctg gcgccggggtg   1980 ccggtggact ccaaggtcac gctgggcctg gcgggggtgg cggtggtgct gggagcagtg   2040
acagcggcca tggcttctt ctcctacctc ggcgtgccgt cctccctggt gatccttcag   2100
gtggtgcctt tcctggtgtt ggccgtgggc gctgacaaca tcttcatctt tgttctggag   2160
taccagaggc tgcccggag gccggggagg ccgcggagg cccacatcgg ccgagcgctg   2220
ggcagtgtgg cccctagcat gttgctctgc agcctgtctg aggccatctg cttctttcta   2280
ggggccctga ccctatgcc cgctgtgaag acctttgccc tgatctcggg cttttgccatc   2340 gtcctggact tcttgctgca ggtgtcagcc tttgtggctc tgctttctct ggacagcagg   2400
aggcaggagg cctcccgctt ggacgtctgc tgctgcgtga gcgccccgaa gctgcctgca   2460
cccggccaga gcgagggact cctgcttcga gtcttccgca agttctacgt cccagtcctg   2520
ctgcaccggg tgacacgggc ggtggtgctg ctgctgttca ccggcctctt cggggtgggg   2580
ctctacttca tgtgccacat ccgcgtggga ttggatcagg agctggccct gcccaaggac   2640
tcatacctgc tggactattt cttcttcctg aaccgctact ttgaggtggg gctcccgtc   2700 tactttgtca ccacgggagg ctacaacttc tccagcgagg cgggcatgaa tgctgtgtgc   2760
tccagtgccg ggtgcgacag ttactcctta acccagaaga tccagtacgc caccgagttc   2820
cccgaggagt cttacctggc catccctgcc tcctcctggg tggatgactt catcgactgg   2880
ctgaccccgt cctcctgctg ccgcctttat gcctttggtg ctaataagga caaattctgc   2940
ccttcgactg tcaactccct agcctgcttg aagaactgcg tgaacttcac actgggccct   3000
gtccggccat ccgtggacca gttccacaag taccttccct ggttcctgag tgacccgccc   3060
aacatcaagt gtcccaaagg tgggctggca gcgtacaaca cctccgtgca tttgggatct   3120
gatggccagg ttttagccct ccggttcatg gcctaccaca agccgctgcg gaactcggag   3180
```

-continued

```
gattacactg aggccctgcg ggtgtcacgg gcgctggcgg ccaacatcac ggcccagctg    3240
cggcaggtgc caggcaccga cccggccttc gaggtcttcc cctacacgat caccaacgtg    3300
ttctacgagc agtacctgag cgtggtcccc gagggcctct tcatgctcgc catctgcctg    3360
ctgcccacct tcgtagtctg ctgcctgctg ctgggcatgg acctacgctc cggcctcctc    3420
aacctgttct ccatcgtcat gatcctcgtg gacaccgtgg gcttcatggc cctgtggggc    3480
atcagttaca atgccgtgtc gctcatcaac ctggtcacgg cggtgggcat ctccgtggaa    3540
tttgtgtccc acatcacccg ctcctttgca gtcagcaccc ggcccacccg gctggagagg    3600
gccaaggagg ccaccatctc catgggcagc gcggtgtttg ctggcgtggc catgaccaac    3660
ctgccgggca tcctcgtcct gggcctggcc aaggcacagc tcatccagat cttcttcttc    3720
cgcctcaacc tcctcatcac cgtgctgggt ctgctgcatg gcctggtctt cctgccagtg    3780
gtcctcagct acctcgggcc tgatatcaat gcagctctcg tgctggacca agaagaaaca    3840
gaagaggcca tcggggcccc tgcccacctg gtcccaacat ccacggccag cagcacctat    3900
gtcaactacg gcttccaaca tcccgccaac ggtgtagtgg gcgacagttc tctgccccgc    3960
agtggaccgg acctctga                                                  3978
```
                                                           (SEQ ID NO: 2)

```
   1 MADTGLRGWL LWALLLHVAQ SELYTPIHQP GYCAFYDECG KNPELSGGLA
  51 PLSNVSCLSN TPALRVTGEH LTLLQRICPR LYTGTTTYAC CSPKQLLSLE
 101 TSLAVTKALL TRCPTCSDNF VNLHCQNTCS PNQSLFINVT RVAGGGGGRP
 151 QAVVAYEAFY QDTFAQQTYD SCSRVRIPAA ATLAVGTMCG VYGSTLCNAQ
 201 RWLNFQGDTS NGLAPLDITF HLMEPGQALG SGMQALTGEI RPCNESQGNG
 251 TVACSCQDCA ASCPTIPQPQ ALDSTFYLGG LEGGLALVII LCSAFALLTT
 301 FLVGTRLASS CGKDKTPDPK AGMSLSDKLS LSTNVILSQC FQNWGTWVAS
 351 WPLTILLVSI AVVLALSGGL AFVELTTDPV ELWSAPSSQA RSEKAFHDQH
 401 FGPFLRTNQV ILTAPNRPSY HYDSLLLGPK NFSGVLASDL LLELLELQET
 451 LRHLQVWSPE EQRHISLQDI CFAPLNPHNA SLSDCCINSL LQYFQSNRTH
 501 LLLTANQTLT GQTSQVDWRD HFLYCANAPL TFKDGTALAL SCMADYGGPV
 551 FPFLAVGGYK GKDYSEAEAL IMTFSLNNYA PGDPRLAQAK LWEAAFLEEM
 601 KAFQRRTAGT FQVTFMAERS LEDEINRTTA EDLPIFGVSY IIIFLYISLA
 651 LGSYSSWRRV PVDSKVTLGL GGVAVVLGAV TAAMGFFSYL GVPSSLVILQ
 701 VVPFLVLAVG ADNIFIFVLE YQRLPRRPGE PREAHIGRAL GSVAPSMLLC
 751 SLSEAICFFL GALTPMPAVK TFALISGFAI VLDFLLQVSA FVALLSLDSR
 801 RQEASRLDVC CCVSAPKLPA PGQSEGLLLR VFRKFYVPVL LHRVTRAVVL
 851 LLFTGLFGVG LYFMCHIRVG LDQELALPKD SYLLDYFFFL NRYFEVGAPV
 901 YFVTTGGYNF SSEAGMNAVC SSAGCDSYSL TQKIQYATEF PEESYLAIPA
 951 SSWVDDFIDW LTPSSCCRLY AFGANKDKFC PSTVNSLACL KNCVNFTLGP
1001 VRPSVDQFHK YLPWFLSDPP NIKCPKGGLA AYNTSVHLGS DGQVLASRFM
1051 AYHKPLRNSE DYTEALRVSR ALAANITAQL RQVPGTDPAF EVFPYTITNV
1101 FYEQYLSVVP EGLFMLAICL LPTFVVCCLL LGMDLRSGLL NLFSIVMILV
1151 DTVGFMALWG ISYNAVSLIN LVTAVGISVE FVSHITRSFA VSTRPTRLER
1201 AKEATISMGS AVFAGVAMTN LPGILVLGLA KAQLIQIFFF RLNLLITVLG
1251 LLHGLVFLPV VLSYLGPDIN AALVLDQKKT EEAIGAPAHL VPTSTASSTY
```

1301 VNYGFQHPAN GVVGDSSLPR SGPDL*

Rabbit NPC1L1 ORF (SEQ ID NO: 3)

```
atggcagggg ctgcgcgggg ctggctgctc tgggccctgc tcctgcacca ggcccaggca    60
gagctgtaca cgcccgtgca ccaggccggc tactgcgcct tctacgagga gtgcgggaag   120
aaccctgagc tgtctggggg cctcacatcg ctgtccaacg tgtcctgcct gtccaacacg   180
cctgcccgcc atgtcacggg cgaccacctg gccctcctgg agcgcatctg cccccgcctc   240
tacaacggcc ccaacaccac ctacgcctgc tgctcgccca ggcagctggt gtcgctggag   300
accagcatgt ccgtcaccaa ggccctgctc acgcgctgcc ccgcctgctc tgacaacttc   360
gtgagcctgc actgccagaa cacctgcagc ccggaccaga gcctcttcat caacgtgacg   420
cgcgtggtct cccagggcgc tgggcagctc caggccgtcg tggcctacga ggcctactac   480
gagcgcagct cgccgagcg ggcctacgag tcctgcagcc gcgtgcgcat ccccgccgcc   540
gccacgctgg ccgtgggcag catgtgcggc gtgtacggct ctgccctctg caacgcccag   600
cgctggctca acttccaggg ggacacgagc aacggcctgg ccccgctgga cattaccttc   660
cacctgcggg agcccgggca ggcgccgggc agcgggatgc aactgctgaa cgcggagatc   720
gcgccctgca acgagtccca ggacagcgcc gcggcctgct cctgccagga ctgtgccgcg   780
tcctgcccgg ccatcacgca gcctgaggcc ctggactcct ccttccgcat ggccgcgtg   840
cggggtgggg tggcactcgt cgtcatcctc tgcagcaccc tgggcgtgct cctcctgggc   900
ctcgtgtgcg cccgcaggta tcggccaag gccaggggca cggcgacggc ccccacggcc   960
tgctccaggc tctcccaccg catcagcctg tccatccaca ccttcctcca tcggctcttc  1020
cagtgctggg gcacgtgggt ggcctcgtgg cccctgacca tcctggccgt gtccatcgcg  1080
gtcgtggtgt ccttggcgtg tggcctggcc ttcacggagc tcacaacgga ccccgtggag  1140
ctgtggtcgg cccccaacag ccaagcccgc agcgagaagg ctttccacga ccagcacttc  1200
ggccccttct tccgaacgaa ccaggtgatc ctgacggcgc ctacccgctc ccgctacact  1260
tacaactccc tgctgctggg gccccggaac ttcagtggga tcctggccat ggacctgctg  1320
ctggagctac tggagctgca ggagcggctg cgggccctgc aggtgtggtc gcccgaggcg  1380
cagcgcaacg tgagcctgcg ggacgtctgc tacgccccgc tcaacccgca caacgccagc  1440
ctcaccgact gctgtatcaa cagcctgctg cagtacttcc agaacaaccg cacgctgctg  1500
cagctcacgg ccaaccagac gctcctgggc cagactgccc aggtcgactg gaggaccac  1560
tttctctact gtgccaatgc cccctcacc ttccaagacg gcacgccct gtccctgagc  1620
tgcatggccg actacggggc gccgtcttc cctttcctcg ccgttggggg atacgaaggc  1680
gaggactact cggatgcgga ggccctcatc ttaaccttct ccctcaacaa ctaccctgcg  1740
ggggaccccc gcctggccca ggtcaagctc tgggaggagg ccttcgtgaa ggagatgcga  1800
gccttgcagc ttgggaagtc cagcaaattc caggtcacgt tcatggccga cgctccctg  1860
gaggatgaga tcaaccgcac cacggctgag gacctgccca tctttgccat cagctacatc  1920
gtcaccttcc tgtacatcgc cctggccctg gccgctact ccagctggcg ccgattgccg  1980
gtggactcca agatcacgct gggcctgggc ggggtggtca tggtgctgag cgcggtcatg  2040
gcttccatgg gcttcttctc ctacctgggc atcccgtcgt ccctgatcat cctgcaagtg  2100
gtgccttcc tggtgctggc cgtgggggcc gacaacatct tcatcctcgt tctcgagtac  2160
cagcggctgc gcggaggcc tgaggagtcg cgggaggccc acatcggccg agccctgggc  2220
agggtggctc ccagcatgct gctgtgcagc ctctccgaga ccatctgctt cttcctgggg  2280
```

```
gccctgaccc ccatgccagc cgtgcgtacc tttgccctga cgtctggcct ggcggtgcaa   2340
ctcgacttcc tgctgcagat gactgccttc gtggccctgc tgtccctgga cagcaagagg   2400
caggaggctt cccggccaga tgtgtgctgc tgcctggagc ccggaagct gccctcccag    2460
cagcagagcg aggggctgct gctgtgtttc ttccgcaaag tctacgcccc gctcctgctg   2520
cacaaggtca cccgcgtggt cgtgctgctg ctctttctgt tcctgttcgg atcgagtctc   2580
tacttcatgt gccaggtcac cgtggggctg gaccaggage tggccctgcc caaggactcg   2640
tacctgatcg actacttcct gtttctgaac cgctactttg aggtggggc cccagtgtac    2700
tttgtcacca cctcgggcta caacttctcc agcgaggcgg gcatgaacgc catctgctcc   2760
agcgcaggct gcgacagctt ctccctcacc cagaagatcc aatacgccac cgagttcccc   2820
gagcagtctt acctggccat ccccgcctcc tcctgggtgg acgacttcat cgactggcta   2880
accccgtcct cctgctgccg cctttacatc ctcggcccca ataaggacga gttctgcccc   2940
tccacagtca actccttgaa ctgcctgagg aattgcatga gcttgacgct gggccctgtg   3000
cggccctcgg tggagcagtt ccacaagtac ctgccctggt ttctgaatga cccccccaac   3060
atccgatgtc ccaagggtgg cctggcggcg tacagcacct ctgtgaacct gagcgccgat   3120
ggccagattg tagccacccg cttcatggcc taccacaagc cgctgaagaa ctcgcaggac   3180
tacaccgagg ccctgcgggc gtcgcgggag ctggcggcca acatcaccgc gagcctgcgg   3240
caggtgccgg gcacggaccc cgccttcgag gtcttcccct cacgatctc caacgtgttc   3300
tacgagcagt acctgaccgt gctcccggag gggctcgcca cgctcggcct ctgcctcgtg   3360
cccaccttcg tcgtctgctg cctcctgctg ggcctggacc tgcgctccgg cctcctcaac   3420
ctgctgacca tcgtcatgat tctcgtggac accgtgggcc tcatgacgct gtggagcatc   3480
agctacaacg ccgtgtccct catcaatctg gtcacggcgg tgggcatgtc cgtggagttc   3540
gtgtcccaca tcacccgctc ctttgccgtc agcaccaagc ccagccggct ggagagagcc   3600
aaggaggcca ccatctccat gggcagtgcg gtgtttgcag gggtggccat gaccaacctg   3660
ccgggcatcc tcatcctggg cctcgccaag gcccagctca tccagatctt cttcttccgc   3720
ctcaacctcc tcatcaccct gctggggctg ctgcacggcc tggtcttcct gcccgtcatc   3780
ctcagctacc ttgggcctga cgtcaacccg gctctggttg ctctggagcg gacgcgagcc   3840
caggaggcgg ctgacgctgc ggcgggctcc tgcccaaatc accccgaccc tacctccaac   3900
atctacgtca actccggctt tgacgaggca gccagggatg tcggcagctc tgcccccacc   3960
agaaagcaga agttctga                                                 3978
```

(SEQ ID NO: 4)

```
  1 MAGAARGWLL WALLLHQAQA ELYTPVHQAG YCAFYEECGK NPELSGGLTS
 51 LSNVSCLSNT PARHVTGDHL ALLERICPRL YNGPNTTYAC CSPRQLVSLE
101 TSMSVTKALL TRCPACSDNF VSLHCQNTCS PDQSLFINVT RVVSQGAGQL
151 QAVVAYEAYY ERSFAERAYE SCSRVRIPAA ATLAVGSMCG VYGSALCNAQ
201 RWLNFQGDTS NGLAPLDITF HLREPGQAPG SGMQLLNAEI APCNESQDSA
251 AACSCQDCAA SCPAITQPEA LDSSFRIGRV RGGVALVVIL CSTLGVLLLG
301 LVCARRYSAK ARGTATAPTA CSRLSHRISL SIHTFLHRLF QCWGTWVASW
351 PLTTLAVSIA VVVSLACGLA FTELTTDPVE LWSAPNSQAR SEKAFHDQHF
401 GPFFRTNQVI LTAPTRSRYT YNSLLLGPRN FSGILAMDLL LELLELQERL
451 RALQVWSPEA QRNVSLRDVC YAPLNPHNAS LTDCCINSLL QYFQNNRTLL
501 QLTANQTLLG QTAQVDWRDH FLYCANAPLT FQDGTALSLS CMADYGAPVF
```

```
 551 PFLAVGGYEG EDYSDAEALI LTFSLNNYPA GDPRLAQVKL WEEAFVKEMR

601 ALQLGKSSKF QVTFMAERSL EDEINRTTAE DLPIFAISYI VTFLYIALAL

651 GRYSSWRRLP VDSKITLGLG GVVMVLSAVM ASMGFFSYLG IPSSLIILQV

701 VPFLVLAVGA DNIFILVLEY QRLPRRPEES REAHIGRALG RVAPSMLLCS

751 LSETICFFLG ALTPMPAVRT FALTSGLAVQ LDFLLQMTAF VALLSLDSKR

801 QEASRPDVCC CLEPRKLPSQ QQSEGLLLCF FRKVYAPLLL HKVTRVVVLL

851 LFLFLFGSSL YFMCQVTVGL DQELALPKDS YLIDYFLFLN RYFEVGAPVY

901 FVTTSGYNFS SEAGMNAICS SAGCDSFSLT QKIQYATEFP EQSYLAIPAS

951 SWVDDFIDWL TPSSCCRLYI LGPNKDEFCP STVNSLNCLR NCMSLTLGPV

1001 RPSVEQFHKY LPWFLNDPPN IRCPKGGLAA YSTSVNLSAD GQIVATRFMA

1051 YHKPLKNSQD YTEALRASRE LAANITASLR QVPGTDPAFE VFPYTISNVF

1101 YEQYLTVLPE GLATLGLCLV PTFVVCCLLL GLDLRSGLLN LLTIVMILVD

1151 TVGLMTLWSI SYNAVSLINL VTAVGMSVEF VSHITRSFAV STKPSRLERA

1201 KEATISMGSA VFAGVAMTNL PGILILGLAK AQLIQIFFFR LNLLITLLGL

1251 LHGLVFLPVI LSYLGPDVNP ALVALERTRA QEAADAAAGS CPNHPDPTSN

1301 IYVNSGFDEA ARDVGSSAPT RKQKF*
```

Hamster NPC1L1 ORF

```
                                                         (SEQ ID NO: 5)
atggcagctg gcctacagag atggctgctc tgggccctac tcctgaatgc ggcccggggt     60
gagatacaca cacccattca taaagctggc gtctgtacct tctatgaaga gtgtgggaag    120
aacccagagc tgtccggagg cctcacgtca ctgtccaatg tatcttgcct gtctaacacc    180
ccagcccgcc gtgtcacagg tgaccacctg accctccttc agcgcatctg cccccgcctg    240
tacaatggcc ccaacaatac ctatgcttgt tgctccgccc agcagctagt ggcattagaa    300
aagagcatgt ctatcaccaa ggccctcctc acccgctgcc cagcctgctc tgacaatttt    360
gtgagcttgc actgccacaa cacctgcagc cctgaccaga gcctcttcat caatgtcacc    420
cgtgtggttg agcaggcgga ccctcagcag cctccagctg tggtggccta tgaagccttt    480
taccagagca gcttttgcaga gaaggcctat gagtcctgta gccgggtacg catccccgcg    540
gctgcctcac tggctgtggg caccatgtgt ggggtgtatg gctctgccct gtgcaatgcc    600
caacgctggc tcaacttcca gggagacaca gggaacggcc tggctcctct cgacatcacc    660
ttccacctcg tggagtccgg ccaggccctg ccagatggga tgcagcctct gaatggggag    720
atcacgccct gcaatcagtc ggagggtgta gagtcggctg cctgttcctg ccaggactgt    780
gcagcgtctt gcctgtcat ccgcagccc tcagccctgc cccttccctt ctacatgggt    840
aaaatgcctg gctggctggc tctcatcatc atcttctgtg cggtcttcgt gctgctcaca    900
gctgtcccta tatatcttcg agtggtttcc aataggagca ggagcaagaa aacaggcctc    960
caggaagccc cgaaccgccc tcctaagcgc agattctcac ctcacatcgt ccttggccgg   1020 ttttccaga gctggggcac aagagtggcc tcatggccac tcactgtctt ggcgctgtcc   1080
tttatggttg tgatagcctt gtcagtgggc atgacctaca tagaactcac cacagaccct   1140
gtggaactgt ggtcagcccc caaaagccaa gctcggaaag agaaggcttt ccacgacgag   1200 catttttggcc cctttcttccg aaccaaccag gttttttgtga cagctcggaa caggtccagc   1260
tatagatatg actcccctgct gctagggccc aagaacttca gtgggctcct gtccctggac   1320
ctggtgctgg agctgctgga gctccaagag aggcttcgac acctgcaggt gtggtcccct   1380
gaggcacagc gcaacatctc cctgcaggac atctgctatg ccccctcaa accgcacaac   1440
```

-continued

```
accagcctct ccgactgctg tgtcaacagt ctccttcagt acttccagaa caaccgcacg   1500
ctcctgctgc tcacagccaa ccagacgctc aatggccaga cttccctggt ggactggagg   1560
gaccacttcc tctactgtgc aaatgcgcct ctcacgttca aagacggcac gtctctggcc   1620
ctgagctgca tcgcggacta tggggcccct atcttcccct tccttgctgt cggggggtac   1680
caagggacgg actactctga ggcagaggcg ctgatcataa ctttctctct caataactac   1740
cctgctgatg atccccgcat ggcccaggcc aagctctggg aggaggcttt tctgaaggaa   1800
atgcaagcct tccagagcag tgtggctgac aagttccagg ttgcattctc agctgagcgc   1860
tctctggagg atgagatcaa ccgcaccacc atccaggacc tgcctgtctt cgccatcagc   1920
tacattatcg tcttcctgta catctctctg gccctgggca gctactccaa atggaagcga   1980
gtagcggtgg attccaaggc tactctgggc ctcggtgggg tggctgtcgt gctgggagca   2040
gtcgtggctg ccatgggttt ctactcctac ctgggtgttc cctcctcact ggttatcatc   2100
caagtggtgc ctttcctggt gctggccgtg ggagctgaca acatcttcat ctttgttctt   2160
gagtaccaga ggctgcctag gaggcctggg gagcagcgag aggcccacat cggccgtacc   2220
ctgggcagtg tggcccccag catgctgctg tgcagcctct ctgaggctgt ctgcttcttt   2280
ctaggggccc tgaccccat gccagctgtg aggaccttg ccttgaccgc tggcctttcg   2340
attatcctcg acttcctgct ccagatgact gccttcgtgg ccctgctctc cctggatagc   2400
aagaggcagg aggcctctcg ccccgacatc ttatgctgtc tttcaccccg gaaactaccc   2460
ccacctgaac agcaagaggg gctcttactc cgcttcttca gaaagatata tgctcccttc   2520
ctgctgcaca ggttcatccg ccctgttgtg ctgctgctgt ttctggccct gtttggagca   2580
aatctctact taatgtgcca catcagcgtg gggttggacc aggagctggc cctgcctaag   2640
gattcctact tgattgacta cttcctcttt ttgaaccgat actttgaggt ggggcctccc   2700
gtgtactttg tcaccacctc gggttacaac ttctccagcg aggcaggcat gaatgccatt   2760
tgctctagtg caggctgtga cagcttctcc atgacccaga agatccaata tgccactgaa   2820
ttccctgagc agtcttacat agggattgct gcatcctcct gggtagacga cttcatcgac   2880
tggctgaccc cgtcctcctg ctgccgcctt tatatctttg gccccaatac gggtgacttc   2940
tgtccttcaa ctgatacttc cttgagctgt ctaaaaaact gcatgaactt cactctgggc   3000
cccgtgaggc ccacagcaga acagtttcac aagtatctgc cctggttcct ggacgatcca   3060
cccaacatca gatgccccaa aggggtctg gcagcatata gaacttccgt gaatttgagc   3120
tcagatggcc agattatago ctcccagttc atggcctacc acaagccgct caggaactca   3180
caggacttca cagaagctct ccggacatcc cgattgctgg cagccaacat cacagctgaa   3240
ctacggaaag tgcctggcac agccccagac tttgaggtct tccccctacac gatctccaac   3300
gtgttctacg agcagtacct gactgtcctc cccgagggca tcttcacact ggctctctgc   3360
ttcgtgccca ccttcgtcgt ctgctacctc tgctgggcc tggacatgcg ctcaggcatc   3420
ctcaacctgc tctccatcat catgatcctt gtggacacca tcgggctcat ggctgtgtgg   3480
ggcatcagct acaatgctgt gtccctcatc aaccttgtca cggcagtggg aatgtctgtg   3540
gagttcgtgt cccacctcac ccggtccttt gctgtcagca ccaagcccac ccggctggag   3600
agggccaagg atgccaccgt ctccatgggc agtgcggtgt ttgctggcgt ggccatgacc   3660
aacttcccag gcatcctcat cctgggcttc gcccaggccc agctaatcca gatcttcttc   3720
ttccgcctca acctcctgat cacccttgctg ggcctgctgc acggcctggt cttcctgccg   3780
gttgtcctca gctatctggg acccgatgtg aacccagagc tggtgctgga ggagaaacta   3840
```

-continued

```
gctacggagg cagcggtggc cccagagcct tccagcccga agtacccctt ccctgataat    3900
gactatgtta atcacagttt tgaggaagcc acccctggag ctgctgctgc tagtagctcc    3960
ttgcctaaaa gcggccaaaa gttttaa                                        3987
```

(SEQ ID NO: 6)

```
   1 MAAGLQRWLL WALLLNAARG EIHTPIHKAG VCTFYEECGK NPELSGGLTS
  51 LSNVSCLSNT PARRVTGDHL TLLQRICPRL YNGPNNTYAC CSAQQLVALE
 101 KSMSITKALL TRCPACSDNF VSLHCHNTCS PDQSLFINVT RVVEQADPQQ
 151 PPAVVAYEAF YQSSFAEKAY ESCSRVRIPA AASLAVGTMC GVYGSALCNA
 201 QRWLNFQGDT GNGLAPLDIT FHLVESGQAL PDGMQPLNGE ITPCNQSEGV
 251 ESAACSCQDC AASCPVIPQP SALPPSFYMG KMPGWLALII IFCAVFVLLT
 301 AVLIYLRVVS NRSRSKKTGL QEAPNRPPKR RFSPHIVLGR FFQSWGTRVA
 351 SWPLTVLALS FMVVIALSVG MTYIELTTDP VELWSAPKSQ ARKEKAFHDE
 401 HFGPFFRTNQ VFVTARNRSS YRYDSLLLGP KNFSGLLSLD LVLELLELQE
 451 RLRHLQVWSP EAQRNISLQD ICYAPLKPHN TSLSDCCVNS LLQYFQNNRT
 501 LLLLTANQTL NGQTSLVDWR DHFLYCANAP LTFKDGTSLA LSCIADYGAP
 551 IFPFLAVGGY QGTDYSEAEA LIITFSLNNY PADDPRMAQA KLWEEAFLKE
 601 MQAFQSSVAD KFQVAFSAER SLEDEINRTT IQDLPVFAIS YIIVFLYISL
 651 ALGSYSKWKR VAVDSKATLG LGGVAVVLGA VVAAMGFYSY LGVPSSLVII
 701 QVVPFLVLAV GADNIFIFVL EYQRLPRRPG EQREAHIGRT LGSVAPSMLL
 751 CSLSEAVCFF LGALTPMPAV RTFALTAGLS IILDFLLQMT AFVALLSLDS
 801 KRQEASRPDI LCCLSPRKLP PPEQQEGLLL RFFRKIYAPF LLHRFIRPVV
 851 LLLFLALFGA NLYLMCHISV GLDQELALPK DSYLIDYFLF LNRYFEVGPP
 901 VYFVTTSGYN FSSEAGMNAI CSSAGCDSFS MTQKIQYATE FPEQSYIGIA
 951 ASSWVDDFID WLTPSSCCRL YIFGPNTGDF CPSTDTSLSC LKNCMNFTLG
1001 PVRPTAEQFH KYLPWFLDDP PNIRCPKGGL AAYRTSVNLS SDGQIIASQF
1051 MAYHKPLRNS QDFTEALRTS RLLAANITAE LRKVPGTAPD FEVFPYTISN
1101 VFYEQYLTVL PEGIFTLALC FVPTFVVCYL LLGLDMRSGI LNLLSIIMIL
1151 VDTIGLMAVW GISYNAVSLI NLVTAVGMSV EFVSHLTRSF AVSTKPTRLE
1201 RAKDATVSMG SAVFAGVAMT NFPGILILGF AQAQLIQIFF FRLNLLITLL
1251 GLLHGLVFLP VVLSYLGPDV NPELVLEEKL ATEAAVAPEP SSPKYPFPDN
1301 DYVNHSFEEA TPGAAAASSS LPKSGQKF*
```

Rhesus Monkey NPC1L1 ORF (SEQ ID NO: 7)

```
atggcggagg ccggcctgag gggctggctg ctgtgggccc tgctcctgca cttggcccag     60
agcgagcctt acacacccat ccaccagcct ggctactgcg ccttctatga cgaatgtggg    120
aagaacccag agctgtctgg aggcctcatg acactctcca acgtgtcctg tctgtccaac    180
acgccagccc gcaacatcac aggtgatcac ctgatcctat acagaggat ctgccccgc     240
ctctacaccg gccccaacac ccaagcctgc tgctccgcca agcagctggt atcattggaa    300
gcgagtctgt cgatcaccaa ggccctcctc acccgctgcc cagcctgctc tgacaatttc    360
gtgagcctgc actgccacaa cacatgcagc cccaaccaga gcctcttcat caatgtgacc    420
cgcgtggctc agctagggc tggacaactc ccagctgtgg tggcctatga ggccttctac    480
cagcacagct ttgccgagca gagctatgac tcctgcagcg tgtgcacat ccctgcggct    540
```

-continued

```
gccacgctgg ctgtgggcag catgtgtggc gtgtatggct ctgcccttttg caatgcccag    600 cgctggctca acttccaggg agacacaggc aatggtctgg ccccactgga catcaccttc    660
cacctcttgg agcccggcca ggctgtgggg agtgggattc agcctctgaa tgagggggtt    720
gcacgttgca atgagtccca aggtgacgac gcagtggcct gctcctgcca ggactgtgct    780
gcatcctgtc ctgccatcgc ccatccccag gccctggact ccaccttccg cctgggccgg    840
atgccgggtg ggctggtcct catcatcatc ctctgttctg tcttcactgt ggtcgccatc    900
ctgctcgtgg gactccgtgt ggcccccacc agggacaaaa gcaagacggt ggaccccaag    960
aagggcacca gcctctctga taagctcagc ttctccaccc acaccctcct tggccagttc   1020
ttccagggct ggggcacctg ggtggcttcg tggcctctga ccatcctggt gctgtctgtc   1080
atcccggtgg tggtcttggc agcgggcctg gtctttacag aactcactac ggaccccgtg   1140
gagctgtggt cggcccccaa cagccaagcc cggagtgaga aggcttttca tgaccagcat   1200
ttcggcccct tcttccgaac caaccaggtg atcctgacgg ctcctaaccg gtccagctac   1260
aggtatgact ccctgctgct ggggcccaag aacttcagcg ggatcctgga cctggacttg   1320
ctgctggagc tgctggagtt gcaggagagg ctgcggcacc tccaggtgtg gtcgcccgaa   1380
gcacagcgca acatctccct gcagcacatc tgctacgccc cctcaatcc ggacaatacc   1440 agtctttccg attgctgcat caacagcctc ctgcagtatt ccagaacaa ccgcacgctc   1500 ctgttgctca cggccaacca gacactgatg gggcagacct cccaagtcga ctggagggac   1560
cattttctgt actgtgccaa tgccccgctc accttcaagg atggcacagc cctggccctg   1620
agctgcatgg ctgactatgg ggcccctgtc ttccccttcc ttgccgttgg ggggtacaaa   1680
gggaaggact attctgaggc ggaggccctg atcatgacgt tctccctcaa caattaccct   1740
gccggggacc cccggctggc ccaggcccag ctgtgggagg aggccttctt ggaggaaatg   1800
cgagccttcc agcgtcggac ggctggcaag ttccaggtca cgttcatggc tgagcgctct   1860
ctggaagatg agatcaatcg caccacagcc gaagacctgc ccatctttgc caccagctac   1920
attgtcatct tcctgtacat ctccctggcc ctgggcagct attccagctg agccgagtg   1980 atggtggact ccaaggccac gctgggcctt ggcggggtgg ccgtggtcct gggagcagtc   2040
atggctgcca tgggcttctt ctcctacctg ggtatccgct cctccctgat catcctgcaa   2100
gtggtgcctt tcctggtgct gtctgtgggg gctgataaca tcttcatctt tgttctcgag   2160
taccagaggc tgcccggag gcctggggag ccgcgagagg ttcacattgg ccgagccctg   2220
ggcagggtgg cccccagcat gctgttgtgc agcctctctg aggccatctg cttcttccta   2280
ggggccctga ccccatgcc agctgtgcgg acctttgccc tgacctctgg ccttgcagtg   2340
gtccttgact tcctcctgca gatgtctgcc tttgtggccc tgctctccct ggacagcaag   2400
aggcaggagg cctcccgatt ggacgtctgc tgctgcgtca agcccgggga gctgcccctg   2460
cctggccagg gagagggggtt cctgcttggc ctcttccgaa aggcctatgt ccccttcctg   2520
ctgcactgga tcactcgagg ggttgtgctg ctgctgtttc tcgccctgtt tggagtgagc   2580
ctctactaca tgtgccacat cagtgttgga ctgaccagg agctggccct gccaaggac   2640 tcgtacctgc ttgactattt cctctttctg aaccgctact cgagacgggg ggccccggtg   2700
tactttgtta ctacctcagg ctacaacttc tccagtgagg ctgggatgaa tgccatctgc   2760
tccagtgcag gctgcaacaa cttctccttc acccagaaga tccagtatgc cacagagttc   2820
cctgagcagt cttaccttgc catccctgcc tcctcctggg tggatgactt cattgactgg   2880 ctgacccat cctcctgctg ccgcctttat atatctggcc ccaataagga ccagttctgc   2940
ccctcgactg tcaactccct gaactgccta aagaactgcc tgagcatcac gatgggctct   3000
```

-continued

```
gtgaggccct cagtggagca gttctataag tatcttccct ggttcctgaa tgaccggccc   3060
aacatcaaat gtcccaaagg cggcctggga gcatacagca cctctgtgaa cttgacttca   3120
gatggccagg ttttagcctc caggttcatg gcctatcaca agcccctgaa aaactcacag   3180
gattacacag aagctctgcg ggcagctcgg gagctggcag ccaacatcac tgctgacctg   3240
cggaaggtgc ctgggacaga cccagctttt gaggtcttcc cctacacggt caccaatgtg   3300
ttttatgagc agtacctgac cattctccct gaggggctct tcatgctcag cctctgcctg   3360
gtgcccacct tcgctgtctg ctgcctcctg ctgggcctgg acctgcgctc cggcctcctc   3420
aacctgctgt ccatcatcat gatcctcgtg gacaccgttg gcttcatggc cctgtggggc   3480
atcagttaca atgctgtgtc cctcatcaac ctggtctcgg cggtgggcat gtctgtggag   3540
ttcgtgtccc acattacccg ctcctttgcc atcagcacca gcccacccg gctggagagg   3600 gccaaagagg ccaccatctc tatgggaagt gcggtgtttg caggtgtggc catgaccaac   3660
ctccctggca tcctggtcct gggccttgcc aaggcccagc tcattcagat cttcttcttc   3720
cgcctcaacc tcctgattac tctgctgggt ctgctgcatg gcttggtctt cctgcctgtc   3780
atcctcagct atgtggggcc tgacatcaac ccagctctgg cactggagca gaagctggct   3840
gaggaggcag cagcggcagc catagcggcc tcctacccaa atcacccctc ccgagtctcc   3900
acagctgaca acatctatgt caaccacagc tttgaaggtt ctatcaaagg tgctggtgcc   3960
gtcagcaact tcttgcccaa caatgggcgg cagttctga                         3999
```

(SEQ ID NO: 8)
```
   1 MAEAGLRGWL LWALLLHLAQ SEPYTPIHQP GYCAFYDECG KNPELSGGLM

51 TLSNVSCLSN TPARNITGDH LILLQRICPR LYTGPNTQAC CSAKQLVSLE

101 ASLSITKALL TRCPACSDNF VSLNCHNTCS PNQSLFINVT RVAQLGAGQL

151 PAVVAYEAFY QHSFAEQSYD SCSRVHIPAA ATLAVGSMCG VYGSALCNAQ

201 RWLNFQGDTG NGLAPLDITF HLLEPGQAVG SGIQPLNEGV ARCNESQGDD

251 AVACSCQDCA ASCPAIAHPQ ALDSTFRLGR MPGGLVLIII LCSVFTVVAI

301 LLVGLRVAPT RDKSKTVDPK KGTSLSDKLS FSTHTLLGQF FQGWGTWVAS

351 WPLTILVLSV IPVVLAAGL VFTELTTDPV ELWSAPNSQA RSEKAFHDQH

401 FGPFFRTNQV ILTAPNRSSY RYDSLLLGPK NFSGILDLDL LLELLELQER

451 LRHLQVWSPE AQRNISLQHI CYAPLNPDNT SLSDCCINSL LQYFQNNRTL

501 LLLTANQTLM GQTSQVDWRD HFLYCANAPL TFKDGTALAL SCMADYGAPV

551 FPFLAVGGYK GKDYSEAEAL IMTFSLNNYP AGDPRLAQAQ LWEEAFLEEM

601 RAFQRRTAGK FQVTFMAERS LEDEINRTTA EDLPIFATSY IVIFLYISLA

651 LGSYSSWSRV MVDSKATLGL GGVAVVLGAV MAAMGFFSYL GIRSSLIILQ

701 VVPFLVLSVG ADNIFIFVLE YQRLPRRPGE PREVHIGRAL GRVAPSMLLC

751 SLSEAICFFL GALTPMPAVR TFALTSGLAV VLDFLLQMSA FVALLSLDSK

801 RQEASRLDVC CCVKPRELPL PGQGEGFLLG LFRKAYVPFL LHWITRGVVL

851 LLFLALFGVS LYYMCHISVG LDQELALPKD SYLLDYFLFL NRYFETGAPV

901 YFVTTSGYNF SSEAGMNAIC SSAGCNNFSF TQKIQYATEF PEQSYLAIPA

951 SSWVDDFIDW LTPSSCCRLY ISGPNKDQFC PSTVNSLNCL KNCLSITMGS

1001 VRPSVEQFYK YLPWFLNDRP NIKCPKGGLG AYSTSVNLTS DGQVLASRFM

1051 AYHKPLKNSQ DYTEALRAAR ELAANITADL RKVPGTDPAF EVFPYTVTNV

1101 FYEQYLTILP EGLFMLSLCL VPTFAVCCLL LGLDLRSGLL NLLSIIMILV
```

-continued

```
1151 DTVGFMALWG ISYNAVSLIN LVSAVGMSVE FVSHITRSFA ISTKPTRLER

1201 AKEATISMGS AVFAGVAMTN LPGILVLGLA KAQLIQIFFF RLNLLITLLG

1251 LLHGLVFLPV ILSYVGPDIN PALALEQKLA EEAAAAAIAA SYPNHPSRVS

1301 TADNIYVNHS FEGSIKGAGA VSNFLPNNGR QF*
```

Cynomolgus Monkey NPC1L1 ORF (SEQ ID NO: 9)

```
atggcggagg ccggcctgag gggctggctg ctgtgggccc tgctcctgca cttggcccag    60
agcgagcctt acacacccat ccaccagcct ggctactgcg ccttctatga cgaatgtggg   120
aagaacccag agctgtctgg aggcctcatg acactctcca acgtgtcctg tctgtccaac   180
acgccagccc gcaacatcac aggtgatcac ctgatcctat tacagaggat ctgccccgc    240
ctctacaccg gccccaacac ccaagcctgc tgctccgcca agcagctggt atcattggaa   300
gcgagtctgt cgatcaccaa ggccctcctc acccgctgcc cagcctgctc tgacaatttc   360
gtgagcctgc actgccacaa cacatgcagc cccaaccaga gcctcttcat caatgtgacc   420
cgcgtggctc agctaggggc tggacaactc ccagctgtgg tggcctatga ggccttctac   480
cagcacagct tgccgagca gagctatgac tcctgcagcc gtgtgcacat ccctgcggct   540
gccacgctgg ctgtgggcag catgtgtggc gtgtatggct ctgccctttg caatgcccag   600
cgctggctca acttccaggg agacacaggc aatggtctgg ccccactgga catcaccttc   660
cacctcttgg agcccggcca ggctgtgggg agtgggattc agcctctgaa tgaggggggtt   720
gcacgttgca atgagtccca aggtgacgac gcagtggcct gctcctgcca ggactgtgct   780
gcatcctgtc ctgccatcgc ccatccccag gccctggact ccaccttccg cctgggccgg   840
atgccgggtg gctggtcct catcatcatc ctctgttctg tcttcactgt ggtcgccatc   900
ctgctcgtgg gactccgtgt ggcccccacc agggacaaaa gcaagacggt ggaccccaag   960
aagggcacca gcctctctga caagctcagc ttctccaccc acacctcct tggccagttc   1020
ttccagggct ggggcacctg ggtggcttcg tggcctctga ccatcctggt gctgtctgtc   1080
atcccggtgg tggtcttggc agcgggcctg tctttacag aactcactac agaccccgtg   1140
gagctgtggt cggccccaa cagccaagcc ggagtgaga aggcttttca tgaccagcat   1200
ttcggcccct tcttccgaac caaccaggtg atcctgacgg ctcctaaccg gtccagctac   1260
aggtatgact ccctgctgct ggggcccaag aacttcagcg ggatcctgga cctgacttg   1320
ctgctggagc tgctggagtt gcaggagagg ctgcggcacc tccaggtgtg gtcgcccgaa   1380
gcacagcgca acatctccct gcagcacatc tgctacgccc cctcaatcc ggacaatacc   1440
agtctctccg attgctgcat caacagcctc ctgcagtatt ccagaacaa ccgcacgctc   1500
ctgttgctca cggccaacca gacactgatg gggcagacct cccaagtcga ctggaggac   1560
cattttctgt actgtgccaa tgccccgctc accttcaagg atggcacagc cctggccctg   1620
agctgcatgg ctgactatgg ggcccctgtc ttccccttcc ttgccgttgg ggggtacaaa   1680
gggaaggact attctgaggc ggaggccctg atcatgacgt tctccctcaa caattaccct   1740
gccgggggacc cccggctggc ccaggcccag ctgtgggagg aggccttctt ggaggaaatg   1800
cgagccttcc agcgtcggac ggctggcaag ttccaggtca cgttcatggc tgagcgctct   1860
ctggaagatg agatcaatcg caccacagcc gaagacctgc catctttgc caccagctac   1920
attgtcatct tcctgtacat ctccctggcc ctgggcagct attccagctg agcagagtg   1980
atggtggact ccaaggccac gctgggcctt gcggggtgg ccgtggtcct gggagcagtc   2040
atggctgcca tgggcttctt ctcctacctg ggtatccgct cctccctgat catcctgcaa   2100
```

-continued

```
gtggtgcctt tcctggtgct gtctgtgggg gctgataaca tcttcatctt tgttctcgag    2160
taccagaggc tgccccggag gcctggggag ccgcgagagg ttcacattgg ccgagccctg    2220
ggcagggtgg cccccagcat gctgttgtgc agcctctctg aggccatctg cttcttccta    2280
ggggccctga cccccatgcc agctgtgcgg acctttgccc tgacctctgg ccttgcagtg    2340
gtccttgact tcctcctgca gatgtctgcc tttgtggccc tgctctccct ggacagcaag    2400
aggcaggagg cctcccgatt ggacgtctgc tgctgcgtca agccccggga gctgcccctg    2460
cctggccagg gagaggggtt cctgcttggc ctcttccgaa aggcctatgt cccttcctg    2520 ctgcactgga tcactcgagg ggttgtgctg ctgctgtttc tcgccctgtt tggagtgagc    2580
ctctactaca tgtgccacat cagtgttgga ctggaccagg agctggccct gcccaaggac    2640
tcgtacctgc ttgactattt cctctttctg aaccgctact cgagacgggg gccccggtg     2700 tactttgtta ctacctcagg ctacaacttc tccagtgagg ctgggatgaa tgccatctgc    2760
tccagtgcag gctgcaacaa cttctccttc acccagaaga tccagtatgc cacagagttc    2820
cctgagcagt cttaccttgc catccctgcc tcctcctggg tggatgactt cattgactgg    2880
ctgaccccat cctcctgctg ccgcctttat atatctggcc caataagga ccagttctgc     2940 ccctcgactg tcaactccct gaactgccta agaactgcc tgagcatcac gatgggctct     3000
gtgaggccct cagtggagca gttctataag tatcttccct ggttcctgaa tgaccggccc    3060
aacatcaaat gtcccaaagg cggcctggga gcatacagca cctctgtgaa cttgacttca    3120
gatggccagg ttttagcctc caggttcatg gcctatcaca gcccctgaa aaactcacag     3180 gattacacag aagctctgcg ggcagctcgg gagctggcag ccaacatcac tgctgacctg    3240
cggaaggtgc ctgggacaga cccagctttt gaggtcttcc cctacacggt caccaatgtg    3300
ttttatgagc agtacctgac cattctccct gagggctct tcatgctcag cctctgcctg      3360
gtgcccacct tcgctgtctg ctgcctcctg ctgggcctgg acctgcgctc cggcctcctc    3420
aacctgctgt ccatcatcat gatcctcgtg gacaccgttg gcttcatggc cctgtgggc     3480 atcagttaca atgctgtgtc cctcatcaac ctggtctcgg cggtgggcat gtctgtggag    3540
ttcgtgtccc acattacccg ctcctttgcc atcagcacca gcccacccg gctggagagg     3600 gccaaagagg ccaccatctc tatgggaagt gcggtgtttg caggtgtggc catgaccaac    3660
ctccctggca tcctggtcct gggccttgcc aaggcccagc tcattcagat cttcttcttc    3720
cgcctcaacc tcctgattac tctgctgggt ctgctgcatg gcttggtctt cctgcctgtc    3780
atcctcagct atgtggggcc tgacatcaac ccagctctgg cactggagca gaagctggct    3840
gaggaggcag cagcggcagc catagcggcc tcctacccaa tcacccctc ccgagtctcc     3900 acagctgaca acatctatgt caaccacagc tttgaaggtt ctatcaaagg tgctggtgcc    3960
gtcagcaact tcttgcccaa caatgggcgg cagttctga                           3999
```

-continued (SEQ ID NO: 10)

```
   1 MAEAGLRGWL LWALLLHLAQ SEPYTPIHQP GYCAFYDECG KNPELSGGLM

51 TLSNVSCLSN TPARNITGDH LILLQRICPR LYTGPNTQAC CSAKQLVSLE

101 ASLSITKALL TRCPACSDNF VSLHCHNTCS PNQSLFINVT RVAQLGAGQL

151 PAVVAYEAFY QHSFAEQSYD SCSRVHIPAA ATLAVGSMCG VYGSALCNAQ

201 RWLNFQGDTG NGLAPLDITF HLLEPGQAVG SGIQPLNEGV ARCNESQGDD

251 AVACSCQDCA ASCPAIAHPQ ALDSTFRLGR MPGGLVLIII LCSVFTVVAI

301 LLVGLRVAPT RDKSKTVDPK KGTSLSDKLS FSTHTLLGQF FQGWGTWVAS

351 WPLTILVLSV IPVVVLAAGL VFTELTTDPV ELWSAPNSQA RSEKAFHDQH

401 FGPFFRTNQV ILTAPNRSSY RYDSLLLGPK NFSGILDLDL LLELLELQER

451 LRHLQVWSPE AQRNISLQHI CYAPLNPDNT SLSDCCINSL LQYFQNNRTL

501 LLLTANQTLM GQTSQVDWRD HFLYCANAPL TFKDGTALAL SCMADYGAPV

551 FPFLAVGGYK GKDYSEAEAL IMTFSLNNYP AGDPRLAQAQ LWEEAFLEEM

601 RAFQRRTAGK FQVTFMAERS LEDEINRTTA EDLPIFATSY IVIFLYISLA

651 LGSYSSWSRV MVDSKATLGL GGVAVVLGAV MAAMGFFSYL GIRSSLIILQ

701 VVPFLVLSVG ADNIFIFVLE YQRLPRRPGE PREVHIGRAL GRVAPSMLLC

751 SLSEAICFFL GALTPMPAVR TFALTSGLAV VLDFLLQMSA FVALLSLDSK

801 RQEASRLDVC CCVKPRELPL PGQGEGFLLG LFRKAYVPFL LHWITRGVVL

851 LLFLALFGVS LYYMCHISVG LDQELALPKD SYLLDYFLFL NRYFETGAPV

901 YFVTTSGYNF SSEAGMNAIC SSAGCNNFSF TQKIQYATEF PEQSYLAIPA

951 SSWVDDFIDW LTPSSCCRLY ISGPNKDQFC PSTVNSLNCL KNCLSITMGS

1001 VRPSVEQFYK YLPWFLNDRP NIKCPKGGLG AYSTSVNLTS DGQVLASRFM

1051 AYHKPLKNSQ DYTEALRAAR ELAANITADL RKVPGTDPAF EVFPYTVTNV

1101 FYEQYLTILP EGLFMLSLCL VPTFAVCCLL LGLDLRSGLL NLLSIIMILV

1151 DTVGFMALWG ISYNAVSLIN LVSAVGMSVE FVSHITRSFA ISTKPTRLER

1201 AKEATISMGS AVFAGVAMTN LPGILVLGLA KAQLIQIFFF RLNLLITLLG

1251 LLHGLVFLPV ILSYVGPDIN PALALEQKLA EEAAAAAIAA SYPNHPSRVS

1301 TADNIYVNHS FEGSIKGAGA VSNFLPNNGR QF*
```

Screening Assays

The invention allows the discovery of selective agonists and antagonists of NPC1L1 (e.g., SEQ ID NO: 2, 4, 6, 8, or 10) that may be useful in treatment, prevention and management of a variety of medical conditions including elevated-serum sterol (e.g., cholesterol) or 5α-stanol. Thus, NPC1L1 of this invention can be employed in screening systems to identify agonists or antagonists. For example, the screening assays of the present invention, comprising use of canine, hamster, rabbit, rhesus monkey or cynomolgus monkey NPC1L1, can be used to identify an agonist or antagonist of NPC1L1 from the same or a different organism (e.g., an antagonist of human NPC1L1). In an embodiment of the invention, these systems provide methods for bringing together NPC1L1, an appropriate, known ligand or agonist or antagonist (e.g., compound 1, 2, 3, 4, 5, 6, 7, 8 or 9), including a sterol (e.g., cholesterol, phytosterols (including, but not limited to, sitosterol, campesterol, stigmasterol and avenosterol)), a cholesterol oxidation product, a 5α-stanol (including but not limited to cholestanol, 5α-campestanol and 5α-sitostanol), a substituted azetidinone (e.g., ezetimibe), BODIPY-ezetimibe (Altmann, et al., (2002) Biochim. Biophys. Acta 1580(1):77-93) or 4", 6"-bis[(2-fluorophenyl)carbamoyl]-beta-D-cellobiosyl derivative of 11-ketotigogenin as described in DeNinno, et al., (1997) (J. Med. Chem. 40(16):2547-54) (Merck; L-166,143) or any substituted azetidinone, and a sample to be tested for the presence of an NPC1L1 agonist or antagonist.

A convenient method by which to evaluate whether a sample contains an NPC1L1 agonist or antagonist is to determine whether the sample contains a substance which competes for binding between the known agonist or antagonist (e.g., ezetimibe) and NPC1L1.

In an embodiment of the invention, an antagonist of an NPC1L1 of the invention (e.g., canine, rabbit, hamster, rhesus monkey or cynomolgus monkey NPC1L1 (e.g., SEQ ID NO: 2, 4, 6, 8, or 10)) is used to treat, prevent or manage hypercholesterolemia (e.g., primary hypercholesterolemia, homozygous familial hypercholesterolemia (HoFH), sitosterolemia (e.g., homozygous sitosterolemia), hyperlipidemia, hypertriglyceridemia, arteriosclerosis, atherosclerosis or hypertension. In an embodiment of the invention, an NPC1L1 antagonist is used to treat, prevent or manage any of the foregoing disorders in human or non-human animals (e.g., dogs, cats, rabbits, hamsters, monkeys, rats, mice, cows). For example, a veterinary hyperlipidemic disorder such as primary idiopathic hyperlipidemia can be treated with an NPC1L1 antagonist. Primary idiopathic hyperlipidemia has been reported in a variety of canine breeds including miniature Schnauzers, beagles, mixed breeds, poodles, shelties as well as in cats. Dogs with diabetes mellitus, hypothyroidism, Cushings disease, liver Disease and nephrotic Syndrome have been reported with hyperlipidemia. Hypercholesterolemia (which may also be treated, prevented or managed with an NPC1L1 antagonist) has also been reported in dogs such as Shetland sheepdogs and has been observed in dogs with canine hypothyroidism.

The term "specific" when used to describe binding of, for example, a ligand or antagonist of NPC1L1 in a screening assay is a term of art which refers to the extent by which the ligand or antagonist (e.g., detectably labeled substituted azetidinone, detectably labeled ezetimibe, detectably labeled sterol (e.g., cholesterol) or detectably labeled 5α-stanol, e.g., [$^3$H]-glucuronidated ezetimibe or BODIPY-labeled ezetimibe) binds preferentially to NPC1L1 over that of other proteins in the assay system. For example, an antagonist or ligand of NPC1L1 binds specifically to NPC1L1 when the signal generated in the assay to indicate such binding exceeds, to any extent, a background signal in a negative control experiment wherein, for example, NPC1L1 or the known antagonist or ligand is absent. Furthermore, "specific binding" includes binding of an antagonist or ligand either directly to NPC1L1 or indirectly, for example via another moiety, in a complex of which NPC1L1 is a part. The moiety to which an NPC1L1 ligand or antagonist binds can be another protein or a post-translational modification of NPC1L1 (e.g., a lipid chain or a carbohydrate chain).

Non-limiting examples of suitable azetidinones include those disclosed in U.S. Pat. Nos. RE37,721; 5,631,365; 5,767,115; 5,846,966; 5,688,990; 5,656,624; 5,624,920; 5,698,548 and 5,756,470 and U.S. Patent Application Publication No 2003/0105028, each of which is herein incorporated by reference in its entirety.

Ezetimibe can be prepared by a variety of methods well know to those skilled in the art, for example such as are disclosed in U.S. Pat. Nos. 5,631,365, 5,767,115, 5,846,966, 6,207,822, U.S. Patent Application Publication No. 2002/0193607 and PCT Patent Application WO 93/02048, each of which is incorporated herein by reference in its entirety.

"Sample", "candidate compound" or "candidate substance" refers to a composition which is evaluated in a test or assay, for example, for the ability to agonize or antagonize NPC1L1 (e.g., SEQ ID NO: 2, 4, 6, 8, or 10) or a functional fragment thereof. The composition may be a small organic or inorganic molecule, peptide, nucleotide, polynucleotide, subatomic particle (e.g., α particles, β particles) or antibody or fragment thereof.

NPC1L1 for use in an assay of the invention (e.g., any set forth below) can be from any suitable source. For example, a nucleic acid encoding an NPC1L1 polypeptide of the invention (e.g., SEQ ID NO: 1, 3, 5, 7, or 9) can be transfected into an appropriate host cell (e.g., HEK293), whereby the receptor will become incorporated into the membrane of the cell. A membrane fraction can then be isolated from the cell and used as a source of the receptor for assay. Alternatively, the whole cell expressing the receptor on the cell surface can be used in an assay. In an embodiment, free NPC1L1 is used or a highly soluble fragment of NPC1L1 is generated and used in an assay of the invention.

Two basic types of screening systems that can be used include, a labeled-ligand binding assay (e.g., direct binding assay or scintillation proximity assay (SPA)) and a "sterol (e.g., cholesterol) or 5α-stanol uptake" assay. A labeled ligand, for use in the binding assay, can be obtained by labeling a sterol (e.g., cholesterol) or a 5α-stanol or a known NPC1L1 agonist or antagonist with a measurable group (e.g., $^{125}$I or $^3$H). Various labeled forms of sterols (e.g., cholesterol) or 5α-stanols are available commercially or can be generated using standard techniques (e.g., Cholesterol-[1,2-$^3$H(N)], Cholesterol-[1,2,6,7-$^3$H(N)] or Cholesterol-[7-$^3$H(N)]; American Radiolabeled Chemicals, Inc; St. Louis, Mo.). In an embodiment of the invention, ezetimibe is fluorescently labeled with a BODIPY group (Altmann, et al., Biochim. Biophys. Acta 1580(1):77-93 (2002)) or labeled with a detectable group such as $^{125}$I or $^3$H.

Direct Binding Assay. Typically, a given amount of NPC1L1 of the invention (e.g., SEQ ID NO: 2, 4, 6, 8 or 10) or an active fragment thereof is contacted with increasing amounts of labeled ligand or known antagonist or agonist (discussed above) and the amount of the bound, labeled ligand or known antagonist or agonist is measured after removing unbound, labeled ligand or known antagonist or agonist by washing. As the amount of the labeled ligand or known agonist or antagonist is increased, a point is eventually reached at which all receptor binding sites are occupied or saturated. Specific receptor binding of the labeled ligand or known agonist or antagonist is abolished by a large excess of unlabeled ligand or known agonist or antagonist.

In an embodiment of the invention, an assay system is used in which non-specific binding of the labeled ligand or known antagonist or agonist to the receptor is minimal. Non-specific binding is typically less than 50%, preferably less than 15%, and more preferably less than 10% of the total binding of the labeled ligand or known antagonist or agonist. Preferably, specific binding of the labeled ligand or known antagonist or agonist to an untransfected/untransformed host cell or to a membrane fraction from an untransfected/untransformed host cell will be negligible.

In the basic binding assay, the method for identifying an NPC1L1 agonist or antagonist includes:
(a) contacting canine, rabbit, hamster, rhesus monkey or cynomolgus monkey NPC1L1 (e.g., SEQ ID NO: 2, 4, 6, 8 or 10) or a subsequence thereof, in the presence of a known amount of detectably labeled sterol (e.g., cholesterol) or 5α-stanol or known antagonist or agonist (e.g., [$^3$H]-glucuronidated ezetimibe or BODIPY-labeled ezetimibe) with a sample to be tested for the presence of an NPC1L1 agonist or antagonist; and
(b) measuring the amount of labeled sterol (e.g., cholesterol) or 5α-stanol or known antagonist or agonist bound to NPC1L1.

An NPC1L1 antagonist or agonist in the sample is identified by measuring substantially reduced binding of the labeled sterol (e.g., cholesterol) or 5α-stanol or known antagonist or agonist to NPC1L1, compared to what would be measured in the absence of such an antagonist or agonist. For example, reduced binding between [$^3$H]-cholesterol and NPC1L1 in the presence of a sample would indicate that the sample contains a substance which is competing against [$^3$H]-cholesterol for NPC1L1 binding.

In an embodiment of the invention, this assay includes a negative-control experiment lacking any NPC1L1-dependent ligand (e.g., [$^3$H]-glucuronidated ezetimibe or BODIPY-labeled ezetimibe) binding. In an embodiment of the invention, for example, a whole cell or cell membrane lacking any functional NPC1L1, e.g., untransformed HEK293, is assayed for ligand binding. When screening a sample for the presence of an NPC1L1 antagonist, it is useful to compare the level of binding observed in the presence of a sample being tested with that of a control experiment, as described herein, which completely lacks NPC1L1-dependent binding. Ideally, though by no means necessarily, the level of binding seen in the presence of a sample containing an antagonist will be similar to that of the negative-control experiment. If no significant binding is observed, then this indicates that the assay is operating properly.

In another embodiment of the invention, a positive-control experiment is performed in conjunction with the assay. In this embodiment, for example, NPC1L1 is bound to a detectably labeled substance which is known to bind (e.g. $^3$H-ezetimibe) and, then, exposed to a blank. If binding is observed (e.g., where the labeled substance is competed off of the NPC1L1 by the unlabeled substance), then this indicates that the assay is working properly.

Alternatively, a sample can be tested directly for binding to canine, rabbit, hamster, rhesus monkey or cynomolgus monkey NPC1L1 (e.g., SEQ ID NO: 2, 4, 6, 8 or 10). In an embodiment of the invention, a basic assay of this type includes the following steps:

(a) contacting canine, rabbit, hamster, rhesus monkey or cynomolgus monkey NPC1L1 (e.g., SEQ ID NO: 2, 4, 6, 8 or 10), a subsequence thereof with a detectable or detectably labeled candidate substance (e.g., small molecule or an antibody); and
(b) detecting direct binding between the candidate substance and NPC1L1.

Again, these experiment can be performed along with a negative-control experiment wherein NPC1L1-dependent binding is completely lacking. For example, the assay can be performed using a whole cell or cell membrane lacking any functional NPC1L1 (e.g., untransformed HEK293 cells) and/or lacking any candidate substance. If no binding is observed, then this indicates that the assay is working properly.

In an embodiment of the invention, a positive-control assay is performed. In such an assay, a detectable or detectably labeled substance known to bind to NPC1L1 (e.g., $^3$H-labeled compound 4) is assayed for binding. If binding is observed, then this indicates that the assay is operating properly.

The scope of the present invention includes a method for assaying candidate inhibitory agents for activity against cholesterol absorption (e.g., intestinal cholesterol absorption, for example, in the intestine of a human) comprising the steps of: providing a cell expressing canine, rabbit, hamster, rhesus monkey or cynomolgus monkey NPC1L1 (e.g., SEQ ID NO: 2, 4, 6, 8 or 10) or a functional fragment or variant thereof which is capable of binding a fluorescent cholesterol absorption inhibitor, e.g., wherein said inhibitor is an azetidinone; contacting said cell with a candidate inhibitory agent in the presence of said fluorescent cholesterol absorption inhibitor; and measuring the inhibition of the fluorescence of said cell, wherein a relative absence of fluorescent cholesterol absorption inhibitor indicates that said candidate inhibitory agent is an inhibitory agent which inhibits cholesterol absorption into the cell (e.g., intestinal cholesterol absorption). In an embodiment of the invention, the fluorescent cholesterol absorption inhibitor is

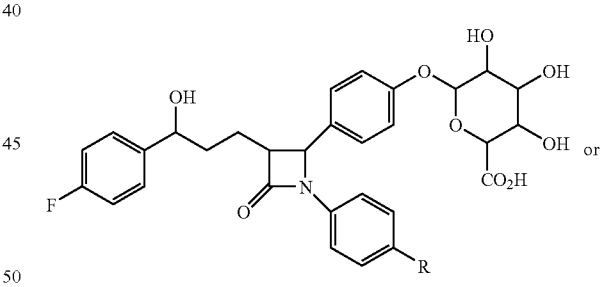

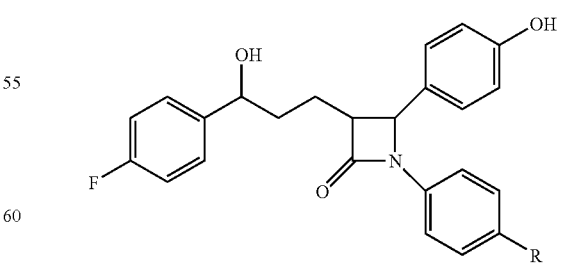

wherein R comprises a fluorescent moiety, e.g., whereing the fluorescent moiety linked by an alkynyl-containing tether group (e.g., C1, C2, C3, C4, C5, C6, C7, C8, C9 or C10 alkynyl group). In an embodiment of the invention, R is

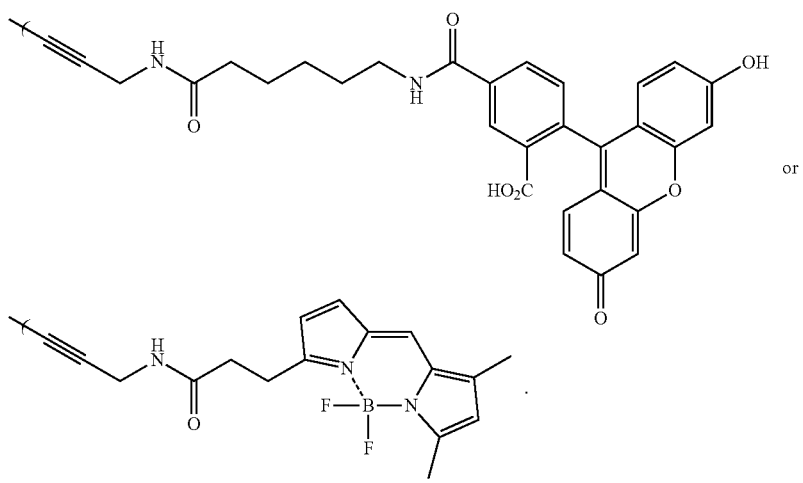

The scope of the present invention includes a method for identifying inhibitory agents which inhibit the absorption of cholesterol into or onto a cell membrane or which inhibit cholesterol absorption e.g., in the intestine of a human, said method comprising the steps of: (a) combining a fluorescent cholesterol absorption inhibitor e.g., wherein said inhibitor is an azetidinone, said cell membrane, wherein the cell membrane comprises canine, rabbit, hamster, rhesus monkey or cynomolgus monkey NPC1L1 (e.g., SEQ ID NO: 2, 4, 6, 8 or 10) or a functional fragment or variant thereof on its surface or embedded within the membrane in such a manner that the NPC1L1 is capable of mediating cholesterol transport across the membrane or binding or transport of a cholesterol absorption inhibitor, and a candidate inhibitory agent, under conditions wherein, but for the presence of said inhibitory agent, said fluorescent cholesterol absorption inhibitor is bound to the membrane e.g., by the NPC1L1; and (b) detecting the relative presence or absence of fluorescent cholesterol absorption inhibitor bound to the membrane, wherein a relative absence of fluorescent cholesterol absorption inhibitor indicates that said candidate inhibitory agent is an inhibitory agent which inhibits cholesterol absorption into or onto the membrane or which inhibits cholesterol absorption into the intestine. In an embodiment of the invention, the cell membrane is an intestinal epithelial cell membrane. In an embodiment of the invention, the fluorescent cholesterol absorption inhibitor is

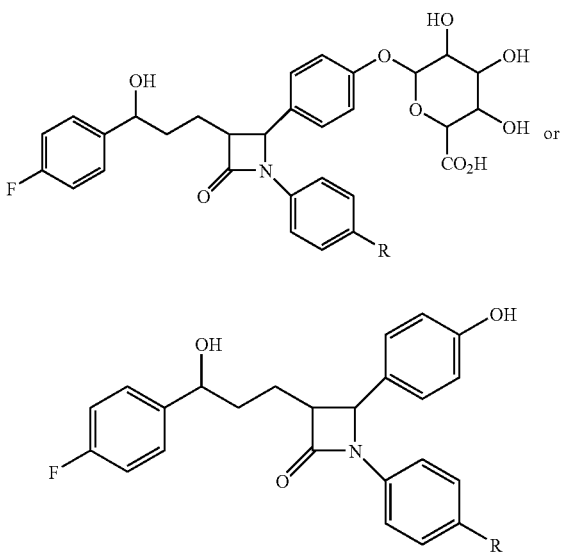

wherein R comprises a fluorescent moiety, e.g., whereing the fluorescent moiety linked by an alkynyl-containing tether group. In an embodiment of the invention, R is

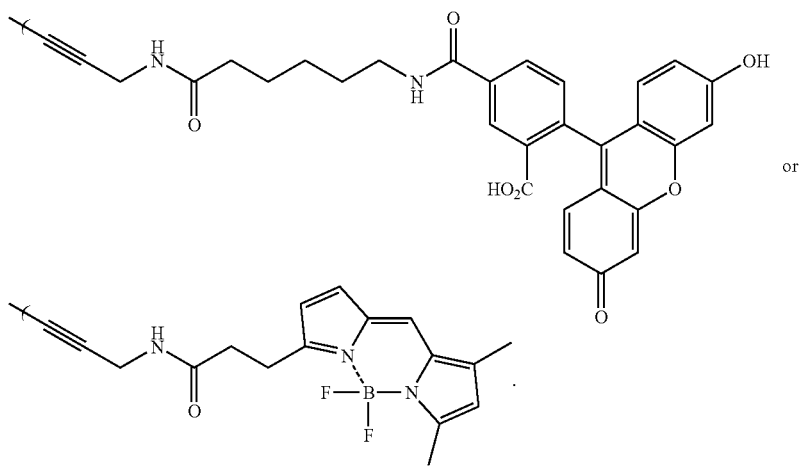

The presence of fluorescent inhibitor in the cell or bound to the membrane in these methods would indicate that the candidate inhibitory agent is not an inhibitor of cholesterol absorption.

The present invention also includes any azetidinone, such as ezetimibe or any fluorescent cholesterol absorption inhibitor (e.g., a fluorescently labeled azetidinone) bound to canine, rabbit, hamster, rhesus monkey or cynomolgus monkey NPC1L1 (e.g., SEQ ID NO: 2, 4, 6, 8 or 10) or a functional fragment or variant thereof (e.g., isolated NPC1L1 e.g., soluble or on the surface of an isolated cell or membrane or non-isolated, in vivo NPC1L1, for example, on the surface of a cell), e.g., wherein the inhibitor is

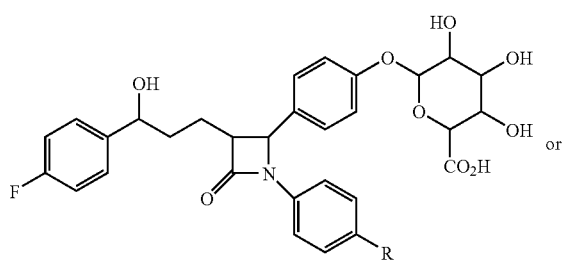

or

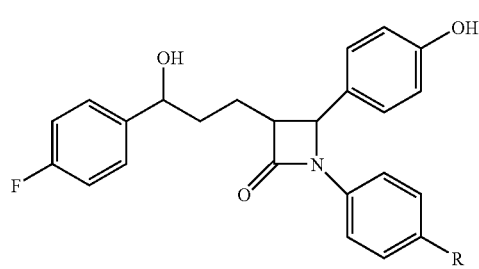

wherein R comprises a fluorescent moiety, e.g., whereing the fluorescent moiety linked by an alkynyl-containing tether group. In an embodiment of the invention, R is U.S. Pat. Nos. 7,144,696; 6,933,107; 6,632,933; and 6,593,078 are herein incorporated by reference in their entireties as is published international application no. WO 00/63703.

A candidate compound which is found to bind to NPC1L1 may function as an agonist or antagonist of NPC1L1 (e.g., by inhibition of sterol (e.g., cholesterol) or 5α-stanol uptake). This may be confirmed, subsequently, in an uptake assay as discussed below.

SPA Assay. NPC1L1 antagonists or agonists may also be measured using scintillation proximity assays (SPA). SPA assays are conventional and very well known in the art; see, for example, U.S. Pat. No. 4,568,649. In SPA, the target of interest is immobilised to a small microsphere approximately 5 microns in diameter. The microsphere, typically, includes a solid scintillant core which has been coated with a polyhydroxy film, which in turn contains coupling molecules, which allow generic links for assay design. When a radioisotopically labeled molecule binds to the microsphere, the radioisotope is brought into close proximity to the scintillant and effective energy transfer from electrons emitted by the isotope will take place resulting in the emission of light. While the radioisotope remains in free solution, it is too distant from the scintillant and the electron will dissipate the energy into the aqueous medium and therefore remain undetected. Scintillation may be detected with a scintillation counter. In general, $^3$H and $^{125}$I labels are well suited to SPA.

For the assay of receptor-mediated binding events, the lectin wheat germ agglutinin (WGA) may be used as the SPA bead coupling molecule (Amersham Biosciences; Piscataway, N.J.). The WGA coupled bead captures glycosylated, cellular membranes and glycoproteins and has been used for a wide variety of receptor sources and cultured cell membranes. The receptor is immobilized onto the WGA-SPA bead and a signal is generated on binding of an isotopically labeled ligand. Other coupling molecules which may be useful for receptor binding SPA assays include poly-L-lysine and WGA/polyethyleneimine (Amersham Biosciences; Piscataway, N.J.). See, for example, Berry, J. A., et al., (1991) Cardiovascular Pharmacol. 17 (Suppl. 7): S143-S145; Hoffman, R., et al., (1992) Anal. Biochem. 203: 70-75; Kienhus, et al., (1992) J. Receptor Research 12: 389-399; Jing, S., et al., (1992) Neuron 9: 1067-1079.

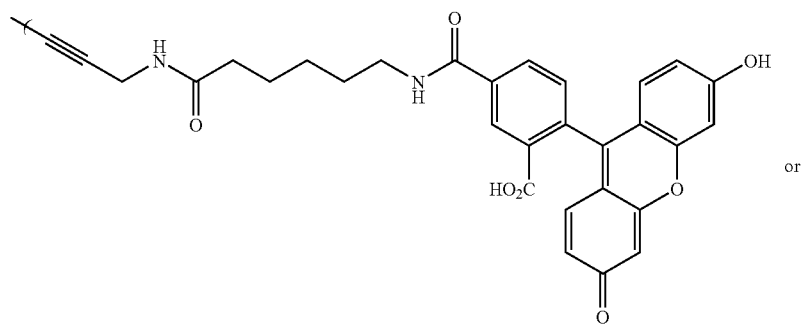

or

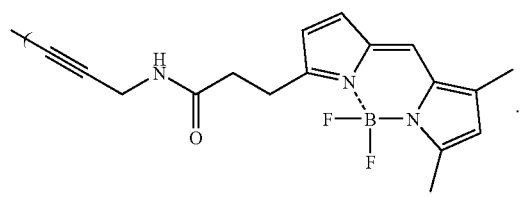

The scintillant contained in SPA beads may include, for example, yttrium silicate (YSi), yttrium oxide (YOx), diphenyloxazole or polyvinyltoluene (PVT) which acts as a solid solvent for diphenylanthracine (DPA).

SPA assays may be used to analyze whether a sample contains an NPC1L1 antagonist or agonist. In these assays, canine, rabbit, hamster, rhesus monkey or cynomolgus monkey NPC1L1 or a host cell which expresses canine, rabbit, hamster, rhesus monkey or cynomolgus monkey NPC1L1 (e.g., SEQ ID NO: 2, 4, 6, 8 or 10) on the cell surface or a membrane fraction thereof is incubated with and captured by SPA beads (e.g., WGA coated YOx beads or WGA coated YSi beads). The beads bearing the NPC1L1 are incubated with labeled, known ligand or agonist or antagonist (e.g., $^3$H-labeled compound 4). The assay mixture further includes either the sample to be tested or a blank (e.g., water). After an optional incubation, scintillation is measured using a scintillation counter. An NPC1L1 agonist or antagonist may be identified in the sample by measuring substantially reduced fluorescence, compared to what would be measured in the absence of such agonist or antagonist (blank). Measuring substantially reduced fluorescence suggests that the sample contains a substance which competes for NPC1L1 binding with the known ligand, agonist or antagonist.

In an embodiment of the invention, a negative-control assay is performed. In a negative-control assay, for example, the assay is performed as set forth above except that no NPC1L1 is present. If no significant fluorescence is observed, then this indicates that the assay is operating properly.

In an embodiment of the invention, a positive-control assay is performed. In a positive-control assay, the substance known to bind to NPC1L1 (e.g., $^3$H-labeled compound 4) is incubated along with an un-radiolabeled substance also known to bind to NPC1L1 (e.g., unlabeled compound 4). If reduced binding of the labeled substance is observed (i.e., reduced fluorescence), relative to an assay wherein a blank is used in place on the unlabeled substance known to bind NPC1L1, then this indicates that the assay is operating properly.

Alternatively, a sample may be identified as an antagonist or agonist of NPC1L1 by directly detecting binding in a SPA assay. In this assay, a labeled version of a candidate compound to be tested is put in contact with canine, rabbit, hamster, rhesus monkey or cynomolgus monkey NPC1L1 or a host cell expressing NPC1L1 or a membrane fraction thereof which is bound to the SPA bead. Fluorescence may then be assayed to detect the presence of a complex between the labeled candidate compound and the NPC1L1. A candidate compound which binds to NPC1L1 may possess NPC1L1 agonistic or antagonistic activity.

SPA Assays can also be performed along with a negative-control experiment lacking any NPC1L1-dependent binding. The control experiment can be performed, for example, with a cell or cell membrane lacking any functional NPC1L1. When the control experiment is performed, the level of binding observed in the presence of sample being tested for the presence of an antagonist can be compared with that observed in the control experiment. If no significant binding is observed, this indicates that the assay is operating properly.

Furthermore, a positive-control experiment can be performed wherein a radiolabeled compound known to bind to NPC1L1 (e.g., $^3$H-labeled compound 4) is assayed. If binding is observed, this indicates that the assay is operating properly.

Host cells expressing NPC1L1 may be prepared by transforming or transfecting a nucleic acid encoding an NPC1L1 of the invention into an appropriate host cell, whereby the receptor becomes incorporated into the membrane of the cell. A membrane fraction can then be isolated from the cell and used as a source of the receptor for assay. Alternatively, the whole cell expressing the receptor on the cell surface can be used in an assay. Preferably, specific binding of the labeled ligand or known antagonist or agonist to an untransfected/untransformed host cell or membrane fraction from an untransfected/untransformed host cell will be negligible. Preferred host cells include Chinese Hamster Ovary (CHO) cells, murine macrophage J774 cells or any other macrophage cell line and human intestinal epithelial Caco2 cells.

Sterol/5α-stanol Uptake Assay. Assays may also be performed to determine if a sample can agonize or antagonize NPC1L1 mediated sterol (e.g., cholesterol) or 5α-stanol uptake. In these assays, a host cell expressing canine, hamster, rabbit, rhesus monkey or cynomolgus monkey NPC1L1 (e.g., SEQ ID NO: 2, 4, 6, 8 or 10) on the cell surface (discussed above) is contacted with detectably labeled sterol (e.g., $^3$H-cholesterol or $^{125}$I-cholesterol)) or 5α-stanol along with a sample to be tested for an agonist or antagonist of NPC1L1. After an optional incubation, the cells can be washed to remove unabsorbed sterol or 5α-stanol. Sterol or 5α-stanol uptake can be determined by detecting the presence of labeled sterol or 5α-stanol in the host cells. For example, assayed cells or lysates or fractions thereof (e.g., fractions resolved by thin-layer chromatography) can be contacted with a liquid scintillant and scintillation can be measured using a scintillation counter.

In these assays, an NPC1L1 antagonist in the sample may be identified by measuring substantially reduced uptake of the labeled sterol (e.g., $^3$H-cholesterol) or 5α-stanol, compared to what would be measured in the absence of such an antagonist and an agonist may be identified by measuring substantially increased uptake of the labeled sterol (e.g., $^3$H-cholesterol) or 5α-stanol, compared to what would be measured in the absence of such an agonist.

Uptake assays can optionally be performed along with a negative-control assay lacking any NPC1L1-dependent uptake. The negative-control assay can be performed, for example, with a cell lacking any functional NPC1L1 (e.g., an untransformed host cell) or lacking any labeled sterol or 5α-stanol. A substantial lack of uptake indicates that the assay is operating correctly. A positive-control assay may also be optionally performed along with an assay of the invention. For example, in a control assay, a cell expressing NPC1L1 is exposed to labeled sterol or 5α-stanol in the absence of any antagonist. A high level of uptake in the cell would indicate that the assay is operating correctly.

In Vivo Assay. The present invention comprises a mutant, transgenic canine, rabbit, hamster, rhesus monkey or cynomolgus monkey which lacks any functional NPC1L1. This canine, rabbit, hamster, rhesus monkey or cynomolgus monkey may serve as a convenient control experiment in screening assays for identifying inhibitors of intestinal sterol (e.g., cholesterol) or 5α-stanol absorption, preferably inhibitors of NPC1L1. In an embodiment of the invention, a canine, rabbit, hamster, rhesus monkey or cynomolgus monkey-based assay of the present invention would comprise the following steps:

(a) feeding a sterol (e.g., cholesterol) or 5α-stanol-containing substance (e.g., comprising radiolabeled cholesterol, such as $^{14}$C-cholesterol or $^3$H-cholesterol) to a first and second canine, rabbit, hamster, rhesus monkey or cynomolgus monkey comprising a functional NPC1L1 gene and to a third, mutant canine, rabbit, hamster, rhesus monkey or cynomolgus monkey lacking a functional NPC1L1;

In an embodiment of the invention, the sterol (e.g., cholesterol) or 5α-stanol containing substance contains labeled cholesterol, such as a radiolabeled cholesterol, for example, $^3$H or $^{14}$C labeled cholesterol. The sterol (e.g., cholesterol) or 5α-stanol containing substance may also include cold, unlabeled sterol (e.g., cholesterol) or 5α-stanol such as in corn oil.

In these assays, the third npc1l1 mutant canine, rabbit, hamster, rhesus monkey or cynomolgus monkey serves as a (+)-control experiment which exhibits low levels of intestinal sterol (e.g., cholesterol) or 5α-stanol absorption and the second canine, rabbit, hamster, rhesus monkey or cynomolgus monkey serves as a (−)-control experiment which exhibits normal, uninhibited levels of intestinal sterol (e.g., cholesterol) or 5α-stanol absorption. The second canine, rabbit, hamster, rhesus monkey or cynomolgus monkey is not administered the sample to be tested for an NPC1L1 antagonist. The first canine, rabbit, hamster, rhesus monkey or cynomolgus monkey is the experimental.

(b) administering the sample to be tested for the presence of the antagonist to the first canine, rabbit, hamster, rhesus monkey or cynomolgus monkey comprising a functional NPC1L1 but not to the second canine, rabbit, hamster, rhesus monkey or cynomolgus monkey;

(c) measuring the amount of sterol (e.g., cholesterol) or 5α-stanol absorption in the intestine of said first, second and third canine, rabbit, hamster, rhesus monkey or cynomolgus monkey;

Intestinal sterol (e.g., cholesterol) or 5α-stanol absorption may be measured by any method known in the art. For example, the level intestinal absorption can be assayed by measuring the level of serum sterol (e.g., cholesterol) or 5α-stanol.

(d) comparing the levels of intestinal sterol (e.g., cholesterol) or 5α-stanol absorption in each canine, rabbit, hamster, rhesus monkey or cynomolgus monkey;

wherein the sample is determined to contain the intestinal sterol (e.g., cholesterol) or 5α-stanol absorption antagonist when the level of intestinal sterol (e.g., cholesterol) or 5α-stanol absorption in the first canine, rabbit, hamster, rhesus monkey or cynomolgus monkey and in the third canine, rabbit, hamster, rhesus monkey or cynomolgus monkey are less than the amount of intestinal sterol (e.g., cholesterol) or 5α-stanol absorption in the second canine, rabbit, hamster, rhesus monkey or cynomolgus monkey.

Preferably, if the sample contains an intestinal sterol (e.g., cholesterol) or 5α-stanol absorption inhibitor (e.g., an NPC1L1 inhibitor), the level of sterol (e.g., cholesterol) or 5α-stanol absorption in the first canine, rabbit, hamster, rhesus monkey or cynomolgus monkey will be similar to that of the third, npc1l1 mutant canine, rabbit, hamster, rhesus monkey or cynomolgus monkey.

An alternative positive-control experiment which may be used in conjunction with these screening assays is to perform the experiment essentially as set forth above, except that the sample tested is ezetimibe. If inhibition of uptake is observed in this assay, this indicates that the assay is operating properly.

Antibodies

The present invention includes any antibody or antigen-binding fragment thereof that binds specifically to canine, hamster, rabbit, rhesus monkey or cynomolgus monkey NPC1L1 or an antigenic fragment thereof. Embodiments of the invention include any anti-canine, hamster, rabbit, rhesus monkey or cynomolgus monkey NPC1L1 antibody or antigen-binding fragment thereof which is a monoclonal antibody, polyclonal antibody, bispecific antibody, linear antibody, chimeric antibody, humanized antibody, anti-idiotypic antibody, recombinant antibody, Fab antibody fragment, F(ab)$_2$ antibody fragment, Fv antibody fragment (e.g., VH or VL), single chain Fv antibody fragment or dsFv antibody fragment.

The present invention also includes any antibody or antigen-binding fragment thereof which binds specifically to canine, hamster, rabbit, rhesus monkey or cynomolgus monkey NPC1L1 or an antigenic fragment thereof which was raised against said NPC1L1 or fragment thereof. For example, an embodiment of the invention includes any anti-canine, hamster, rabbit, rhesus monkey or cynomolgus monkey NPC1L1 antibody or antigen-binding fragment thereof produced by immunization of an animal with said NPC1L1 or an antigenic fragment thereof.

In an embodiment of the invention, a polyclonal antibody is raised in animals by multiple subcutaneous (sc) or intraperitoneal (ip) injections of the relevant antigen (e.g., canine, hamster, rabbit, rhesus monkey or cynomolgus monkey NPC1L1 or an antigenic fragment thereof) and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl$_2$, or R1N=C=NR, where R and R1 are different alkyl groups. In an embodiment of the invention, animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. In an embodiment of the invention, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

In an embodiment of the invention, a monoclonal antibody is made using the hybridoma method first described by Kohler et al., Nature, 256:495 (1975), or by recombinant DNA methods (see e.g., U.S. Pat. No. 4,816,567). In an embodiment of the invention, in the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)). In an embodiment of the invention, the hybridoma cells thus prepared are seeded and grown in a suitable culture medium that, in an embodiment of the invention, contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. In an embodiment of the invention, myeloma cells are those that fuse efficiently, support stable high-level production of antibody by the selected antibody-producing cells, and are sensitive to a medium such as HAT medium. Among these, myeloma cell lines are murine myeloma lines. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

In an embodiment of the invention, culture medium in which hybridoma cells are growing is assayed for production of monoclonal antibodies directed against the antigen. In an embodiment of the invention, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). In an embodiment of the invention, after hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. In an embodiment of the invention, the monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. In an embodiment of the invention, DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells.

In an embodiment of the invention, antibodies or antibody fragments of the invention can be isolated from antibody phage libraries generated using the techniques described in McCafferty et al., Nature, 348:552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

In an embodiment of the invention, single-chain Fv or sFv antibody fragments comprise the VH and VL domains of an antibody, wherein these domains are present in a single polypeptide chain. Generally, the Fv polypeptide further comprises a polypeptide linker between the VH and VL domains which enables the sFv to form the desired structure for antigen binding. For a review of sFv see Pluckthun in The Pharmacology of Monoclonal Antibodies, vol. 113, Rosenburg and Moore eds. Springer-Verlag, New York, pp. 269-315 (1994).

In an embodiment of the invention, humanized antibody forms of non-human (e.g., murine) antibodies are chimeric antibodies which contain minimal sequence derived from non-human immunoglobulin. In general, humanized antibodies are human immunoglobulins (recipient antibody) in which residues from a hypervariable region (e.g., CDRs) of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues.

A linear antibody is an antibody fragment as described in Zapata et al. Protein Eng. 8(10):1057-1062 (1995). Briefly, these fragments comprise a pair of tandem Fd segments (VH—CH1-VH—CH1) which form a pair of antigen binding regions. Linear antibodies can be bispecific or monospecific.

A species-dependent antibody is one which has a stronger binding affinity for an antigen from a first species than it has for a homologue of that antigen from a second species. In an embodiment of the invention, a species-dependent antibody "binds specifically" to a canine, hamster, rabbit, rhesus monkey or cynomolgus monkey NPC1L1 antigen (e.g., has a binding affinity (Kd) value of no more than about $1 \times 10^{-7}$ M) but has a binding affinity for a homologue of the antigen from a second species (e.g., another mammalian species such as human NPC1L1) which is at least about 50 fold, or at least about 500 fold, or at least about 1000 fold, weaker than its binding affinity for the canine, hamster, rabbit, rhesus monkey or cynomolgus monkey NPC1L1 antigen. The present invention comprises species dependent anti-canine, rabbit, hamster, cynomolgus monkey and rhesus monkey NPC1L1 antibodies and antigen-binding fragments thereof.

The present invention also includes an anti-canine, hamster, rabbit, rhesus monkey or cynomolgus monkey NPC1L1 antibody or antigen-binding fragment thereof produced by a process including introduction of an expression vector comprising the light and/or heavy chain of said antibody into a suitable host cell, expressing said chain(s) in said cell and, optionally isolating said chain(s). For example, an embodiment of the invention includes expressing an anti-canine, hamster, rabbit, rhesus monkey or cynomolgus monkey NPC1L1 antibody or antigen-binding fragment thereof of the invention in the plasmid system set forth in published international application no. WO2005/047512.

The present invention also includes any immunoliposome including any anti-canine, hamster, rabbit, rhesus monkey or cynomolgus monkey NPC1L1 antibody or antigen-binding fragment thereof of the invention. An immunoliposome is a liposome including said antibody or fragment. Liposomes containing the antibody or fragment can be prepared by methods known in the art, such as described in Epstein et al., Proc. Natl. Acad. Sci. USA, 82:3688 (1985); Hwang et al., Proc. Natl. Acad. Sci. USA, 77:4030 (1980); and U.S. Pat. Nos. 4,485,045 and 4,544,545. Liposomes with enhanced circulation time are disclosed in U.S. Pat. No. 5,013,556. Other useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab fragments of an antibody of the present invention can be conjugated to the liposomes as described in Martin et al. J. Biol. Chem. 257: 286-288 (1982) via a disulfide interchange reaction. In an embodiment, a chemotherapeutic agent (such as ezetimibe) is optionally contained within the liposome.

In an embodiment of the invention, an anti-canine NPC1L1 antibody, an anti-hamster NPC1L1 antibody, an anti-rabbit NPC1L1 antibody, an anti-rhesus monkey NPC1L1 antibody or an anti-cynomolgus monkey NPC1L1 antibody that "specifically binds" to or is "specific for" canine, hamster, rabbit, rhesus monkey or cynomolgus monkey NPC1L1, respectively, is one that binds to that particular polypeptide or an epitope on the polypeptide without substantially binding to any other polypeptide or epitope.

In an embodiment of the invention, an anti-canine NPC1L1 antibody, an anti-hamster NPC1L1 antibody, an anti-rabbit NPC1L1 antibody, an anti-rhesus monkey NPC1L1 antibody or an anti-cynomolgus monkey NPC1L1 antibody that "specifically binds" to or is "specific for" canine, hamster, rabbit, rhesus monkey or cynomolgus monkey NPC1L1, respectively, is one that binds to that particular polypeptide or an epitope on the polypeptide with an affinity constant of at least $10^{-6}$ M, or at least $10^{-8}$ M.

If necessary, non-specific binding can be reduced without substantially affecting specific binding by varying the binding conditions. The appropriate binding conditions such as concentration of antibodies, ionic strength of the solution, temperature, time allowed for binding, concentration of a blocking agent (e.g., serum albumin, milk casein), etc., may be optimized by a skilled artisan using routine techniques The present invention further comprises a complex comprising an antibody (e.g., an isolated antibody) or antigen-binding fragment thereof of the present invention (e.g., an anti-canine, rabbit, hamster, rhesus monkey or cynomolgus monkey NPC1L1 antibody) bound to a polypeptide of the present invention (e.g., canine, rabbit, hamster, rhesus monkey or cynomolgus monkey NPC1L1 (e.g., SEQ ID NO: 2, 4, 6, 8, or 10) or any fragment thereof (e.g., an antigenic fragment)). In an embodiment of the invention, the polypeptide is isolated. The present invention includes complexes existing both in vitro as well as in vivo (e.g., in the body of a subject). For example, the present invention includes a complex comprising an isolated antibody of the invention, that was administered to a subject, existing in a complex with an NPC1L1 polypeptide of the present invention, in the body of said subject. Furthermore, the present invention includes a complex comprising a non-isolated antibody, bound to an isolated NPC1L1 polypeptide of the present invention that was administered to a subject (e.g., for the purpose of generating anti-NPC1L1 antibodies), inside or outside the body of said subject.

Pharmaceutical Compositions

NPC1L1 agonists and antagonists discovered, for example, by the screening methods described above may be used therapeutically (e.g., in a pharmaceutical composition) to stimulate or block the activity of NPC1L1 and, thereby, to treat any medical condition caused or mediated by NPC1L1. In addition, the antibodies and antigen-binding fragments thereof of the invention may also be used therapeutically (e.g., in a pharmaceutical composition) to bind NPC1L1 and, thereby, block the ability of NPC1L1 to bind a sterol (e.g., cholesterol) or 5α-stanol. Blocking the binding of a sterol (e.g., cholesterol) or 5α-stanol to NPC1L1 prevents absorption of the molecule (e.g., by intestinal cells such as enterocytes). Blocking absorption of sterol (e.g., cholesterol) or 5α-stanol is a useful way to lower serum sterol (e.g., cholesterol) or 5α-stanol levels in a subject and, thereby, reduce the incidence of, for example, hyperlipidemia, atherosclerosis, coronary heart disease, stroke or arteriosclerosis.

The term "subject" or "patient" includes any organism, preferably animals, more preferably mammals such as humans, hamsters, rhesus monkeys, cynomolgus monkeys, mice, rats, rabbits, dogs, canines, horses, primates, cats).

The term "pharmaceutical composition" refers to a composition including an active ingredient and a pharmaceutically acceptable carrier and/or adjuvant.

Although the compositions of this invention could be administered in simple solution, they may be used in combination with other materials such as carriers, preferably pharmaceutically acceptable carriers. Useful, pharmaceutically acceptable carriers can be any compatible, non-toxic substances suitable for delivering the compositions of the invention to a subject. Sterile water, alcohol, fats, waxes, and inert solids may be included in a pharmaceutically acceptable carrier. Buffering agents or dispersing agents may also be incorporated into the pharmaceutical composition.

In an embodiment of the invention, the pharmaceutical compositions of the invention are in the form of a pill or capsule. Methods for formulating pills and capsules are very well known in the art. For example, for oral administration in the form of tablets or capsules, the active drug component may be combined with any oral, non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Suitable binders include, for example, starch, gelatin, natural sugars, corn sweeteners, natural and synthetic gums such as acacia, sodium alginate, carboxymethylcellulose, polyethylene glycol and waxes. Among the lubricants that may be used in a pharmaceutical composition are boric acid, sodium benzoate, sodium acetate, sodium chloride, and the like. Disintegrants include starch, methylcellulose, guar gum and the like. Sweetening and flavoring agents and preservatives may also be included where appropriate.

The pharmaceutical compositions of the invention may be administered in association with a second pharmaceutical composition or substance. In an embodiment of the invention, the second composition includes a cholesterol-lowering drug (e.g., simvastatin, atorvastatin, lovastatin, pravastatin, rosuvastatin or fluvastatin). The term "in association with" indicates that the components of the combinations of the invention can be formulated into a single composition for simultaneous delivery or formulated separately into two or more compositions (e.g., a kit). Furthermore, each component of a combination of the invention can be administered to a subject at a different time than when the other component is administered; for example, each administration may be given non-simultaneously (e.g., separately or sequentially) at several intervals over a given period of time. Moreover, the separate components may be administered to a subject by the same or by a different route (e.g., orally, intravenously, subcutaneously).

The formulations may conveniently be presented in unit dosage form and may be prepared by any methods well known in the art of pharmacy. See, e.g., Gilman et al. (eds.) (1990), *The Pharmacological Bases of Therapeutics*, 8th Ed., Pergamon Press; and *Remington's Pharmaceutical Sciences*, supra, Easton, Pa.; Avis et al. (eds.) (1993) *Pharmaceutical Dosage Forms: Parenteral Medications* Dekker, New York; Lieberman et al. (eds.) (1990) *Pharmaceutical Dosage*

Forms: Tablets Dekker, New York; and Lieberman et al. (eds.) (1990), *Pharmaceutical Dosage Forms: Disperse Systems* Dekker, New York.

The dosage regimen involved in a therapeutic application may be determined by a physician, considering various factors which may modify the action of the therapeutic substance, e.g., the condition, body weight, sex and diet of the patient, the severity of any infection, time of administration, and other clinical factors. Often, treatment dosages are titrated upward from a low level to optimize safety and efficacy. Dosages may be adjusted to account for the smaller molecular sizes and possibly decreased half-lives (clearance times) following administration.

An "effective amount" of an antagonist of the invention may be an amount that will detectably reduce the level of intestinal sterol (e.g., cholesterol) or 5α-stanol absorption or detectably reduce the level of serum sterol (e.g., cholesterol) or 5α-stanol in a subject administered the composition.

Typical protocols for the therapeutic administration of such substances are well known in the art. Pharmaceutical composition of the invention may be administered, for example, by any parenteral or non-parenteral route.

Pills and capsules of the invention can be administered orally. Injectable compositions can be administered with medical devices known in the art; for example, by injection with a hypodermic needle.

Injectable pharmaceutical compositions of the invention may also be administered with a needleless hypodermic injection device; such as the devices disclosed in U.S. Pat. Nos. 5,399,163; 5,383,851; 5,312,335; 5,064,413; 4,941,880; 4,790,824 or 4,596,556.

Anti-Sense

The present invention also encompasses anti-sense oligonucleotides capable of specifically hybridizing to mRNA encoding NPC1L1 (e.g., any of SEQ ID NOs: 1, 3, 5, 7, or 9) having an amino acid sequence defined by, for example, SEQ ID NO: 2, 4, 6, 8, or 10 or a subsequence thereof so as to prevent translation of the mRNA. Additionally, this invention contemplates anti-sense oligonucleotides capable of specifically hybridizing to the genomic DNA molecule encoding NPC1L1.

This invention further provides pharmaceutical compositions comprising (a) an amount of an oligonucleotide effective to reduce NPC1L1-mediated sterol (e.g., cholesterol) or 5α-stanol absorption by passing through a cell membrane and binding specifically with mRNA encoding NPC1L1 in the cell so as to prevent its translation and (b) a pharmaceutically acceptable carrier capable of passing through a cell membrane. In an embodiment, the oligonucleotide is coupled to a substance that inactivates mRNA. In another embodiment, the substance that inactivates mRNA is a ribozyme.

Reducing the level of NPC1L1 expression by introducing anti-sense NPC1L1 RNA into the cells of a patient is a useful method reducing intestinal sterol (e.g., cholesterol) or 5α-stanol absorption and serum cholesterol in the patient.

Kits

Kits of the present invention include ezetimibe, e.g., combined with a pharmaceutically acceptable carrier, in a pharmaceutical formulation, e.g., in a pharmaceutical dosage form such as a pill, a powder, an injectable liquid, a tablet, dispersible granules, a capsule, a cachet or a suppository. See for example, Gilman et al. (eds.) (1990), *The Pharmacological Bases of Therapeutics*, 8th Ed., Pergamon Press; and *Remington's Pharmaceutical Sciences*, supra, Easton, Pa.; Avis et al. (eds.) (1993) *Pharmaceutical Dosage Forms: Parenteral Medications* Dekker, New York; Lieberman et al. (eds.) (1990) *Pharmaceutical Dosage Forms: Tablets* Dekker, New York; and Lieberman et al. (eds.) (1990), *Pharmaceutical Dosage Forms: Disperse Systems* Dekker, New York. In an embodiment of the invention, the dosage form is a Zetia® (ezetimibe) or Vytorin® (ezetimibe/simvastatin) tablet (Merck/Schering-Plough Corp.).

The kits of the present invention also include information, for example in the form of a package insert, indicating that the target of ezetimibe is NPC1L1. The term "target of ezetimibe" indicates that ezetimibe reduces intestinal sterol (e.g., cholesterol) or 5α-stanol absorption, either directly or indirectly, by antagonizing NPC1L1. The form of the insert may take any form, such as paper or on electronic media such as a magnetically recorded medium (e.g., floppy disk) or a CD-ROM.

The package insert may also include other information concerning the pharmaceutical compositions and dosage forms in the kit. Generally, such information aids patients and physicians in using the enclosed pharmaceutical compositions and dosage forms effectively and safely. For example, the following information may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references and patent information.

The kits of the invention may also include simvastatin (

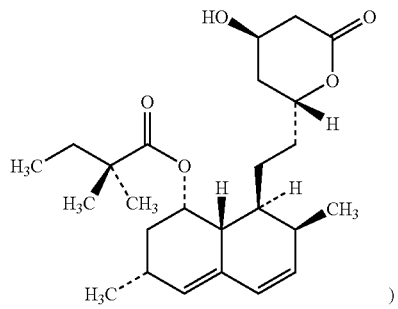

)

combined, in an embodiment of the invention, with a pharmaceutically acceptable carrier, in a pharmaceutical formulation, more preferably in a pharmaceutical dosage form such as a pill, a powder, an injectable liquid, a tablet, dispersible granules, a capsule, a cachet or a suppository. In an embodiment of the invention, the dosage form of simvastatin is a Zocor® tablet (Merck & Co.; Whitehouse Station, N.J.).

Ezetimibe and simvastatin may be supplied, in the kit, as separate compositions or combined into a single composition. For example, ezetimibe and simvastatin may be supplied within a single, common pharmaceutical dosage form (e.g., pill or tablet) or in separate pharmaceutical dosage forms (e.g., two separate pills or tablets).

npc1l1⁻ Cells

The present invention provides any isolated canine, rabbit, hamster, rhesus monkey or cynomolgus monkey cell which lacks an NPC1L1 gene which encodes or can produce a functional NPC1L1 protein. Included within this embodiment are mutant npc1l1 genes comprising a point mutation, truncation or deletion of the genetic coding region (partly or in its entirety) or of any regulatory element (e.g., a promoter).

For example, the cell can be isolated from a mutant animal comprising a homozygous or heterozygous mutation of endogenous, chromosomal NPC1L1 wherein the animal does not produce any functional NPC1L1 protein. Moreover, the present invention comprises any cell, tissue, organ, fluid, nucleic acid, peptide or other biological substance derived or isolated from such an animal. The isolated cell can be isolated or derived, for example, from the duodenum, gall bladder, liver, small intestine or stomach of the mutant animal. Further, the cell can be an enterocyte.

The npc1l1⁻ mutant cells are useful, for example, for use in control experiments in screening assays (see e.g., supra) since they lack any NPC1L1-dependent uptake or binding of sterol, 5α-stanol or ezetimibe. The level of inhibition caused by a particular sample, in a screening assay, can be compared to that of an assay performed with the mutant cell. Ideally, though by no means necessarily, in a screening assay, for example, as described herein, the same amount of binding will be observed by a non-mutant cell or cell membrane, in the presence of an antagonist, as is observed in connection with a mutant npc1l1⁻ cell or cell membrane alone.

Transgenic Animals

Genetically engineered host cells can be further used to produce non-human transgenic animals such as canines (e.g., dogs), rabbits, hamsters, cynomolgus monkeys and rhesus monkeys. A transgene is exogenous DNA which is integrated into the genome of a cell from which a transgenic animal develops and which remains in the genome of the mature animal in one or more cell types or tissues of the transgenic animal. These animals are useful for studying the function of NPC1L1 and identifying and evaluating modulators (e.g., inhibitors) thereof. The present invention includes for example, knock-out canines (e.g., dogs), rabbits, hamsters, cynomolgus monkeys and rhesus monkeys which lack any functional NPC1L1 protein in their cells. The present invention also includes any transgenic non-human animal comprising a supra-normal level of an NPC1L1 of the invention in its cells.

A transgenic animal can be produced by introducing nucleic acid into the male pronuclei of a fertilized oocyte, e.g., by microinjection or retroviral infection, and allowing the oocyte to develop in a pseudopregnant female foster animal. Any of the NPC1L1 nucleotide sequences of the invention can be introduced as a transgene into the genome of an animal.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of NPC1L1 protein to particular cells.

Methods for generating transgenic animals via embryo manipulation and microinjection have become conventional in the art and are described. Any technique known in the art may be used to introduce the transgene (i.e., nucleic acids of the invention) into animals to produce the founder lines of transgenic animals. Such techniques include, but are not limited to, pronuclear microinjection (Paterson et al., Appl. Microbiol. Biotechnol. 40:691-698 (1994); Carver et al., Biotechnology (NY) 11:1263-1270 (1993); Wright et al., Biotechnology (NY) 9:830-834 (1991); and Hoppe et al., U.S. Pat. No. 4,873,191 (1989)); retrovirus mediated gene transfer into germ lines (Van der Putten et al., Proc. Natl. Acad. Sci., USA 82:6148-6152 (1985)), blastocysts or embryos; gene targeting in embryonic stem cells (Thompson et al., Cell 56:313-321 (1989)); electroporation of cells or embryos (Lo, Mol Cell. Biol. 3:1803-1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717-723 (1989); etc. For a review of such techniques, see Gordon, "Transgenic Animals," Intl. Rev. Cytol. 115:171-229 (1989), which is incorporated by reference herein in its entirety. See also Gordon, "Transgenic Animals," Intl. Rev. Cytol. 115: 171-229 (1989); U.S. Pat. No. 5,464,764 (Capecchi, et al., Positive-Negative Selection Methods and Vectors); U.S. Pat. No. 5,631,153 (Capecchi, et al., Cells and Non-Human Organisms Containing Predetermined Genomic Modifications and Positive-Negative Selection Methods and Vectors for Making Same); U.S. Pat. No. 4,736,866 (Leder, et al., Transgenic Non-Human Animals); and U.S. Pat. No. 4,873,191 (Wagner, et al., Genetic Transformation of Zygotes). As stated, any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64-66 (1996); Wilmut et al., Nature 385:810-813 (1997)).

In one embodiment of the invention, a transgenic canine (e.g., dog), hamster, rabbit, cynomolgus monkey or rhesus monkey is a "knock-out" animal having a heterozygous or homozygous alteration in the sequence of an endogenous NPC1L1 gene that results in a decrease of NPC1L1 function, e.g., such that NPC1L1 expression is undetectable or insignificant. Knock-out animals are typically generated by homologous recombination with a vector comprising a transgene having at least a portion of the gene to be knocked out. A deletion, addition or substitution can be introduced into the transgene to functionally disrupt it. Detailed methodologies for homologous recombination in transgenic animals are available (see Capecchi, Science (1989) 244:1288-1292; Joyner et al., Nature (1989) 338:153-156). Other procedures for the production of transgenic animals are also available (Pursel et al., Science (1989) 244:1281-1288; Simms et al., Bio/Technology (1988) 6:179-183).

A transgenic founder animal can be identified based upon the presence of the transgene in its genome and/or expression of transgenic mRNA in tissues or cells of the animals. For example, once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product. A transgenic founder animal can then be used to breed additional animals carrying the transgene. Moreover, transgenic animals carrying a transgene can further be bred to other transgenic animals carrying other transgenes.

Any cell, tissue, gamete, organ, fluid, nucleic acid, peptide or other biological substance derived or isolated from a transgenic animal of the invention is within the scope of the present invention as is any offspring of such an animal (e.g., any offspring inheriting the transgene).

EXAMPLES

The invention is further illustrated by the following non-limiting example.

Example 1

Binding and Inhibition of NPC1L1 Orthologues by Ezetimibe and Related Compounds

This example demonstrates that the NPC1L1 genes set forth herein bind to ezetimibe and structurally related compounds.

Materials and Methods

Materials. The [$^3$H]-ezetimibe glucuronide (EZE-gluc) [1-([2, 6-3H]-4-fluorophenyl)-(3R)-[3-(4-fluorophenyl)-(3S)-hydroxypropyl]-(4S)-[3,5-$^3$H]-4-hydroxyphenyl)-2-azetidinone; 34.5 Ci/mmol (Garcia-Calvo et al., Proc. Natl. Acad. Sci. U.S.A. 102:8132-8137 (2005)) and several 2-azetidinone based compounds.

cDNA cloning. Cloning and sequencing of NPC1L1 from human (Genbank AY437865), rat (Genbank AY437867) and mouse (Genbank AY437865) have been reported (Altmann et al., Science 303:1201-1204 (2004) and U.S. published patent application nos. US2004/0093629; US 2004/0137467; US 2004/0132058 and US 2004/0161838). Jejunal enterocytes were isolated as previously described (Altmann et al., Biochim. Biophys. Acta 1580:77-93 (2002)) from freshly isolated tissue samples from rhesus monkey, cynomolgus monkey, hamster, rabbit and beagle dog. Isolated enterocytes were immediately extracted with Tri-reagent and the total RNA isolated following manufacturer's instructions (Molecular Research Center Inc.; Cincinnati, Ohio). Messenger RNA was isolated using FastTrack 2.0 (Invitrogen; Carlsbad, Calif.) and cDNA prepared using superscript Choice System (Life Technologies; Gaithersburg, Md.) following oligo-(dT) primed first strand synthesis. NPC1L1 specific oligo primers corresponding to highly conserved regions in the human, mouse and rat were used in varied combinations to polymerase chain reaction (PCR) amplify each cDNA sample. PCR products were sequenced to determine species specific NPC1L1 sequence. To obtain species-specific gene sequences from the 5'-start codon region and the 3'-stop codon region, 5'- and 3' RACE PCR were performed using Marathon-Ready cDNA Amplification Kit, or Smart RACE cDNA Amplification Kit according to the manufacturer's instructions (BD Biosciences Clontech; Mountain View, Calif.). The species-specific oligonucleotide primers for 5' and 3' RACE PCR were designed according to available species-specific NPC1L1 gene sequences. In some cases, oligo primers based upon consensus gene sequences among species were also used in the 5' and 3'-RACE PCR reaction. Sequence analysis of RACE PCR products identified coding sequence for the start and stop of the protein open reading frame. Preparation of the final NPC1L1 cDNA was carried out by PCR amplification of the complete ORF using species specific forward and reverse primers encompassing the start and stop codons respectively:

Rabbit NPC1L1:
    5'-end sequence was obtained by 5'-RACE PCR with primer set of S1352 (TAGGCCCGCTCGGCGAAGCT-GCGCTCG) (SEQ ID NO: 11) and primer #98 (AGCTAGCTTGCCAAACCTACAGGT) (SEQ ID NO: 12).

3'-end sequence was obtained by 3'-RACE PCR with primer set of S1299 (CATGTCTGTGGAGTTYGT-GTCCCACAT) (SEQ ID NO: 13) and primer #98 (AGCTAGC TTGCCAAACCTACAGGT) (SEQ ID NO: 12).

The complete ORF sequence was obtained by PCR with primer set of S1368 (ATGGCAGGGGCT-GCGCGGGGCTGGCTG) (SEQ ID NO: 14) and S1317 (TCAGAACTTC TGCTTTCTGGTGGG) (SEQ ID NO: 15)

Rhesus Monkey NPC1L1
    5'-end sequence was obtained by 5'-RACE PCR with primer S1320R (TARAAGGCCTCATAGGCCAC-CAC) (SEQ ID NO: 16).

3'-end sequence was obtained by 3'-RACE PCR with primer set of S1299 (CATGTCTGTGGAGTTYGT-GTCCCACAT) (SEQ ID NO: 13) and primer #98 (AGCTAGC TTGCCAAACCTACAGGT) (SEQ ID NO: 12).

The complete ORF sequence was obtained by PCR with primer set of monkey 5' primer (ATGGCGGAGGCCG-GCCTGAGGGGCTGGCTG) (SEQ ID NO: 17) and Monkey 3' primer (TCAGAA CTGCCGCCCATTGT-TGGGCAAGAA) (SEQ ID NO: 18)

Hamster NPC1L1
    5'-end sequence was obtained by 5'-RACE PCR with 5' hamster GSP2 primer (TGACATTGATGAAGAG-GCTCTGGTCAGG) (SEQ ID NO: 19).

3'-end sequence was obtained by 3'-RACE PCR with 5' hamster GSP2 primer (TCAGGCATCCTCAACCT-GCTCTCCATCAT) (SEQ ID NO: 20).

The complete ORF sequence was obtained by PCR with primer set of hamster 5' primer (ATGGCAGCTGGC-CTAACGAGATGGCTG) (SEQ ID NO: 21) and hamster 3' primer (TTAAAACTT TTGGCCGCTTTTAG-GCAAG) (SEQ ID NO: 22)

Canine NPC1L1
    The complete ORF sequence was obtained by PCR with primer set of S1406 (ATGGCGGACACTGGC-CAGGGGCT) (SEQ ID NO: 23) and S1414 (TCAGAG-GTCCGGT CCACTGCGGGG) (SEQ ID NO: 24)

Cynomologus Monkey NPC1L1
    The complete ORF sequence was obtained by PCR with primer set of monkey 5' primer (ATGGCGGAGGCCG-GCCTGAGGGGCTGGCTG) (SEQ ID NO: 17) and Monkey 3' primer (TCAGAACTGCCGCCCATTGT-TGGGCAAGAA) (SEQ ID NO: 18)

Sequencing of multiple clones from independent PCR reactions resulted in cDNA sequences free from nucleotide errors introduced by Taq polymerase.

Cell Culture and Membrane Preparation. Each plasmid pCR3.1 harboring NPC1L1 was prepared using standard molecular biology protocols. Stable cell lines expressing human, rhesus monkey, mouse, rat, hamster, canine or rabbit NPC1L1 were generated using Lipofectamine 2000 transfection reagent in HEK-293 cells according to the manufacturer's protocol. Cells were maintained in DMEM supplemented with 10% FBS, 100 U/ml pen/strep, and 500 µg/ml geneticin at 37° C., 5% $CO_2$. All cell culture reagents were obtained from Invitrogen Life Technologies, (Carlsbad, Calif.). Cell membranes were prepared by lysing cells in 5 mM HEPES with protease inhibitors (Complete™ Protease Inhibitor Cocktail Tablets; Roche Diagnostics Corp., Indianapolis Ind.) for 15 min at 4° C. A membrane pellet was obtained by centrifuging the cell lysates at 12,000×g for 25 min. The membranes were resuspended in 5 mM HEPES with protease inhibitors and triturated with a 21 G needle.

NPC1L1 Binding Assays

Fluorescence. Cells were plated into 384-well black/clear plates (BD Biosciences, Bedford Mass.) for binding experiments the following day. The media was aspirated. Media (20 µl) containing 250 nM BODIPY-labeled glucuronidated ezetimibe (compound 1; Burnett et al., Bioorganic and Medicinal Chemistry Letters 12:315-318 (2002)) was added to each well. Media (20 µl) containing the indicated concentration of compound was then added to the wells. Unlabeled glucuronidated ezetimibe (compound 4; 100 µM) was used to determine nonspecific binding. The binding reaction was allowed to proceed for 4 hours at 37° C. Subsequently the media was aspirated and the cells washed once with PBS. The remaining BODIPY-labeled glucuronidated ezetimibe (compound 1) bound to the cells was quantified using a FlexStation plate reader (Molecular Devices, Sunnyvale Calif.).

Radioligand. Binding of [$^3$H]-glucuronidated ezetimibe (compound 4) to membranes from cells expressing NPC1L1 was measured using filtration (Garcia-Calvo et al., Proc. Natl. Acad. Sci. U.S.A. 102:8132-8137 (2005)). Reactions were performed in binding buffer (5 mM HEPES, 5.5 mM glucose, 117 mM NaCl and 5.4 mM KCl, pH 7.4). Cell membranes (50 µg in 20 µl) were added to each well. Subsequently, [$^3$H]-glucuronidated ezetimibe (compound 4; 20 nM; 20 µl) was added to each well. Compounds (20 µl) were then added to the wells as indicated in the figure legends. Nonspecific binding was determined by including unlabeled glucuronidated ezetimibe (compound 4; 100 µM) in the binding reaction. Binding reactions were incubated for 2 hours at 37° C. Samples were transferred to Unifilter-96 GF/C plates (Perkin Elmer, Wellesley Mass.) and filtered using a Brandel harvester (Gaithersburg Md.). The plates were washed several times with cold wash buffer (120 mM NaCl, 0.1% Sodium Cholate, 20 mM MES pH 6.7) and dried. Liquid scintillant (50 µl; Microscint-20, Perkin Elmer, Wellesley Mass.) was added and the bound radioactivity was measured using a microplate scintillation counter.

Acute cholesterol absorption assay. $^{14}$C-cholesterol absorption was determined acutely in rats using conditions previously described (Van Heek et al., J. Pharmacol. Exp. Ther. 283: 157-163 (1997)). Compounds were dissolved in rat bile and delivered (1.0 ml) intraduodenally by bolus injection via an intestinal catheter, followed by 1.0 ml saline rinse (0.9%). Following a 30 min incubation, a cholesterol emulsion containing 3 mg cholesterol and 2 µCi $^{14}$C-cholesterol (3 ml) was delivered to each rat as a bolus via intestinal catheter, followed by 1 ml saline rinse. Animals were sacrificed 90 min later and $^{14}$C-cholesterol levels in plasma, liver, intestinal contents, and intestinal wall were determined.

Results

Figure 2:
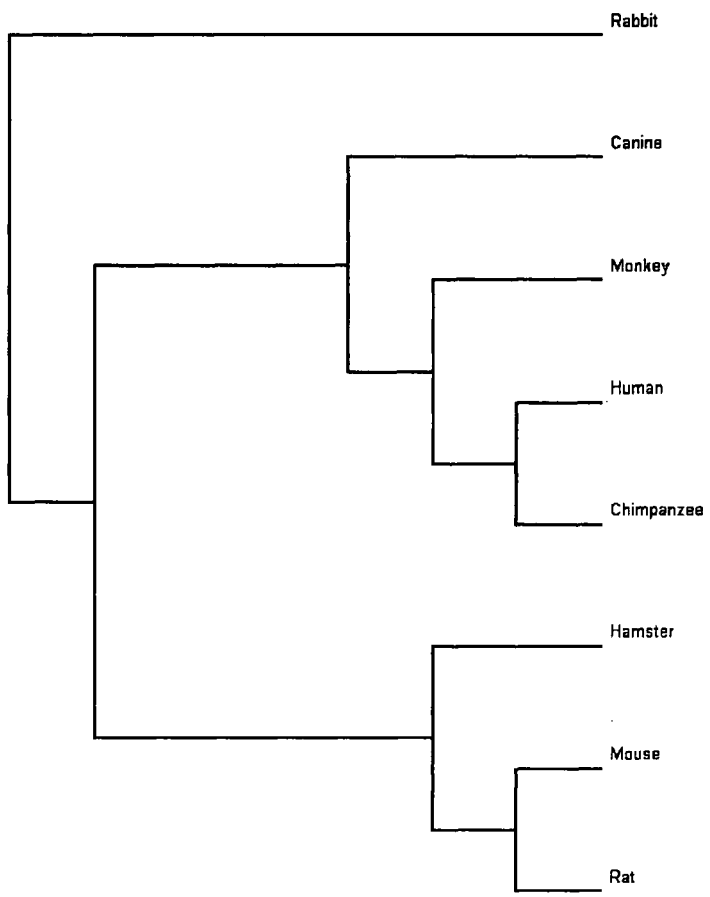
FIG. 2. Progressive multiple amino acid sequence alignment using the Clustal W method (Thompson et al., Nucleic Acid Research 22; 4673-80 (1994)). (A) NPC1L1 amino acid sequence pair distances between species comparing percent identity and percent divergence. (B) Phylogenetic tree representation of amino acid sequence alignment using Treeview (Page, 1996).
Figure 7:
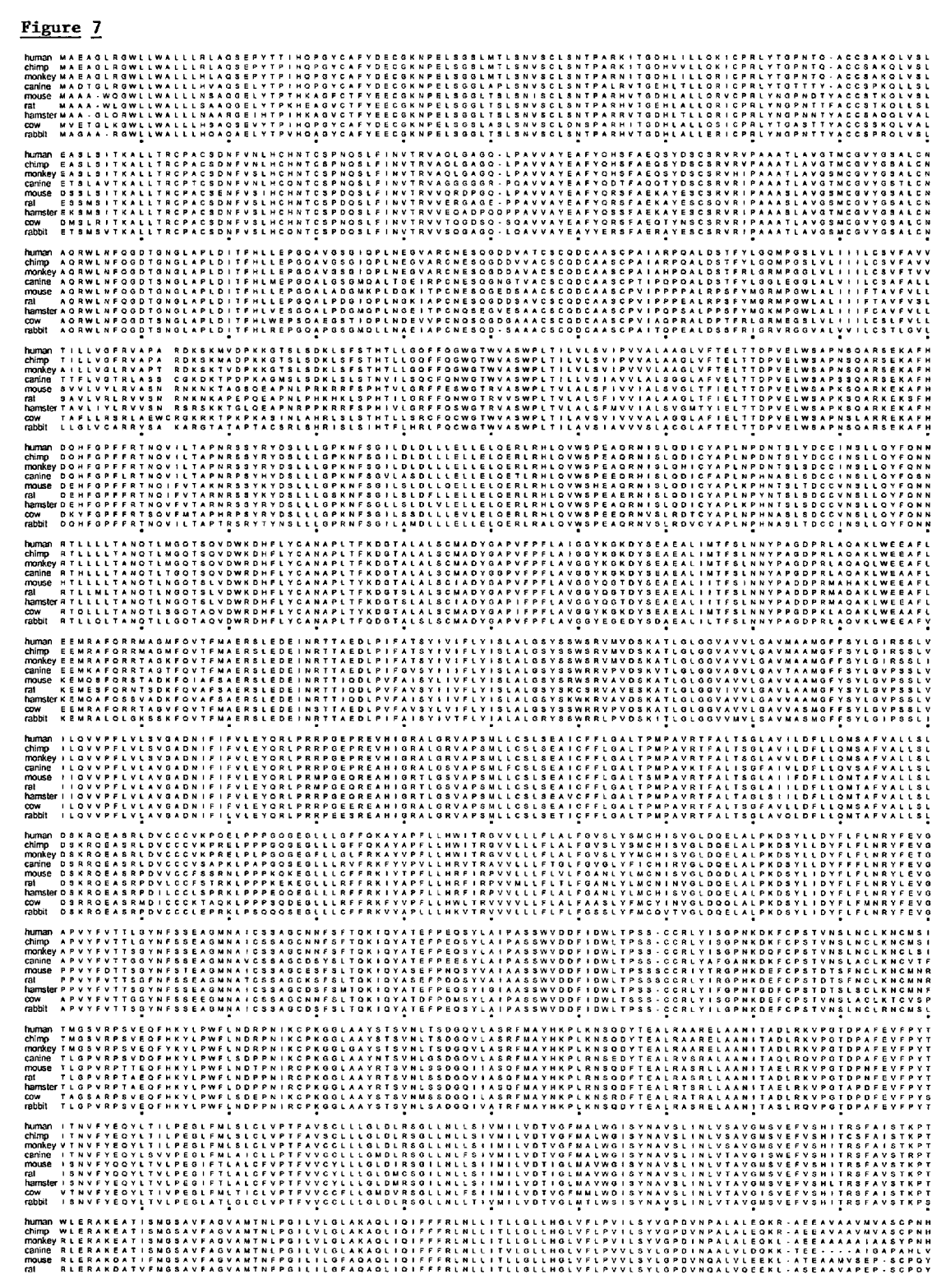

The effective dose of ezetimibe that inhibits cholesterol absorption varies among several species that have been studied. Since NPC1L1 has been identified as the direct proximal target of ezetimibe, we cloned NPC1L1 from jejunal enterocytes of rhesus and cynomolgus monkey, canine, hamster, and rabbit (see SEQ ID NOs: 1-10). Comparison of the amino acid sequences of NPC1L1 in those species along with previously published amino acid sequences of human, rat, and mouse NPC1L1 (Altmann et al., Science 303:1201-1204 (2004)) and predicted sequences from chimpanzee (Genbank XM_519072) and cow (Genbank XM_588051) are shown in FIG. 7. At the sequence level, the positions of the Cys residues, of which there are ~40, are highly conserved across all species and suggestive of a highly constrained structure. Several Cys residues are located within predicted transmembrane helices 1, 6 and 9 with the potential of fixing these transmembrane helices in close proximity. The proposed protein topology defined by the predicted transmembrane helices is consistent with the location of the putative N-linked glycosylation sites which reside in three large extracellular loops exposed to the intestinal lumen. FIG. 1 presents a ball model of the predicted membrane topology of human NPC1L1 (Iyer et al., Biochim. Biophys. Acta 1722:382-392 (2005)). Residues in black constitute the sterol sensing domain (SSD) (Carstea et al., Science 277:228-231 (1997)) and residues shaded gray identify non-conserved positions between human and monkey NPC1L1. NPC1L1 is most highly conserved among the primates with human, chimpanzee and monkey exhibiting >95% amino acid identity (FIG. 2A). Nucleotide sequences in rhesus and cynomolgus monkey coding regions show only 9 substitutions, none of which result in amino acid differences (data not shown). Human and monkey NPC1L1 amino acid sequences are highly homologous being less than 5% divergent. Of the 53 amino acid substitutions in monkey, 28 reside in the extracellular domain and 17 are located within the cytoplasmic domains. The remaining 8 changes occur in the transmembrane domains, 2 of which are located in the SSD.

The rodent family, consisting of sequences from hamster, rat, and mouse, also exhibit strong homology to each other with close to 90% identity in amino acid sequences. Primates and rodents share only 77-78% amino acid sequence identity with each other. The homology of canine NPC1L1 compared to the other species is relatively low (74-81%) as is cow (75-81%). Rabbit NPC1L1 also exhibits relatively low homology to the other species examined (75-79%) but is most closely associated with rodents. A phylogenetic tree representing the homology of NPC1L1 in the various species is shown in FIG. 2B. As expected, canine and cow NPC1L1 are more divergent compared to both primate and rodent families.

Figure 3:
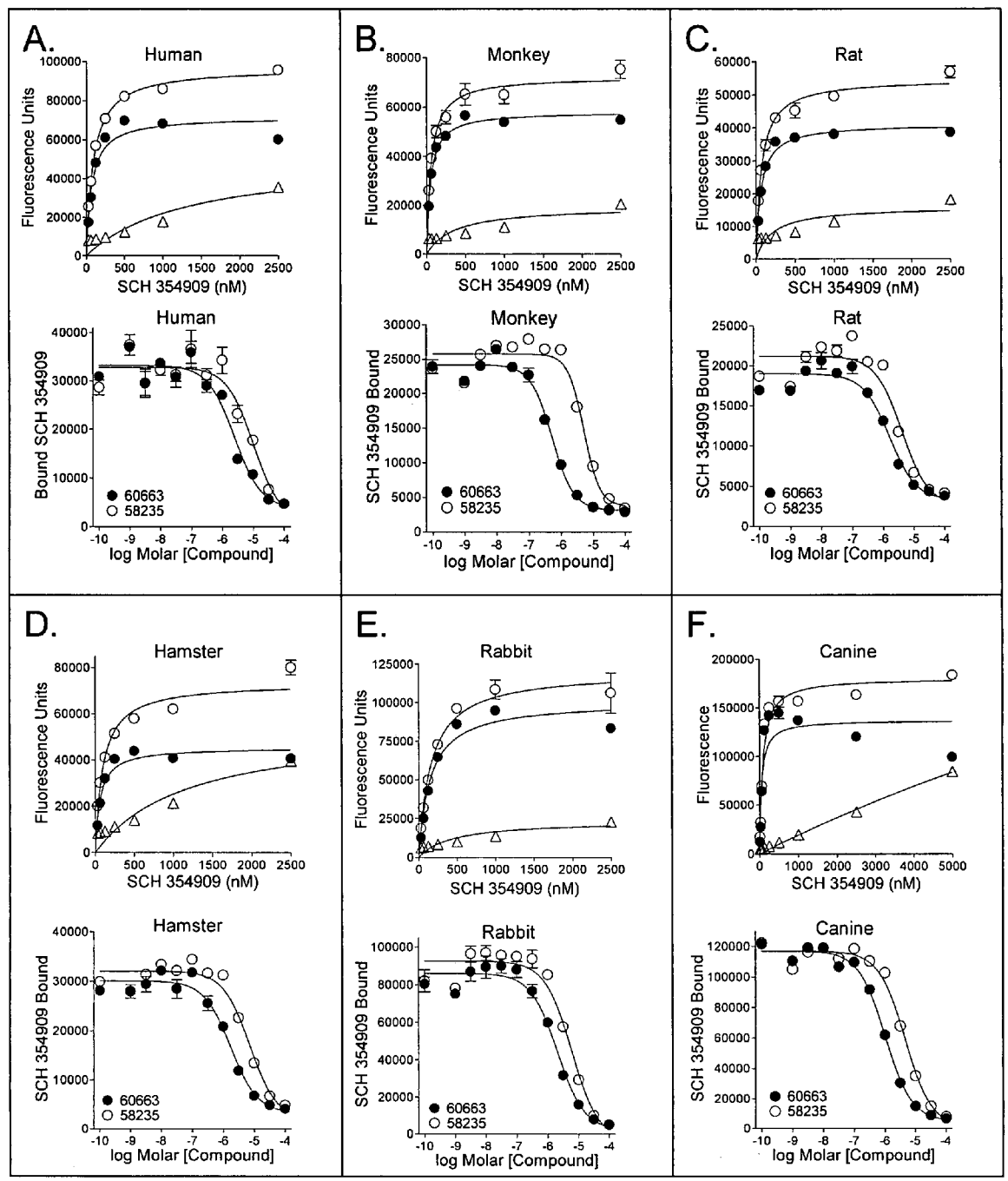
FIG. 3. Characterization of NPC1L1 binding in multiple species. HEK 293 cells expressing human (A), monkey (B), rat (C), hamster (D), rabbit (E), or canine (F) NPC1L1 were exposed to the indicated concentration of compound 1 for 4 h. The amount of fluorescence bound to the cells was quantified as total binding (open circles). Addition of 100 uM compound 4 was used to determine nonspecific binding (open triangles). Specific binding (filled circles) was determined by subtraction of nonspecific from total binding. The Kd values were calculated using Prism software and are the mean of at least three separate experiments. Competition binding of compound 3 and compound 4 to NPC1L1 is also shown. Binding of compound 1 to HEK 293 cells expressing each species NPC1L1 in the presence of the indicated concentration of compound 3 (open circles) or compound 4 (filled circles) was determined. Ki values were calculated using Prism software and are the mean of at least three separate experiments.

Binding characteristics of ezetimibe (compound 3) and its glucuronidated metabolite (compound 4) to the NPC1L1 orthologs of several species were examined herein. Stable HEK-293 cell lines expressing human, rhesus monkey, canine, rat, mouse, hamster, rabbit, or mouse NPC1L1 cDNA were derived and used in subsequent experiments. The saturation binding curves of a fluorescently-labeled (BODIPY) ezetimibe glucuronide (compound 1) to each species NPC1L1 ortholog (except mouse) are shown in FIG. 3. The calculated Kd values were: monkey 46 nM; hamster 49 nM, canine 52 nM; rat 58 nM; human 61 nM, rabbit 151 nM. Fluorescently-labeled (BODIPY) ezetimibe glucuronide (compound 1) binding to mouse NPC1L1 could not be detected despite demonstrable expression of mouse NPC1L1 in HEK-293 cells by western blot analysis (data not shown).

In an effort to show binding to mouse NPC1L1, several related ezetimibe analogs were examined as possible alternatives to fluorescently-labeled (BODIPY) ezetimibe glucuronide (compound 1) in the binding assay. Compound 2, which is a fluorescently labeled synthetic precursor for fluorescently-labeled (BODIPY) ezetimibe glucuronide (compound 1; Burnett et al., Bioorganic and Medicinal Chemistry Letters 12:315-318 (2002)), was identified as a viable option for detection of mouse NPC1L1 binding. Compound 2 contains a methyl ester substitution for the carboxylic acid on the glucuronide portion of the molecule (compound structures shown in FIG. 4A). Saturation binding analysis with compound 2 (FIG. 4B) demonstrated binding to mouse NPC1L1 with a Kd of 118 nM.

Figure 4:
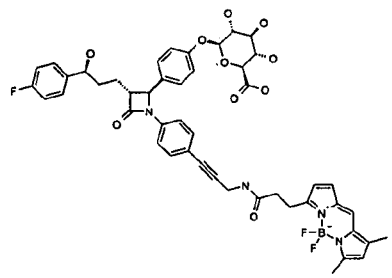
FIG. 4. Comparison of binding characteristics of compound 1 and compound 2. (A) Structure of compound 1 and compound 2. Saturation binding of [$^3$H]-labeled compound 4 to membranes derived from HEK 293 cells expressing human NPC1L1 (B) or mouse NPC1L1 (C). [$^3$H]compound 4 bound was determined in the absence (total, filled circles) or presence (nonspecific, open circles) of 100 μM unlabeled compound 4. Specific binding (filled triangles) was determined by subtracting nonspecific from total binding. Kd values were determined using Prism software. The Ki of compound 1 and compound 2 at human NPC1L1 (D) and monkey NPC1L1 (E) was determined by competition binding studies using [$^3$H]-labeled compound 4. Studies were performed on membranes from HEK 293 cells expressing human or monkey NPC1L1. Ki values are the mean from at least three separate experiments.
Figure 4:
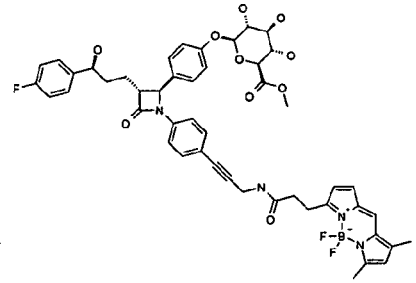
Figure 4:
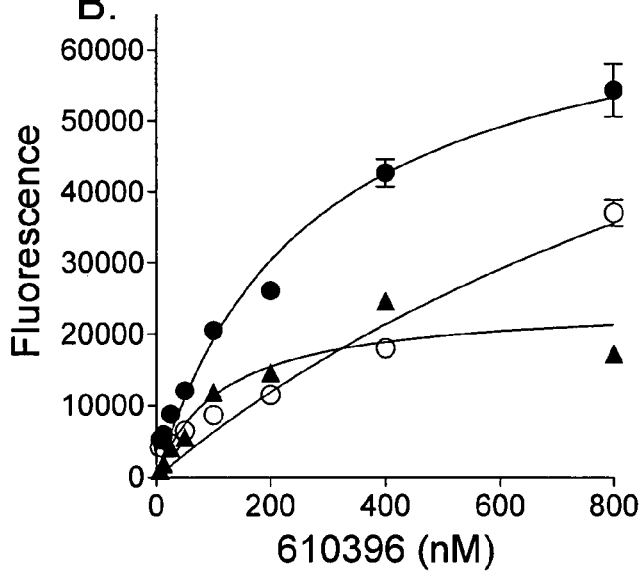
Figure 4:
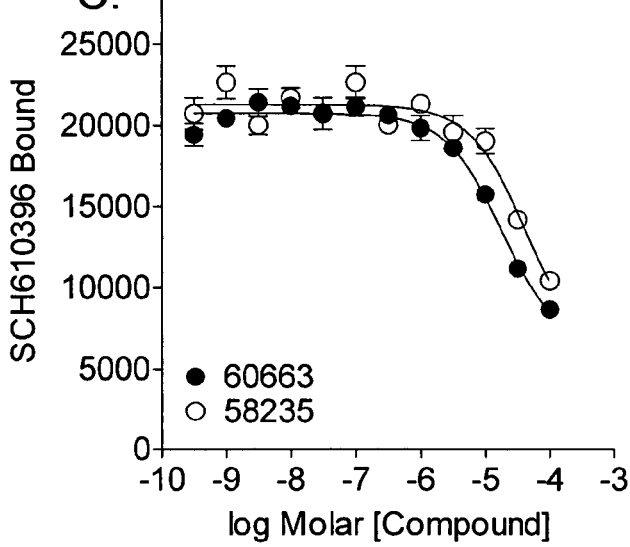
Figure 5:
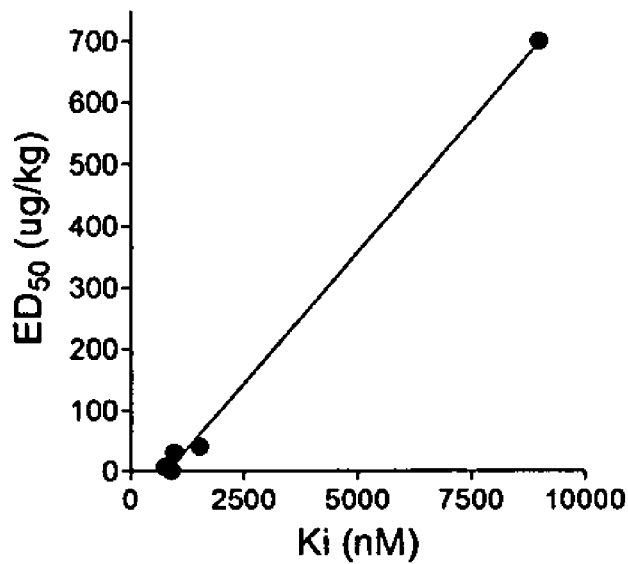
FIG. 5. Correlation of NPC1L1 binding and in vivo efficacy. Data (ED50) from studies assessing in vivo efficacy of compound 3 in human, monkey, hamster, canine, rat, rabbit, and mouse species is plotted as a function of the ability of compound 3 (A) or compound 4 (B) to bind to each species NPC1L1 ortholog.
Figure 5:
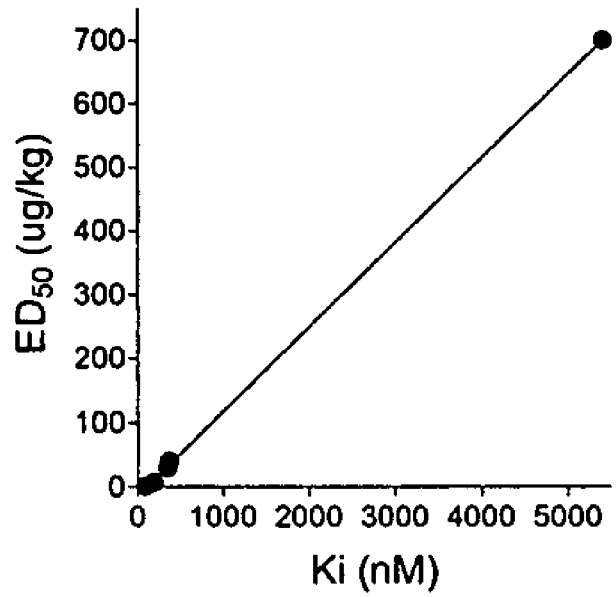

Binding affinities at each species NPC1L1 ortholog were determined for both ezetimibe (compound 3) and compound 4 (FIGS. 3 and 4C). The calculated Ki values are listed in Table 2 (columns 1 and 2) and are compared with in vivo ED50 values derived for each species tested (column 3). Divergence in the affinities of ezetimibe (compound 3) and compound 4 for NPC1L1 is consistently observed across species. For all species tested, the affinity of compound 4 for NPC1L1 is greater than that of ezetimibe (compound 3) (compare column 1 versus column 2). Against monkey NPC1L1, the difference in affinity of these two compounds is most obvious at nearly 10-fold, whereas the difference in affinity is less than 3-fold against rabbit or mouse NPC1L1. Rank order species affinity for ezetimibe (compound 3) is (monkey, dog, rat)>hamster>(human and rabbit)>>mouse. The rank order species affinity for compound 4 is slightly modified with monkey>dog>(rat and hamster)>(human and rabbit)>>mouse. By comparison, the rank order of in vivo potency of ezetimibe among species is monkey>dog>(rat and hamster)>>mouse. It should be noted that following oral administration, 90% of ezetimibe is glucuronidated thereby converting ezetimibe (compound 3) to compound 4. Therefore, the predominant form of ezetimibe present at the site of action in vivo (NPC1L1 in the jejunum) is the glucuronide compound 4. FIG. 5 shows the correlation between compound 4 or ezetimibe (compound 3) affinity and in vivo potency across multiple species. The results indicate that stronger binding to NPC1L1 by the compound produces more profound cholesterol lowering activity in vivo.

TABLE 2

Binding affinities of NPC1L1 orthologues for ezetimibe or compound 4.

|  | ezetimibe Ki (nM) | cpd. 4 Ki (nM) | ezetimibe ED50 (ug/kg) |
|---|---|---|---|
| Human | 2240 | 660 | ND |
| Monkey | 900 | 92 | 0.5 |
| Hamster | 1530 | 370 | 40 |

TABLE 2-continued

Binding affinities of NPC1L1 orthologues for ezetimibe or compound 4.

|  | ezetimibe Ki (nM) | cpd. 4 Ki (nM) | ezetimibe ED50 (ug/kg) |
|---|---|---|---|
| Canine | 770 | 192 | 7 |
| Rat | 970 | 352 | 30 |
| Rabbit | 2125 | 830 | ND |
| Mouse | 5400 | 9000 | 700 |

Expanding the study to several other ezetimibe analogs confirms the observation that NPC1L1 binding correlates with in vivo cholesterol lowering activity. Ezetimibe analogs exhibiting in vivo cholesterol lowering activity (compound 5, compound 6 and compound 7) as well as analogs displaying no in vivo cholesterol lowering activity (compound 8 and compound 9) were evaluated for binding to NPC1L1 orthologs of multiple species. The compound structures and the Ki values at each species NPC1L1 are listed in Table 3. The in vivo data measuring inhibition of cholesterol absorption in rat ($ED_{50}$) and percent cholesterol lowering in plasma and liver in hamster are also provided for comparison in Table 3. The three active compounds exhibit variable affinity when evaluated against each species of NPC1L1 with the rank order of affinity among species similar to that of ezetimibe (compound 3) and compound 4. Higher affinity is observed at monkey, dog, and rat NPC1L1 and lower affinity at human and rabbit NPC1L1 with affinity for hamster NPC1L1 somewhat intermediate. In comparison, the affinities of the compounds are markedly lower at mouse NPC1L1. Compounds that lack in vivo efficacy exhibit no detectable binding to NPC1L1 orthologs from any of the species tested. These data demonstrate that compound binding to NPC1L1 translates into in vivo activity. Prediction of the extent of in vivo potency is confounded by metabolic parameters following oral administration. Glucuronidation of ezetimibe (compound 3) produces a metabolite (compound 4) with higher affinity for NPC1L1. Similar metabolism may affect related compounds. The ability to generate metabolites with high affinity for NPC1L1 will affect overall in vivo responsiveness. A determinant of in vivo efficacy is the ability of the predominant compound metabolite to bind to NPC1L1. Minor changes in compound structure or NPC1L1 amino acid sequence can affect binding affinity and consequently in vivo efficacy.

TABLE 3

Inhibition of NPC1L1 orthologues with ezetimibe and related compounds.

| Compound | Human | Monkey | Mouse | Hamster | Rat | Dog |
|---|---|---|---|---|---|---|
| compound 3 | 2.24 | 0.9 | 9 | 1.53 | 0.97 | 0.77 |

TABLE 3-continued
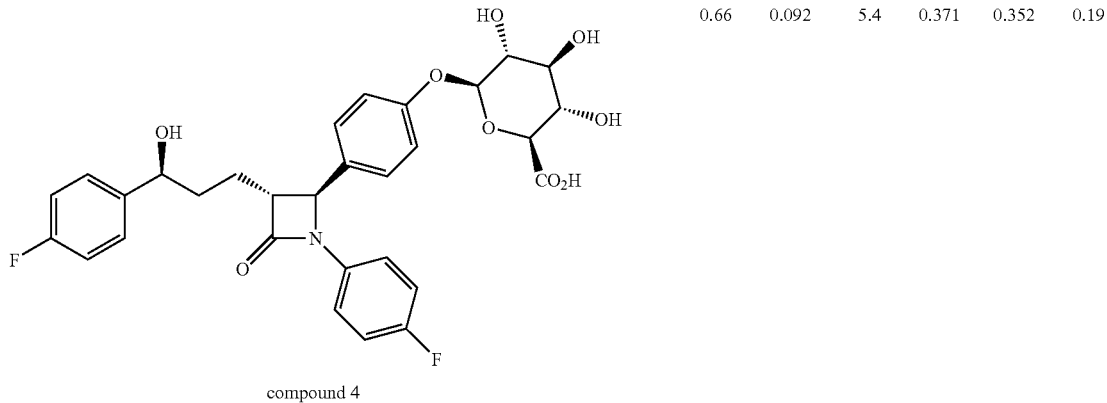
compound 4
0.66  0.092  5.4  0.371  0.352  0.19
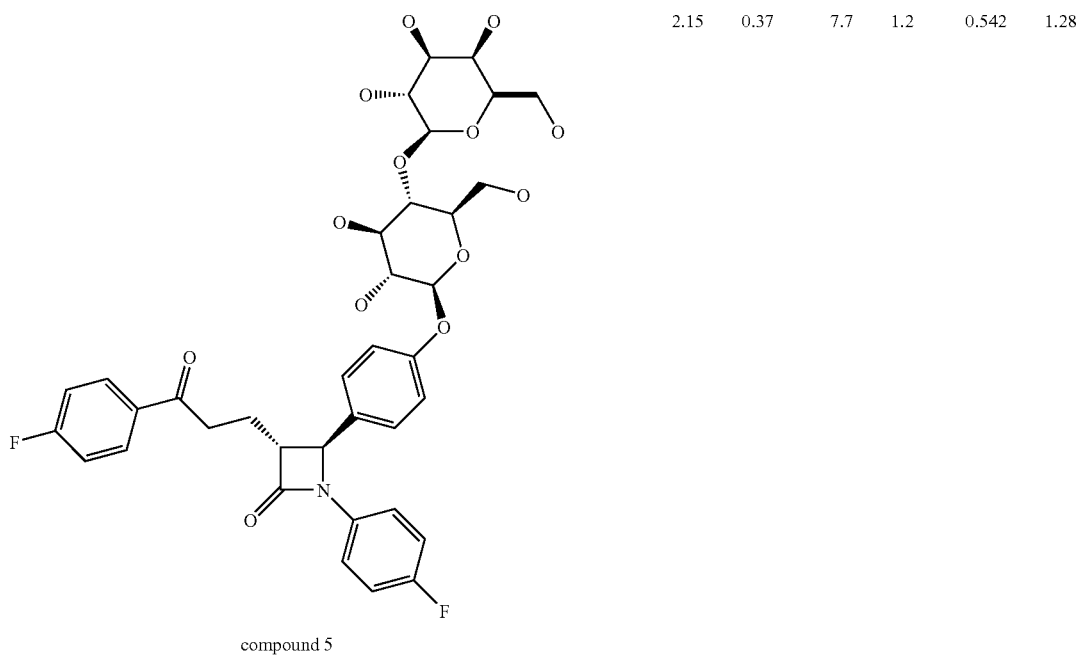
compound 5
2.15  0.37  7.7  1.2  0.542  1.28
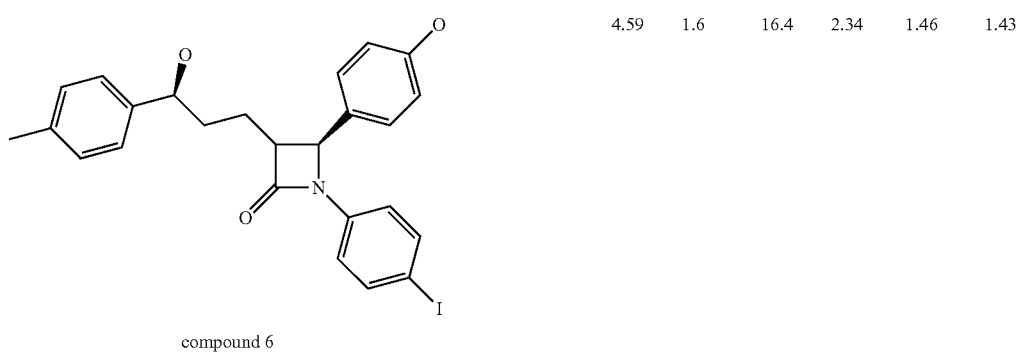
compound 6
4.59  1.6  16.4  2.34  1.46  1.43

TABLE 3-continued
| Compound | | | | | | |
|---|---|---|---|---|---|---|
| 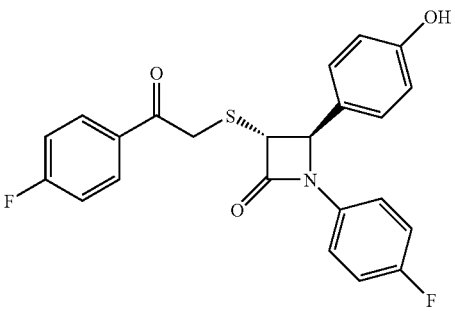compound 7 | 3.23 | 3.23 | 21.6 | 4.28 | 2.1 | 2.3 |
| 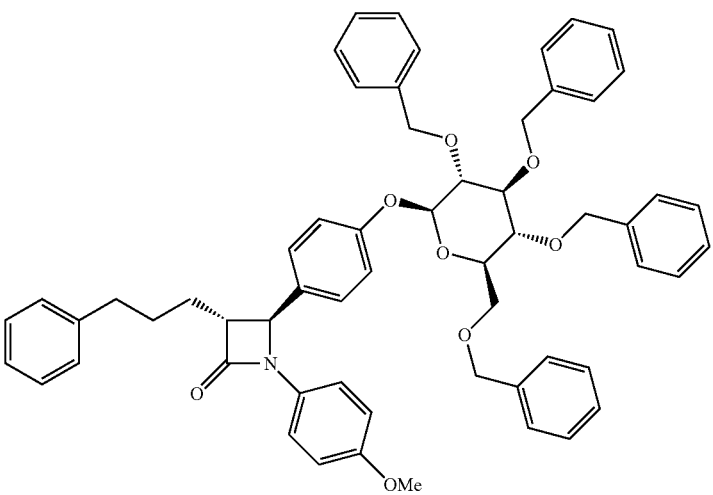compound 8 | Inactive | Inactive | Inactive | Inactive | Inactive | Inactive |
| 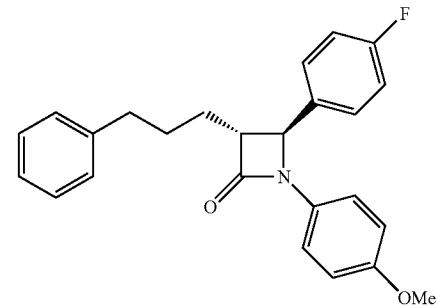compound 9 | Inactive | Inactive | Inactive | Inactive | Inactive | Inactive |
| Compound | Rabbit | rat ED50 | Liver | Plasma |
|---|---|---|---|---|
| 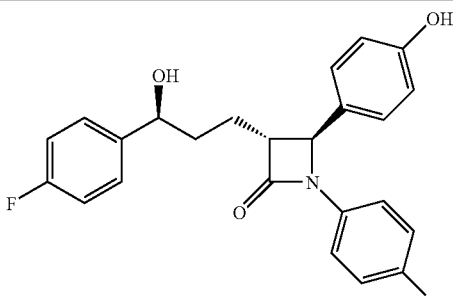compound 3 | 2.1 | 1.6 | 96 | 26 |

TABLE 3-continued
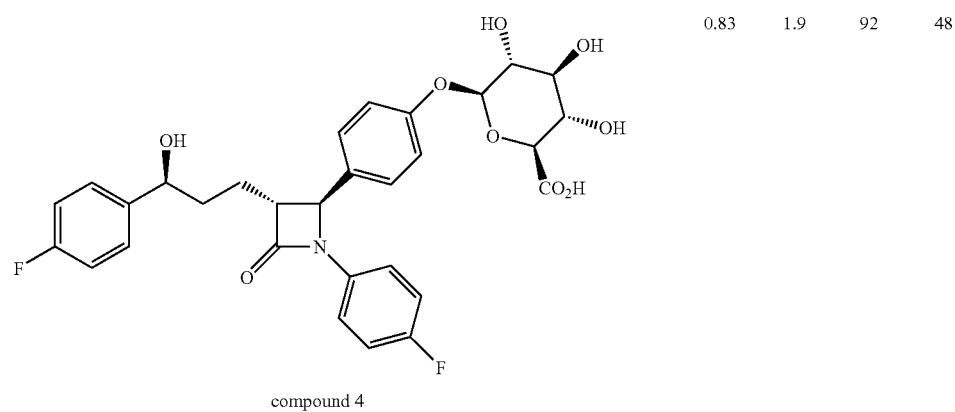
compound 4
0.83　1.9　92　48
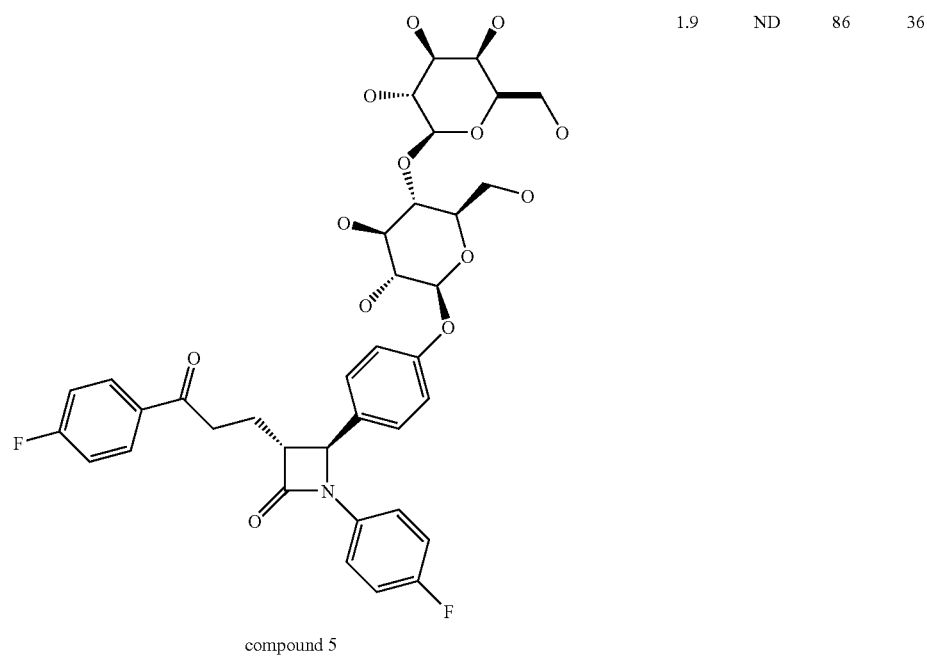
compound 5
1.9　ND　86　36
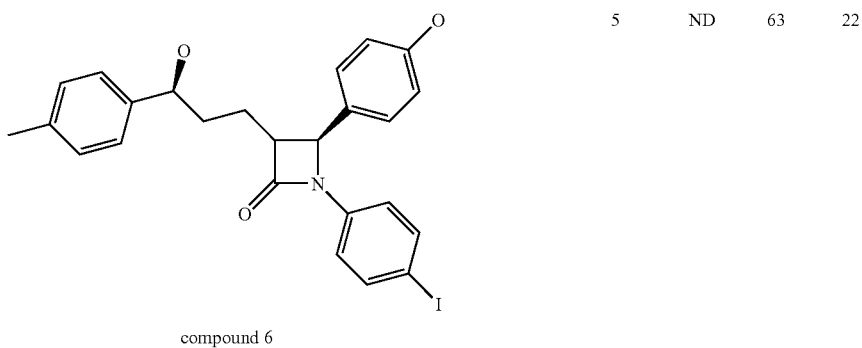
compound 6
5　ND　63　22

TABLE 3-continued

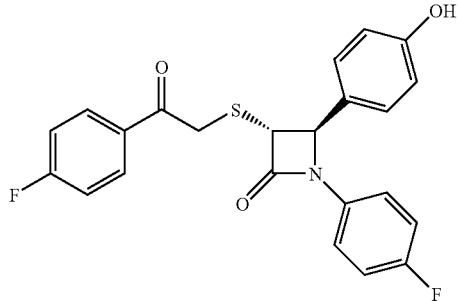

compound 7    5.6   36   96   47

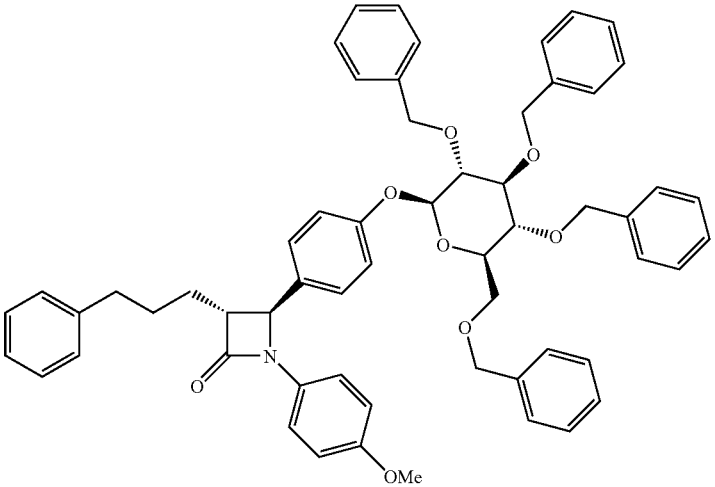

compound 8    Inactive   Inactive   ND   ND

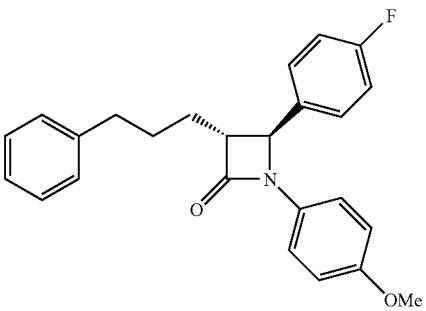

compound 9    Inactive   Inactive   Inactive   Inactive

ND = experiment not done

An example of the effects of small modifications on the binding affinity of related compounds for NPC1L1 is provided by comparison of the binding characteristics of compound 2 and compound 1 (fluorescently labeled (BODIPY) ezetimibe). The Kd of [$^3$H]-labeled compound 4 was determined for both human and monkey NPC1L1 in saturation binding assays (FIGS. 6A & 6B). A Kd of 206 nM for human and 102 nM for monkey are consistent with previously reported values of 220 nM and 41 nM respectively (Garcia-Calvo et al., Proc. Natl. Acad. Sci. U.S.A. 102:8132-8137 (2005)). Competition binding studies using [$^3$H]-labeled compound 4 were performed to derive Ki values for compound 1 (fluorescently labeled (BODIPY) ezetimibe) and compound 2 at both human NPC1L1 (FIG. 6C) and monkey NPC1L1 (FIG. 6D). The Ki of compound 1 (fluorescently labeled (BODIPY) ezetimibe) at human NPC1L1 is calculated to be 2.5 µM and 210 nM at monkey NPC1L1. By comparison, the Ki of compound 2 is calculated to be 120 nM and 70 nM at human and monkey NPC1L1 respectively. The results demonstrate that the small modification of substituting the methyl ester for the carboxylic acid on the glucuronide dramatically increases the affinity for human NPC1L1 (over 20-fold). In comparison, the compound modification increased affinity for monkey NPC1L1 by 3-fold. This illustrates that small variations in ezetimibe related compounds can result in markedly diverse binding interactions. Likewise, diversity in NPC1L1 may also affect the binding interaction. Although human and monkey NPC1L1 share 95% homology, the binding affinity of specific compounds varies markedly between the two species orthologs. Given the data demonstrating the correlation between NPC1L1 binding affinity and in vivo efficacy, the diversity in NPC1L1 among species may be a determinant regulating in vivo responsiveness.

Discussion

Recently, NPC1L1, an intestinally expressed protein critical to the absorption of sterols was identified as the molecular target of ezetimibe (Altmann et al., Science 303:1201-1204 (2004); Davis et al., J. Biol. Chem., 279:33586-33592 (2004), Garcia-Calvo et al., Proc. Natl. Acad. Sci. U.S.A. 102:8132-8137 (2005)). Discovery of the drug target enabled in vitro analysis of drug binding and experimental opportunities to explore the inter-species variability in ezetimibe potency and efficacy. Herein, we describe the cloning and expression of NPC1L1 in multiple species for studies comparing target interaction of ezetimibe (compound 3) and the active in vivo glucuronidated metabolite, compound 4. A novel fluorescent compound binding assay is utilized to assess the binding properties of several ezetimibe related compounds at the NPC1L1 orthologs of multiple species enabling structure activity relationships to be developed and the interaction of ezetimibe and NPC1L1 to be better understood.

Intraduodenal delivery of ezetimibe (compound 3) leads to significant levels of the compound detected in portal plasma of which >95% is the glucuronide compound 4 following first pass metabolism in the intestine. Traveling from portal plasma to the liver and back to the intestine via bile, compound 4 is redelivered to the site of action where it accumulates in the intestinal lumen (van Heek et al., Br. J. Pharmacol. 129:1748-1754 (2000)). Although both ezetimibe (compound 3) and compound 4 bind to NPC1L1, the binding affinity of compound 4 is greater than that of ezetimibe (compound 3) in all species examined consistent with the stronger potency of compound 4 observed in in vivo efficacy studies (van Heek et al., Br. J. Pharmacol. 129:1748-1754 (2000)). The compounds differ in affinity by as much as 10-fold in monkey and as little as 2-fold in mouse (Table 2), but the rank order of potency is similar for both compounds, (monkey, rat, dog, and hamster>human and rabbit>mouse) and correlates well with animal efficacy studies (Table 2). This indicates that compound potency is affected by the binding affinity of the compound for NPC1L1 of a particular species. However, the rate and efficiency of glucuronidation in each species also likely contribute to the diversity in species responsiveness to oral administration of ezetimibe given the binding differential between ezetimibe and compound 4. Indeed, compound metabolism may be a factor in determination of ezetimibe potency in species that exhibit the highest degree of separation between ezetimibe (compound 3) and compound 4 binding affinities and that are particularly responsive to ezetimibe therapy in vivo (e.g., monkey). Recently, the UDP-glucuronosyltransferase enzyme(s) responsible for glucuronidating ezetimibe (compound 3) in humans was identified (Ghosal et al., Drug. Metab. Dispos. 32: 314-320 (2004)), however little comparative information is available for this enzyme or related enzymes across multiple species.

Changes in compound structure affect NPC1L1 binding ability (Table 3). Glucuronidation of ezetimibe (compound 3) following oral administration (forming compound 4) enhances NPC1L1 binding and improves in vivo potency. By contrast, addition of a protective aromatic group to the glucuronide moiety (compound 5) causes the Ki value to revert to that observed for the nonglucuronidated form. It has previously been reported that hydroxylation of the 3-phenylpropyl side chain improves in vivo potency of this class of compounds (Burnett et al., Curr. Medicinal Chem. 11:1873-1887 (2004); Clader et al., J. Med Chem. 39:3684-3693 (1996)). Consistent with that conclusion, compounds that lack the hydroxyl group at the 3-phenylpropyl side chain exhibit decreased (compound 7) or total loss (compound 8, compound 9) of NPC1L1 binding activity.

Figure 6:
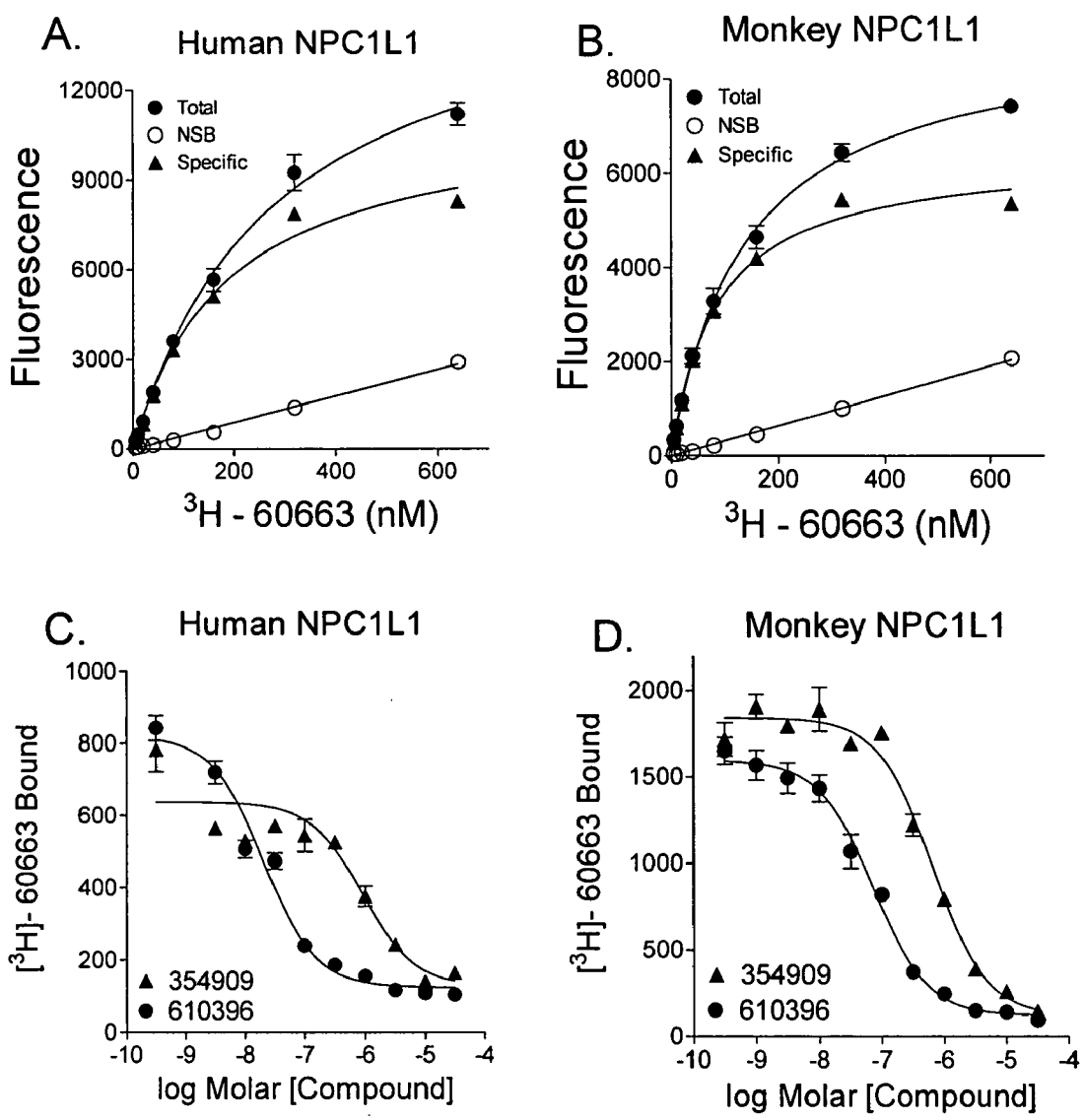
FIG. 6. Comparison of compound 1 and compound 2 binding to human and monkey NPC1L1. Saturation binding of [$^3$H]-labeled compound 4 to human (A) and monkey (B) NPC1L1 was performed to determine Kd values. The Ki values of compound 1 (triangles) and compound 2 (circles) at human (C) and monkey (D) NPC1L1 were then determined. Ki values were calculated using Prism software and are the mean of three separate experiments.

Diversity in compounds or NPC1L1 can affect NPC1L1 binding. In FIG. 6, binding of compound 1 and compound 2 to human and monkey NPC1L1 are compared. Compound 1 is BODIPY-labeled compound 4 and differs from compound 2 only by a substitution of a methyl ester for the carboxylic acid on the glucuronide moiety (FIG. 4A) (Burnett et al., Curr. Medicinal Chem. 11:1873-1887 (2004)). Consistent with other ezetimibe analogs, both compound 1 and compound 2 exhibit stronger affinity for monkey NPC1L1 compared to human NPC1L1. The substitution of the methyl ester on the glucuronide in compound 2 confers much higher affinity to both human and monkey NPC1L1. The methyl ester conveys a 20-fold increase in binding to human NPC1L1 and a 3-fold increase at monkey NPC1L1.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

We claim:

1. An isolated polypeptide comprising an amino acid sequence that is at least 97% identical to the amino acid sequence set forth in SEQ ID NO: 8 wherein said polypeptide binds to the compound having the structural formula

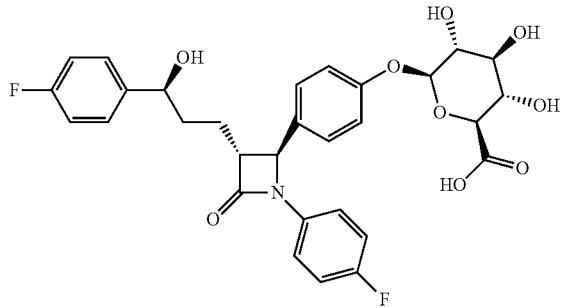

with a $K_i$ of 92 nM or lower.

2. The isolated polypeptide of claim 1 comprising the amino acid sequence set forth in SEQ ID NO: 8.

3. The polypeptide of claim 1 which is antigenic.

4. An isolated fusion polypeptide comprising the polypeptide of claim 1 which is radiolabeled or fused to a heterologous polypeptide.

5. The fusion polypeptide of claim 4 wherein:

(a) the heterologous polypeptide is a member selected from the group consisting of: glutathione-S-transferase, a hexahistidine tag, a green fluorescent protein tag, a maltose binding protein tag, a haemagglutinin tag, a cellulose binding protein tag and a myc tag; or (b) the radiolabel is a member selected from the group consisting of $^{32}P$, $^{35}S$, $^{3}H$, $^{14}C$, $^{123}I$, $^{111}In$, $^{68}Ga$, $^{18}F$, $^{125}I$, $^{131}I$, $^{113m}In$, $^{76}Br$, $^{67}Ga$ and $^{99m}Tc$.

6. The polypeptide of claim 1 complexed with a compound selected from the group consisting of structural formula 1, 2, 3, 4, 5, 6, 7, 8, 9, a sterol, and a 5α-stanol.

7. The polypeptide of claim 6 wherein the sterol is cholesterol.

8. The polypeptide of claim 6 wherein said compound represented by structural formula 1, 2, 3, 4, 5, 6, 7, 8 or 9, the sterol or the 5α-stanol is detectably labeled.

9. The polypeptide of claim 8 wherein the label is $^3$H or $^{125}$I.

10. An isolated polypeptide comprising an amino acid sequence that is at least 97% identical to the amino acid sequence set forth in SEQ ID NO: 8 wherein said polypeptide binds to the compound having the structural formula

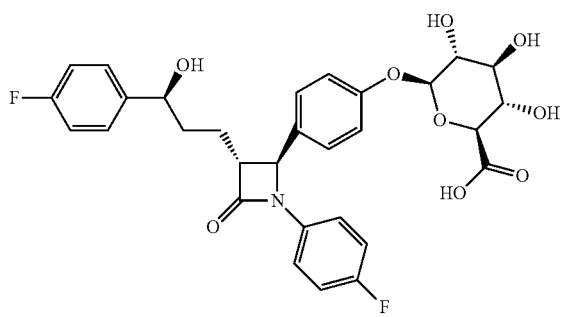

with a $K_i$ of 92 nM or lower; wherein the polypeptide is produced by a method comprising culturing a host cell comprising a polynucleotide encoding said polypeptide, in a vector, under conditions in which the polypeptide is expressed.

11. A method for identifying an antagonist of NPC1L1 comprising:
(a) contacting the polypeptide of claim 1, in the presence of a known amount of a detectable or detectably labeled substance which is known to bind to said polypeptide, with a sample to be tested for the presence of the antagonist; and
(b) measuring the amount of the detectable or detectably labeled substance specifically bound to the polypeptide;
wherein an NPC1L1 antagonist in the sample is identified by measuring substantially reduced binding of the detectable or detectably labeled substance to the polypeptide, compared to what would be measured in the absence of such an antagonist.

12. A method for identifying an antagonist of NPC1L1 comprising:
(a) placing, in an aqueous suspension, a plurality of support particles, impregnated with a fluorescer, to which the polypeptide of claim 1 is attached;
(b) adding, to the suspension, a radiolabeled substance which is known to bind said polypeptide and a sample to be tested for the presence of the antagonist, wherein the radiolabel emits radiation energy capable of activating the fluorescer upon binding of the substance to the polypeptide to produce light energy, whereas radiolabeled substance that does not bind to the polypeptide is, generally, too far removed from the support particles to enable the radioactive energy to activate the fluorescer; and
(c) measuring the light energy emitted by the fluorescer in the suspension;
wherein an NPC1L1 antagonist in the sample is identified by measuring substantially reduced light energy emission, compared to what would be measured in the absence of such an antagonist.

13. The method of claim 12 wherein the fluorescer is selected from yttrium silicate, yttrium oxide, diphenyloxazole and polyvinyltoluene.

14. A method of claim 11 wherein the substance is a radiolabeled sterol, a radiolabeled 5α-stanol or a radiolabeled compound represented by a structural formula selected from 1-9.

15. A method of claim 12 wherein the substance is a radiolabeled sterol, a radiolabeled 5α-stanol or a radiolabeled compound represented by a structural formula selected from 1-9.

16. A method for identifying an antagonist of NPC1L1 comprising:
(a) contacting a host cell expressing, on its cell surface, the polypeptide of claim 1 with a detectably labeled sterol or 5α-stanol and with a sample to be tested for the presence of the antagonist; and
(b) measuring the amount of detectably labeled sterol or 5α-stanol in the cell;
wherein an NPC1L1 antagonist in the sample is identified by measuring substantially reduced detectably labeled sterol or 5α-stanol within the host cell, compared to what would be measured in the absence of such an antagonist.

17. The method of claim 16 wherein the sterol or 5α-stanol is detectably labeled with a radiolabel selected from $^3$H, $^{14}$C and $^{125}$I.

18. The method of claim 16 wherein the sterol is cholesterol.

19. A method of claim 11 wherein the polypeptide is on a cell membrane of a host cell or in a membrane fraction thereof.

20. A method according to claim 12 wherein the polypeptide is on a cell membrane of a host cell or in a membrane fraction thereof.

21. A method according to claim 16 wherein the polypeptide is on a cell membrane of a host cell or in a membrane fraction thereof.

22. A method for screening a sample for an intestinal sterol or 5α-stanol absorption antagonist comprising:
(a) feeding a sterol or 5α-stanol-containing substance to a first and second animal which is a rhesus monkey comprising a functional NPC1L1 gene that encodes the polypeptide of claim 1 and to a third, mutant animal which is a rhesus monkey which does not comprise a functional NPC1L1 gene;
(b) administering the sample to be tested for the presence of the antagonist to the first animal, and optionally to the third animal, but not the second animal;
(c) measuring the amount of sterol or 5α-stanol absorption in the intestine of said first, second and third animals; and
(d) comparing the levels of intestinal sterol or 5α-stanol absorption in said first, second and third animals;
wherein the sample is determined to contain the intestinal sterol or 5α-stanol absorption antagonist when the level of intestinal sterol or 5α-stanol absorption in the first animal and the third animal are less than the amount of intestinal sterol or 5α-stanol absorption in the second animal.

23. The method of claim 22 wherein the sterol is cholesterol.

24. The method of claim 23 wherein the cholesterol is radiolabeled.

25. The method of claim 22 wherein the level of sterol or 5α-stanol cholesterol absorption is determined by measuring the level of serum sterol or 5α-stanol in the animal.

26. A method for identifying an inhibitor of cholesterol absorption comprising the steps of:

providing a cell expressing the polypeptide of claim 1 which cell is capable of binding a fluorescent cholesterol absorption inhibitor; contacting said cell with a candidate inhibitor of cholesterol absorption in the presence of said fluorescent cholesterol absorption inhibitor; and measuring fluorescence of said cell, wherein a relative absence of fluorescent cholesterol absorption inhibitor indicates that said candidate inhibitory agent is an inhibitor of cholesterol absorption which inhibits cholesterol absorption.

27. The method of claim 26 wherein the inhibitor is an azetidinone.

28. The method of claim 26 wherein the fluorescent cholesterol absorption inhibitor is

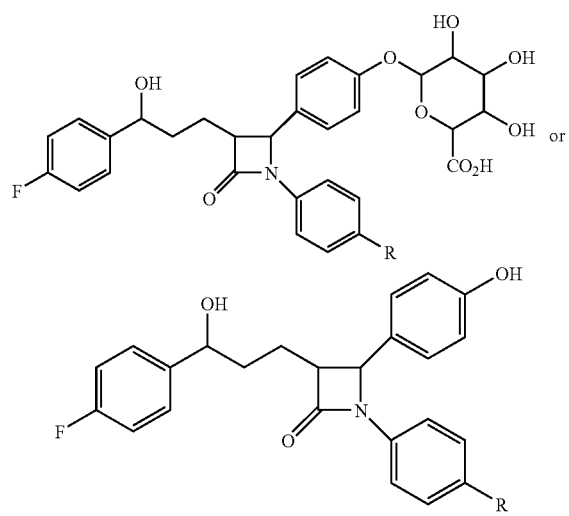

wherein R comprises a fluorescent moiety.

29. The method of claim 28, wherein R is a fluorescent moiety linked by an alkynyl-containing tether group.

30. The method of claim 29, wherein R is selected from the group consisting of:

31. A method for identifying an inhibitor of intestinal absorption of cholesterol, said method comprising the steps of: (a) combining a fluorescent cholesterol absorption inhibitor, a cell membrane comprising the polypeptide of claim 1, and a candidate inhibitor of intestinal cholesterol absorption, under conditions wherein, but for the presence of said inhibitor, said fluorescent cholesterol absorption inhibitor is bound to the NPC1L1 in the membrane; and (b) detecting the relative presence or absence of fluorescent cholesterol absorption inhibitor bound to the membrane, wherein a relative absence of fluorescent cholesterol absorption inhibitor indicates that said candidate inhibitor of intestinal cholesterol absorption is an inhibitor of intestinal cholesterol absorption which inhibits intestinal cholesterol absorption.

32. The method of claim 31 wherein the inhibitor is an azetidinone.

33. The method of claim 31 wherein the fluorescent cholesterol absorption inhibitor is

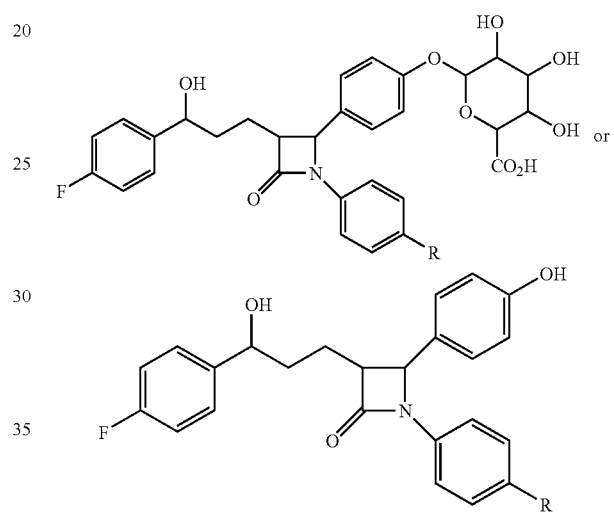

wherein R comprises a fluorescent moiety.

34. The method of claim 33, wherein R is a fluorescent moiety linked by an alkynyl-containing tether group.

35. The method of claim 34, wherein R is selected from the group consisting of:

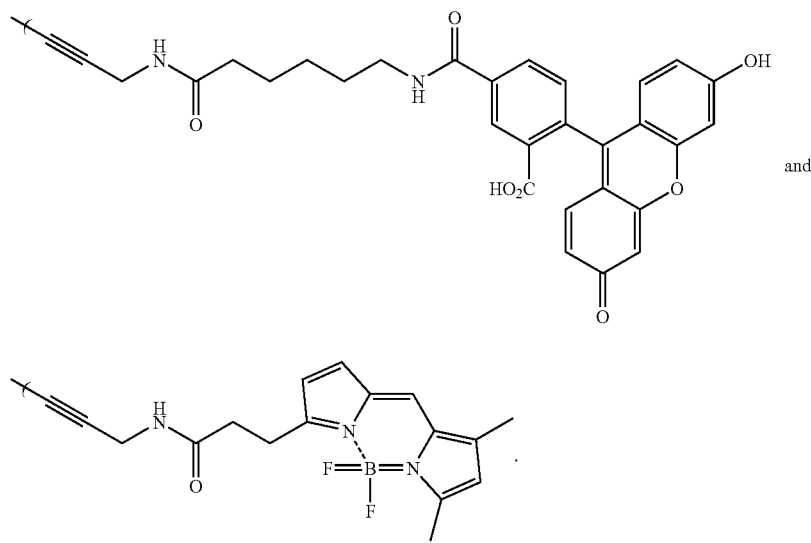

and

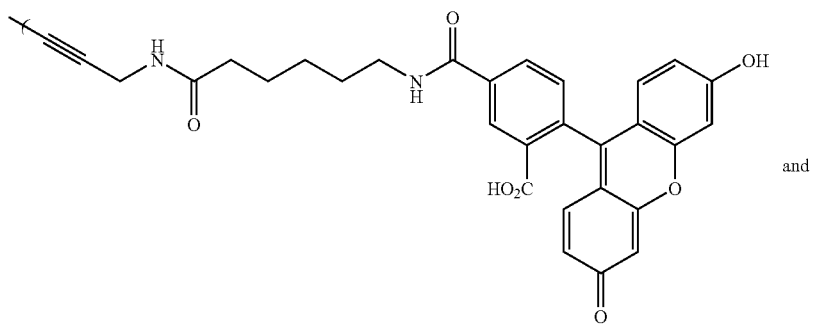
and
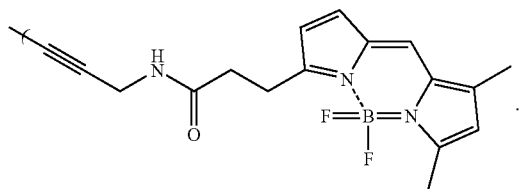
* * * * *

SEQUENCE LISTING

```
<160> NUMBER OF SEQ ID NOS: 29

<210> SEQ ID NO 1
<211> LENGTH: 3978
<212> TYPE: DNA
<213> ORGANISM: Canis sp.
<220> FEATURE:
<221> NAME/KEY: CDS
<222> LOCATION: (1)..(3978)

<400> SEQUENCE: 1 atg gcg gac act ggc ctg agg ggc tgg ctg cta tgg gca ctg ctc ctg      48
Met Ala Asp Thr Gly Leu Arg Gly Trp Leu Leu Trp Ala Leu Leu Leu
1               5                   10                  15 cat gtg gcc cag agt gag ctg tac aca ccc atc cac cag cct ggc tac      96
```

-continued

```
                His Val Ala Gln Ser Glu Leu Tyr Thr Pro Ile His Gln Pro Gly Tyr
                             20                  25                  30 tgc gct ttc tac gac gag tgt ggg aag aac cca gag ctg tct ggg gga        144
Cys Ala Phe Tyr Asp Glu Cys Gly Lys Asn Pro Glu Leu Ser Gly Gly
             35                  40                  45 ctg gcg cct ctg tct aat gtg tcc tgc ctg tcc aac acg ccc gcc ctc        192
Leu Ala Pro Leu Ser Asn Val Ser Cys Leu Ser Asn Thr Pro Ala Leu
 50                  55                  60 cgt gtc act ggt gag cac ctg acc ctc cta cag cgc atc tgc ccc cgc        240
Arg Val Thr Gly Glu His Leu Thr Leu Leu Gln Arg Ile Cys Pro Arg
 65                  70                  75                  80 ctc tac acg ggc acc acc acc tat gcc tgc tgc tcc ccc aag cag ctg        288
Leu Tyr Thr Gly Thr Thr Thr Tyr Ala Cys Cys Ser Pro Lys Gln Leu
             85                  90                  95 ctg tcc ctg gag acg agc ctg gcg gtc acc aag gcc ctc ctc acc cgc        336
Leu Ser Leu Glu Thr Ser Leu Ala Val Thr Lys Ala Leu Leu Thr Arg
            100                 105                 110 tgc ccc acc tgc tcc gac aac ttt gtg aac ctg cac tgc caa aac acc        384
Cys Pro Thr Cys Ser Asp Asn Phe Val Asn Leu His Cys Gln Asn Thr
            115                 120                 125 tgc agc ccc aac caa agt ctc ttc atc aac gtg acc cgc gtg gct ggg        432
Cys Ser Pro Asn Gln Ser Leu Phe Ile Asn Val Thr Arg Val Ala Gly
130                 135                 140 ggc ggg ggt ggc cgg ccc cag gct gtg gtg gcc tat gag gcc ttc tac        480
Gly Gly Gly Gly Arg Pro Gln Ala Val Val Ala Tyr Glu Ala Phe Tyr
145                 150                 155                 160 cag gac acc ttt gcc cag cag acc tac gac tct tgc agc cgg gtg cgc        528
Gln Asp Thr Phe Ala Gln Gln Thr Tyr Asp Ser Cys Ser Arg Val Arg
            165                 170                 175 atc cct gcg gct gcc acg ctg gcc gtg ggc acc atg tgt ggc gtt tat        576
Ile Pro Ala Ala Ala Thr Leu Ala Val Gly Thr Met Cys Gly Val Tyr
            180                 185                 190 ggc tcc acc ctc tgc aat gct cag cgc tgg ctc aat ttc cag ggg gac        624
Gly Ser Thr Leu Cys Asn Ala Gln Arg Trp Leu Asn Phe Gln Gly Asp
            195                 200                 205 act tcg aat ggc ctg gct ccc cta gac atc acc ttc cac ctg atg gag        672
Thr Ser Asn Gly Leu Ala Pro Leu Asp Ile Thr Phe His Leu Met Glu
            210                 215                 220 ccc ggc cag gcc cta ggg agt ggg atg cag gct ctg acc ggg gag atc        720
Pro Gly Gln Ala Leu Gly Ser Gly Met Gln Ala Leu Thr Gly Glu Ile
225                 230                 235                 240 agg ccc tgc aac gag tcc cag ggc aat ggc acg gtg gcc tgc tcc tgc        768
Arg Pro Cys Asn Glu Ser Gln Gly Asn Gly Thr Val Ala Cys Ser Cys
            245                 250                 255 cag gac tgt gct gcg tcc tgc ccc acc atc ccc cag ccc cag gca ctg        816
Gln Asp Cys Ala Ala Ser Cys Pro Thr Ile Pro Gln Pro Gln Ala Leu
            260                 265                 270 gac tcc acc ttc tac ctg ggc ggg ctg gaa ggt ggg ctg gcc ctt gtc        864
Asp Ser Thr Phe Tyr Leu Gly Gly Leu Glu Gly Gly Leu Ala Leu Val
            275                 280                 285 atc atc ctc tgc tct gct ttt gcc ctg ctt acc acc ttc ctg gtg ggt        912
Ile Ile Leu Cys Ser Ala Phe Ala Leu Leu Thr Thr Phe Leu Val Gly
            290                 295                 300 acc cgc ctg gcc tcc tcc tgt ggc aag gac aag acg cca gac ccc aag        960
Thr Arg Leu Ala Ser Ser Cys Gly Lys Asp Lys Thr Pro Asp Pro Lys
305                 310                 315                 320 gca ggc atg agc ctg tct gac aaa ctc agc ctc tcc acc aac gtc atc        1008
Ala Gly Met Ser Leu Ser Asp Lys Leu Ser Leu Ser Thr Asn Val Ile
            325                 330                 335 ctt agc cag tgc ttc cag aac tgg ggc aca tgg gtg gcc tca tgg ccg        1056
```

```
                    -continued

Leu Ser Gln Cys Phe Gln Asn Trp Gly Thr Trp Val Ala Ser Trp Pro
            340                 345                 350 ctg acc atc ctg ttg gtg tcc atc gcc gtg gta ttg gcc ttg tca gga      1104
Leu Thr Ile Leu Leu Val Ser Ile Ala Val Val Leu Ala Leu Ser Gly
355                 360                 365 ggc ctg gcc ttt gtg gaa ctg acc acg gac cca gtg gag ctg tgg tcg      1152
Gly Leu Ala Phe Val Glu Leu Thr Thr Asp Pro Val Glu Leu Trp Ser
        370                 375                 380 gcc ccc agc agc caa gcc cgg agt gag aag gct ttc cac gac cag cat      1200
Ala Pro Ser Ser Gln Ala Arg Ser Glu Lys Ala Phe His Asp Gln His
385                 390                 395                 400 ttt ggc ccc ttc ctc cga acc aac cag gtg atc ttg acg gct ccc aac      1248
Phe Gly Pro Phe Leu Arg Thr Asn Gln Val Ile Leu Thr Ala Pro Asn
                405                 410                 415 cgg ccc agc tac cac tac gac tcc ctg ctc ctg ggg ccc aag aac ttc      1296
Arg Pro Ser Tyr His Tyr Asp Ser Leu Leu Leu Gly Pro Lys Asn Phe
            420                 425                 430 agt ggg gtc ctg gcc tct gac ctc ctg ctg gag ctg ctg gag cta cag      1344
Ser Gly Val Leu Ala Ser Asp Leu Leu Leu Glu Leu Leu Glu Leu Gln
        435                 440                 445 gag acg ctg cgg cac ctc cag gtg tgg tcg ccc gag gag cag cgc cac      1392
Glu Thr Leu Arg His Leu Gln Val Trp Ser Pro Glu Glu Gln Arg His
450                 455                 460 atc tcg ctg cag gac atc tgc ttc gcg ccc ctc aac cct cac aat gcc      1440
Ile Ser Leu Gln Asp Ile Cys Phe Ala Pro Leu Asn Pro His Asn Ala
465                 470                 475                 480 agc ctc tcc gac tgc tgc atc aac agc ctc ctg cag tat ttc cag agc      1488
Ser Leu Ser Asp Cys Cys Ile Asn Ser Leu Leu Gln Tyr Phe Gln Ser
                485                 490                 495 aac cgc acg cac ctg ctc ctc acg gcc aac cag acg ctg acg ggc cag      1536
Asn Arg Thr His Leu Leu Leu Thr Ala Asn Gln Thr Leu Thr Gly Gln
            500                 505                 510 acc tcc cag gtg gac tgg agg gac cac ttt ctc tac tgt gct aac gcc      1584
Thr Ser Gln Val Asp Trp Arg Asp His Phe Leu Tyr Cys Ala Asn Ala
        515                 520                 525 cca ctc acc ttc aag gat ggc aca gcc cta gcc ctg agc tgc atg gct      1632
Pro Leu Thr Phe Lys Asp Gly Thr Ala Leu Ala Leu Ser Cys Met Ala
530                 535                 540 gac tat ggg ggc cct gtc ttc ccc ttc ctt gcc gtg ggt ggc tac aaa      1680
Asp Tyr Gly Gly Pro Val Phe Pro Phe Leu Ala Val Gly Gly Tyr Lys
545                 550                 555                 560 ggg aag gac tac tct gag gcg gag gcc ctg att atg acc ttc tcc ctc      1728
Gly Lys Asp Tyr Ser Glu Ala Glu Ala Leu Ile Met Thr Phe Ser Leu
                565                 570                 575 aac aac tat gcc cct ggg gac ccc cgg ctg gcc cag gct aag ctc tgg      1776
Asn Asn Tyr Ala Pro Gly Asp Pro Arg Leu Ala Gln Ala Lys Leu Trp
            580                 585                 590 gag gca gcc ttc ttg gag gag atg aaa gcc ttc cag cgg cgg aca gct      1824
Glu Ala Ala Phe Leu Glu Glu Met Lys Ala Phe Gln Arg Arg Thr Ala
        595                 600                 605 ggc act ttc cag gtc aca ttc atg gct gag cgc tcc ctg gag gac gag      1872
Gly Thr Phe Gln Val Thr Phe Met Ala Glu Arg Ser Leu Glu Asp Glu
610                 615                 620 att aac cgc acg acg gcg gag gac ctc ccc atc ttc gga gtc agc tac      1920
Ile Asn Arg Thr Thr Ala Glu Asp Leu Pro Ile Phe Gly Val Ser Tyr
625                 630                 635                 640 atc atc atc ttc ctg tac atc tcc ctg gcg ctg ggc agc tac tcc agc      1968
Ile Ile Ile Phe Leu Tyr Ile Ser Leu Ala Leu Gly Ser Tyr Ser Ser
                645                 650                 655 tgg cgc cgg gtg ccg gtg gac tcc aag gtc acg ctg ggc ctg ggc ggg      2016
```

-continued

| | |
|---|---|
| Trp Arg Arg Val Pro Val Asp Ser Lys Val Thr Leu Gly Leu Gly Gly<br>              660                    665                  670 | |
| gtg gcg gtg gtg ctg gga gca gtg aca gcg gcc atg ggc ttc ttc tcc<br>Val Ala Val Val Leu Gly Ala Val Thr Ala Ala Met Gly Phe Phe Ser<br>        675                    680                  685 | 2064 |
| tac ctc ggc gtg ccg tcc tcc ctg gtg atc ctt cag gtg gtg cct ttc<br>Tyr Leu Gly Val Pro Ser Ser Leu Val Ile Leu Gln Val Val Pro Phe<br>    690                    695                  700 | 2112 |
| ctg gtg ttg gcc gtg ggc gct gac aac atc ttc atc ttt gtt ctg gag<br>Leu Val Leu Ala Val Gly Ala Asp Asn Ile Phe Ile Phe Val Leu Glu<br>705                  710                  715                  720 | 2160 |
| tac cag agg ctg ccc cgg agg ccg gga gag ccg cgg gag gcc cac atc<br>Tyr Gln Arg Leu Pro Arg Arg Pro Gly Glu Pro Arg Glu Ala His Ile<br>              725                    730                  735 | 2208 |
| ggc cga gcg ctg ggc agt gtg gcc cct agc atg ttg ctc tgc agc ctg<br>Gly Arg Ala Leu Gly Ser Val Ala Pro Ser Met Leu Leu Cys Ser Leu<br>        740                    745                  750 | 2256 |
| tct gag gcc atc tgc ttc ttt cta ggg gcc ctg acc cct atg ccc gct<br>Ser Glu Ala Ile Cys Phe Phe Leu Gly Ala Leu Thr Pro Met Pro Ala<br>              755                    760                  765 | 2304 |
| gtg aag acc ttt gcc ctg atc tcg ggc ttt gcc atc gtc ctg gac ttc<br>Val Lys Thr Phe Ala Leu Ile Ser Gly Phe Ala Ile Val Leu Asp Phe<br>770                  775                  780 | 2352 |
| ttg ctg cag gtg tca gcc ttt gtg gct ctg ctt tct ctg gac agc agg<br>Leu Leu Gln Val Ser Ala Phe Val Ala Leu Leu Ser Leu Asp Ser Arg<br>785                  790                  795                  800 | 2400 |
| agg cag gag gcc tcc cgc ttg gac gtc tgc tgc tgc gtg agc gcc ccg<br>Arg Gln Glu Ala Ser Arg Leu Asp Val Cys Cys Cys Val Ser Ala Pro<br>                  805                    810                  815 | 2448 |
| aag ctg cct gca ccc ggc cag agc gag gga ctc ctg ctt cga gtc ttc<br>Lys Leu Pro Ala Pro Gly Gln Ser Glu Gly Leu Leu Leu Arg Val Phe<br>        820                    825                  830 | 2496 |
| cgc aag ttc tac gtc cca gtg ctg ctg cac cgg gtg aca cgg gcg gtg<br>Arg Lys Phe Tyr Val Pro Val Leu Leu His Arg Val Thr Arg Ala Val<br>              835                    840                  845 | 2544 |
| gtg ctg ctg ctg ttc acc ggc ctc ttc ggg gtg ggg ctc tac ttc atg<br>Val Leu Leu Leu Phe Thr Gly Leu Phe Gly Val Gly Leu Tyr Phe Met<br>850                  855                  860 | 2592 |
| tgc cac atc cgc gtg gga ttg gat cag gag ctg gcc ctg ccc aag gac<br>Cys His Ile Arg Val Gly Leu Asp Gln Glu Leu Ala Leu Pro Lys Asp<br>865                  870                  875                  880 | 2640 |
| tca tac ctg ctg gac tat ttc ttc ttc ctg aac cgc tac ttt gag gtg<br>Ser Tyr Leu Leu Asp Tyr Phe Phe Phe Leu Asn Arg Tyr Phe Glu Val<br>              885                    890                  895 | 2688 |
| ggg gct ccc gtc tac ttt gtc acc acg gga ggc tac aac ttc tcc agc<br>Gly Ala Pro Val Tyr Phe Val Thr Thr Gly Gly Tyr Asn Phe Ser Ser<br>        900                    905                  910 | 2736 |
| gag gcg ggc atg aat gct gtg tgc tcc agt gcc ggg tgc gac agt tac<br>Glu Ala Gly Met Asn Ala Val Cys Ser Ser Ala Gly Cys Asp Ser Tyr<br>              915                    920                  925 | 2784 |
| tcc tta acc cag aag atc cag tac gcc acc gag ttc ccc gag gag tct<br>Ser Leu Thr Gln Lys Ile Gln Tyr Ala Thr Glu Phe Pro Glu Glu Ser<br>930                  935                  940 | 2832 |
| tac ctg gcc atc cct gcc tcc tcc tgg gtg gat gac ttc atc gac tgg<br>Tyr Leu Ala Ile Pro Ala Ser Ser Trp Val Asp Asp Phe Ile Asp Trp<br>945                  950                  955                  960 | 2880 |
| ctg acc ccg tcc tcc tgc tgc cgc ctt tat gcc ttt ggt gct aat aag<br>Leu Thr Pro Ser Ser Cys Cys Arg Leu Tyr Ala Phe Gly Ala Asn Lys<br>              965                    970                  975 | 2928 |
| gac aaa ttc tgc cct tcg act gtc aac tcc cta gcc tgc ttg aag aac | 2976 |

-continued

```
                Asp Lys Phe Cys Pro Ser Thr Val Asn Ser Leu Ala Cys Leu Lys Asn
                                980                 985                 990 tgc gtg aac ttc aca ctg ggc cct gtc cgg cca tcc gtg gac cag ttc        3024
Cys Val Asn Phe Thr Leu Gly Pro Val Arg Pro Ser Val Asp Gln Phe
            995                 1000                1005 cac aag tac ctt ccc tgg ttc ctg agt gac ccg ccc aac atc aag            3069
His Lys Tyr Leu Pro Trp Phe Leu Ser Asp Pro Pro Asn Ile Lys
        1010                1015                1020 tgt ccc aaa ggt ggg ctg gca gcg tac aac acc tcc gtg cat ttg            3114
Cys Pro Lys Gly Gly Leu Ala Ala Tyr Asn Thr Ser Val His Leu
        1025                1030                1035 gga tct gat ggc cag gtt tta gcc tcc cgg ttc atg gcc tac cac            3159
Gly Ser Asp Gly Gln Val Leu Ala Ser Arg Phe Met Ala Tyr His
        1040                1045                1050 aag ccg ctg cgg aac tcg gag gat tac act gag gcc ctg cgg gtg            3204
Lys Pro Leu Arg Asn Ser Glu Asp Tyr Thr Glu Ala Leu Arg Val
        1055                1060                1065 tca cgg gcg ctg gcg gcc aac atc acg gcc cag ctg cgg cag gtg            3249
Ser Arg Ala Leu Ala Ala Asn Ile Thr Ala Gln Leu Arg Gln Val
        1070                1075                1080 cca ggc acc gac ccg gcc ttc gag gtc ttc ccc tac acg atc acc            3294
Pro Gly Thr Asp Pro Ala Phe Glu Val Phe Pro Tyr Thr Ile Thr
        1085                1090                1095 aac gtg ttc tac gag cag tac ctg agc gtg gtc ccc gag ggc ctc            3339
Asn Val Phe Tyr Glu Gln Tyr Leu Ser Val Val Pro Glu Gly Leu
        1100                1105                1110 ttc atg ctc gcc atc tgc ctg ctg ccc acc ttc gta gtc tgc tgc            3384
Phe Met Leu Ala Ile Cys Leu Leu Pro Thr Phe Val Val Cys Cys
        1115                1120                1125 ctg ctg ctg ggc atg gac cta cgc tcc ggc ctc ctc aac ctg ttc            3429
Leu Leu Leu Gly Met Asp Leu Arg Ser Gly Leu Leu Asn Leu Phe
        1130                1135                1140 tcc atc gtc atg atc ctc gtg gac acc gtg ggc ttc atg gcc ctg            3474
Ser Ile Val Met Ile Leu Val Asp Thr Val Gly Phe Met Ala Leu
        1145                1150                1155 tgg ggc atc agt tac aat gcc gtg tcg ctc atc aac ctg gtc acg            3519
Trp Gly Ile Ser Tyr Asn Ala Val Ser Leu Ile Asn Leu Val Thr
        1160                1165                1170 gcg gtg ggc atc tcc gtg gag ttt gtg tcc cac atc acc cgc tcc            3564
Ala Val Gly Ile Ser Val Glu Phe Val Ser His Ile Thr Arg Ser
        1175                1180                1185 ttt gca gtc agc acc cgg ccc acc cgg ctg gag agg gcc aag gag            3609
Phe Ala Val Ser Thr Arg Pro Thr Arg Leu Glu Arg Ala Lys Glu
        1190                1195                1200 gcc acc atc tcc atg ggc agc gcg gtg ttt gct ggc gtg gcc atg            3654
Ala Thr Ile Ser Met Gly Ser Ala Val Phe Ala Gly Val Ala Met
        1205                1210                1215 acc aac ctg ccg ggc atc ctc gtc ctg ggc ctg gcc aag gca cag            3699
Thr Asn Leu Pro Gly Ile Leu Val Leu Gly Leu Ala Lys Ala Gln
        1220                1225                1230 ctc atc cag atc ttc ttc ttc cgc ctc aac ctc ctc atc acc gtg            3744
Leu Ile Gln Ile Phe Phe Phe Arg Leu Asn Leu Leu Ile Thr Val
        1235                1240                1245 ctg ggt ctg ctg cat ggc ctg gtc ttc ctg cca gtg gtc ctc agc            3789
Leu Gly Leu Leu His Gly Leu Val Phe Leu Pro Val Val Leu Ser
        1250                1255                1260 tac ctc ggg cct gat atc aat gca gct ctc gtg ctg gac cag aag            3834
Tyr Leu Gly Pro Asp Ile Asn Ala Ala Leu Val Leu Asp Gln Lys
        1265                1270                1275 aag aca gaa gag gcc atc ggg gcc cct gcc cac ctg gtc cca aca            3879
```

```
Lys Thr Glu Glu Ala Ile Gly Ala Pro Ala His Leu Val Pro Thr
    1280            1285                1290 tcc acg gcc agc agc acc tat gtc aac tac ggc ttc caa cat ccc      3924
Ser Thr Ala Ser Ser Thr Tyr Val Asn Tyr Gly Phe Gln His Pro
    1295            1300                1305 gcc aac ggt gta gtg ggc gac agt tct ctg ccc cgc agt gga ccg      3969
Ala Asn Gly Val Val Gly Asp Ser Ser Leu Pro Arg Ser Gly Pro
1310            1315                1320 gac ctc tga                                                      3978
Asp Leu
    1325

<210> SEQ ID NO 2
<211> LENGTH: 1325
<212> TYPE: PRT
<213> ORGANISM: Canis sp.

<400> SEQUENCE: 2

Met Ala Asp Thr Gly Leu Arg Gly Trp Leu Leu Trp Ala Leu Leu Leu
1               5                   10                  15

His Val Ala Gln Ser Glu Leu Tyr Thr Pro Ile His Gln Pro Gly Tyr
                20                  25                  30

Cys Ala Phe Tyr Asp Glu Cys Gly Lys Asn Pro Glu Leu Ser Gly Gly
            35                  40                  45

Leu Ala Pro Leu Ser Asn Val Ser Cys Leu Ser Asn Thr Pro Ala Leu
        50                  55                  60

Arg Val Thr Gly Glu His Leu Thr Leu Leu Gln Arg Ile Cys Pro Arg
65                  70                  75                  80

Leu Tyr Thr Gly Thr Thr Thr Tyr Ala Cys Cys Ser Pro Lys Gln Leu
                85                  90                  95

Leu Ser Leu Glu Thr Ser Leu Ala Val Thr Lys Ala Leu Leu Thr Arg
            100                 105                 110

Cys Pro Thr Cys Ser Asp Asn Phe Val Asn Leu His Cys Gln Asn Thr
        115                 120                 125

Cys Ser Pro Asn Gln Ser Leu Phe Ile Asn Val Thr Arg Val Ala Gly
    130                 135                 140

Gly Gly Gly Gly Arg Pro Gln Ala Val Val Ala Tyr Glu Ala Phe Tyr
145                 150                 155                 160

Gln Asp Thr Phe Ala Gln Gln Thr Tyr Asp Ser Cys Ser Arg Val Arg
                165                 170                 175

Ile Pro Ala Ala Ala Thr Leu Ala Val Gly Thr Met Cys Gly Val Tyr
            180                 185                 190

Gly Ser Thr Leu Cys Asn Ala Gln Arg Trp Leu Asn Phe Gln Gly Asp
        195                 200                 205

Thr Ser Asn Gly Leu Ala Pro Leu Asp Ile Thr Phe His Leu Met Glu
    210                 215                 220

Pro Gly Gln Ala Leu Gly Ser Gly Met Gln Ala Leu Thr Gly Glu Ile
225                 230                 235                 240

Arg Pro Cys Asn Glu Ser Gln Gly Asn Gly Thr Val Ala Cys Ser Cys
                245                 250                 255

Gln Asp Cys Ala Ala Ser Cys Pro Thr Ile Pro Gln Pro Gln Ala Leu
            260                 265                 270

Asp Ser Thr Phe Tyr Leu Gly Gly Leu Glu Gly Gly Leu Ala Leu Val
        275                 280                 285

Ile Ile Leu Cys Ser Ala Phe Ala Leu Leu Thr Thr Phe Leu Val Gly
    290                 295                 300
```

-continued

```
Thr Arg Leu Ala Ser Ser Cys Gly Lys Asp Lys Thr Pro Asp Pro Lys
305                 310                 315                 320

Ala Gly Met Ser Leu Ser Asp Lys Leu Ser Leu Ser Thr Asn Val Ile
            325                 330                 335

Leu Ser Gln Cys Phe Gln Asn Trp Gly Thr Trp Val Ala Ser Trp Pro
        340                 345                 350

Leu Thr Ile Leu Leu Val Ser Ile Ala Val Val Leu Ala Leu Ser Gly
    355                 360                 365

Gly Leu Ala Phe Val Glu Leu Thr Thr Asp Pro Val Glu Leu Trp Ser
370                 375                 380

Ala Pro Ser Ser Gln Ala Arg Ser Glu Lys Ala Phe His Asp Gln His
385                 390                 395                 400

Phe Gly Pro Phe Leu Arg Thr Asn Gln Val Ile Leu Thr Ala Pro Asn
                405                 410                 415

Arg Pro Ser Tyr His Tyr Asp Ser Leu Leu Leu Gly Pro Lys Asn Phe
            420                 425                 430

Ser Gly Val Leu Ala Ser Asp Leu Leu Glu Leu Leu Glu Leu Gln
        435                 440                 445

Glu Thr Leu Arg His Leu Gln Val Trp Ser Pro Glu Glu Gln Arg His
450                 455                 460

Ile Ser Leu Gln Asp Ile Cys Phe Ala Pro Leu Asn Pro His Asn Ala
465                 470                 475                 480

Ser Leu Ser Asp Cys Cys Ile Asn Ser Leu Leu Gln Tyr Phe Gln Ser
                485                 490                 495

Asn Arg Thr His Leu Leu Leu Thr Ala Asn Gln Thr Leu Thr Gly Gln
            500                 505                 510

Thr Ser Gln Val Asp Trp Arg Asp His Phe Leu Tyr Cys Ala Asn Ala
        515                 520                 525

Pro Leu Thr Phe Lys Asp Gly Thr Ala Leu Ala Leu Ser Cys Met Ala
530                 535                 540

Asp Tyr Gly Gly Pro Val Phe Pro Phe Leu Ala Val Gly Gly Tyr Lys
545                 550                 555                 560

Gly Lys Asp Tyr Ser Glu Ala Glu Ala Leu Ile Met Thr Phe Ser Leu
                565                 570                 575

Asn Asn Tyr Ala Pro Gly Asp Pro Arg Leu Ala Gln Ala Lys Leu Trp
            580                 585                 590

Glu Ala Ala Phe Leu Glu Glu Met Lys Ala Phe Gln Arg Arg Thr Ala
        595                 600                 605

Gly Thr Phe Gln Val Thr Phe Met Ala Glu Arg Ser Leu Glu Asp Glu
610                 615                 620

Ile Asn Arg Thr Thr Ala Glu Asp Leu Pro Ile Phe Gly Val Ser Tyr
625                 630                 635                 640

Ile Ile Ile Phe Leu Tyr Ile Ser Leu Ala Leu Gly Ser Tyr Ser Ser
                645                 650                 655

Trp Arg Arg Val Pro Val Asp Ser Lys Val Thr Leu Gly Leu Gly Gly
            660                 665                 670

Val Ala Val Val Leu Gly Ala Val Thr Ala Ala Met Gly Phe Phe Ser
        675                 680                 685

Tyr Leu Gly Val Pro Ser Ser Leu Val Ile Leu Gln Val Val Pro Phe
690                 695                 700

Leu Val Leu Ala Val Gly Ala Asp Asn Ile Phe Ile Phe Val Leu Glu
705                 710                 715                 720

Tyr Gln Arg Leu Pro Arg Arg Pro Gly Glu Pro Arg Glu Ala His Ile
                725                 730                 735
```

-continued

```
Gly Arg Ala Leu Gly Ser Val Ala Pro Ser Met Leu Leu Cys Ser Leu
            740                 745                 750

Ser Glu Ala Ile Cys Phe Phe Leu Gly Ala Leu Thr Pro Met Pro Ala
            755                 760                 765

Val Lys Thr Phe Ala Leu Ile Ser Gly Phe Ala Ile Val Leu Asp Phe
        770                 775                 780

Leu Leu Gln Val Ser Ala Phe Val Ala Leu Leu Ser Leu Asp Ser Arg
785                 790                 795                 800

Arg Gln Glu Ala Ser Arg Leu Asp Val Cys Cys Val Ser Ala Pro
                805                 810                 815

Lys Leu Pro Ala Pro Gly Gln Ser Glu Gly Leu Leu Leu Arg Val Phe
                820                 825                 830

Arg Lys Phe Tyr Val Pro Val Leu Leu His Arg Val Thr Arg Ala Val
            835                 840                 845

Val Leu Leu Leu Phe Thr Gly Leu Phe Gly Val Gly Leu Tyr Phe Met
        850                 855                 860

Cys His Ile Arg Val Gly Leu Asp Gln Glu Leu Ala Leu Pro Lys Asp
865                 870                 875                 880

Ser Tyr Leu Leu Asp Tyr Phe Phe Leu Asn Arg Tyr Phe Glu Val
                885                 890                 895

Gly Ala Pro Val Tyr Phe Val Thr Thr Gly Gly Tyr Asn Phe Ser Ser
                900                 905                 910

Glu Ala Gly Met Asn Ala Val Cys Ser Ser Ala Gly Cys Asp Ser Tyr
            915                 920                 925

Ser Leu Thr Gln Lys Ile Gln Tyr Ala Thr Glu Phe Pro Glu Glu Ser
        930                 935                 940

Tyr Leu Ala Ile Pro Ala Ser Ser Trp Val Asp Phe Ile Asp Trp
945                 950                 955                 960

Leu Thr Pro Ser Ser Cys Cys Arg Leu Tyr Ala Phe Gly Ala Asn Lys
                965                 970                 975

Asp Lys Phe Cys Pro Ser Thr Val Asn Ser Leu Ala Cys Leu Lys Asn
                980                 985                 990

Cys Val Asn Phe Thr Leu Gly Pro Val Arg Pro Ser Val Asp Gln Phe
            995                 1000                1005

His Lys Tyr Leu Pro Trp Phe Leu Ser Asp Pro Asn Ile Lys
        1010                1015                1020

Cys Pro Lys Gly Gly Leu Ala Ala Tyr Asn Thr Ser Val His Leu
        1025                1030                1035

Gly Ser Asp Gly Gln Val Leu Ala Ser Arg Phe Met Ala Tyr His
        1040                1045                1050

Lys Pro Leu Arg Asn Ser Glu Asp Tyr Thr Glu Ala Leu Arg Val
        1055                1060                1065

Ser Arg Ala Leu Ala Ala Asn Ile Thr Ala Gln Leu Arg Gln Val
        1070                1075                1080

Pro Gly Thr Asp Pro Ala Phe Glu Val Phe Pro Tyr Thr Ile Thr
        1085                1090                1095

Asn Val Phe Tyr Glu Gln Tyr Leu Ser Val Val Pro Glu Gly Leu
        1100                1105                1110

Phe Met Leu Ala Ile Cys Leu Leu Pro Thr Phe Val Val Cys Cys
        1115                1120                1125

Leu Leu Leu Gly Met Asp Leu Arg Ser Gly Leu Leu Asn Leu Phe
        1130                1135                1140

Ser Ile Val Met Ile Leu Val Asp Thr Val Gly Phe Met Ala Leu
```

-continued

```
                1145                1150                1155

Trp Gly Ile Ser Tyr Asn Ala Val Ser Leu Ile Asn  Leu Val Thr
    1160                1165                1170

Ala Val Gly Ile Ser Val Glu Phe Val Ser His Ile  Thr Arg Ser
    1175                1180                1185

Phe Ala Val Ser Thr Arg Pro Thr Arg Leu Glu Arg  Ala Lys Glu
    1190                1195                1200

Ala Thr Ile Ser Met Gly Ser Ala Val Phe Ala Gly  Val Ala Met
    1205                1210                1215

Thr Asn Leu Pro Gly Ile Leu Val Leu Gly Leu Ala  Lys Ala Gln
    1220                1225                1230

Leu Ile Gln Ile Phe Phe Phe Arg Leu Asn Leu Leu  Ile Thr Val
    1235                1240                1245

Leu Gly Leu Leu His Gly Leu Val Phe Leu Pro Val  Val Leu Ser
    1250                1255                1260

Tyr Leu Gly Pro Asp Ile Asn Ala Ala Leu Val Leu  Asp Gln Lys
    1265                1270                1275

Lys Thr Glu Glu Ala Ile Gly Ala Pro Ala His Leu  Val Pro Thr
    1280                1285                1290

Ser Thr Ala Ser Ser Thr Tyr Val Asn Tyr Gly Phe  Gln His Pro
    1295                1300                1305

Ala Asn Gly Val Val Gly Asp Ser Ser Leu Pro Arg  Ser Gly Pro
    1310                1315                1320

Asp Leu
    1325

<210> SEQ ID NO 3
<211> LENGTH: 3978
<212> TYPE: DNA
<213> ORGANISM: Oryctolagus sp.
<220> FEATURE:
<221> NAME/KEY: CDS
<222> LOCATION: (1)..(3978)

<400> SEQUENCE: 3 atg gca ggg gct gcg cgg ggc tgg ctg ctc tgg gcc ctg ctc ctg cac      48
Met Ala Gly Ala Ala Arg Gly Trp Leu Leu Trp Ala Leu Leu Leu His
1               5                   10                  15 cag gcc cag gca gag ctg tac acg ccc gtg cac cag gcc ggc tac tgc      96
Gln Ala Gln Ala Glu Leu Tyr Thr Pro Val His Gln Ala Gly Tyr Cys
            20                  25                  30 gcc ttc tac gag gag tgc ggg aag aac cct gag ctg tct ggg ggc ctc     144
Ala Phe Tyr Glu Glu Cys Gly Lys Asn Pro Glu Leu Ser Gly Gly Leu
        35                  40                  45 aca tcg ctg tcc aac gtg tcc tgc ctg tcc aac acg cct gcc cgc cat     192
Thr Ser Leu Ser Asn Val Ser Cys Leu Ser Asn Thr Pro Ala Arg His
    50                  55                  60 gtc acg ggc gac cac ctg gcc ctc ctg gag cgc atc tgc ccc cgc ctc     240
Val Thr Gly Asp His Leu Ala Leu Leu Glu Arg Ile Cys Pro Arg Leu
65                  70                  75                  80 tac aac ggc ccc aac acc acc tac gcc tgc tgc tcg ccc agg cag ctg     288
Tyr Asn Gly Pro Asn Thr Thr Tyr Ala Cys Cys Ser Pro Arg Gln Leu
                85                  90                  95 gtg tcg ctg gag acc agc atg tcc gtc acc aag gcc ctg ctc acg cgc     336
Val Ser Leu Glu Thr Ser Met Ser Val Thr Lys Ala Leu Leu Thr Arg
            100                 105                 110 tgc ccc gcc tgc tct gac aac ttc gtg agc ctg cac tgc cag aac acc     384
Cys Pro Ala Cys Ser Asp Asn Phe Val Ser Leu His Cys Gln Asn Thr
        115                 120                 125
```

```
tgc agc ccg gac cag agc ctc ttc atc aac gtg acg cgc gtg gtc tcc       432
Cys Ser Pro Asp Gln Ser Leu Phe Ile Asn Val Thr Arg Val Val Ser
    130                 135                 140 cag ggc gct ggg cag ctc cag gcc gtc gtg gcc tac gag gcc tac tac       480
Gln Gly Ala Gly Gln Leu Gln Ala Val Val Ala Tyr Glu Ala Tyr Tyr
145                 150                 155                 160 gag cgc agc ttc gcc gag cgg gcc tac gag tcc tgc agc cgc gtg cgc       528
Glu Arg Ser Phe Ala Glu Arg Ala Tyr Glu Ser Cys Ser Arg Val Arg
                165                 170                 175 atc ccc gcc gcc gcc acg ctg gcc gtg ggc agc atg tgc ggc gtg tac       576
Ile Pro Ala Ala Ala Thr Leu Ala Val Gly Ser Met Cys Gly Val Tyr
            180                 185                 190 ggc tct gcc ctc tgc aac gcc cag cgc tgg ctc aac ttc cag ggg gac       624
Gly Ser Ala Leu Cys Asn Ala Gln Arg Trp Leu Asn Phe Gln Gly Asp
        195                 200                 205 acg agc aac ggc ctg gcc ccg ctg gac att acc ttc cac ctg cgg gag       672
Thr Ser Asn Gly Leu Ala Pro Leu Asp Ile Thr Phe His Leu Arg Glu
    210                 215                 220 ccc ggg cag gcg ccg ggc agc ggg atg caa ctg ctg aac gcg gag atc       720
Pro Gly Gln Ala Pro Gly Ser Gly Met Gln Leu Leu Asn Ala Glu Ile
225                 230                 235                 240 gcg ccc tgc aac gag tcc cag gac agc gcc gcg gcc tgc tcc tgc cag       768
Ala Pro Cys Asn Glu Ser Gln Asp Ser Ala Ala Ala Cys Ser Cys Gln
                245                 250                 255 gac tgt gcc gcg tcc tgc ccg gcc atc acg cag cct gag gcc ctg gac       816
Asp Cys Ala Ala Ser Cys Pro Ala Ile Thr Gln Pro Glu Ala Leu Asp
            260                 265                 270 tcc tcc ttc cgc att ggc cgc gtg cgg ggt ggg gtg gca ctc gtc gtc       864
Ser Ser Phe Arg Ile Gly Arg Val Arg Gly Gly Val Ala Leu Val Val
        275                 280                 285 atc ctc tgc agc acc ctg ggc gtg ctc ctg ggc ctc gtg tgc gcc           912
Ile Leu Cys Ser Thr Leu Gly Val Leu Leu Gly Leu Val Cys Ala
    290                 295                 300 cgc agg tac tcg gcc aag gcc agg ggc acg gcg acg gcc ccc acg gcc       960
Arg Arg Tyr Ser Ala Lys Ala Arg Gly Thr Ala Thr Ala Pro Thr Ala
305                 310                 315                 320 tgc tcc agg ctc tcc cac cgc atc agc ctg tcc atc cac acc ttc ctc      1008
Cys Ser Arg Leu Ser His Arg Ile Ser Leu Ser Ile His Thr Phe Leu
                325                 330                 335 cat cgg ctc ttc cag tgc tgg ggc acg tgg gtg gcc tcg tgg ccc ctg      1056
His Arg Leu Phe Gln Cys Trp Gly Thr Trp Val Ala Ser Trp Pro Leu
            340                 345                 350 acc atc ctg gcc gtg tcc atc gcg gtc gtg gtg tcc ttg gcg tgt ggc      1104
Thr Ile Leu Ala Val Ser Ile Ala Val Val Val Ser Leu Ala Cys Gly
        355                 360                 365 ctg gcc ttc acg gag ctc aca acg gac ccc gtg gag ctg tgg tcg gcc      1152
Leu Ala Phe Thr Glu Leu Thr Thr Asp Pro Val Glu Leu Trp Ser Ala
370                 375                 380 ccc aac agc caa gcc cgc agc gag aag gct ttc cac gac cag cac ttc      1200
Pro Asn Ser Gln Ala Arg Ser Glu Lys Ala Phe His Asp Gln His Phe
385                 390                 395                 400 ggc ccc ttc ttc cga acg aac cag gtg atc ctg acg gcg cct acc cgc      1248
Gly Pro Phe Phe Arg Thr Asn Gln Val Ile Leu Thr Ala Pro Thr Arg
                405                 410                 415 tcc cgc tac act tac aac tcc ctg ctg ctg ggc ccc cgg aac ttc agt      1296
Ser Arg Tyr Thr Tyr Asn Ser Leu Leu Leu Gly Pro Arg Asn Phe Ser
            420                 425                 430 ggg atc ctg gcc atg gac ctg ctg ctg gag cta ctg gag ctg cag gag      1344
Gly Ile Leu Ala Met Asp Leu Leu Leu Glu Leu Leu Glu Leu Gln Glu
        435                 440                 445
```

```
cgg ctg cgg gcc ctg cag gtg tgg tcg ccc gag gcg cag cgc aac gtg      1392
Arg Leu Arg Ala Leu Gln Val Trp Ser Pro Glu Ala Gln Arg Asn Val
    450                 455                 460 agc ctg cgg gac gtc tgc tac gcc ccg ctc aac ccg cac aac gcc agc      1440
Ser Leu Arg Asp Val Cys Tyr Ala Pro Leu Asn Pro His Asn Ala Ser
465                 470                 475                 480 ctc acc gac tgc tgt atc aac agc ctg ctg cag tac ttc cag aac aac      1488
Leu Thr Asp Cys Cys Ile Asn Ser Leu Leu Gln Tyr Phe Gln Asn Asn
                485                 490                 495 cgc acg ctg ctg cag ctc acg gcc aac cag acg ctg ctg ggc cag act      1536
Arg Thr Leu Leu Gln Leu Thr Ala Asn Gln Thr Leu Leu Gly Gln Thr
            500                 505                 510 gcc cag gtc gac tgg agg gac cac ttt ctc tac tgt gcc aat gcc ccc      1584
Ala Gln Val Asp Trp Arg Asp His Phe Leu Tyr Cys Ala Asn Ala Pro
        515                 520                 525 ctc acc ttc caa gac ggc acg gcc ctg tcc ctg agc tgc atg gcc gac      1632
Leu Thr Phe Gln Asp Gly Thr Ala Leu Ser Leu Ser Cys Met Ala Asp
    530                 535                 540 tac ggg gcg ccc gtc ttc cct ttc ctc gcc gtt gga gga tac gaa ggc      1680
Tyr Gly Ala Pro Val Phe Pro Phe Leu Ala Val Gly Gly Tyr Glu Gly
545                 550                 555                 560 gag gac tac tcg gat gcg gag gcc ctc atc tta acc ttc tcc ctc aac      1728
Glu Asp Tyr Ser Asp Ala Glu Ala Leu Ile Leu Thr Phe Ser Leu Asn
                565                 570                 575 aac tac cct gcg ggg gac ccc cgc ctg gcc cag gtc aag ctc tgg gag      1776
Asn Tyr Pro Ala Gly Asp Pro Arg Leu Ala Gln Val Lys Leu Trp Glu
            580                 585                 590 gag gcc ttc gtg aag gag atg cga gcc ttg cag ctt ggg aag tcc agc      1824
Glu Ala Phe Val Lys Glu Met Arg Ala Leu Gln Leu Gly Lys Ser Ser
        595                 600                 605 aaa ttc cag gtc acg ttc atg gcc gag cgc tcc ctg gag gat gag atc      1872
Lys Phe Gln Val Thr Phe Met Ala Glu Arg Ser Leu Glu Asp Glu Ile
    610                 615                 620 aac cgc acc acg gct gag gac ctg ccc atc ttt gcc atc agc tac atc      1920
Asn Arg Thr Thr Ala Glu Asp Leu Pro Ile Phe Ala Ile Ser Tyr Ile
625                 630                 635                 640 gtc acc ttc ctg tac atc gcc ctg gcc ctg ggc cgc tac tcc agc tgg      1968
Val Thr Phe Leu Tyr Ile Ala Leu Ala Leu Gly Arg Tyr Ser Ser Trp
                645                 650                 655 cgc cga ttg ccg gtg gac tcc aag atc acg ctg ggc ctg ggc ggg gtg      2016
Arg Arg Leu Pro Val Asp Ser Lys Ile Thr Leu Gly Leu Gly Gly Val
            660                 665                 670 gtc atg gtg ctg agc gcg gtc atg gct tcc atg ggc ttc ttc tcc tac      2064
Val Met Val Leu Ser Ala Val Met Ala Ser Met Gly Phe Phe Ser Tyr
        675                 680                 685 ctg ggc atc ccg tcg tcc ctg atc atc ctg caa gtg gtg cct ttc ctg      2112
Leu Gly Ile Pro Ser Ser Leu Ile Ile Leu Gln Val Val Pro Phe Leu
    690                 695                 700 gtg ctg gcc gtg ggg gcc gac aac atc ttc atc ctc gtt ctc gag tac      2160
Val Leu Ala Val Gly Ala Asp Asn Ile Phe Ile Leu Val Leu Glu Tyr
705                 710                 715                 720 cag cgg ctg ccg cgg agg cct gag gag tcg cgg gag gcc cac atc ggc      2208
Gln Arg Leu Pro Arg Arg Pro Glu Glu Ser Arg Glu Ala His Ile Gly
                725                 730                 735 cga gcc ctg ggc agg gtg gct ccc agc atg ctg ctg tgc agc ctc tcc      2256
Arg Ala Leu Gly Arg Val Ala Pro Ser Met Leu Leu Cys Ser Leu Ser
            740                 745                 750 gag acc atc tgc ttc ttc ctg ggg gcc ctg acc ccc atg cca gcc gtg      2304
Glu Thr Ile Cys Phe Phe Leu Gly Ala Leu Thr Pro Met Pro Ala Val
        755                 760                 765
```

```
cgt acc ttt gcc ctg acg tct ggc ctg gcg gtg caa ctc gac ttc ctg      2352
Arg Thr Phe Ala Leu Thr Ser Gly Leu Ala Val Gln Leu Asp Phe Leu
    770             775             780 ctg cag atg act gcc ttc gtg gcc ctg ctg tcc ctg gac agc aag agg      2400
Leu Gln Met Thr Ala Phe Val Ala Leu Leu Ser Leu Asp Ser Lys Arg
785             790             795             800 cag gag gct tcc cgg cca gat gtg tgc tgc tgc ctg gag ccc cgg aag      2448
Gln Glu Ala Ser Arg Pro Asp Val Cys Cys Cys Leu Glu Pro Arg Lys
            805             810             815 ctg ccc tcc cag cag cag agc gag ggg ctg ctg ctg tgt ttc ttc cgc      2496
Leu Pro Ser Gln Gln Gln Ser Glu Gly Leu Leu Leu Cys Phe Phe Arg
        820             825             830 aaa gtc tac gcc ccg ctc ctg ctg cac aag gtc acc cgc gtg gtc gtg      2544
Lys Val Tyr Ala Pro Leu Leu Leu His Lys Val Thr Arg Val Val Val
    835             840             845 ctg ctg ctc ttt ctg ttc ctg ttc gga tcg agt ctc tac ttc atg tgc      2592
Leu Leu Leu Phe Leu Phe Leu Phe Gly Ser Ser Leu Tyr Phe Met Cys
850             855             860 cag gtc acc gtg ggg ctg gac cag gag ctg gcc ctg ccc aag gac tcg      2640
Gln Val Thr Val Gly Leu Asp Gln Glu Leu Ala Leu Pro Lys Asp Ser
865             870             875             880 tac ctg atc gac tac ttc ctg ttt ctg aac cgc tac ttt gag gtg ggg      2688
Tyr Leu Ile Asp Tyr Phe Leu Phe Leu Asn Arg Tyr Phe Glu Val Gly
            885             890             895 gcc cca gtg tac ttt gtc acc acc tcg ggc tac aac ttc tcc agc gag      2736
Ala Pro Val Tyr Phe Val Thr Thr Ser Gly Tyr Asn Phe Ser Ser Glu
        900             905             910 gcg ggc atg aac gcc atc tgc tcc agc gca ggc tgc gac agc ttc tcc      2784
Ala Gly Met Asn Ala Ile Cys Ser Ser Ala Gly Cys Asp Ser Phe Ser
    915             920             925 ctc acc cag aag atc caa tac gcc acc gag ttc ccc gag cag tct tac      2832
Leu Thr Gln Lys Ile Gln Tyr Ala Thr Glu Phe Pro Glu Gln Ser Tyr
930             935             940 ctg gcc atc ccc gcc tcc tcc tgg gtg gac gac ttc atc gac tgg cta      2880
Leu Ala Ile Pro Ala Ser Ser Trp Val Asp Asp Phe Ile Asp Trp Leu
945             950             955             960 acc ccg tcc tcc tgc tgc cgc ctt tac atc ctc ggc ccc aat aag gac      2928
Thr Pro Ser Ser Cys Cys Arg Leu Tyr Ile Leu Gly Pro Asn Lys Asp
            965             970             975 gag ttc tgc ccc tcc aca gtc aac tcc ttg aac tgc ctg agg aat tgc      2976
Glu Phe Cys Pro Ser Thr Val Asn Ser Leu Asn Cys Leu Arg Asn Cys
        980             985             990 atg agc ttg acg ctg ggc cct gtg cgg ccc tcg gtg gag cag ttc cac      3024
Met Ser Leu Thr Leu Gly Pro Val Arg Pro Ser Val Glu Gln Phe His
    995             1000            1005 aag tac ctg ccc tgg ttt ctg aat gac ccc ccc aac atc cga tgt           3069
Lys Tyr Leu Pro Trp Phe Leu Asn Asp Pro Pro Asn Ile Arg Cys
1010            1015            1020 ccc aag ggt ggc ctg gcg gcg tac agc acc tct gtg aac ctg agc           3114
Pro Lys Gly Gly Leu Ala Ala Tyr Ser Thr Ser Val Asn Leu Ser
    1025            1030            1035 gcc gat ggc cag att gta gcc acc cgc ttc atg gcc tac cac aag           3159
Ala Asp Gly Gln Ile Val Ala Thr Arg Phe Met Ala Tyr His Lys
1040            1045            1050 ccg ctg aag aac tcg cag gac tac acc gag gcc ctg cgg gcg tcg           3204
Pro Leu Lys Asn Ser Gln Asp Tyr Thr Glu Ala Leu Arg Ala Ser
    1055            1060            1065 cgg gag ctg gcg gcc aac atc acc gcg agc ctg cgg cag gtg ccg           3249
Arg Glu Leu Ala Ala Asn Ile Thr Ala Ser Leu Arg Gln Val Pro
1070            1075            1080
```

```
ggc acg gac ccc gcc ttc gag gtc ttc ccc tac acg atc tcc aac        3294
Gly Thr Asp Pro Ala Phe Glu Val Phe Pro Tyr Thr Ile Ser Asn
       1085                1090                1095 gtg ttc tac gag cag tac ctg acc gtg ctc ccg gag ggg ctc gcc        3339
Val Phe Tyr Glu Gln Tyr Leu Thr Val Leu Pro Glu Gly Leu Ala
   1100                1105                1110 acg ctc ggc ctc tgc ctc gtc ccc acc ttc gtc gtc tgc tgc ctc        3384
Thr Leu Gly Leu Cys Leu Val Pro Thr Phe Val Val Cys Cys Leu
       1115                1120                1125 ctg ctg ggc ctg gac ctg cgc tcc ggc ctc ctc aac ctg ctg acc        3429
Leu Leu Gly Leu Asp Leu Arg Ser Gly Leu Leu Asn Leu Leu Thr
   1130                1135                1140 atc gtc atg att ctc gtg gac acc gtg ggc ctc atg acg ctg tgg        3474
Ile Val Met Ile Leu Val Asp Thr Val Gly Leu Met Thr Leu Trp
       1145                1150                1155 agc atc agc tac aac gcc gtg tcc ctc atc aat ctg gtc acg gcg        3519
Ser Ile Ser Tyr Asn Ala Val Ser Leu Ile Asn Leu Val Thr Ala
   1160                1165                1170 gtg ggc atg tcc gtg gag ttc gtg tcc cac atc acc cgc tcc ttt        3564
Val Gly Met Ser Val Glu Phe Val Ser His Ile Thr Arg Ser Phe
       1175                1180                1185 gcc gtc agc acc aag ccc agc cgg ctg gag aga gcc aag gag gcc        3609
Ala Val Ser Thr Lys Pro Ser Arg Leu Glu Arg Ala Lys Glu Ala
   1190                1195                1200 acc atc tcc atg ggc agt gcg gtg ttt gca ggg gtg gcc atg acc        3654
Thr Ile Ser Met Gly Ser Ala Val Phe Ala Gly Val Ala Met Thr
       1205                1210                1215 aac ctg ccg ggc atc ctc atc ctg ggc ctc gcc aag gcc cag ctc        3699
Asn Leu Pro Gly Ile Leu Ile Leu Gly Leu Ala Lys Ala Gln Leu
   1220                1225                1230 atc cag atc ttc ttc ttc cgc ctc aac ctc ctc atc acc ctg ctg        3744
Ile Gln Ile Phe Phe Phe Arg Leu Asn Leu Leu Ile Thr Leu Leu
       1235                1240                1245 ggg ctg ctg cac ggc ctg gtc ttc ctg ccc gtc atc ctc agc tac        3789
Gly Leu Leu His Gly Leu Val Phe Leu Pro Val Ile Leu Ser Tyr
   1250                1255                1260 ctt ggg cct gac gtc aac ccg gct ctg gtt gct ctg gag cgg acg        3834
Leu Gly Pro Asp Val Asn Pro Ala Leu Val Ala Leu Glu Arg Thr
       1265                1270                1275 cga gcc cag gag gcg gct gac gct gcg gcg ggc tcc tgc cca aat        3879
Arg Ala Gln Glu Ala Ala Asp Ala Ala Ala Gly Ser Cys Pro Asn
   1280                1285                1290 cac ccc gac cct acc tcc aac atc tac gtc aac tcc ggc ttt gac        3924
His Pro Asp Pro Thr Ser Asn Ile Tyr Val Asn Ser Gly Phe Asp
       1295                1300                1305 gag gca gcc agg gat gtc ggc agc tct gcc ccc acc aga aag cag        3969
Glu Ala Ala Arg Asp Val Gly Ser Ser Ala Pro Thr Arg Lys Gln
   1310                1315                1320 aag ttc tga                                                         3978
Lys Phe
    1325

<210> SEQ ID NO 4
<211> LENGTH: 1325
<212> TYPE: PRT
<213> ORGANISM: Oryctolagus sp.

<400> SEQUENCE: 4

Met Ala Gly Ala Ala Arg Gly Trp Leu Leu Trp Ala Leu Leu Leu His
1               5                   10                  15
```

-continued

```
Gln Ala Gln Ala Glu Leu Tyr Thr Pro Val His Gln Ala Gly Tyr Cys
         20                  25                  30
Ala Phe Tyr Glu Glu Cys Gly Lys Asn Pro Glu Leu Ser Gly Gly Leu
         35                  40                  45
Thr Ser Leu Ser Asn Val Ser Cys Leu Ser Asn Thr Pro Ala Arg His
 50                  55                  60
Val Thr Gly Asp His Leu Ala Leu Leu Glu Arg Ile Cys Pro Arg Leu
 65                  70                  75                  80
Tyr Asn Gly Pro Asn Thr Thr Tyr Ala Cys Cys Ser Pro Arg Gln Leu
                 85                  90                  95
Val Ser Leu Glu Thr Ser Met Ser Val Thr Lys Ala Leu Leu Thr Arg
            100                 105                 110
Cys Pro Ala Cys Ser Asp Asn Phe Val Ser Leu His Cys Gln Asn Thr
            115                 120                 125
Cys Ser Pro Asp Gln Ser Leu Phe Ile Asn Val Thr Arg Val Val Ser
130                 135                 140
Gln Gly Ala Gly Gln Leu Gln Ala Val Val Ala Tyr Glu Ala Tyr Tyr
145                 150                 155                 160
Glu Arg Ser Phe Ala Glu Arg Ala Tyr Glu Ser Cys Ser Arg Val Arg
                165                 170                 175
Ile Pro Ala Ala Ala Thr Leu Ala Val Gly Ser Met Cys Gly Val Tyr
            180                 185                 190
Gly Ser Ala Leu Cys Asn Ala Gln Arg Trp Leu Asn Phe Gln Gly Asp
            195                 200                 205
Thr Ser Asn Gly Leu Ala Pro Leu Asp Ile Thr Phe His Leu Arg Glu
210                 215                 220
Pro Gly Gln Ala Pro Gly Ser Gly Met Gln Leu Leu Asn Ala Glu Ile
225                 230                 235                 240
Ala Pro Cys Asn Glu Ser Gln Asp Ser Ala Ala Cys Ser Cys Gln
                245                 250                 255
Asp Cys Ala Ala Ser Cys Pro Ala Ile Thr Gln Pro Glu Ala Leu Asp
            260                 265                 270
Ser Ser Phe Arg Ile Gly Arg Val Arg Gly Val Ala Leu Val Val
            275                 280                 285
Ile Leu Cys Ser Thr Leu Gly Val Leu Leu Gly Leu Val Cys Ala
290                 295                 300
Arg Arg Tyr Ser Ala Lys Ala Arg Gly Thr Ala Thr Ala Pro Thr Ala
305                 310                 315                 320
Cys Ser Arg Leu Ser His Arg Ile Ser Leu Ser Ile His Thr Phe Leu
                325                 330                 335
His Arg Leu Phe Gln Cys Trp Gly Thr Trp Val Ala Ser Trp Pro Leu
            340                 345                 350
Thr Ile Leu Ala Val Ser Ile Ala Val Val Val Ser Leu Ala Cys Gly
            355                 360                 365
Leu Ala Phe Thr Glu Leu Thr Thr Asp Pro Val Glu Leu Trp Ser Ala
            370                 375                 380
Pro Asn Ser Gln Ala Arg Ser Glu Lys Ala Phe His Asp Gln His Phe
385                 390                 395                 400
Gly Pro Phe Phe Arg Thr Asn Gln Val Ile Leu Thr Ala Pro Thr Arg
                405                 410                 415
Ser Arg Tyr Thr Tyr Asn Ser Leu Leu Leu Gly Pro Arg Asn Phe Ser
            420                 425                 430
Gly Ile Leu Ala Met Asp Leu Leu Leu Glu Leu Leu Glu Leu Gln Glu
            435                 440                 445
```

```
Arg Leu Arg Ala Leu Gln Val Trp Ser Pro Glu Ala Gln Arg Asn Val
    450                 455                 460

Ser Leu Arg Asp Val Cys Tyr Ala Pro Leu Asn Pro His Asn Ala Ser
465                 470                 475                 480

Leu Thr Asp Cys Cys Ile Asn Ser Leu Leu Gln Tyr Phe Gln Asn Asn
                485                 490                 495

Arg Thr Leu Leu Gln Leu Thr Ala Asn Gln Thr Leu Leu Gly Gln Thr
            500                 505                 510

Ala Gln Val Asp Trp Arg Asp His Phe Leu Tyr Cys Ala Asn Ala Pro
        515                 520                 525

Leu Thr Phe Gln Asp Gly Thr Ala Leu Ser Leu Ser Cys Met Ala Asp
    530                 535                 540

Tyr Gly Ala Pro Val Phe Pro Phe Leu Ala Val Gly Gly Tyr Glu Gly
545                 550                 555                 560

Glu Asp Tyr Ser Asp Ala Glu Ala Leu Ile Leu Thr Phe Ser Leu Asn
                565                 570                 575

Asn Tyr Pro Ala Gly Asp Pro Arg Leu Ala Gln Val Lys Leu Trp Glu
            580                 585                 590

Glu Ala Phe Val Lys Glu Met Arg Ala Leu Gln Leu Gly Lys Ser Ser
        595                 600                 605

Lys Phe Gln Val Thr Phe Met Ala Glu Arg Ser Leu Glu Asp Glu Ile
    610                 615                 620

Asn Arg Thr Thr Ala Glu Asp Leu Pro Ile Phe Ala Ile Ser Tyr Ile
625                 630                 635                 640

Val Thr Phe Leu Tyr Ile Ala Leu Ala Leu Gly Arg Tyr Ser Ser Trp
                645                 650                 655

Arg Arg Leu Pro Val Asp Ser Lys Ile Thr Leu Gly Leu Gly Gly Val
            660                 665                 670

Val Met Val Leu Ser Ala Val Met Ala Ser Met Gly Phe Phe Ser Tyr
        675                 680                 685

Leu Gly Ile Pro Ser Ser Leu Ile Ile Leu Gln Val Val Pro Phe Leu
    690                 695                 700

Val Leu Ala Val Gly Ala Asp Asn Ile Phe Ile Leu Val Leu Glu Tyr
705                 710                 715                 720

Gln Arg Leu Pro Arg Arg Pro Glu Glu Ser Arg Glu Ala His Ile Gly
                725                 730                 735

Arg Ala Leu Gly Arg Val Ala Pro Ser Met Leu Leu Cys Ser Leu Ser
            740                 745                 750

Glu Thr Ile Cys Phe Phe Leu Gly Ala Leu Thr Pro Met Pro Ala Val
        755                 760                 765

Arg Thr Phe Ala Leu Thr Ser Gly Leu Ala Val Gln Leu Asp Phe Leu
    770                 775                 780

Leu Gln Met Thr Ala Phe Val Ala Leu Leu Ser Leu Asp Ser Lys Arg
785                 790                 795                 800

Gln Glu Ala Ser Arg Pro Asp Val Cys Cys Cys Leu Glu Pro Arg Lys
                805                 810                 815

Leu Pro Ser Gln Gln Ser Glu Gly Leu Leu Leu Cys Phe Phe Arg
            820                 825                 830

Lys Val Tyr Ala Pro Leu Leu His Lys Val Thr Arg Val Val Val
        835                 840                 845

Leu Leu Leu Phe Leu Phe Leu Phe Gly Ser Ser Leu Tyr Phe Met Cys
850                 855                 860

Gln Val Thr Val Gly Leu Asp Gln Glu Leu Ala Leu Pro Lys Asp Ser
```

```
                865               870                875                880
Tyr Leu Ile Asp Tyr Phe Leu Phe Leu Asn Arg Tyr Phe Glu Val Gly
                    885                890                895

Ala Pro Val Tyr Phe Val Thr Thr Ser Gly Tyr Asn Phe Ser Ser Glu
                900                905                910

Ala Gly Met Asn Ala Ile Cys Ser Ser Ala Gly Cys Asp Ser Phe Ser
                915                920                925

Leu Thr Gln Lys Ile Gln Tyr Ala Thr Glu Phe Pro Glu Gln Ser Tyr
            930                935                940

Leu Ala Ile Pro Ala Ser Ser Trp Val Asp Asp Phe Ile Asp Trp Leu
945                950                955                960

Thr Pro Ser Ser Cys Cys Arg Leu Tyr Ile Leu Gly Pro Asn Lys Asp
                965                970                975

Glu Phe Cys Pro Ser Thr Val Asn Ser Leu Asn Cys Leu Arg Asn Cys
                980                985                990

Met Ser Leu Thr Leu Gly Pro Val  Arg Pro Ser Val Glu  Gln Phe His
                995               1000                1005

Lys Tyr  Leu Pro Trp Phe Leu  Asn Asp Pro Pro Asn  Ile Arg Cys
    1010                1015                1020

Pro Lys  Gly Gly Leu Ala Ala  Tyr Ser Thr Ser Val  Asn Leu Ser
    1025                1030                1035

Ala Asp  Gly Gln Ile Val Ala  Thr Arg Phe Met Ala  Tyr His Lys
    1040                1045                1050

Pro Leu  Lys Asn Ser Gln Asp  Tyr Thr Glu Ala Leu  Arg Ala Ser
    1055                1060                1065

Arg Glu  Leu Ala Ala Asn Ile  Thr Ala Ser Leu Arg  Gln Val Pro
    1070                1075                1080

Gly Thr  Asp Pro Ala Phe Glu  Val Phe Pro Tyr Thr  Ile Ser Asn
    1085                1090                1095

Val Phe  Tyr Glu Gln Tyr Leu  Thr Val Leu Pro Glu  Gly Leu Ala
    1100                1105                1110

Thr Leu  Gly Leu Cys Leu Val  Pro Thr Phe Val Val  Cys Cys Leu
    1115                1120                1125

Leu Leu  Gly Leu Asp Leu Arg  Ser Gly Leu Leu Asn  Leu Leu Thr
    1130                1135                1140

Ile Val  Met Ile Leu Val Asp  Thr Val Gly Leu Met  Thr Leu Trp
    1145                1150                1155

Ser Ile  Ser Tyr Asn Ala Val  Ser Leu Ile Asn Leu  Val Thr Ala
    1160                1165                1170

Val Gly  Met Ser Val Glu Phe  Val Ser His Ile Thr  Arg Ser Phe
    1175                1180                1185

Ala Val  Ser Thr Lys Pro Ser  Arg Leu Glu Arg Ala  Lys Glu Ala
    1190                1195                1200

Thr Ile  Ser Met Gly Ser Ala  Val Phe Ala Gly Val  Ala Met Thr
    1205                1210                1215

Asn Leu  Pro Gly Ile Leu Ile  Leu Gly Leu Ala Lys  Ala Gln Leu
    1220                1225                1230

Ile Gln  Ile Phe Phe Phe Arg  Leu Asn Leu Leu Ile  Thr Leu Leu
    1235                1240                1245

Gly Leu  Leu His Gly Leu Val  Phe Leu Pro Val Ile  Leu Ser Tyr
    1250                1255                1260

Leu Gly  Pro Asp Val Asn Pro  Ala Leu Val Ala Leu  Glu Arg Thr
    1265                1270                1275
```

```
Arg Ala Gln Glu Ala Ala Asp Ala Ala Ala Gly Ser Cys Pro Asn
    1280            1285                1290

His Pro Asp Pro Thr Ser Asn Ile Tyr Val Asn Ser Gly Phe Asp
    1295                1300                1305

Glu Ala Ala Arg Asp Val Gly Ser Ser Ala Pro Thr Arg Lys Gln
    1310                1315                1320

Lys Phe
    1325

<210> SEQ ID NO 5
<211> LENGTH: 3987
<212> TYPE: DNA
<213> ORGANISM: hamster
<220> FEATURE:
<221> NAME/KEY: CDS
<222> LOCATION: (1)..(3987)

<400> SEQUENCE: 5
```

| | | | | | | | | | | | | | | | |
|---|---|---|---|---|---|---|---|---|---|---|---|---|---|---|---|
| atg | gca | gct | ggc | cta | cag | aga | tgg | ctg | ctc | tgg | gcc | cta | ctc | ctg | aat | 48 |
| Met | Ala | Ala | Gly | Leu | Gln | Arg | Trp | Leu | Leu | Trp | Ala | Leu | Leu | Leu | Asn | |
| 1 | | | | 5 | | | | | 10 | | | | | 15 | | |

```
gcg gcc cgg ggt gag ata cac aca ccc att cat aaa gct ggc gtc tgt      96
Ala Ala Arg Gly Glu Ile His Thr Pro Ile His Lys Ala Gly Val Cys
            20                  25                  30 acc ttc tat gaa gag tgt ggg aag aac cca gag ctg tcc gga ggc ctc      144
Thr Phe Tyr Glu Glu Cys Gly Lys Asn Pro Glu Leu Ser Gly Gly Leu
        35                  40                  45 acg tca ctg tcc aat gta tct tgc ctg tct aac acc cca gcc cgc cgt      192
Thr Ser Leu Ser Asn Val Ser Cys Leu Ser Asn Thr Pro Ala Arg Arg
50                  55                  60 gtc aca ggt gac cac ctg acc ctc ctt cag cgc atc tgc ccc cgc ctg      240
Val Thr Gly Asp His Leu Thr Leu Leu Gln Arg Ile Cys Pro Arg Leu
65                  70                  75                  80 tac aat ggc ccc aac aat acc tat gct tgt tgc tcc gcc cag cag cta      288
Tyr Asn Gly Pro Asn Asn Thr Tyr Ala Cys Cys Ser Ala Gln Gln Leu
                85                  90                  95 gtg gca tta gaa aag agc atg tct atc acc aag gcc ctc ctc acc cgc      336
Val Ala Leu Glu Lys Ser Met Ser Ile Thr Lys Ala Leu Leu Thr Arg
            100                 105                 110 tgc cca gcc tgc tct gac aat ttt gtg agc ttg cac tgc cac aac acc      384
Cys Pro Ala Cys Ser Asp Asn Phe Val Ser Leu His Cys His Asn Thr
        115                 120                 125 tgc agc cct gac cag agc ctc ttc atc aat gtc acc cgt gtg gtt gag      432
Cys Ser Pro Asp Gln Ser Leu Phe Ile Asn Val Thr Arg Val Val Glu
    130                 135                 140 cag gcg gac cct cag cag cct cca gct gtg gtg gcc tat gaa gcc ttt      480
Gln Ala Asp Pro Gln Gln Pro Pro Ala Val Val Ala Tyr Glu Ala Phe
145                 150                 155                 160 tac cag agc agc ttt gca gag aag gcc tat gag tcc tgt agc cgg gta      528
Tyr Gln Ser Ser Phe Ala Glu Lys Ala Tyr Glu Ser Cys Ser Arg Val
                165                 170                 175 cgc atc ccc gcg gct gcc tca ctg gct gtg ggc acc atg tgt ggg gtg      576
Arg Ile Pro Ala Ala Ala Ser Leu Ala Val Gly Thr Met Cys Gly Val
            180                 185                 190 tat ggc tct gcc ctg tgc aat gcc caa cgc tgg ctc aac ttc cag gga      624
Tyr Gly Ser Ala Leu Cys Asn Ala Gln Arg Trp Leu Asn Phe Gln Gly
        195                 200                 205 gac aca ggg aac ggc ctg gct cct ctc gac atc acc ttc cac ctc gtg      672
Asp Thr Gly Asn Gly Leu Ala Pro Leu Asp Ile Thr Phe His Leu Val
    210                 215                 220 gag tcc ggc cag gcc ctg cca gat ggg atg cag cct ctg aat ggg gag      720
```

| | | | | | | | | | | | | | | | | |
|---|---|---|---|---|---|---|---|---|---|---|---|---|---|---|---|---|
| Glu | Ser | Gly | Gln | Ala | Leu | Pro | Asp | Gly | Met | Gln | Pro | Leu | Asn | Gly | Glu | |
| 225 | | | | 230 | | | | 235 | | | | 240 | | | | |

| atc | acg | ccc | tgc | aat | cag | tcg | gag | ggt | gta | gag | tcg | gct | gcc | tgt | tcc | 768 |
|---|---|---|---|---|---|---|---|---|---|---|---|---|---|---|---|---|
| Ile | Thr | Pro | Cys | Asn | Gln | Ser | Glu | Gly | Val | Glu | Ser | Ala | Ala | Cys | Ser | |
| | | | | 245 | | | | | 250 | | | | | 255 | | |

| tgc | cag | gac | tgt | gca | gcg | tct | tgc | cct | gtc | att | ccg | cag | ccc | tca | gcc | 816 |
|---|---|---|---|---|---|---|---|---|---|---|---|---|---|---|---|---|
| Cys | Gln | Asp | Cys | Ala | Ala | Ser | Cys | Pro | Val | Ile | Pro | Gln | Pro | Ser | Ala | |
| | | | 260 | | | | | 265 | | | | | 270 | | | |

| ctg | ccc | cct | tcc | ttc | tac | atg | ggt | aaa | atg | cct | ggc | tgg | ctg | gct | ctc | 864 |
|---|---|---|---|---|---|---|---|---|---|---|---|---|---|---|---|---|
| Leu | Pro | Pro | Ser | Phe | Tyr | Met | Gly | Lys | Met | Pro | Gly | Trp | Leu | Ala | Leu | |
| | | 275 | | | | | 280 | | | | | 285 | | | | |

| atc | atc | atc | ttc | tgt | gcg | gtc | ttc | gtg | ctg | ctc | aca | gct | gtc | ctt | ata | 912 |
|---|---|---|---|---|---|---|---|---|---|---|---|---|---|---|---|---|
| Ile | Ile | Ile | Phe | Cys | Ala | Val | Phe | Val | Leu | Leu | Thr | Ala | Val | Leu | Ile | |
| | 290 | | | | | 295 | | | | | 300 | | | | | |

| tat | ctt | cga | gtg | gtt | tcc | aat | agg | agc | agg | agc | aag | aaa | aca | ggc | ctc | 960 |
|---|---|---|---|---|---|---|---|---|---|---|---|---|---|---|---|---|
| Tyr | Leu | Arg | Val | Val | Ser | Asn | Arg | Ser | Arg | Ser | Lys | Lys | Thr | Gly | Leu | |
| 305 | | | | | 310 | | | | | 315 | | | | | 320 | |

| cag | gaa | gcc | ccg | aac | cgc | cct | cct | aag | cgc | aga | ttc | tca | cct | cac | atc | 1008 |
|---|---|---|---|---|---|---|---|---|---|---|---|---|---|---|---|---|
| Gln | Glu | Ala | Pro | Asn | Arg | Pro | Pro | Lys | Arg | Arg | Phe | Ser | Pro | His | Ile | |
| | | | | 325 | | | | | 330 | | | | | 335 | | |

| gtc | ctt | ggc | cgg | ttt | ttc | cag | agc | tgg | ggc | aca | aga | gtg | gcc | tca | tgg | 1056 |
|---|---|---|---|---|---|---|---|---|---|---|---|---|---|---|---|---|
| Val | Leu | Gly | Arg | Phe | Phe | Gln | Ser | Trp | Gly | Thr | Arg | Val | Ala | Ser | Trp | |
| | | | 340 | | | | | 345 | | | | | 350 | | | |

| cca | ctc | act | gtc | ttg | gcg | ctg | tcc | ttt | atg | gtt | gtg | ata | gcc | ttg | tca | 1104 |
|---|---|---|---|---|---|---|---|---|---|---|---|---|---|---|---|---|
| Pro | Leu | Thr | Val | Leu | Ala | Leu | Ser | Phe | Met | Val | Val | Ile | Ala | Leu | Ser | |
| | | 355 | | | | | 360 | | | | | 365 | | | | |

| gtg | ggc | atg | acc | tac | ata | gaa | ctc | acc | aca | gac | cct | gtg | gaa | ctg | tgg | 1152 |
|---|---|---|---|---|---|---|---|---|---|---|---|---|---|---|---|---|
| Val | Gly | Met | Thr | Tyr | Ile | Glu | Leu | Thr | Thr | Asp | Pro | Val | Glu | Leu | Trp | |
| | 370 | | | | | 375 | | | | | 380 | | | | | |

| tca | gcc | ccc | aaa | agc | caa | gct | cgg | aaa | gag | aag | gct | ttc | cac | gac | gag | 1200 |
|---|---|---|---|---|---|---|---|---|---|---|---|---|---|---|---|---|
| Ser | Ala | Pro | Lys | Ser | Gln | Ala | Arg | Lys | Glu | Lys | Ala | Phe | His | Asp | Glu | |
| 385 | | | | | 390 | | | | | 395 | | | | | 400 | |

| cat | ttt | ggc | ccc | ttc | ttc | cga | acc | aac | cag | gtt | ttt | gtg | aca | gct | cgg | 1248 |
|---|---|---|---|---|---|---|---|---|---|---|---|---|---|---|---|---|
| His | Phe | Gly | Pro | Phe | Phe | Arg | Thr | Asn | Gln | Val | Phe | Val | Thr | Ala | Arg | |
| | | | | 405 | | | | | 410 | | | | | 415 | | |

| aac | agg | tcc | agc | tat | aga | tat | gac | tcc | ctg | ctg | cta | ggg | ccc | aag | aac | 1296 |
|---|---|---|---|---|---|---|---|---|---|---|---|---|---|---|---|---|
| Asn | Arg | Ser | Ser | Tyr | Arg | Tyr | Asp | Ser | Leu | Leu | Leu | Gly | Pro | Lys | Asn | |
| | | | 420 | | | | | 425 | | | | | 430 | | | |

| ttc | agt | ggg | ctc | ctg | tcc | ctg | gac | ctg | gtg | ctg | gag | ctg | ctg | gag | ctc | 1344 |
|---|---|---|---|---|---|---|---|---|---|---|---|---|---|---|---|---|
| Phe | Ser | Gly | Leu | Leu | Ser | Leu | Asp | Leu | Val | Leu | Glu | Leu | Leu | Glu | Leu | |
| | | 435 | | | | | 440 | | | | | 445 | | | | |

| caa | gag | agg | ctt | cga | cac | ctg | cag | gtg | tgg | tcc | cct | gag | gca | cag | cgc | 1392 |
|---|---|---|---|---|---|---|---|---|---|---|---|---|---|---|---|---|
| Gln | Glu | Arg | Leu | Arg | His | Leu | Gln | Val | Trp | Ser | Pro | Glu | Ala | Gln | Arg | |
| | 450 | | | | | 455 | | | | | 460 | | | | | |

| aac | atc | tcc | ctg | cag | gac | atc | tgc | tat | gcc | ccc | ctc | aaa | ccg | cac | aac | 1440 |
|---|---|---|---|---|---|---|---|---|---|---|---|---|---|---|---|---|
| Asn | Ile | Ser | Leu | Gln | Asp | Ile | Cys | Tyr | Ala | Pro | Leu | Lys | Pro | His | Asn | |
| 465 | | | | | 470 | | | | | 475 | | | | | 480 | |

| acc | agc | ctc | tcc | gac | tgc | tgt | gtc | aac | agt | ctc | ctt | cag | tac | ttc | cag | 1488 |
|---|---|---|---|---|---|---|---|---|---|---|---|---|---|---|---|---|
| Thr | Ser | Leu | Ser | Asp | Cys | Cys | Val | Asn | Ser | Leu | Leu | Gln | Tyr | Phe | Gln | |
| | | | | 485 | | | | | 490 | | | | | 495 | | |

| aac | aac | cgc | acg | ctc | ctg | ctc | aca | gcc | aac | cag | acg | ctc | aat | ggc | 1536 |
|---|---|---|---|---|---|---|---|---|---|---|---|---|---|---|---|
| Asn | Asn | Arg | Thr | Leu | Leu | Leu | Thr | Ala | Asn | Gln | Thr | Leu | Asn | Gly | |
| | | | 500 | | | | | 505 | | | | | 510 | | |

| cag | act | tcc | ctg | gtg | gac | tgg | agg | gac | cac | ttc | ctc | tac | tgt | gca | aat | 1584 |
|---|---|---|---|---|---|---|---|---|---|---|---|---|---|---|---|---|
| Gln | Thr | Ser | Leu | Val | Asp | Trp | Arg | Asp | His | Phe | Leu | Tyr | Cys | Ala | Asn | |
| | | 515 | | | | | 520 | | | | | 525 | | | | |

| gcg | cct | ctc | acg | ttc | aaa | gac | ggc | acg | tct | ctg | gcc | ctg | agc | tgc | atc | 1632 |
|---|---|---|---|---|---|---|---|---|---|---|---|---|---|---|---|---|
| Ala | Pro | Leu | Thr | Phe | Lys | Asp | Gly | Thr | Ser | Leu | Ala | Leu | Ser | Cys | Ile | |
| | 530 | | | | | 535 | | | | | 540 | | | | | |

| gcg | gac | tat | ggg | gcc | cct | atc | ttc | ccc | ttc | ctt | gct | gtc | ggg | ggg | tac | 1680 |

```
                            -continued
Ala Asp Tyr Gly Ala Pro Ile Phe Pro Phe Leu Ala Val Gly Gly Tyr
545                 550                 555                 560 caa ggg acg gac tac tct gag gca gag gcg ctg atc ata act ttc tct      1728
Gln Gly Thr Asp Tyr Ser Glu Ala Glu Ala Leu Ile Ile Thr Phe Ser
            565                 570                 575 ctc aat aac tac cct gct gat gat ccc cgc atg gcc cag gcc aag ctc      1776
Leu Asn Asn Tyr Pro Ala Asp Asp Pro Arg Met Ala Gln Ala Lys Leu
        580                 585                 590 tgg gag gag gct ttt ctg aag gaa atg caa gcc ttc cag agc agt gtg      1824
Trp Glu Glu Ala Phe Leu Lys Glu Met Gln Ala Phe Gln Ser Ser Val
    595                 600                 605 gct gac aag ttc cag gtt gca ttc tca gct gag cgc tct ctg gag gat      1872
Ala Asp Lys Phe Gln Val Ala Phe Ser Ala Glu Arg Ser Leu Glu Asp
610                 615                 620 gag atc aac cgc acc acc atc cag gac ctg cct gtc ttc gcc atc agc      1920
Glu Ile Asn Arg Thr Thr Ile Gln Asp Leu Pro Val Phe Ala Ile Ser
625                 630                 635                 640 tac att atc gtc ttc ctg tac atc tct ctg gcc ctg ggc agc tac tcc      1968
Tyr Ile Ile Val Phe Leu Tyr Ile Ser Leu Ala Leu Gly Ser Tyr Ser
                645                 650                 655 aaa tgg aag cga gta gcg gtg gat tcc aag gct act ctg ggc ctc ggt      2016
Lys Trp Lys Arg Val Ala Val Asp Ser Lys Ala Thr Leu Gly Leu Gly
            660                 665                 670 ggg gtg gct gtc gtg ctg gga gca gtc gtg gct gcc atg ggt ttc tac      2064
Gly Val Ala Val Val Leu Gly Ala Val Val Ala Ala Met Gly Phe Tyr
        675                 680                 685 tcc tac ctg ggt gtt ccc tcc tca ctg gtt atc atc caa gtg gtg cct      2112
Ser Tyr Leu Gly Val Pro Ser Ser Leu Val Ile Ile Gln Val Val Pro
    690                 695                 700 ttc ctg gtg ctg gcc gtg gga gct gac aac atc ttc atc ttt gtt ctt      2160
Phe Leu Val Leu Ala Val Gly Ala Asp Asn Ile Phe Ile Phe Val Leu
705                 710                 715                 720 gag tac cag agg ctg cct agg agg cct ggg gag cag cga gag gcc cac      2208
Glu Tyr Gln Arg Leu Pro Arg Arg Pro Gly Glu Gln Arg Glu Ala His
                725                 730                 735 atc ggc cgt acc ctg ggc agt gtg gcc ccc agc atg ctg ctg tgc agc      2256
Ile Gly Arg Thr Leu Gly Ser Val Ala Pro Ser Met Leu Leu Cys Ser
            740                 745                 750 ctc tct gag gct gtc tgc ttt ttt cta ggg gcc ctg acc ccc atg cca      2304
Leu Ser Glu Ala Val Cys Phe Phe Leu Gly Ala Leu Thr Pro Met Pro
        755                 760                 765 gct gtg agg acc ttt gcc ttg acc gct ggc ctt tcg att atc ctc gac      2352
Ala Val Arg Thr Phe Ala Leu Thr Ala Gly Leu Ser Ile Ile Leu Asp
    770                 775                 780 ttc ctg ctc cag atg act gcc ttc gtg gcc ctg ctc tcc ctg gat agc      2400
Phe Leu Leu Gln Met Thr Ala Phe Val Ala Leu Leu Ser Leu Asp Ser
785                 790                 795                 800 aag agg cag gag gcc tct cgc ccc gac atc tta tgc tgt ctt tca ccc      2448
Lys Arg Gln Glu Ala Ser Arg Pro Asp Ile Leu Cys Cys Leu Ser Pro
                805                 810                 815 cgg aaa cta ccc cca cct gaa cag caa gag ggg ctc tta ctc cgc ttc      2496
Arg Lys Leu Pro Pro Pro Glu Gln Gln Glu Gly Leu Leu Leu Arg Phe
            820                 825                 830 ttc aga aag ata tat gct ccc ttc ctg ctg cac agg ttc atc cgc cct      2544
Phe Arg Lys Ile Tyr Ala Pro Phe Leu Leu His Arg Phe Ile Arg Pro
        835                 840                 845 gtt gtg ctg ctg ctg ttt ctg gcc ctg ttt gga gca aat ctc tac tta      2592
Val Val Leu Leu Leu Phe Leu Ala Leu Phe Gly Ala Asn Leu Tyr Leu
    850                 855                 860 atg tgc cac atc agc gtg ggg ttg gac cag gag ctg gcc ctg cct aag      2640
```

```
        Met Cys His Ile Ser Val Gly Leu Asp Gln Glu Leu Ala Leu Pro Lys
        865                 870                 875                 880 gat tcc tac ttg att gac tac ttc ctc ttt ttg aac cga tac ttt gag    2688
Asp Ser Tyr Leu Ile Asp Tyr Phe Leu Phe Leu Asn Arg Tyr Phe Glu
                885                 890                 895 gtg ggg cct ccc gtg tac ttt gtc acc acc tcg ggt tac aac ttc tcc    2736
Val Gly Pro Pro Val Tyr Phe Val Thr Thr Ser Gly Tyr Asn Phe Ser
            900                 905                 910 agc gag gca ggc atg aat gcc att tgc tct agt gca ggc tgt gac agc    2784
Ser Glu Ala Gly Met Asn Ala Ile Cys Ser Ser Ala Gly Cys Asp Ser
            915                 920                 925 ttc tcc atg acc cag aag atc caa tat gcc act gaa ttc cct gag cag    2832
Phe Ser Met Thr Gln Lys Ile Gln Tyr Ala Thr Glu Phe Pro Glu Gln
        930                 935                 940 tct tac ata ggg att gct gca tcc tcc tgg gta gac gac ttc atc gac    2880
Ser Tyr Ile Gly Ile Ala Ala Ser Ser Trp Val Asp Asp Phe Ile Asp
945                 950                 955                 960 tgg ctg acc ccg tcc tcc tgc tgc cgc ctt tat atc ttt ggc ccc aat    2928
Trp Leu Thr Pro Ser Ser Cys Cys Arg Leu Tyr Ile Phe Gly Pro Asn
                965                 970                 975 acg ggt gac ttc tgt cct tca act gat act tcc ttg agc tgt cta aaa    2976
Thr Gly Asp Phe Cys Pro Ser Thr Asp Thr Ser Leu Ser Cys Leu Lys
            980                 985                 990 aac tgc atg aac ttc act ctg ggc  ccc gtg agg ccc aca  gca gaa cag  3024
Asn Cys Met Asn Phe Thr Leu Gly  Pro Val Arg Pro Thr  Ala Glu Gln
            995                  1000                 1005 ttt cac aag tat ctg ccc tgg  ttc ctg gac gat cca  ccc aac atc      3069
Phe His Lys Tyr Leu Pro Trp  Phe Leu Asp Asp Pro  Pro Asn Ile
    1010                1015                 1020 aga tgc ccc aaa ggg ggt ctg  gca gca tat aga act  tcc gtg aat      3114
Arg Cys Pro Lys Gly Gly Leu  Ala Ala Tyr Arg Thr  Ser Val Asn
    1025                1030                 1035 ttg agc tca gat ggc cag att  ata gcc tcc cag ttc  atg gcc tac      3159
Leu Ser Ser Asp Gly Gln Ile  Ile Ala Ser Gln Phe  Met Ala Tyr
    1040                1045                 1050 cac aag ccg ctc agg aac tca  cag gac ttc aca gaa  gct ctc cgg      3204
His Lys Pro Leu Arg Asn Ser  Gln Asp Phe Thr Glu  Ala Leu Arg
    1055                1060                 1065 aca tcc cga ttg ctg gca gcc  aac atc aca gct gaa  cta cgg aaa      3249
Thr Ser Arg Leu Leu Ala Ala  Asn Ile Thr Ala Glu  Leu Arg Lys
    1070                1075                 1080 gtg cct ggc aca gcc cca gac  ttt gag gtc ttc ccc  tac acg atc      3294
Val Pro Gly Thr Ala Pro Asp  Phe Glu Val Phe Pro  Tyr Thr Ile
    1085                1090                 1095 tcc aac gtg ttc tac gag cag  tac ctg act gtc ctc  ccc gag ggc      3339
Ser Asn Val Phe Tyr Glu Gln  Tyr Leu Thr Val Leu  Pro Glu Gly
    1100                1105                 1110 atc ttc aca ctg gct ctc tgc  ttc gtg ccc acc ttc  gtc gtc tgc      3384
Ile Phe Thr Leu Ala Leu Cys  Phe Val Pro Thr Phe  Val Val Cys
    1115                1120                 1125 tac ctc ctg ctg ggc ctg gac  atg cgc tca ggc atc  ctc aac ctg      3429
Tyr Leu Leu Leu Gly Leu Asp  Met Arg Ser Gly Ile  Leu Asn Leu
    1130                1135                 1140 ctc tcc atc atc atg atc ctt  gtg gac acc atc ggg  ctc atg gct      3474
Leu Ser Ile Ile Met Ile Leu  Val Asp Thr Ile Gly  Leu Met Ala
    1145                1150                 1155 gtg tgg ggc atc agc tac aat  gct gtg tcc ctc atc  aac ctt gtc      3519
Val Trp Gly Ile Ser Tyr Asn  Ala Val Ser Leu Ile  Asn Leu Val
    1160                1165                 1170 acg gca gtg gga atg tct gtg  gag ttc gtg tcc cac  ctc acc cgg      3564
```

-continued

```
Thr Ala Val Gly Met Ser Val Glu Phe Val Ser His Leu Thr Arg
1175             1180                 1185 tcc ttt gct gtc agc acc aag ccc acc cgg ctg gag agg gcc aag    3609
Ser Phe Ala Val Ser Thr Lys Pro Thr Arg Leu Glu Arg Ala Lys
1190             1195                 1200 gat gcc acc gtc tcc atg ggc agt gcg gtg ttt gct ggc gtg gcc    3654
Asp Ala Thr Val Ser Met Gly Ser Ala Val Phe Ala Gly Val Ala
1205             1210                 1215 atg acc aac ttc cca ggc atc ctc atc ctg ggc ttc gcc cag gcc    3699
Met Thr Asn Phe Pro Gly Ile Leu Ile Leu Gly Phe Ala Gln Ala
1220             1225                 1230 cag cta atc cag atc ttc ttc ttc cgc ctc aac ctc ctg atc acc    3744
Gln Leu Ile Gln Ile Phe Phe Phe Arg Leu Asn Leu Leu Ile Thr
1235             1240                 1245 ttg ctg ggc ctg ctg cac ggc ctg gtc ttc ctg ccg gtt gtc ctc    3789
Leu Leu Gly Leu Leu His Gly Leu Val Phe Leu Pro Val Val Leu
1250             1255                 1260 agc tat ctg gga ccc gat gtg aac cca gag ctg gtg ctg gag gag    3834
Ser Tyr Leu Gly Pro Asp Val Asn Pro Glu Leu Val Leu Glu Glu
1265             1270                 1275 aaa cta gct acg gag gca gcg gtg gcc cca gag cct tcc agc ccg    3879
Lys Leu Ala Thr Glu Ala Ala Val Ala Pro Glu Pro Ser Ser Pro
1280             1285                 1290 aag tac ccc ttc cct gat aat gac tat gtt aat cac agt ttt gag    3924
Lys Tyr Pro Phe Pro Asp Asn Asp Tyr Val Asn His Ser Phe Glu
1295             1300                 1305 gaa gcc acc cct gga gct gct gct gct agt agc tcc ttg cct aaa    3969
Glu Ala Thr Pro Gly Ala Ala Ala Ala Ser Ser Ser Leu Pro Lys
1310             1315                 1320 agc ggc caa aag ttt taa                                        3987
Ser Gly Gln Lys Phe
1325

<210> SEQ ID NO 6
<211> LENGTH: 1328
<212> TYPE: PRT
<213> ORGANISM: hamster

<400> SEQUENCE: 6

Met Ala Ala Gly Leu Gln Arg Trp Leu Leu Trp Ala Leu Leu Leu Asn
1               5                   10                  15

Ala Ala Arg Gly Glu Ile His Thr Pro Ile His Lys Ala Gly Val Cys
            20                  25                  30

Thr Phe Tyr Glu Glu Cys Gly Lys Asn Pro Glu Leu Ser Gly Gly Leu
        35                  40                  45

Thr Ser Leu Ser Asn Val Ser Cys Leu Ser Asn Thr Pro Ala Arg Arg
    50                  55                  60

Val Thr Gly Asp His Leu Thr Leu Leu Gln Arg Ile Cys Pro Arg Leu
65                  70                  75                  80

Tyr Asn Gly Pro Asn Asn Thr Tyr Ala Cys Cys Ser Ala Gln Gln Leu
                85                  90                  95

Val Ala Leu Glu Lys Ser Met Ser Ile Thr Lys Ala Leu Leu Thr Arg
            100                 105                 110

Cys Pro Ala Cys Ser Asp Asn Phe Val Ser Leu His Cys His Asn Thr
        115                 120                 125

Cys Ser Pro Asp Gln Ser Leu Phe Ile Asn Val Thr Arg Val Val Glu
    130                 135                 140

Gln Ala Asp Pro Gln Gln Pro Ala Val Val Ala Tyr Glu Ala Phe
145                 150                 155                 160
```

-continued

```
Tyr Gln Ser Ser Phe Ala Glu Lys Ala Tyr Glu Ser Cys Ser Arg Val
                165                 170                 175
Arg Ile Pro Ala Ala Ala Ser Leu Ala Val Gly Thr Met Cys Gly Val
                180                 185                 190
Tyr Gly Ser Ala Leu Cys Asn Ala Gln Arg Trp Leu Asn Phe Gln Gly
                195                 200                 205
Asp Thr Gly Asn Gly Leu Ala Pro Leu Asp Ile Thr Phe His Leu Val
                210                 215                 220
Glu Ser Gly Gln Ala Leu Pro Asp Gly Met Gln Pro Leu Asn Gly Glu
225                 230                 235                 240
Ile Thr Pro Cys Asn Gln Ser Glu Gly Val Glu Ser Ala Ala Cys Ser
                245                 250                 255
Cys Gln Asp Cys Ala Ala Ser Cys Pro Val Ile Pro Gln Pro Ser Ala
                260                 265                 270
Leu Pro Pro Ser Phe Tyr Met Gly Lys Met Pro Gly Trp Leu Ala Leu
                275                 280                 285
Ile Ile Ile Phe Cys Ala Val Phe Val Leu Leu Thr Ala Val Leu Ile
                290                 295                 300
Tyr Leu Arg Val Val Ser Asn Arg Ser Arg Ser Lys Lys Thr Gly Leu
305                 310                 315                 320
Gln Glu Ala Pro Asn Arg Pro Pro Lys Arg Arg Phe Ser Pro His Ile
                325                 330                 335
Val Leu Gly Arg Phe Phe Gln Ser Trp Gly Thr Arg Val Ala Ser Trp
                340                 345                 350
Pro Leu Thr Val Leu Ala Leu Ser Phe Met Val Val Ile Ala Leu Ser
                355                 360                 365
Val Gly Met Thr Tyr Ile Glu Leu Thr Thr Asp Pro Val Glu Leu Trp
                370                 375                 380
Ser Ala Pro Lys Ser Gln Ala Arg Lys Glu Lys Ala Phe His Asp Glu
385                 390                 395                 400
His Phe Gly Pro Phe Phe Arg Thr Asn Gln Val Phe Val Thr Ala Arg
                405                 410                 415
Asn Arg Ser Ser Tyr Arg Tyr Asp Ser Leu Leu Leu Gly Pro Lys Asn
                420                 425                 430
Phe Ser Gly Leu Leu Ser Leu Asp Leu Val Leu Glu Leu Leu Glu Leu
                435                 440                 445
Gln Glu Arg Leu Arg His Leu Gln Val Trp Ser Pro Glu Ala Gln Arg
450                 455                 460
Asn Ile Ser Leu Gln Asp Ile Cys Tyr Ala Pro Leu Lys Pro His Asn
465                 470                 475                 480
Thr Ser Leu Ser Asp Cys Cys Val Asn Ser Leu Leu Gln Tyr Phe Gln
                485                 490                 495
Asn Asn Arg Thr Leu Leu Leu Leu Thr Ala Asn Gln Thr Leu Asn Gly
                500                 505                 510
Gln Thr Ser Leu Val Asp Trp Arg Asp His Phe Leu Tyr Cys Ala Asn
                515                 520                 525
Ala Pro Leu Thr Phe Lys Asp Gly Thr Ser Leu Ala Leu Ser Cys Ile
                530                 535                 540
Ala Asp Tyr Gly Ala Pro Ile Phe Pro Phe Leu Ala Val Gly Gly Tyr
545                 550                 555                 560
Gln Gly Thr Asp Tyr Ser Glu Ala Glu Ala Leu Ile Ile Thr Phe Ser
                565                 570                 575
Leu Asn Asn Tyr Pro Ala Asp Asp Pro Arg Met Ala Gln Ala Lys Leu
```

```
              580             585             590
Trp Glu Glu Ala Phe Leu Lys Glu Met Gln Ala Phe Gln Ser Ser Val
            595                 600                 605

Ala Asp Lys Phe Gln Val Ala Phe Ser Ala Glu Arg Ser Leu Glu Asp
            610                 615                 620

Glu Ile Asn Arg Thr Thr Ile Gln Asp Leu Pro Val Phe Ala Ile Ser
625                 630                 635                 640

Tyr Ile Ile Val Phe Leu Tyr Ile Ser Leu Ala Leu Gly Ser Tyr Ser
                645                 650                 655

Lys Trp Lys Arg Val Ala Val Asp Ser Lys Ala Thr Leu Gly Leu Gly
                660                 665                 670

Gly Val Ala Val Leu Gly Ala Val Ala Ala Met Gly Phe Tyr
                675                 680                 685

Ser Tyr Leu Gly Val Pro Ser Ser Leu Val Ile Ile Gln Val Val Pro
            690                 695                 700

Phe Leu Val Leu Ala Val Gly Ala Asp Asn Ile Phe Ile Phe Val Leu
705                 710                 715                 720

Glu Tyr Gln Arg Leu Pro Arg Arg Pro Gly Glu Gln Arg Glu Ala His
                725                 730                 735

Ile Gly Arg Thr Leu Gly Ser Val Ala Pro Ser Met Leu Leu Cys Ser
                740                 745                 750

Leu Ser Glu Ala Val Cys Phe Phe Leu Gly Ala Leu Thr Pro Met Pro
            755                 760                 765

Ala Val Arg Thr Phe Ala Leu Thr Ala Gly Leu Ser Ile Ile Leu Asp
            770                 775                 780

Phe Leu Leu Gln Met Thr Ala Phe Val Ala Leu Leu Ser Leu Asp Ser
785                 790                 795                 800

Lys Arg Gln Glu Ala Ser Arg Pro Asp Ile Leu Cys Cys Leu Ser Pro
                805                 810                 815

Arg Lys Leu Pro Pro Pro Glu Gln Gln Glu Gly Leu Leu Leu Arg Phe
                820                 825                 830

Phe Arg Lys Ile Tyr Ala Pro Phe Leu Leu His Arg Phe Ile Arg Pro
            835                 840                 845

Val Val Leu Leu Leu Phe Leu Ala Leu Phe Gly Ala Asn Leu Tyr Leu
            850                 855                 860

Met Cys His Ile Ser Val Gly Leu Asp Gln Glu Leu Ala Leu Pro Lys
865                 870                 875                 880

Asp Ser Tyr Leu Ile Asp Tyr Phe Leu Phe Leu Asn Arg Tyr Phe Glu
                885                 890                 895

Val Gly Pro Pro Val Tyr Phe Val Thr Thr Ser Gly Tyr Asn Phe Ser
            900                 905                 910

Ser Glu Ala Gly Met Asn Ala Ile Cys Ser Ser Ala Gly Cys Asp Ser
            915                 920                 925

Phe Ser Met Thr Gln Lys Ile Gln Tyr Ala Thr Glu Phe Pro Glu Gln
            930                 935                 940

Ser Tyr Ile Gly Ile Ala Ala Ser Ser Trp Val Asp Asp Phe Ile Asp
945                 950                 955                 960

Trp Leu Thr Pro Ser Ser Cys Cys Arg Leu Tyr Ile Phe Gly Pro Asn
                965                 970                 975

Thr Gly Asp Phe Cys Pro Ser Thr Asp Thr Ser Leu Ser Cys Leu Lys
            980                 985                 990

Asn Cys Met Asn Phe Thr Leu Gly Pro Val Arg Pro Thr Ala Glu Gln
            995                 1000                1005
```

```
Phe His Lys Tyr Leu Pro Trp Phe Leu Asp Pro Pro Asn Ile
    1010                1015                1020

Arg Cys Pro Lys Gly Gly Leu Ala Ala Tyr Arg Thr Ser Val Asn
    1025                1030                1035

Leu Ser Ser Asp Gly Gln Ile Ile Ala Ser Gln Phe Met Ala Tyr
    1040                1045                1050

His Lys Pro Leu Arg Asn Ser Gln Asp Phe Thr Glu Ala Leu Arg
    1055                1060                1065

Thr Ser Arg Leu Leu Ala Ala Asn Ile Thr Ala Glu Leu Arg Lys
    1070                1075                1080

Val Pro Gly Thr Ala Pro Asp Phe Glu Val Phe Pro Tyr Thr Ile
    1085                1090                1095

Ser Asn Val Phe Tyr Glu Gln Tyr Leu Thr Val Leu Pro Glu Gly
    1100                1105                1110

Ile Phe Thr Leu Ala Leu Cys Phe Val Pro Thr Phe Val Val Cys
    1115                1120                1125

Tyr Leu Leu Leu Gly Leu Asp Met Arg Ser Gly Ile Leu Asn Leu
    1130                1135                1140

Leu Ser Ile Ile Met Ile Leu Val Asp Thr Ile Gly Leu Met Ala
    1145                1150                1155

Val Trp Gly Ile Ser Tyr Asn Ala Val Ser Leu Ile Asn Leu Val
    1160                1165                1170

Thr Ala Val Gly Met Ser Val Glu Phe Val Ser His Leu Thr Arg
    1175                1180                1185

Ser Phe Ala Val Ser Thr Lys Pro Thr Arg Leu Glu Arg Ala Lys
    1190                1195                1200

Asp Ala Thr Val Ser Met Gly Ser Ala Val Phe Ala Gly Val Ala
    1205                1210                1215

Met Thr Asn Phe Pro Gly Ile Leu Ile Leu Gly Phe Ala Gln Ala
    1220                1225                1230

Gln Leu Ile Gln Ile Phe Phe Phe Arg Leu Asn Leu Leu Ile Thr
    1235                1240                1245

Leu Leu Gly Leu Leu His Gly Leu Val Phe Leu Pro Val Val Leu
    1250                1255                1260

Ser Tyr Leu Gly Pro Asp Val Asn Pro Glu Leu Val Leu Glu Glu
    1265                1270                1275

Lys Leu Ala Thr Glu Ala Ala Val Ala Pro Glu Pro Ser Ser Pro
    1280                1285                1290

Lys Tyr Pro Phe Pro Asp Asn Asp Tyr Val Asn His Ser Phe Glu
    1295                1300                1305

Glu Ala Thr Pro Gly Ala Ala Ala Ala Ser Ser Ser Leu Pro Lys
    1310                1315                1320

Ser Gly Gln Lys Phe
    1325

<210> SEQ ID NO 7
<211> LENGTH: 3999
<212> TYPE: DNA
<213> ORGANISM: Macaca mulatta
<220> FEATURE:
<221> NAME/KEY: CDS
<222> LOCATION: (1)..(3999)

<400> SEQUENCE: 7 atg gcg gag gcc ggc ctg agg ggc tgg ctg ctg tgg gcc ctg ctc ctg     48
Met Ala Glu Ala Gly Leu Arg Gly Trp Leu Leu Trp Ala Leu Leu Leu
1               5                   10                  15
```

```
cac ttg gcc cag agc gag cct tac aca ccc atc cac cag cct ggc tac        96
His Leu Ala Gln Ser Glu Pro Tyr Thr Pro Ile His Gln Pro Gly Tyr
         20                  25                  30 tgc gcc ttc tat gac gaa tgt ggg aag aac cca gag ctg tct gga ggc       144
Cys Ala Phe Tyr Asp Glu Cys Gly Lys Asn Pro Glu Leu Ser Gly Gly
             35                  40                  45 ctc atg aca ctc tcc aac gtg tcc tgt ctg tcc aac acg cca gcc cgc       192
Leu Met Thr Leu Ser Asn Val Ser Cys Leu Ser Asn Thr Pro Ala Arg
 50                  55                  60 aac atc aca ggt gat cac ctg atc cta tta cag agg atc tgc ccc cgc       240
Asn Ile Thr Gly Asp His Leu Ile Leu Leu Gln Arg Ile Cys Pro Arg
 65                  70                  75                  80 ctc tac acc ggc ccc aac acc caa gcc tgc tgc tcc gcc aag cag ctg       288
Leu Tyr Thr Gly Pro Asn Thr Gln Ala Cys Cys Ser Ala Lys Gln Leu
             85                  90                  95 gta tca ttg gaa gcg agt ctg tcg atc acc aag gcc ctc ctc acc cgc       336
Val Ser Leu Glu Ala Ser Leu Ser Ile Thr Lys Ala Leu Leu Thr Arg
                100                 105                 110 tgc cca gcc tgc tct gac aat ttc gtg agc ctg cac tgc cac aac aca       384
Cys Pro Ala Cys Ser Asp Asn Phe Val Ser Leu His Cys His Asn Thr
            115                 120                 125 tgc agc ccc aac cag agc ctc ttc atc aat gtg acc cgc gtg gct cag       432
Cys Ser Pro Asn Gln Ser Leu Phe Ile Asn Val Thr Arg Val Ala Gln
130                 135                 140 cta ggg gct gga caa ctc cca gct gtg gtg gcc tat gag gcc ttc tac       480
Leu Gly Ala Gly Gln Leu Pro Ala Val Val Ala Tyr Glu Ala Phe Tyr
145                 150                 155                 160 cag cac agc ttt gcc gag cag agc tat gac tcc tgc agc cgt gtg cac       528
Gln His Ser Phe Ala Glu Gln Ser Tyr Asp Ser Cys Ser Arg Val His
            165                 170                 175 atc cct gcg gct gcc acg ctg gct gtg ggc agc atg tgt ggc gtg tat       576
Ile Pro Ala Ala Ala Thr Leu Ala Val Gly Ser Met Cys Gly Val Tyr
            180                 185                 190 ggc tct gcc ctt tgc aat gcc cag cgc tgg ctc aac ttc cag gga gac       624
Gly Ser Ala Leu Cys Asn Ala Gln Arg Trp Leu Asn Phe Gln Gly Asp
            195                 200                 205 aca ggc aat ggt ctg gcc cca ctg gac atc acc ttc cac ctc ttg gag       672
Thr Gly Asn Gly Leu Ala Pro Leu Asp Ile Thr Phe His Leu Leu Glu
210                 215                 220 ccc ggc cag gct gtg ggg agt ggg att cag cct ctg aat gag ggg gtt       720
Pro Gly Gln Ala Val Gly Ser Gly Ile Gln Pro Leu Asn Glu Gly Val
225                 230                 235                 240 gca cgt tgc aat gag tcc caa ggt gac gac gca gtg gcc tgc tcc tgc       768
Ala Arg Cys Asn Glu Ser Gln Gly Asp Asp Ala Val Ala Cys Ser Cys
                245                 250                 255 cag gac tgt gct gca tcc tgt cct gcc atc gcc cat ccc cag gcc ctg       816
Gln Asp Cys Ala Ala Ser Cys Pro Ala Ile Ala His Pro Gln Ala Leu
            260                 265                 270 gac tcc acc ttc cgc ctg ggc cgg atg ccg ggt ggg ctg gtc ctc atc       864
Asp Ser Thr Phe Arg Leu Gly Arg Met Pro Gly Gly Leu Val Leu Ile
            275                 280                 285 atc atc ctc tgt tct gtc ttc act gtg gtc gcc atc ctg ctc gtg gga       912
Ile Ile Leu Cys Ser Val Phe Thr Val Val Ala Ile Leu Leu Val Gly
        290                 295                 300 ctc cgt gtg gcc ccc acc agg gac aaa agc aag acg gtg gac ccc aag       960
Leu Arg Val Ala Pro Thr Arg Asp Lys Ser Lys Thr Val Asp Pro Lys
305                 310                 315                 320 aag ggc acc agc ctc tct gat aag ctc agc ttc tcc acc cac acc ctc      1008
Lys Gly Thr Ser Leu Ser Asp Lys Leu Ser Phe Ser Thr His Thr Leu
            325                 330                 335
```

| | |
|---|---|
| ctt ggc cag ttc ttc cag ggc tgg ggc acc tgg gtg gct tcg tgg cct<br>Leu Gly Gln Phe Phe Gln Gly Trp Gly Thr Trp Val Ala Ser Trp Pro<br>340 345 350 | 1056 |
| ctg acc atc ctg gtg ctg tct gtc atc ccg gtg gtg gtc ttg gca gcg<br>Leu Thr Ile Leu Val Leu Ser Val Ile Pro Val Val Val Leu Ala Ala<br>355 360 365 | 1104 |
| ggc ctg gtc ttt aca gaa ctc act acg gac ccc gtg gag ctg tgg tcg<br>Gly Leu Val Phe Thr Glu Leu Thr Thr Asp Pro Val Glu Leu Trp Ser<br>370 375 380 | 1152 |
| gcc ccc aac agc caa gcc cgg agt gag aag gct ttt cat gac cag cat<br>Ala Pro Asn Ser Gln Ala Arg Ser Glu Lys Ala Phe His Asp Gln His<br>385 390 395 400 | 1200 |
| ttc ggc ccc ttc ttc cga acc aac cag gtg atc ctg acg gct cct aac<br>Phe Gly Pro Phe Phe Arg Thr Asn Gln Val Ile Leu Thr Ala Pro Asn<br>405 410 415 | 1248 |
| cgg tcc agc tac agg tat gac tcc ctg ctg ctg ggg ccc aag aac ttc<br>Arg Ser Ser Tyr Arg Tyr Asp Ser Leu Leu Leu Gly Pro Lys Asn Phe<br>420 425 430 | 1296 |
| agc ggg atc ctg gac ctg gac ttg ctg ctg gag ctg ctg gag ttg cag<br>Ser Gly Ile Leu Asp Leu Asp Leu Leu Leu Glu Leu Leu Glu Leu Gln<br>435 440 445 | 1344 |
| gag agg ctg cgg cac ctc cag gtg tgg tcg ccc gaa gca cag cgc aac<br>Glu Arg Leu Arg His Leu Gln Val Trp Ser Pro Glu Ala Gln Arg Asn<br>450 455 460 | 1392 |
| atc tcc ctg cag cac atc tgc tac gcc ccc ctc aat ccg gac aat acc<br>Ile Ser Leu Gln His Ile Cys Tyr Ala Pro Leu Asn Pro Asp Asn Thr<br>465 470 475 480 | 1440 |
| agt ctt tcc gat tgc tgc atc aac agc ctc ctg cag tat ttc cag aac<br>Ser Leu Ser Asp Cys Cys Ile Asn Ser Leu Leu Gln Tyr Phe Gln Asn<br>485 490 495 | 1488 |
| aac cgc acg ctc ctg ttg ctc acg gcc aac cag aca ctg atg ggg cag<br>Asn Arg Thr Leu Leu Leu Leu Thr Ala Asn Gln Thr Leu Met Gly Gln<br>500 505 510 | 1536 |
| acc tcc caa gtc gac tgg agg gac cat ttt ctg tac tgt gcc aat gcc<br>Thr Ser Gln Val Asp Trp Arg Asp His Phe Leu Tyr Cys Ala Asn Ala<br>515 520 525 | 1584 |
| ccg ctc acc ttc aag gat ggc aca gcc ctg gcc ctg agc tgc atg gct<br>Pro Leu Thr Phe Lys Asp Gly Thr Ala Leu Ala Leu Ser Cys Met Ala<br>530 535 540 | 1632 |
| gac tat ggg gcc cct gtc ttc ccc ttc ctt gcc gtt ggg ggg tac aaa<br>Asp Tyr Gly Ala Pro Val Phe Pro Phe Leu Ala Val Gly Gly Tyr Lys<br>545 550 555 560 | 1680 |
| ggg aag gac tat tct gag gcg gag gcc ctg atc atg acg ttc tcc ctc<br>Gly Lys Asp Tyr Ser Glu Ala Glu Ala Leu Ile Met Thr Phe Ser Leu<br>565 570 575 | 1728 |
| aac aat tac cct gcc ggg gac ccc cgg ctg gcc cag gcc cag ctg tgg<br>Asn Asn Tyr Pro Ala Gly Asp Pro Arg Leu Ala Gln Ala Gln Leu Trp<br>580 585 590 | 1776 |
| gag gag gcc ttc ttg gag gaa atg cga gcc ttc cag cgt cgg acg gct<br>Glu Glu Ala Phe Leu Glu Glu Met Arg Ala Phe Gln Arg Arg Thr Ala<br>595 600 605 | 1824 |
| ggc aag ttc cag gtc acg ttc atg gct gag cgc tct ctg gaa gat gag<br>Gly Lys Phe Gln Val Thr Phe Met Ala Glu Arg Ser Leu Glu Asp Glu<br>610 615 620 | 1872 |
| atc aat cgc acc aca gcc gaa gac ctg ccc atc ttt gcc acc agc tac<br>Ile Asn Arg Thr Thr Ala Glu Asp Leu Pro Ile Phe Ala Thr Ser Tyr<br>625 630 635 640 | 1920 |
| att gtc atc ttc ctg tac atc tcc ctg gcc ctg ggc agc tat tcc agc<br>Ile Val Ile Phe Leu Tyr Ile Ser Leu Ala Leu Gly Ser Tyr Ser Ser<br>645 650 655 | 1968 |

```
tgg agc cga gtg atg gtg gac tcc aag gcc acg ctg ggc ctt ggc ggg      2016
Trp Ser Arg Val Met Val Asp Ser Lys Ala Thr Leu Gly Leu Gly Gly
            660                 665                 670 gtg gcc gtg gtc ctg gga gca gtc atg gct gcc atg ggc ttc ttc tcc      2064
Val Ala Val Val Leu Gly Ala Val Met Ala Ala Met Gly Phe Phe Ser
675                 680                 685 tac ctg ggt atc cgc tcc tcc ctg atc atc ctg caa gtg gtg cct ttc      2112
Tyr Leu Gly Ile Arg Ser Ser Leu Ile Ile Leu Gln Val Val Pro Phe
        690                 695                 700 ctg gtg ctg tct gtg ggg gct gat aac atc ttc atc ttt gtt ctc gag      2160
Leu Val Leu Ser Val Gly Ala Asp Asn Ile Phe Ile Phe Val Leu Glu
705                 710                 715                 720 tac cag agg ctg ccc cgg agg cct ggg gag ccg cga gag gtt cac att      2208
Tyr Gln Arg Leu Pro Arg Arg Pro Gly Glu Pro Arg Glu Val His Ile
            725                 730                 735 ggc cga gcc ctg ggc agg gtg gcc ccc agc atg ctg ttg tgt agc ctc      2256
Gly Arg Ala Leu Gly Arg Val Ala Pro Ser Met Leu Leu Cys Ser Leu
        740                 745                 750 tct gag gcc atc tgc ttc ttc cta ggg gcc ctg acc ccc atg cca gct      2304
Ser Glu Ala Ile Cys Phe Phe Leu Gly Ala Leu Thr Pro Met Pro Ala
755                 760                 765 gtg cgg acc ttt gcc ctg acc tct ggc ctt gca gtg gtc ctt gac ttc      2352
Val Arg Thr Phe Ala Leu Thr Ser Gly Leu Ala Val Val Leu Asp Phe
            770                 775                 780 ctc ctg cag atg tct gcc ttt gtg gcc ctg ctc tcc ctg gac agc aag      2400
Leu Leu Gln Met Ser Ala Phe Val Ala Leu Leu Ser Leu Asp Ser Lys
785                 790                 795                 800 agg cag gag gcc tcc cga ttg gac gtc tgc tgc tgc gtc aag ccc cgg      2448
Arg Gln Glu Ala Ser Arg Leu Asp Val Cys Cys Cys Val Lys Pro Arg
            805                 810                 815 gag ctg ccc ctg cct ggc cag gga gag ggg ttc ctg ctt ggc ctc ttc      2496
Glu Leu Pro Leu Pro Gly Gln Gly Glu Gly Phe Leu Leu Gly Leu Phe
        820                 825                 830 cga aag gcc tat gtc ccc ttc ctg ctg cac tgg atc act cga ggg gtt      2544
Arg Lys Ala Tyr Val Pro Phe Leu Leu His Trp Ile Thr Arg Gly Val
            835                 840                 845 gtg ctg ctg ctg ttt ctc gcc ctg ttt gga gtg agc ctc tac tac atg      2592
Val Leu Leu Leu Phe Leu Ala Leu Phe Gly Val Ser Leu Tyr Tyr Met
850                 855                 860 tgc cac atc agt gtt gga ctg gac cag gag ctg gcc ctg ccc aag gac      2640
Cys His Ile Ser Val Gly Leu Asp Gln Glu Leu Ala Leu Pro Lys Asp
865                 870                 875                 880 tcg tac ctg ctt gac tat ttc ctc ttt ctg aac cgc tac ttc gag acg      2688
Ser Tyr Leu Leu Asp Tyr Phe Leu Phe Leu Asn Arg Tyr Phe Glu Thr
            885                 890                 895 ggg gcc ccg gtg tac ttt gtt act acc tca ggc tac aac ttc tcc agt      2736
Gly Ala Pro Val Tyr Phe Val Thr Thr Ser Gly Tyr Asn Phe Ser Ser
        900                 905                 910 gag gct ggg atg aat gcc atc tgc tcc agt gca ggc tgc aac aac ttc      2784
Glu Ala Gly Met Asn Ala Ile Cys Ser Ser Ala Gly Cys Asn Asn Phe
            915                 920                 925 tcc ttc acc cag aag atc cag tat gcc aca gag ttc cct gag cag tct      2832
Ser Phe Thr Gln Lys Ile Gln Tyr Ala Thr Glu Phe Pro Glu Gln Ser
930                 935                 940 tac ctt gcc atc cct gcc tcc tcc tgg gtg gat gac ttc att gac tgg      2880
Tyr Leu Ala Ile Pro Ala Ser Ser Trp Val Asp Asp Phe Ile Asp Trp
945                 950                 955                 960 ctg acc cca tcc tcc tgc tgc cgc ctt tat ata tct ggc ccc aat aag      2928
Leu Thr Pro Ser Ser Cys Cys Arg Leu Tyr Ile Ser Gly Pro Asn Lys
            965                 970                 975
```

```
gac cag ttc tgc ccc tcg act gtc aac tcc ctg aac tgc cta aag aac     2976
Asp Gln Phe Cys Pro Ser Thr Val Asn Ser Leu Asn Cys Leu Lys Asn
            980                 985                 990 tgc ctg agc atc acg atg ggc tct gtg agg ccc tca gtg gag cag ttc     3024
Cys Leu Ser Ile Thr Met Gly Ser Val Arg Pro Ser Val Glu Gln Phe
        995                 1000                1005 tat aag tat ctt ccc tgg ttc ctg aat gac cgg ccc aac atc aaa         3069
Tyr Lys Tyr Leu Pro Trp Phe Leu Asn Asp Arg Pro Asn Ile Lys
    1010                1015                1020 tgt ccc aaa ggc ggc ctg gga gca tac agc acc tct gtg aac ttg         3114
Cys Pro Lys Gly Gly Leu Gly Ala Tyr Ser Thr Ser Val Asn Leu
    1025                1030                1035 act tca gat ggc cag gtt tta gcc tcc agg ttc atg gcc tat cac         3159
Thr Ser Asp Gly Gln Val Leu Ala Ser Arg Phe Met Ala Tyr His
    1040                1045                1050 aag ccc ctg aaa aac tca cag gat tac aca gaa gct ctg cgg gca         3204
Lys Pro Leu Lys Asn Ser Gln Asp Tyr Thr Glu Ala Leu Arg Ala
    1055                1060                1065 gct cgg gag ctg gca gcc aac atc act gct gac ctg cgg aag gtg         3249
Ala Arg Glu Leu Ala Ala Asn Ile Thr Ala Asp Leu Arg Lys Val
    1070                1075                1080 cct ggg aca gac cca gct ttt gag gtc ttc ccc tac acg gtc acc         3294
Pro Gly Thr Asp Pro Ala Phe Glu Val Phe Pro Tyr Thr Val Thr
    1085                1090                1095 aat gtg ttt tat gag cag tac ctg acc att ctc cct gag ggg ctc         3339
Asn Val Phe Tyr Glu Gln Tyr Leu Thr Ile Leu Pro Glu Gly Leu
    1100                1105                1110 ttc atg ctc agc ctc tgc ctg gtg ccc acc ttc gct gtc tgc tgc         3384
Phe Met Leu Ser Leu Cys Leu Val Pro Thr Phe Ala Val Cys Cys
    1115                1120                1125 ctc ctg ctg ggc ctg gac ctg cgc tcc ggc ctc ctc aac ctg ctg         3429
Leu Leu Leu Gly Leu Asp Leu Arg Ser Gly Leu Leu Asn Leu Leu
    1130                1135                1140 tcc atc atc atg atc ctc gtg gac acc gtt ggc ttc atg gcc ctg         3474
Ser Ile Ile Met Ile Leu Val Asp Thr Val Gly Phe Met Ala Leu
    1145                1150                1155 tgg ggc atc agt tac aat gct gtg tcc ctc atc aac ctg gtc tcg         3519
Trp Gly Ile Ser Tyr Asn Ala Val Ser Leu Ile Asn Leu Val Ser
    1160                1165                1170 gcg gtg ggc atg tct gtg gag ttc gtg tcc cac att acc cgc tcc         3564
Ala Val Gly Met Ser Val Glu Phe Val Ser His Ile Thr Arg Ser
    1175                1180                1185 ttt gcc atc agc acc aag ccc acc cgg ctg gag agg gcc aaa gag         3609
Phe Ala Ile Ser Thr Lys Pro Thr Arg Leu Glu Arg Ala Lys Glu
    1190                1195                1200 gcc acc atc tct atg gga agt gcg gtg ttt gca ggt gtg gcc atg         3654
Ala Thr Ile Ser Met Gly Ser Ala Val Phe Ala Gly Val Ala Met
    1205                1210                1215 acc aac ctc cct ggc atc ctg gtc ctg ggc ctt gcc aag gcc cag         3699
Thr Asn Leu Pro Gly Ile Leu Val Leu Gly Leu Ala Lys Ala Gln
    1220                1225                1230 ctc att cag atc ttc ttc ttc cgc ctc aac ctc ctg att act ctg         3744
Leu Ile Gln Ile Phe Phe Phe Arg Leu Asn Leu Leu Ile Thr Leu
    1235                1240                1245 ctg ggt ctg ctg cat ggc ttg gtc ttc ctg cct gtc atc ctc agc         3789
Leu Gly Leu Leu His Gly Leu Val Phe Leu Pro Val Ile Leu Ser
    1250                1255                1260 tat gtg ggg cct gac atc aac cca gct ctg gca ctg gag cag aag         3834
Tyr Val Gly Pro Asp Ile Asn Pro Ala Leu Ala Leu Glu Gln Lys
    1265                1270                1275
```

```
ctg gct gag gag gca gca gcg gca gcc ata gcg gcc tcc tac cca   3879
Leu Ala Glu Glu Ala Ala Ala Ala Ala Ile Ala Ala Ser Tyr Pro
    1280            1285            1290 aat cac ccc tcc cga gtc tcc aca gct gac aac atc tat gtc aac   3924
Asn His Pro Ser Arg Val Ser Thr Ala Asp Asn Ile Tyr Val Asn
1295            1300            1305 cac agc ttt gaa ggt tct atc aaa ggt gct ggt gcc gtc agc aac   3969
His Ser Phe Glu Gly Ser Ile Lys Gly Ala Gly Ala Val Ser Asn
    1310            1315            1320 ttc ttg ccc aac aat ggg cgg cag ttc tga                       3999
Phe Leu Pro Asn Asn Gly Arg Gln Phe
    1325            1330
```

<210> SEQ ID NO 8
<211> LENGTH: 1332
<212> TYPE: PRT
<213> ORGANISM: Macaca mulatta

<400> SEQUENCE: 8

```
Met Ala Glu Ala Gly Leu Arg Gly Trp Leu Leu Trp Ala Leu Leu Leu
1               5                   10                  15

His Leu Ala Gln Ser Glu Pro Tyr Thr Pro Ile His Gln Pro Gly Tyr
            20                  25                  30

Cys Ala Phe Tyr Asp Glu Cys Gly Lys Asn Pro Glu Leu Ser Gly Gly
        35                  40                  45

Leu Met Thr Leu Ser Asn Val Ser Cys Leu Ser Asn Thr Pro Ala Arg
    50                  55                  60

Asn Ile Thr Gly Asp His Leu Ile Leu Leu Gln Arg Ile Cys Pro Arg
65                  70                  75                  80

Leu Tyr Thr Gly Pro Asn Thr Gln Ala Cys Cys Ser Ala Lys Gln Leu
                85                  90                  95

Val Ser Leu Glu Ala Ser Leu Ser Ile Thr Lys Ala Leu Leu Thr Arg
            100                 105                 110

Cys Pro Ala Cys Ser Asp Asn Phe Val Ser Leu His Cys His Asn Thr
        115                 120                 125

Cys Ser Pro Asn Gln Ser Leu Phe Ile Asn Val Thr Arg Val Ala Gln
    130                 135                 140

Leu Gly Ala Gly Gln Leu Pro Ala Val Val Ala Tyr Glu Ala Phe Tyr
145                 150                 155                 160

Gln His Ser Phe Ala Glu Gln Ser Tyr Asp Ser Cys Ser Arg Val His
                165                 170                 175

Ile Pro Ala Ala Ala Thr Leu Ala Val Gly Ser Met Cys Gly Val Tyr
            180                 185                 190

Gly Ser Ala Leu Cys Asn Ala Gln Arg Trp Leu Asn Phe Gln Gly Asp
        195                 200                 205

Thr Gly Asn Gly Leu Ala Pro Leu Asp Ile Thr Phe His Leu Leu Glu
    210                 215                 220

Pro Gly Gln Ala Val Gly Ser Gly Ile Gln Pro Leu Asn Glu Gly Val
225                 230                 235                 240

Ala Arg Cys Asn Glu Ser Gln Gly Asp Asp Ala Val Ala Cys Ser Cys
                245                 250                 255

Gln Asp Cys Ala Ala Ser Cys Pro Ala Ile Ala His Pro Gln Ala Leu
            260                 265                 270

Asp Ser Thr Phe Arg Leu Gly Arg Met Pro Gly Gly Leu Val Leu Ile
        275                 280                 285

Ile Ile Leu Cys Ser Val Phe Thr Val Val Ala Ile Leu Leu Val Gly
```

```
              290                 295                 300
Leu Arg Val Ala Pro Thr Arg Asp Lys Ser Lys Thr Val Asp Pro Lys
305                 310                 315                 320

Lys Gly Thr Ser Leu Ser Asp Lys Leu Ser Phe Ser Thr His Thr Leu
                325                 330                 335

Leu Gly Gln Phe Phe Gln Gly Trp Gly Thr Trp Val Ala Ser Trp Pro
                340                 345                 350

Leu Thr Ile Leu Val Leu Ser Val Ile Pro Val Val Leu Ala Ala
                355                 360                 365

Gly Leu Val Phe Thr Glu Leu Thr Thr Asp Pro Val Glu Leu Trp Ser
370                 375                 380

Ala Pro Asn Ser Gln Ala Arg Ser Glu Lys Ala Phe His Asp Gln His
385                 390                 395                 400

Phe Gly Pro Phe Phe Arg Thr Asn Gln Val Ile Leu Thr Ala Pro Asn
                405                 410                 415

Arg Ser Ser Tyr Arg Tyr Asp Ser Leu Leu Gly Pro Lys Asn Phe
                420                 425                 430

Ser Gly Ile Leu Asp Leu Asp Leu Leu Glu Leu Leu Glu Leu Gln
                435                 440                 445

Glu Arg Leu Arg His Leu Gln Val Trp Ser Pro Glu Ala Gln Arg Asn
450                 455                 460

Ile Ser Leu Gln His Ile Cys Tyr Ala Pro Leu Asn Pro Asp Asn Thr
465                 470                 475                 480

Ser Leu Ser Asp Cys Cys Ile Asn Ser Leu Leu Gln Tyr Phe Gln Asn
                485                 490                 495

Asn Arg Thr Leu Leu Leu Thr Ala Asn Gln Thr Leu Met Gly Gln
                500                 505                 510

Thr Ser Gln Val Asp Trp Arg Asp His Phe Leu Tyr Cys Ala Asn Ala
                515                 520                 525

Pro Leu Thr Phe Lys Asp Gly Thr Ala Leu Ala Leu Ser Cys Met Ala
                530                 535                 540

Asp Tyr Gly Ala Pro Val Phe Pro Phe Leu Ala Val Gly Gly Tyr Lys
545                 550                 555                 560

Gly Lys Asp Tyr Ser Glu Ala Glu Ala Leu Ile Met Thr Phe Ser Leu
                565                 570                 575

Asn Asn Tyr Pro Ala Gly Asp Pro Arg Leu Ala Gln Ala Gln Leu Trp
                580                 585                 590

Glu Glu Ala Phe Leu Glu Glu Met Arg Ala Phe Gln Arg Arg Thr Ala
                595                 600                 605

Gly Lys Phe Gln Val Thr Phe Met Ala Glu Arg Ser Leu Glu Asp Glu
                610                 615                 620

Ile Asn Arg Thr Thr Ala Glu Asp Leu Pro Ile Phe Ala Thr Ser Tyr
625                 630                 635                 640

Ile Val Ile Phe Leu Tyr Ile Ser Leu Ala Leu Gly Ser Tyr Ser Ser
                645                 650                 655

Trp Ser Arg Val Met Val Asp Ser Lys Ala Thr Leu Gly Leu Gly Gly
                660                 665                 670

Val Ala Val Val Leu Gly Ala Val Met Ala Ala Met Gly Phe Phe Ser
                675                 680                 685

Tyr Leu Gly Ile Arg Ser Ser Leu Ile Ile Leu Gln Val Val Pro Phe
                690                 695                 700

Leu Val Leu Ser Val Gly Ala Asp Asn Ile Phe Ile Phe Val Leu Glu
705                 710                 715                 720
```

```
Tyr Gln Arg Leu Pro Arg Arg Pro Gly Glu Pro Arg Glu Val His Ile
                725                 730                 735

Gly Arg Ala Leu Gly Arg Val Ala Pro Ser Met Leu Leu Cys Ser Leu
            740                 745                 750

Ser Glu Ala Ile Cys Phe Phe Leu Gly Ala Leu Thr Pro Met Pro Ala
            755                 760                 765

Val Arg Thr Phe Ala Leu Thr Ser Gly Leu Ala Val Val Leu Asp Phe
    770                 775                 780

Leu Leu Gln Met Ser Ala Phe Val Ala Leu Leu Ser Leu Asp Ser Lys
785                 790                 795                 800

Arg Gln Glu Ala Ser Arg Leu Asp Val Cys Cys Val Lys Pro Arg
            805                 810                 815

Glu Leu Pro Leu Pro Gly Gln Gly Glu Gly Phe Leu Leu Gly Leu Phe
            820                 825                 830

Arg Lys Ala Tyr Val Pro Phe Leu Leu His Trp Ile Thr Arg Gly Val
            835                 840                 845

Val Leu Leu Leu Phe Leu Ala Leu Phe Gly Val Ser Leu Tyr Tyr Met
    850                 855                 860

Cys His Ile Ser Val Gly Leu Asp Gln Glu Leu Ala Leu Pro Lys Asp
865                 870                 875                 880

Ser Tyr Leu Leu Asp Tyr Phe Leu Phe Leu Asn Arg Tyr Phe Glu Thr
            885                 890                 895

Gly Ala Pro Val Tyr Phe Val Thr Thr Ser Gly Tyr Asn Phe Ser Ser
            900                 905                 910

Glu Ala Gly Met Asn Ala Ile Cys Ser Ser Ala Gly Cys Asn Asn Phe
            915                 920                 925

Ser Phe Thr Gln Lys Ile Gln Tyr Ala Thr Glu Phe Pro Glu Gln Ser
    930                 935                 940

Tyr Leu Ala Ile Pro Ala Ser Ser Trp Val Asp Asp Phe Ile Asp Trp
945                 950                 955                 960

Leu Thr Pro Ser Ser Cys Cys Arg Leu Tyr Ile Ser Gly Pro Asn Lys
            965                 970                 975

Asp Gln Phe Cys Pro Ser Thr Val Asn Ser Leu Asn Cys Leu Lys Asn
            980                 985                 990

Cys Leu Ser Ile Thr Met Gly Ser Val Arg Pro Ser Val Glu Gln Phe
    995                 1000                1005

Tyr Lys Tyr Leu Pro Trp Phe Leu Asn Asp Arg Pro Asn Ile Lys
    1010                1015                1020

Cys Pro Lys Gly Gly Leu Gly Ala Tyr Ser Thr Ser Val Asn Leu
    1025                1030                1035

Thr Ser Asp Gly Gln Val Leu Ala Ser Arg Phe Met Ala Tyr His
    1040                1045                1050

Lys Pro Leu Lys Asn Ser Gln Asp Tyr Thr Glu Ala Leu Arg Ala
    1055                1060                1065

Ala Arg Glu Leu Ala Ala Asn Ile Thr Ala Asp Leu Arg Lys Val
    1070                1075                1080

Pro Gly Thr Asp Pro Ala Phe Glu Val Phe Pro Tyr Thr Val Thr
    1085                1090                1095

Asn Val Phe Tyr Glu Gln Tyr Leu Thr Ile Leu Pro Glu Gly Leu
    1100                1105                1110

Phe Met Leu Ser Leu Cys Leu Val Pro Thr Phe Ala Val Cys Cys
    1115                1120                1125

Leu Leu Leu Gly Leu Asp Leu Arg Ser Gly Leu Leu Asn Leu Leu
    1130                1135                1140
```

```
Ser Ile Ile Met Ile Leu Val Asp Thr Val Gly Phe Met Ala Leu
    1145                1150                1155

Trp Gly Ile Ser Tyr Asn Ala Val Ser Leu Ile Asn Leu Val Ser
    1160                1165                1170

Ala Val Gly Met Ser Val Glu Phe Val Ser His Ile Thr Arg Ser
    1175                1180                1185

Phe Ala Ile Ser Thr Lys Pro Thr Arg Leu Glu Arg Ala Lys Glu
    1190                1195                1200

Ala Thr Ile Ser Met Gly Ser Ala Val Phe Ala Gly Val Ala Met
    1205                1210                1215

Thr Asn Leu Pro Gly Ile Leu Val Leu Gly Leu Ala Lys Ala Gln
    1220                1225                1230

Leu Ile Gln Ile Phe Phe Arg Leu Asn Leu Leu Ile Thr Leu
    1235                1240                1245

Leu Gly Leu Leu His Gly Leu Val Phe Leu Pro Val Ile Leu Ser
    1250                1255                1260

Tyr Val Gly Pro Asp Ile Asn Pro Ala Leu Ala Leu Glu Gln Lys
    1265                1270                1275

Leu Ala Glu Glu Ala Ala Ala Ala Ile Ala Ala Ser Tyr Pro
    1280                1285                1290

Asn His Pro Ser Arg Val Ser Thr Ala Asp Asn Ile Tyr Val Asn
    1295                1300                1305

His Ser Phe Glu Gly Ser Ile Lys Gly Ala Gly Ala Val Ser Asn
    1310                1315                1320

Phe Leu Pro Asn Asn Gly Arg Gln Phe
    1325                1330
```

```
<210> SEQ ID NO 9
<211> LENGTH: 3999
<212> TYPE: DNA
<213> ORGANISM: Macaca fascicularis
<220> FEATURE:
<221> NAME/KEY: CDS
<222> LOCATION: (1)..(3999)

<400> SEQUENCE: 9 atg gcg gag gcc ggc ctg agg ggc tgg ctg ctg tgg gcc ctg ctc ctg      48
Met Ala Glu Ala Gly Leu Arg Gly Trp Leu Leu Trp Ala Leu Leu Leu
1               5                   10                  15 cac ttg gcc cag agc gag cct tac aca ccc atc cac cag cct ggc tac      96
His Leu Ala Gln Ser Glu Pro Tyr Thr Pro Ile His Gln Pro Gly Tyr
            20                  25                  30 tgc gcc ttc tat gac gaa tgt ggg aag aac cca gag ctg tct gga ggc     144
Cys Ala Phe Tyr Asp Glu Cys Gly Lys Asn Pro Glu Leu Ser Gly Gly
        35                  40                  45 ctc atg aca ctc tcc aac gtg tcc tgt ctg tcc aac acg cca gcc cgc     192
Leu Met Thr Leu Ser Asn Val Ser Cys Leu Ser Asn Thr Pro Ala Arg
    50                  55                  60 aac atc aca ggt gat cac ctg atc cta tta cag agg atc tgc ccc cgc     240
Asn Ile Thr Gly Asp His Leu Ile Leu Leu Gln Arg Ile Cys Pro Arg
65                  70                  75                  80 ctc tac acc ggc ccc aac acc caa gcc tgc tgc tcc gcc aag cag ctg     288
Leu Tyr Thr Gly Pro Asn Thr Gln Ala Cys Cys Ser Ala Lys Gln Leu
                85                  90                  95 gta tca ttg gaa gcg agt ctg tcg atc acc aag gcc ctc ctc acc cgc     336
Val Ser Leu Glu Ala Ser Leu Ser Ile Thr Lys Ala Leu Leu Thr Arg
            100                 105                 110 tgc cca gcc tgc tct gac aat ttc gtg agc ctg cac tgc cac aac aca     384
```

```
                Cys Pro Ala Cys Ser Asp Asn Phe Val Ser Leu His Cys His Asn Thr
                        115                 120                 125 tgc agc ccc aac cag agc ctc ttc atc aat gtg acc cgc gtg gct cag       432
Cys Ser Pro Asn Gln Ser Leu Phe Ile Asn Val Thr Arg Val Ala Gln
    130                 135                 140 cta ggg gct gga caa ctc cca gct gtg gtg gcc tat gag gcc ttc tac       480
Leu Gly Ala Gly Gln Leu Pro Ala Val Val Ala Tyr Glu Ala Phe Tyr
145                 150                 155                 160 cag cac agc ttt gcc gag cag agc tat gac tcc tgc agc cgt gtg cac       528
Gln His Ser Phe Ala Glu Gln Ser Tyr Asp Ser Cys Ser Arg Val His
            165                 170                 175 atc cct gcg gct gcc acg ctg gct gtg ggc agc atg tgt ggc gtg tat       576
Ile Pro Ala Ala Ala Thr Leu Ala Val Gly Ser Met Cys Gly Val Tyr
                180                 185                 190 ggc tct gcc ctt tgc aat gcc cag cgc tgg ctc aac ttc cag gga gac       624
Gly Ser Ala Leu Cys Asn Ala Gln Arg Trp Leu Asn Phe Gln Gly Asp
                    195                 200                 205 aca ggc aat ggt ctg gcc cca ctg gac atc acc ttc cac ctc ttg gag       672
Thr Gly Asn Gly Leu Ala Pro Leu Asp Ile Thr Phe His Leu Leu Glu
    210                 215                 220 ccc ggc cag gct gtg ggg agt ggg att cag cct ctg aat gag ggg gtt       720
Pro Gly Gln Ala Val Gly Ser Gly Ile Gln Pro Leu Asn Glu Gly Val
225                 230                 235                 240 gca cgt tgc aat gag tcc caa ggt gac gac gca gtg gcc tgc tcc tgc       768
Ala Arg Cys Asn Glu Ser Gln Gly Asp Asp Ala Val Ala Cys Ser Cys
            245                 250                 255 cag gac tgt gct gca tcc tgt cct gcc atc gcc cat ccc cag gcc ctg       816
Gln Asp Cys Ala Ala Ser Cys Pro Ala Ile Ala His Pro Gln Ala Leu
                260                 265                 270 gac tcc acc ttc cgc ctg ggc cgg atg ccg ggt ggg ctg gtc ctc atc       864
Asp Ser Thr Phe Arg Leu Gly Arg Met Pro Gly Gly Leu Val Leu Ile
                    275                 280                 285 atc atc ctc tgt tct gtc ttc act gtg gtc gcc atc ctg ctc gtg gga       912
Ile Ile Leu Cys Ser Val Phe Thr Val Val Ala Ile Leu Leu Val Gly
    290                 295                 300 ctc cgt gtg gcc ccc acc agg gac aaa agc aag acg gtg gac ccc aag       960
Leu Arg Val Ala Pro Thr Arg Asp Lys Ser Lys Thr Val Asp Pro Lys
305                 310                 315                 320 aag ggc acc agc ctc tct gac aag ctc agc ttc tcc acc cac acc ctc      1008
Lys Gly Thr Ser Leu Ser Asp Lys Leu Ser Phe Ser Thr His Thr Leu
            325                 330                 335 ctt ggc cag ttc ttc cag ggc tgg ggc acc tgg gtg gct tcg tgg cct      1056
Leu Gly Gln Phe Phe Gln Gly Trp Gly Thr Trp Val Ala Ser Trp Pro
                340                 345                 350 ctg acc atc ctg gtg ctg tct gtc atc ccg gtg gtg gtc ttg gca gcg      1104
Leu Thr Ile Leu Val Leu Ser Val Ile Pro Val Val Val Leu Ala Ala
                    355                 360                 365 ggc ctg gtc ttt aca gaa ctc act aca gac ccc gtg gag ctg tgg tcg      1152
Gly Leu Val Phe Thr Glu Leu Thr Thr Asp Pro Val Glu Leu Trp Ser
    370                 375                 380 gcc ccc aac agc caa gcc cgg agt gag aag gct ttt cat gac cag cat      1200
Ala Pro Asn Ser Gln Ala Arg Ser Glu Lys Ala Phe His Asp Gln His
385                 390                 395                 400 ttc ggc ccc ttc ttc cga acc aac cag gtg atc ctg acg gct cct aac      1248
Phe Gly Pro Phe Phe Arg Thr Asn Gln Val Ile Leu Thr Ala Pro Asn
            405                 410                 415 cgg tcc agc tac agg tat gac tcc ctg ctg ctg ggg ccc aag aac ttc      1296
Arg Ser Ser Tyr Arg Tyr Asp Ser Leu Leu Leu Gly Pro Lys Asn Phe
                420                 425                 430 agc ggg atc ctg gac ctg gac ttg ctg ctg gag ctg ctg gag ttg cag      1344
```

```
                    Ser Gly Ile Leu Asp Leu Asp Leu Leu Glu Leu Leu Glu Leu Gln
                            435                 440                 445 gag agg ctg cgg cac ctc cag gtg tgg tcg ccc gaa gca cag cgc aac          1392
Glu Arg Leu Arg His Leu Gln Val Trp Ser Pro Glu Ala Gln Arg Asn
    450                 455                 460 atc tcc ctg cag cac atc tgc tac gcc ccc ctc aat ccg gac aat acc          1440
Ile Ser Leu Gln His Ile Cys Tyr Ala Pro Leu Asn Pro Asp Asn Thr
465                 470                 475                 480 agt ctc tcc gat tgc tgc atc aac agc ctc ctg cag tat ttc cag aac          1488
Ser Leu Ser Asp Cys Cys Ile Asn Ser Leu Leu Gln Tyr Phe Gln Asn
                485                 490                 495 aac cgc acg ctc ctg ttg ctc acg gcc aac cag aca ctg atg ggg cag          1536
Asn Arg Thr Leu Leu Leu Leu Thr Ala Asn Gln Thr Leu Met Gly Gln
            500                 505                 510 acc tcc caa gtc gac tgg agg gac cat ttt ctg tac tgt gcc aat gcc          1584
Thr Ser Gln Val Asp Trp Arg Asp His Phe Leu Tyr Cys Ala Asn Ala
        515                 520                 525 ccg ctc acc ttc aag gat ggc aca gcc ctg gcc ctg agc tgc atg gct          1632
Pro Leu Thr Phe Lys Asp Gly Thr Ala Leu Ala Leu Ser Cys Met Ala
530                 535                 540 gac tat ggg gcc cct gtc ttc ccc ttc ctt gcc gtt ggg ggg tac aaa          1680
Asp Tyr Gly Ala Pro Val Phe Pro Phe Leu Ala Val Gly Gly Tyr Lys
545                 550                 555                 560 ggg aag gac tat tct gag gcg gag gcc ctg atc atg acg ttc tcc ctc          1728
Gly Lys Asp Tyr Ser Glu Ala Glu Ala Leu Ile Met Thr Phe Ser Leu
                565                 570                 575 aac aat tac cct gcc ggg gac ccc cgg ctg gcc cag gcc cag ctg tgg          1776
Asn Asn Tyr Pro Ala Gly Asp Pro Arg Leu Ala Gln Ala Gln Leu Trp
            580                 585                 590 gag gag gcc ttc ttg gag gaa atg cga gcc ttc cag cgt cgg acg gct          1824
Glu Glu Ala Phe Leu Glu Glu Met Arg Ala Phe Gln Arg Arg Thr Ala
        595                 600                 605 ggc aag ttc cag gtc acg ttc atg gct gag cgc tct ctg gaa gat gag          1872
Gly Lys Phe Gln Val Thr Phe Met Ala Glu Arg Ser Leu Glu Asp Glu
610                 615                 620 atc aat cgc acc aca gcc gaa gac ctg ccc atc ttt gcc acc agc tac          1920
Ile Asn Arg Thr Thr Ala Glu Asp Leu Pro Ile Phe Ala Thr Ser Tyr
625                 630                 635                 640 att gtc atc ttc ctg tac atc tcc ctg gcc ctg ggc agc tat tcc agc          1968
Ile Val Ile Phe Leu Tyr Ile Ser Leu Ala Leu Gly Ser Tyr Ser Ser
                645                 650                 655 tgg agc aga gtg atg gtg gac tcc aag gcc acg ctg ggc ctt ggc ggg          2016
Trp Ser Arg Val Met Val Asp Ser Lys Ala Thr Leu Gly Leu Gly Gly
            660                 665                 670 gtg gcc gtg gtc ctg gga gca gtc atg gct gcc atg ggc ttc ttc tcc          2064
Val Ala Val Val Leu Gly Ala Val Met Ala Ala Met Gly Phe Phe Ser
        675                 680                 685 tac ctg ggt atc cgc tcc tcc ctg atc atc ctg caa gtg gtg cct ttc          2112
Tyr Leu Gly Ile Arg Ser Ser Leu Ile Ile Leu Gln Val Val Pro Phe
690                 695                 700 ctg gtg ctg tct gtg ggg gct gat aac atc ttc atc ttt gtt ctc gag          2160
Leu Val Leu Ser Val Gly Ala Asp Asn Ile Phe Ile Phe Val Leu Glu
705                 710                 715                 720 tac cag agg ctg ccc cgg agg cct ggg gag ccg cga gag gtt cac att          2208
Tyr Gln Arg Leu Pro Arg Arg Pro Gly Glu Pro Arg Glu Val His Ile
                725                 730                 735 ggc cga gcc ctg ggc agg gtg gcc ccc agc atg ctg ttg tgc agc ctc          2256
Gly Arg Ala Leu Gly Arg Val Ala Pro Ser Met Leu Leu Cys Ser Leu
            740                 745                 750 tct gag gcc atc tgc ttc ttc cta ggg gcc ctg acc ccc atg cca gct          2304
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Ser | Glu | Ala | Ile | Cys | Phe | Phe | Leu | Gly | Ala | Leu | Thr | Pro | Met | Pro | Ala  |
|     | 755 |     |     |     | 760 |     |     |     |     | 765 |     |     |     |     |      |

| gtg | cgg | acc | ttt | gcc | ctg | acc | tct | ggc | ctt | gca | gtg | gtc | ctt | gac | ttc | 2352 |
| --- | --- | --- | --- | --- | --- | --- | --- | --- | --- | --- | --- | --- | --- | --- | --- | --- |
| Val | Arg | Thr | Phe | Ala | Leu | Thr | Ser | Gly | Leu | Ala | Val | Val | Leu | Asp | Phe |  |
|  | 770 |  |  |  | 775 |  |  |  |  | 780 |  |  |  |  |  |  |

| ctc | ctg | cag | atg | tct | gcc | ttt | gtg | gcc | ctg | ctc | tcc | ctg | gac | agc | aag | 2400 |
| --- | --- | --- | --- | --- | --- | --- | --- | --- | --- | --- | --- | --- | --- | --- | --- | --- |
| Leu | Leu | Gln | Met | Ser | Ala | Phe | Val | Ala | Leu | Leu | Ser | Leu | Asp | Ser | Lys |  |
| 785 |  |  |  |  | 790 |  |  |  |  | 795 |  |  |  |  | 800 |  |

| agg | cag | gag | gcc | tcc | cga | ttg | gac | gtc | tgc | tgc | gtc | aag | ccc | cgg |  | 2448 |
| --- | --- | --- | --- | --- | --- | --- | --- | --- | --- | --- | --- | --- | --- | --- | --- | --- |
| Arg | Gln | Glu | Ala | Ser | Arg | Leu | Asp | Val | Cys | Cys | Val | Lys | Pro | Arg |  |  |
|  |  |  |  | 805 |  |  |  |  | 810 |  |  |  |  | 815 |  |  |

| gag | ctg | ccc | ctg | cct | ggc | cag | gga | gag | ggg | ttc | ctg | ctt | ggc | ctc | ttc | 2496 |
| --- | --- | --- | --- | --- | --- | --- | --- | --- | --- | --- | --- | --- | --- | --- | --- | --- |
| Glu | Leu | Pro | Leu | Pro | Gly | Gln | Gly | Glu | Gly | Phe | Leu | Leu | Gly | Leu | Phe |  |
|  |  | 820 |  |  |  |  | 825 |  |  |  |  | 830 |  |  |  |  |

| cga | aag | gcc | tat | gtc | ccc | ttc | ctg | ctg | cac | tgg | atc | act | cga | ggg | gtt | 2544 |
| --- | --- | --- | --- | --- | --- | --- | --- | --- | --- | --- | --- | --- | --- | --- | --- | --- |
| Arg | Lys | Ala | Tyr | Val | Pro | Phe | Leu | Leu | His | Trp | Ile | Thr | Arg | Gly | Val |  |
|  |  |  | 835 |  |  |  |  | 840 |  |  |  |  | 845 |  |  |  |

| gtg | ctg | ctg | ctg | ttt | ctc | gcc | ctg | ttt | gga | gtg | agc | ctc | tac | tac | atg | 2592 |
| --- | --- | --- | --- | --- | --- | --- | --- | --- | --- | --- | --- | --- | --- | --- | --- | --- |
| Val | Leu | Leu | Leu | Phe | Leu | Ala | Leu | Phe | Gly | Val | Ser | Leu | Tyr | Tyr | Met |  |
| 850 |  |  |  |  | 855 |  |  |  |  | 860 |  |  |  |  |  |  |

| tgc | cac | atc | agt | gtt | gga | ctg | gac | cag | gag | ctg | gcc | ctg | ccc | aag | gac | 2640 |
| --- | --- | --- | --- | --- | --- | --- | --- | --- | --- | --- | --- | --- | --- | --- | --- | --- |
| Cys | His | Ile | Ser | Val | Gly | Leu | Asp | Gln | Glu | Leu | Ala | Leu | Pro | Lys | Asp |  |
| 865 |  |  |  |  | 870 |  |  |  |  | 875 |  |  |  |  | 880 |  |

| tcg | tac | ctg | ctt | gac | tat | ttc | ctc | ttt | ctg | aac | cgc | tac | ttc | gag | acg | 2688 |
| --- | --- | --- | --- | --- | --- | --- | --- | --- | --- | --- | --- | --- | --- | --- | --- | --- |
| Ser | Tyr | Leu | Leu | Asp | Tyr | Phe | Leu | Phe | Leu | Asn | Arg | Tyr | Phe | Glu | Thr |  |
|  |  |  |  | 885 |  |  |  |  | 890 |  |  |  |  | 895 |  |  |

| ggg | gcc | ccg | gtg | tac | ttt | gtt | act | acc | tca | ggc | tac | aac | ttc | tcc | agt | 2736 |
| --- | --- | --- | --- | --- | --- | --- | --- | --- | --- | --- | --- | --- | --- | --- | --- | --- |
| Gly | Ala | Pro | Val | Tyr | Phe | Val | Thr | Thr | Ser | Gly | Tyr | Asn | Phe | Ser | Ser |  |
|  |  | 900 |  |  |  |  | 905 |  |  |  |  | 910 |  |  |  |  |

| gag | gct | ggg | atg | aat | gcc | atc | tgc | tcc | agt | gca | ggc | tgc | aac | aac | ttc | 2784 |
| --- | --- | --- | --- | --- | --- | --- | --- | --- | --- | --- | --- | --- | --- | --- | --- | --- |
| Glu | Ala | Gly | Met | Asn | Ala | Ile | Cys | Ser | Ser | Ala | Gly | Cys | Asn | Asn | Phe |  |
|  |  |  | 915 |  |  |  |  | 920 |  |  |  |  | 925 |  |  |  |

| tcc | ttc | acc | cag | aag | atc | cag | tat | gcc | aca | gag | ttc | cct | gag | cag | tct | 2832 |
| --- | --- | --- | --- | --- | --- | --- | --- | --- | --- | --- | --- | --- | --- | --- | --- | --- |
| Ser | Phe | Thr | Gln | Lys | Ile | Gln | Tyr | Ala | Thr | Glu | Phe | Pro | Glu | Gln | Ser |  |
|  | 930 |  |  |  |  | 935 |  |  |  |  | 940 |  |  |  |  |  |

| tac | ctt | gcc | atc | cct | gcc | tcc | tcc | tgg | gtg | gat | gac | ttc | att | gac | tgg | 2880 |
| --- | --- | --- | --- | --- | --- | --- | --- | --- | --- | --- | --- | --- | --- | --- | --- | --- |
| Tyr | Leu | Ala | Ile | Pro | Ala | Ser | Ser | Trp | Val | Asp | Asp | Phe | Ile | Asp | Trp |  |
| 945 |  |  |  |  | 950 |  |  |  |  | 955 |  |  |  |  | 960 |  |

| ctg | acc | cca | tcc | tcc | tgc | tgc | cgc | ctt | tat | ata | tct | ggc | ccc | aat | aag | 2928 |
| --- | --- | --- | --- | --- | --- | --- | --- | --- | --- | --- | --- | --- | --- | --- | --- | --- |
| Leu | Thr | Pro | Ser | Ser | Cys | Cys | Arg | Leu | Tyr | Ile | Ser | Gly | Pro | Asn | Lys |  |
|  |  |  |  | 965 |  |  |  |  | 970 |  |  |  |  | 975 |  |  |

| gac | cag | ttc | tgc | ccc | tcg | act | gtc | aac | tcc | ctg | aac | tgc | cta | aag | aac | 2976 |
| --- | --- | --- | --- | --- | --- | --- | --- | --- | --- | --- | --- | --- | --- | --- | --- | --- |
| Asp | Gln | Phe | Cys | Pro | Ser | Thr | Val | Asn | Ser | Leu | Asn | Cys | Leu | Lys | Asn |  |
|  |  |  | 980 |  |  |  |  | 985 |  |  |  |  | 990 |  |  |  |

| tgc | ctg | agc | atc | acg | atg | ggc | tct | gtg | agg | ccc | tca | gtg | gag | cag | ttc | 3024 |
| --- | --- | --- | --- | --- | --- | --- | --- | --- | --- | --- | --- | --- | --- | --- | --- | --- |
| Cys | Leu | Ser | Ile | Thr | Met | Gly | Ser | Val | Arg | Pro | Ser | Val | Glu | Gln | Phe |  |
| 995 |  |  |  |  | 1000 |  |  |  |  | 1005 |  |  |  |  |  |  |

| tat | aag | tat | ctt | ccc | tgg | ttc | ctg | aat | gac | cgg | ccc | aac | atc | aaa |  | 3069 |
| --- | --- | --- | --- | --- | --- | --- | --- | --- | --- | --- | --- | --- | --- | --- | --- | --- |
| Tyr | Lys | Tyr | Leu | Pro | Trp | Phe | Leu | Asn | Asp | Arg | Pro | Asn | Ile | Lys |  |  |
| 1010 |  |  |  |  | 1015 |  |  |  |  | 1020 |  |  |  |  |  |  |

| tgt | ccc | aaa | ggc | ggc | ctg | gga | gca | tac | agc | acc | tct | gtg | aac | ttg |  | 3114 |
| --- | --- | --- | --- | --- | --- | --- | --- | --- | --- | --- | --- | --- | --- | --- | --- | --- |
| Cys | Pro | Lys | Gly | Gly | Leu | Gly | Ala | Tyr | Ser | Thr | Ser | Val | Asn | Leu |  |  |
| 1025 |  |  |  |  | 1030 |  |  |  |  | 1035 |  |  |  |  |  |  |

| act | tca | gat | ggc | cag | gtt | tta | gcc | tcc | agg | ttc | atg | gcc | tat | cac |  | 3159 |
| --- | --- | --- | --- | --- | --- | --- | --- | --- | --- | --- | --- | --- | --- | --- | --- | --- |
| Thr | Ser | Asp | Gly | Gln | Val | Leu | Ala | Ser | Arg | Phe | Met | Ala | Tyr | His |  |  |
| 1040 |  |  |  |  | 1045 |  |  |  |  | 1050 |  |  |  |  |  |  |

| aag | ccc | ctg | aaa | aac | tca | cag | gat | tac | aca | gaa | gct | ctg | cgg | gca |  | 3204 |
| --- | --- | --- | --- | --- | --- | --- | --- | --- | --- | --- | --- | --- | --- | --- | --- | --- |
| Lys | Pro | Leu | Lys | Asn | Ser | Gln | Asp | Tyr | Thr | Glu | Ala | Leu | Arg | Ala |  |  |
| 1055 |  |  |  |  | 1060 |  |  |  |  | 1065 |  |  |  |  |  |  |

| gct | cgg | gag | ctg | gca | gcc | aac | atc | act | gct | gac | ctg | cgg | aag | gtg |  | 3249 |
| --- | --- | --- | --- | --- | --- | --- | --- | --- | --- | --- | --- | --- | --- | --- | --- | --- |

```
Ala Arg Glu Leu Ala Ala Asn Ile Thr Ala Asp Leu Arg Lys Val
    1070                1075                1080 cct ggg aca gac cca gct ttt gag gtc ttc ccc tac acg gtc acc          3294
Pro Gly Thr Asp Pro Ala Phe Glu Val Phe Pro Tyr Thr Val Thr
    1085                1090                1095 aat gtg ttt tat gag cag tac ctg acc att ctc cct gag ggg ctc          3339
Asn Val Phe Tyr Glu Gln Tyr Leu Thr Ile Leu Pro Glu Gly Leu
    1100                1105                1110 ttc atg ctc agc ctc tgc ctg gtg ccc acc ttc gct gtc tgc tgc          3384
Phe Met Leu Ser Leu Cys Leu Val Pro Thr Phe Ala Val Cys Cys
    1115                1120                1125 ctc ctg ctg ggc ctg gac ctc cgc tcc ggc ctc ctc aac ctg ctg          3429
Leu Leu Leu Gly Leu Asp Leu Arg Ser Gly Leu Leu Asn Leu Leu
    1130                1135                1140 tcc atc atc atg atc ctc gtg gac acc gtt ggc ttc atg gcc ctg          3474
Ser Ile Ile Met Ile Leu Val Asp Thr Val Gly Phe Met Ala Leu
    1145                1150                1155 tgg ggc atc agt tac aat gct gtg tcc ctc atc aac ctg gtc tcg          3519
Trp Gly Ile Ser Tyr Asn Ala Val Ser Leu Ile Asn Leu Val Ser
    1160                1165                1170 gcg gtg ggc atg tct gtg gag ttc gtg tcc cac att acc cgc tcc          3564
Ala Val Gly Met Ser Val Glu Phe Val Ser His Ile Thr Arg Ser
    1175                1180                1185 ttt gcc atc agc acc aag ccc acc cgg ctg gag agg gcc aaa gag          3609
Phe Ala Ile Ser Thr Lys Pro Thr Arg Leu Glu Arg Ala Lys Glu
    1190                1195                1200 gcc acc atc tct atg gga agt gcg gtg ttt gca ggt gtg gcc atg          3654
Ala Thr Ile Ser Met Gly Ser Ala Val Phe Ala Gly Val Ala Met
    1205                1210                1215 acc aac ctc cct ggc atc ctg gtc ctg ggc ctt gcc aag gcc cag          3699
Thr Asn Leu Pro Gly Ile Leu Val Leu Gly Leu Ala Lys Ala Gln
    1220                1225                1230 ctc att cag atc ttc ttc cgc ctc aac ctg ctg att act ctg              3744
Leu Ile Gln Ile Phe Phe Phe Arg Leu Asn Leu Leu Ile Thr Leu
    1235                1240                1245 ctg ggt ctg ctg cat ggc ttg gtc ttc ctg cct gtc atc ctc agc          3789
Leu Gly Leu Leu His Gly Leu Val Phe Leu Pro Val Ile Leu Ser
    1250                1255                1260 tat gtg ggg cct gac atc aac cca gct ctg gca ctg gag cag aag          3834
Tyr Val Gly Pro Asp Ile Asn Pro Ala Leu Ala Leu Glu Gln Lys
    1265                1270                1275 ctg gct gag gag gca gca gcg gca gcc ata gcg gcc tcc tac cca          3879
Leu Ala Glu Glu Ala Ala Ala Ala Ile Ala Ala Ser Tyr Pro
    1280                1285                1290 aat cac ccc tcc cga gtc tcc aca gct gac aac atc tat gtc aac          3924
Asn His Pro Ser Arg Val Ser Thr Ala Asp Asn Ile Tyr Val Asn
    1295                1300                1305 cac agc ttt gaa ggt tct atc aaa ggt gct ggt gcc gtc agc aac          3969
His Ser Phe Glu Gly Ser Ile Lys Gly Ala Gly Ala Val Ser Asn
    1310                1315                1320 ttc ttg ccc aac aat ggg cgg cag ttc tga                              3999
Phe Leu Pro Asn Asn Gly Arg Gln Phe
    1325                1330

<210> SEQ ID NO 10
<211> LENGTH: 1332
<212> TYPE: PRT
<213> ORGANISM: Macaca fascicularis

<400> SEQUENCE: 10

Met Ala Glu Ala Gly Leu Arg Gly Trp Leu Leu Trp Ala Leu Leu Leu
```

```
  1               5                  10                 15
His Leu Ala Gln Ser Glu Pro Tyr Thr Pro Ile His Gln Pro Gly Tyr
             20                  25                 30

Cys Ala Phe Tyr Asp Glu Cys Gly Lys Asn Pro Glu Leu Ser Gly Gly
             35                  40              45

Leu Met Thr Leu Ser Asn Val Ser Cys Leu Ser Asn Thr Pro Ala Arg
 50                  55                  60

Asn Ile Thr Gly Asp His Leu Ile Leu Leu Gln Arg Ile Cys Pro Arg
 65                  70                  75                  80

Leu Tyr Thr Gly Pro Asn Thr Gln Ala Cys Cys Ser Ala Lys Gln Leu
                 85                  90                  95

Val Ser Leu Glu Ala Ser Leu Ser Ile Thr Lys Ala Leu Leu Thr Arg
             100                 105                110

Cys Pro Ala Cys Ser Asp Asn Phe Val Ser Leu His Cys His Asn Thr
             115                 120                 125

Cys Ser Pro Asn Gln Ser Leu Phe Ile Asn Val Thr Arg Val Ala Gln
             130                 135                 140

Leu Gly Ala Gly Gln Leu Pro Ala Val Val Ala Tyr Glu Ala Phe Tyr
145                 150                 155                 160

Gln His Ser Phe Ala Glu Gln Ser Tyr Asp Ser Cys Ser Arg Val His
                 165                 170                 175

Ile Pro Ala Ala Ala Thr Leu Ala Val Gly Ser Met Cys Gly Val Tyr
             180                 185                 190

Gly Ser Ala Leu Cys Asn Ala Gln Arg Trp Leu Asn Phe Gln Gly Asp
             195                 200                 205

Thr Gly Asn Gly Leu Ala Pro Leu Asp Ile Thr Phe His Leu Leu Glu
             210                 215                 220

Pro Gly Gln Ala Val Gly Ser Gly Ile Gln Pro Leu Asn Glu Gly Val
225                 230                 235                 240

Ala Arg Cys Asn Glu Ser Gln Gly Asp Asp Ala Val Ala Cys Ser Cys
                 245                 250                 255

Gln Asp Cys Ala Ala Ser Cys Pro Ala Ile Ala His Pro Gln Ala Leu
             260                 265                 270

Asp Ser Thr Phe Arg Leu Gly Arg Met Pro Gly Gly Leu Val Leu Ile
             275                 280                 285

Ile Ile Leu Cys Ser Val Phe Thr Val Val Ala Ile Leu Leu Val Gly
             290                 295                 300

Leu Arg Val Ala Pro Thr Arg Asp Lys Ser Lys Thr Val Asp Pro Lys
305                 310                 315                 320

Lys Gly Thr Ser Leu Ser Asp Lys Leu Ser Phe Ser Thr His Thr Leu
                 325                 330                 335

Leu Gly Gln Phe Phe Gln Gly Trp Gly Thr Trp Val Ala Ser Trp Pro
             340                 345                 350

Leu Thr Ile Leu Val Leu Ser Val Ile Pro Val Val Leu Ala Ala
             355                 360                 365

Gly Leu Val Phe Thr Glu Leu Thr Thr Asp Pro Val Glu Leu Trp Ser
370                 375                 380

Ala Pro Asn Ser Gln Ala Arg Ser Glu Lys Ala Phe His Asp Gln His
385                 390                 395                 400

Phe Gly Pro Phe Phe Arg Thr Asn Gln Val Ile Leu Thr Ala Pro Asn
                 405                 410                 415

Arg Ser Ser Tyr Arg Tyr Asp Ser Leu Leu Leu Gly Pro Lys Asn Phe
             420                 425                 430
```

-continued

Ser Gly Ile Leu Asp Leu Asp Leu Leu Glu Leu Leu Glu Leu Gln
        435                 440                 445

Glu Arg Leu Arg His Leu Gln Val Trp Ser Pro Glu Ala Gln Arg Asn
    450                 455                 460

Ile Ser Leu Gln His Ile Cys Tyr Ala Pro Leu Asn Pro Asp Asn Thr
465                 470                 475                 480

Ser Leu Ser Asp Cys Cys Ile Asn Ser Leu Leu Gln Tyr Phe Gln Asn
                485                 490                 495

Asn Arg Thr Leu Leu Leu Leu Thr Ala Asn Gln Thr Leu Met Gly Gln
            500                 505                 510

Thr Ser Gln Val Asp Trp Arg Asp His Phe Leu Tyr Cys Ala Asn Ala
        515                 520                 525

Pro Leu Thr Phe Lys Asp Gly Thr Ala Leu Ala Leu Ser Cys Met Ala
    530                 535                 540

Asp Tyr Gly Ala Pro Val Phe Pro Phe Leu Ala Val Gly Gly Tyr Lys
545                 550                 555                 560

Gly Lys Asp Tyr Ser Glu Ala Glu Ala Leu Ile Met Thr Phe Ser Leu
                565                 570                 575

Asn Asn Tyr Pro Ala Gly Asp Pro Arg Leu Ala Gln Ala Gln Leu Trp
            580                 585                 590

Glu Glu Ala Phe Leu Glu Glu Met Arg Ala Phe Gln Arg Arg Thr Ala
        595                 600                 605

Gly Lys Phe Gln Val Thr Phe Met Ala Glu Arg Ser Leu Glu Asp Glu
    610                 615                 620

Ile Asn Arg Thr Thr Ala Glu Asp Leu Pro Ile Phe Ala Thr Ser Tyr
625                 630                 635                 640

Ile Val Ile Phe Leu Tyr Ile Ser Leu Ala Leu Gly Ser Tyr Ser Ser
                645                 650                 655

Trp Ser Arg Val Met Val Asp Ser Lys Ala Thr Leu Gly Leu Gly Gly
            660                 665                 670

Val Ala Val Val Leu Gly Ala Val Met Ala Ala Met Gly Phe Phe Ser
        675                 680                 685

Tyr Leu Gly Ile Arg Ser Ser Leu Ile Ile Leu Gln Val Val Pro Phe
    690                 695                 700

Leu Val Leu Ser Val Gly Ala Asp Asn Ile Phe Ile Phe Val Leu Glu
705                 710                 715                 720

Tyr Gln Arg Leu Pro Arg Arg Pro Gly Glu Pro Arg Glu Val His Ile
                725                 730                 735

Gly Arg Ala Leu Gly Arg Val Ala Pro Ser Met Leu Leu Cys Ser Leu
            740                 745                 750

Ser Glu Ala Ile Cys Phe Phe Leu Gly Ala Leu Thr Pro Met Pro Ala
        755                 760                 765

Val Arg Thr Phe Ala Leu Thr Ser Gly Leu Ala Val Val Leu Asp Phe
    770                 775                 780

Leu Leu Gln Met Ser Ala Phe Val Ala Leu Leu Ser Leu Asp Ser Lys
785                 790                 795                 800

Arg Gln Glu Ala Ser Arg Leu Asp Val Cys Cys Cys Val Lys Pro Arg
                805                 810                 815

Glu Leu Pro Leu Pro Gly Gln Gly Glu Gly Phe Leu Leu Gly Leu Phe
            820                 825                 830

Arg Lys Ala Tyr Val Pro Phe Leu Leu His Trp Ile Thr Arg Gly Val
        835                 840                 845

Val Leu Leu Leu Phe Leu Ala Leu Phe Gly Val Ser Leu Tyr Tyr Met
850                 855                 860

```
Cys His Ile Ser Val Gly Leu Asp Gln Glu Leu Ala Leu Pro Lys Asp
865                 870                 875                 880

Ser Tyr Leu Leu Asp Tyr Phe Leu Phe Leu Asn Arg Tyr Phe Glu Thr
            885                 890                 895

Gly Ala Pro Val Tyr Phe Val Thr Thr Ser Gly Tyr Asn Phe Ser Ser
            900                 905                 910

Glu Ala Gly Met Asn Ala Ile Cys Ser Ser Ala Gly Cys Asn Asn Phe
            915                 920                 925

Ser Phe Thr Gln Lys Ile Gln Tyr Ala Thr Glu Phe Pro Glu Gln Ser
        930                 935                 940

Tyr Leu Ala Ile Pro Ala Ser Ser Trp Val Asp Asp Phe Ile Asp Trp
945                 950                 955                 960

Leu Thr Pro Ser Ser Cys Cys Arg Leu Tyr Ile Ser Gly Pro Asn Lys
                965                 970                 975

Asp Gln Phe Cys Pro Ser Thr Val Asn Ser Leu Asn Cys Leu Lys Asn
            980                 985                 990

Cys Leu Ser Ile Thr Met Gly Ser  Val Arg Pro Ser Val  Glu Gln Phe
            995                 1000                1005

Tyr Lys  Tyr Leu Pro Trp Phe  Leu Asn Asp Arg Pro  Asn Ile Lys
1010                 1015                1020

Cys Pro  Lys Gly Gly Leu Gly  Ala Tyr Ser Thr Ser  Val Asn Leu
1025                 1030                1035

Thr Ser  Asp Gly Gln Val Leu  Ala Ser Arg Phe Met  Ala Tyr His
1040                 1045                1050

Lys Pro  Leu Lys Asn Ser Gln  Asp Tyr Thr Glu Ala  Leu Arg Ala
1055                 1060                1065

Ala Arg  Glu Leu Ala Ala Asn  Ile Thr Ala Asp Leu  Arg Lys Val
1070                 1075                1080

Pro Gly  Thr Asp Pro Ala Phe  Glu Val Phe Pro Tyr  Thr Val Thr
1085                 1090                1095

Asn Val  Phe Tyr Glu Gln Tyr  Leu Thr Ile Leu Pro  Glu Gly Leu
1100                 1105                1110

Phe Met  Leu Ser Leu Cys Leu  Val Pro Thr Phe Ala  Val Cys Cys
1115                 1120                1125

Leu Leu  Leu Gly Leu Asp Leu  Arg Ser Gly Leu Leu  Asn Leu Leu
1130                 1135                1140

Ser Ile  Ile Met Ile Leu Val  Asp Thr Val Gly Phe  Met Ala Leu
1145                 1150                1155

Trp Gly  Ile Ser Tyr Asn Ala  Val Ser Leu Ile Asn  Leu Val Ser
1160                 1165                1170

Ala Val  Gly Met Ser Val Glu  Phe Val Ser His Ile  Thr Arg Ser
1175                 1180                1185

Phe Ala  Ile Ser Thr Lys Pro  Thr Arg Leu Glu Arg  Ala Lys Glu
1190                 1195                1200

Ala Thr  Ile Ser Met Gly Ser  Ala Val Phe Ala Gly  Val Ala Met
1205                 1210                1215

Thr Asn  Leu Pro Gly Ile Leu  Val Leu Gly Leu Ala  Lys Ala Gln
1220                 1225                1230

Leu Ile  Gln Ile Phe Phe  Arg Leu Asn Leu Leu  Ile Thr Leu
1235                 1240                1245

Leu Gly  Leu Leu His Gly Leu  Val Phe Leu Pro Val  Ile Leu Ser
1250                 1255                1260

Tyr Val  Gly Pro Asp Ile Asn  Pro Ala Leu Ala Leu  Glu Gln Lys
```

```
                1265                1270                1275

Leu Ala Glu Glu Ala Ala Ala Ala Ile Ala Ala Ser Tyr Pro
    1280                1285                1290

Asn His Pro Ser Arg Val Ser Thr Ala Asp Asn Ile Tyr Val Asn
    1295                1300                1305

His Ser Phe Glu Gly Ser Ile Lys Gly Ala Gly Ala Val Ser Asn
    1310                1315                1320

Phe Leu Pro Asn Asn Gly Arg Gln Phe
    1325                1330

<210> SEQ ID NO 11
<211> LENGTH: 27
<212> TYPE: DNA
<213> ORGANISM: Artificial Sequence
<220> FEATURE:
<223> OTHER INFORMATION: S1352

<400> SEQUENCE: 11
taggcccgct cggcgaagct gcgctcg                                          27

<210> SEQ ID NO 12
<211> LENGTH: 24
<212> TYPE: DNA
<213> ORGANISM: Artificial Sequence
<220> FEATURE:
<223> OTHER INFORMATION: primer #98

<400> SEQUENCE: 12
agctagcttg ccaaacctac aggt                                             24

<210> SEQ ID NO 13
<211> LENGTH: 27
<212> TYPE: DNA
<213> ORGANISM: Artificial Sequence
<220> FEATURE:
<223> OTHER INFORMATION: S1299

<400> SEQUENCE: 13
catgtctgtg gagttygtgt cccacat                                          27

<210> SEQ ID NO 14
<211> LENGTH: 27
<212> TYPE: DNA
<213> ORGANISM: Artificial Sequence
<220> FEATURE:
<223> OTHER INFORMATION: S1368

<400> SEQUENCE: 14
atggcagggg ctgcgcgggg ctggctg                                          27

<210> SEQ ID NO 15
<211> LENGTH: 24
<212> TYPE: DNA
<213> ORGANISM: Artificial Sequence
<220> FEATURE:
<223> OTHER INFORMATION: S1317

<400> SEQUENCE: 15
tcagaacttc tgctttctgg tggg                                             24

<210> SEQ ID NO 16
<211> LENGTH: 23
<212> TYPE: DNA
<213> ORGANISM: Artificial Sequence
<220> FEATURE:
```

```
<223> OTHER INFORMATION: S1320R

<400> SEQUENCE: 16
taraaggcct cataggccac cac                                           23

<210> SEQ ID NO 17
<211> LENGTH: 30
<212> TYPE: DNA
<213> ORGANISM: Artificial Sequence
<220> FEATURE:
<223> OTHER INFORMATION: monkey 5' primer

<400> SEQUENCE: 17
atggcggagg ccggcctgag gggctggctg                                    30

<210> SEQ ID NO 18
<211> LENGTH: 30
<212> TYPE: DNA
<213> ORGANISM: Artificial Sequence
<220> FEATURE:
<223> OTHER INFORMATION: Monkey 3' primer

<400> SEQUENCE: 18
tcagaactgc cgcccattgt tgggcaagaa                                    30

<210> SEQ ID NO 19
<211> LENGTH: 28
<212> TYPE: DNA
<213> ORGANISM: Artificial Sequence
<220> FEATURE:
<223> OTHER INFORMATION: 5'-RACE PCR 5' hamster GSP2 primer

<400> SEQUENCE: 19
tgacattgat gaagaggctc tggtcagg                                      28

<210> SEQ ID NO 20
<211> LENGTH: 29
<212> TYPE: DNA
<213> ORGANISM: Artificial Sequence
<220> FEATURE:
<223> OTHER INFORMATION: 3'-RACE PCR 5' hamster GSP2 primer

<400> SEQUENCE: 20
tcaggcatcc tcaacctgct ctccatcat                                     29

<210> SEQ ID NO 21
<211> LENGTH: 27
<212> TYPE: DNA
<213> ORGANISM: Artificial Sequence
<220> FEATURE:
<223> OTHER INFORMATION: hamster 5' primer

<400> SEQUENCE: 21
atggcagctg gcctaacgag atggctg                                       27

<210> SEQ ID NO 22
<211> LENGTH: 28
<212> TYPE: DNA
<213> ORGANISM: Artificial Sequence
<220> FEATURE:
<223> OTHER INFORMATION: hamster 3' primer

<400> SEQUENCE: 22
ttaaaacttt tggccgcttt taggcaag                                      28

<210> SEQ ID NO 23
```

```
<211> LENGTH: 23
<212> TYPE: DNA
<213> ORGANISM: Artificial Sequence
<220> FEATURE:
<223> OTHER INFORMATION: S1406

<400> SEQUENCE: 23
atggcggaca ctggccaggg gct                                              23

<210> SEQ ID NO 24
<211> LENGTH: 24
<212> TYPE: DNA
<213> ORGANISM: Artificial Sequence
<220> FEATURE:
<223> OTHER INFORMATION: S1414

<400> SEQUENCE: 24
tcagaggtcc ggtccactgc gggg                                             24

<210> SEQ ID NO 25
<211> LENGTH: 1332
<212> TYPE: PRT
<213> ORGANISM: Homo sapiens

<400> SEQUENCE: 25
```

Met Ala Glu Ala Gly Leu Arg Gly Trp Leu Leu Trp Ala Leu Leu Leu
1               5                   10                  15

Arg Leu Ala Gln Ser Glu Pro Tyr Thr Thr Ile His Gln Pro Gly Tyr
            20                  25                  30

Cys Ala Phe Tyr Asp Glu Cys Gly Lys Asn Pro Glu Leu Ser Gly Ser
        35                  40                  45

Leu Met Thr Leu Ser Asn Val Ser Cys Leu Ser Asn Thr Pro Ala Arg
    50                  55                  60

Lys Ile Thr Gly Asp His Leu Ile Leu Leu Gln Lys Ile Cys Pro Arg
65                  70                  75                  80

Leu Tyr Thr Gly Pro Asn Thr Gln Ala Cys Ser Ala Lys Gln Leu
            85                  90                  95

Val Ser Leu Glu Ala Ser Leu Ser Ile Thr Lys Ala Leu Leu Thr Arg
            100                 105                 110

Cys Pro Ala Cys Ser Asp Asn Phe Val Asn Leu His Cys His Asn Thr
        115                 120                 125

Cys Ser Pro Asn Gln Ser Leu Phe Ile Asn Val Thr Arg Val Ala Gln
    130                 135                 140

Leu Gly Ala Gly Gln Leu Pro Ala Val Val Ala Tyr Glu Ala Phe Tyr
145                 150                 155                 160

Gln His Ser Phe Ala Glu Gln Ser Tyr Asp Ser Cys Ser Arg Val Arg
            165                 170                 175

Val Pro Ala Ala Ala Thr Leu Ala Val Gly Thr Met Cys Gly Val Tyr
            180                 185                 190

Gly Ser Ala Leu Cys Asn Ala Gln Arg Trp Leu Asn Phe Gln Gly Asp
        195                 200                 205

Thr Gly Asn Gly Leu Ala Pro Leu Asp Ile Thr Phe His Leu Leu Glu
    210                 215                 220

Pro Gly Gln Ala Val Gly Ser Gly Ile Gln Pro Leu Asn Glu Gly Val
225                 230                 235                 240

Ala Arg Cys Asn Glu Ser Gln Gly Asp Val Ala Thr Cys Ser Cys
            245                 250                 255

Gln Asp Cys Ala Ala Ser Cys Pro Ala Ile Ala Arg Pro Gln Ala Leu
            260                 265                 270

```
Asp Ser Thr Phe Tyr Leu Gly Gln Met Pro Gly Ser Leu Val Leu Ile
    275                 280                 285

Ile Ile Leu Cys Ser Val Phe Ala Val Val Thr Ile Leu Leu Val Gly
    290                 295                 300

Phe Arg Val Ala Pro Ala Arg Asp Lys Ser Lys Met Val Asp Pro Lys
305                 310                 315                 320

Lys Gly Thr Ser Leu Ser Asp Lys Leu Ser Phe Ser Thr His Thr Leu
                325                 330                 335

Leu Gly Gln Phe Phe Gln Gly Trp Gly Thr Trp Val Ala Ser Trp Pro
                340                 345                 350

Leu Thr Ile Leu Val Leu Ser Val Ile Pro Val Val Ala Leu Ala Ala
            355                 360                 365

Gly Leu Val Phe Thr Glu Leu Thr Thr Asp Pro Val Glu Leu Trp Ser
    370                 375                 380

Ala Pro Asn Ser Gln Ala Arg Ser Glu Lys Ala Phe His Asp Gln His
385                 390                 395                 400

Phe Gly Pro Phe Phe Arg Thr Asn Gln Val Ile Leu Thr Ala Pro Asn
                405                 410                 415

Arg Ser Ser Tyr Arg Tyr Asp Ser Leu Leu Gly Pro Lys Asn Phe
                420                 425                 430

Ser Gly Ile Leu Asp Leu Asp Leu Leu Glu Leu Leu Glu Leu Gln
                435                 440                 445

Glu Arg Leu Arg His Leu Gln Val Trp Ser Pro Glu Ala Gln Arg Asn
    450                 455                 460

Ile Ser Leu Gln Asp Ile Cys Tyr Ala Pro Leu Asn Pro Asp Asn Thr
465                 470                 475                 480

Ser Leu Tyr Asp Cys Cys Ile Asn Ser Leu Leu Gln Tyr Phe Gln Asn
                485                 490                 495

Asn Arg Thr Leu Leu Leu Leu Thr Ala Asn Gln Thr Leu Met Gly Gln
                500                 505                 510

Thr Ser Gln Val Asp Trp Lys Asp His Phe Leu Tyr Cys Ala Asn Ala
    515                 520                 525

Pro Leu Thr Phe Lys Asp Gly Thr Ala Leu Ala Leu Ser Cys Met Ala
    530                 535                 540

Asp Tyr Gly Ala Pro Val Phe Pro Phe Leu Ala Ile Gly Gly Tyr Lys
545                 550                 555                 560

Gly Lys Asp Tyr Ser Glu Ala Glu Ala Leu Ile Met Thr Phe Ser Leu
                565                 570                 575

Asn Asn Tyr Pro Ala Gly Asp Pro Arg Leu Ala Gln Ala Lys Leu Trp
                580                 585                 590

Glu Glu Ala Phe Leu Glu Met Arg Ala Phe Gln Arg Arg Met Ala
    595                 600                 605

Gly Met Phe Gln Val Thr Phe Met Ala Glu Arg Ser Leu Glu Asp Glu
    610                 615                 620

Ile Asn Arg Thr Thr Ala Glu Asp Leu Pro Ile Phe Ala Thr Ser Tyr
625                 630                 635                 640

Ile Val Ile Phe Leu Tyr Ile Ser Leu Ala Leu Gly Ser Tyr Ser Ser
                645                 650                 655

Trp Ser Arg Val Met Val Asp Ser Lys Ala Thr Leu Gly Leu Gly Gly
                660                 665                 670

Val Ala Val Val Leu Gly Ala Val Met Ala Ala Met Gly Phe Phe Ser
                675                 680                 685

Tyr Leu Gly Ile Arg Ser Ser Leu Val Ile Leu Gln Val Val Pro Phe
```

```
             690                 695                 700
Leu Val Leu Ser Val Gly Ala Asp Asn Ile Phe Ile Phe Val Leu Glu
705                 710                 715                 720

Tyr Gln Arg Leu Pro Arg Arg Pro Gly Glu Pro Arg Glu Val His Ile
                725                 730                 735

Gly Arg Ala Leu Gly Arg Val Ala Pro Ser Met Leu Leu Cys Ser Leu
                740                 745                 750

Ser Glu Ala Ile Cys Phe Phe Leu Gly Ala Leu Thr Pro Met Pro Ala
                755                 760                 765

Val Arg Thr Phe Ala Leu Thr Ser Gly Leu Ala Val Ile Leu Asp Phe
770                 775                 780

Leu Leu Gln Met Ser Ala Phe Val Ala Leu Leu Ser Leu Asp Ser Lys
785                 790                 795                 800

Arg Gln Glu Ala Ser Arg Leu Asp Val Cys Cys Val Lys Pro Gln
                805                 810                 815

Glu Leu Pro Pro Pro Gly Gln Gly Glu Gly Leu Leu Leu Gly Phe Phe
                820                 825                 830

Gln Lys Ala Tyr Ala Pro Phe Leu Leu His Trp Ile Thr Arg Gly Val
                835                 840                 845

Val Leu Leu Leu Phe Leu Ala Leu Phe Gly Val Ser Leu Tyr Ser Met
850                 855                 860

Cys His Ile Ser Val Gly Leu Asp Gln Glu Leu Ala Leu Pro Lys Asp
865                 870                 875                 880

Ser Tyr Leu Leu Asp Tyr Phe Leu Phe Leu Asn Arg Tyr Phe Glu Val
                885                 890                 895

Gly Ala Pro Val Tyr Phe Val Thr Thr Leu Gly Tyr Asn Phe Ser Ser
                900                 905                 910

Glu Ala Gly Met Asn Ala Ile Cys Ser Ser Ala Gly Cys Asn Asn Phe
                915                 920                 925

Ser Phe Thr Gln Lys Ile Gln Tyr Ala Thr Glu Phe Pro Glu Gln Ser
                930                 935                 940

Tyr Leu Ala Ile Pro Ala Ser Ser Trp Val Asp Asp Phe Ile Asp Trp
945                 950                 955                 960

Leu Thr Pro Ser Ser Cys Cys Arg Leu Tyr Ile Ser Gly Pro Asn Lys
                965                 970                 975

Asp Lys Phe Cys Pro Ser Thr Val Asn Ser Leu Asn Cys Leu Lys Asn
                980                 985                 990

Cys Met Ser Ile Thr Met Gly Ser  Val Arg Pro Ser Val  Glu Gln Phe
                995                1000                1005

His Lys  Tyr Leu Pro Trp Phe  Leu Asn Asp Arg Pro  Asn Ile Lys
   1010                1015                1020

Cys Pro Lys Gly Gly Leu Ala  Ala Tyr Ser Thr Ser  Val Asn Leu
   1025                1030                1035

Thr Ser  Asp Gly Gln Val Leu  Ala Ser Arg Phe Met  Ala Tyr His
   1040                1045                1050

Lys Pro  Leu Lys Asn Ser Gln  Asp Tyr Thr Glu Ala  Leu Arg Ala
   1055                1060                1065

Ala Arg  Glu Leu Ala Ala Asn  Ile Thr Ala Asp Leu  Arg Lys Val
   1070                1075                1080

Pro Gly  Thr Asp Pro Ala Phe  Glu Val Phe Pro Tyr  Thr Ile Thr
   1085                1090                1095

Asn Val  Phe Tyr Glu Gln Tyr  Leu Thr Ile Leu Pro  Glu Gly Leu
   1100                1105                1110
```

```
Phe Met Leu Ser Leu Cys Leu Val Pro Thr Phe Ala Val Ser Cys
    1115            1120            1125

Leu Leu Leu Gly Leu Asp Leu Arg Ser Gly Leu Leu Asn Leu Leu
    1130            1135            1140

Ser Ile Val Met Ile Leu Val Asp Thr Val Gly Phe Met Ala Leu
    1145            1150            1155

Trp Gly Ile Ser Tyr Asn Ala Val Ser Leu Ile Asn Leu Val Ser
    1160            1165            1170

Ala Val Gly Met Ser Val Glu Phe Val Ser His Ile Thr Arg Ser
    1175            1180            1185

Phe Ala Ile Ser Thr Lys Pro Thr Trp Leu Glu Arg Ala Lys Glu
    1190            1195            1200

Ala Thr Ile Ser Met Gly Ser Ala Val Phe Ala Gly Val Ala Met
    1205            1210            1215

Thr Asn Leu Pro Gly Ile Leu Val Leu Gly Leu Ala Lys Ala Gln
    1220            1225            1230

Leu Ile Gln Ile Phe Phe Phe Arg Leu Asn Leu Leu Ile Thr Leu
    1235            1240            1245

Leu Gly Leu Leu His Gly Leu Val Phe Leu Pro Val Ile Leu Ser
    1250            1255            1260

Tyr Val Gly Pro Asp Val Asn Pro Ala Leu Ala Leu Glu Gln Lys
    1265            1270            1275

Arg Ala Glu Glu Ala Val Ala Ala Val Met Val Ala Ser Cys Pro
    1280            1285            1290

Asn His Pro Ser Arg Val Ser Thr Ala Asp Asn Ile Tyr Val Asn
    1295            1300            1305

His Ser Phe Glu Gly Ser Ile Lys Gly Ala Gly Ala Ile Ser Asn
    1310            1315            1320

Phe Leu Pro Asn Asn Gly Arg Gln Phe
    1325            1330

<210> SEQ ID NO 26
<211> LENGTH: 1332
<212> TYPE: PRT
<213> ORGANISM: Pan troglodytes

<400> SEQUENCE: 26

Met Ala Glu Ala Gly Leu Arg Gly Trp Leu Trp Ala Leu Leu Leu
1               5               10              15

Arg Leu Ala Gln Ser Glu Pro Tyr Thr Pro Ile His Gln Pro Gly Tyr
                20              25              30

Cys Ala Phe Tyr Asp Glu Cys Gly Lys Asn Pro Glu Leu Ser Gly Ser
                35              40              45

Leu Met Thr Leu Ser Asn Val Ser Cys Leu Ser Asn Thr Pro Ala Arg
50              55              60

Lys Ile Thr Gly Asp His Val Leu Leu Gln Lys Ile Cys Pro Arg
65              70              75              80

Leu Tyr Thr Gly Pro Asn Thr Gln Ala Cys Cys Ser Ala Lys Gln Leu
                85              90              95

Val Ser Leu Glu Ala Ser Leu Ser Ile Thr Lys Ala Leu Leu Thr Arg
                100             105             110

Cys Pro Ala Cys Ser Asp Asn Phe Val Asn Leu His Cys His Asn Thr
                115             120             125

Cys Ser Pro Asn Gln Ser Leu Phe Ile Asn Val Thr Arg Val Ala Gln
                130             135             140
```

```
Leu Gly Ala Gly Gln Leu Pro Ala Val Val Ala Tyr Glu Ala Phe Tyr
145                 150                 155                 160

Gln His Ser Phe Ala Glu Gln Ser Tyr Asp Ser Cys Ser Arg Val Arg
            165                 170                 175

Val Pro Ala Ala Ala Thr Leu Ala Val Gly Thr Met Cys Gly Val Tyr
                180                 185                 190

Gly Ser Ala Leu Cys Asn Ala Gln Arg Trp Leu Asn Phe Gln Gly Asp
            195                 200                 205

Thr Gly Asn Gly Leu Ala Pro Leu Asp Ile Thr Phe His Leu Leu Glu
210                 215                 220

Pro Gly Gln Ala Val Gly Ser Gly Ile Gln Pro Leu Asn Glu Gly Val
225                 230                 235                 240

Ala Arg Cys Asn Glu Ser Gln Gly Asp Asp Val Val Ala Cys Ser Cys
                245                 250                 255

Gln Asp Cys Ala Ala Ser Cys Pro Ala Ile Ala Arg Pro Gln Ala Leu
            260                 265                 270

Asp Ser Thr Phe Tyr Leu Gly Gln Met Pro Gly Ser Leu Val Leu Ile
            275                 280                 285

Ile Ile Leu Cys Ser Val Phe Ala Val Val Thr Ile Leu Leu Val Gly
290                 295                 300

Phe Arg Val Ala Pro Ala Arg Asp Lys Ser Lys Met Ala Asp Pro Lys
305                 310                 315                 320

Lys Gly Thr Ser Leu Ser Asp Lys Leu Ser Phe Ser Thr His Thr Leu
                325                 330                 335

Leu Gly Gln Phe Phe Gln Gly Trp Gly Thr Trp Val Ala Ser Trp Pro
            340                 345                 350

Leu Thr Ile Leu Val Leu Ser Val Ile Pro Val Val Ala Leu Ala Ala
            355                 360                 365

Gly Leu Val Phe Thr Glu Leu Thr Thr Asp Pro Val Glu Leu Trp Ser
370                 375                 380

Ala Pro Asn Ser Gln Ala Arg Ser Glu Lys Ala Phe His Asp Gln His
385                 390                 395                 400

Phe Gly Pro Phe Phe Arg Thr Asn Gln Val Ile Leu Thr Ala Pro Asn
                405                 410                 415

Arg Ser Ser Tyr Arg Tyr Asp Ser Leu Leu Leu Gly Pro Lys Asn Phe
            420                 425                 430

Ser Gly Ile Leu Asp Leu Asp Leu Leu Leu Glu Leu Leu Glu Leu Gln
            435                 440                 445

Glu Arg Leu Arg His Leu Gln Val Trp Ser Pro Glu Ala Gln Arg Asn
450                 455                 460

Ile Ser Leu Gln Asp Ile Cys Tyr Ala Pro Leu Asn Pro Asp Asn Thr
465                 470                 475                 480

Ser Leu Tyr Asp Cys Cys Ile Asn Ser Leu Leu Gln Tyr Phe Gln Asn
                485                 490                 495

Asn Arg Thr Leu Leu Leu Leu Thr Ala Asn Gln Thr Leu Met Gly Gln
            500                 505                 510

Thr Ser Gln Val Asp Trp Lys Asp His Phe Leu Tyr Cys Ala Asn Ala
            515                 520                 525

Pro Leu Thr Phe Lys Asp Gly Thr Ala Leu Ala Leu Ser Cys Met Ala
530                 535                 540

Asp Tyr Gly Ala Pro Val Phe Pro Phe Leu Ala Ile Gly Gly Tyr Lys
545                 550                 555                 560

Gly Lys Asp Tyr Ser Glu Ala Glu Ala Leu Ile Met Thr Phe Ser Leu
                565                 570                 575
```

```
Asn Asn Tyr Pro Ala Gly Asp Pro Arg Leu Ala Gln Ala Lys Leu Trp
            580                 585                 590
Glu Glu Ala Phe Leu Glu Glu Met Arg Ala Phe Gln Arg Arg Met Ala
        595                 600                 605
Gly Met Phe Gln Val Thr Phe Met Ala Glu Arg Ser Leu Glu Asp Glu
    610                 615                 620
Ile Asn Arg Thr Thr Ala Glu Asp Leu Pro Ile Phe Ala Thr Ser Tyr
625                 630                 635                 640
Ile Val Ile Phe Leu Tyr Ile Ser Leu Ala Leu Gly Ser Tyr Ser Ser
                645                 650                 655
Trp Ser Arg Val Met Val Asp Ser Lys Ala Thr Leu Gly Leu Gly Gly
            660                 665                 670
Val Ala Val Val Leu Gly Ala Val Met Ala Ala Met Gly Phe Phe Ser
        675                 680                 685
Tyr Leu Gly Ile Arg Ser Ser Leu Val Ile Leu Gln Val Val Pro Phe
    690                 695                 700
Leu Val Leu Ser Val Gly Ala Asp Asn Ile Phe Ile Phe Val Leu Glu
705                 710                 715                 720
Tyr Gln Arg Leu Pro Arg Arg Pro Gly Glu Pro Arg Glu Val His Ile
                725                 730                 735
Gly Arg Ala Leu Gly Arg Val Ala Pro Ser Met Leu Leu Cys Ser Leu
            740                 745                 750
Ser Glu Ala Ile Cys Phe Phe Leu Gly Ala Leu Thr Pro Met Pro Ala
        755                 760                 765
Val Arg Thr Phe Ala Leu Thr Ser Gly Leu Ala Val Ile Leu Asp Phe
    770                 775                 780
Leu Leu Gln Met Ser Ala Phe Val Ala Leu Leu Ser Leu Asp Ser Lys
785                 790                 795                 800
Arg Gln Glu Ala Ser Arg Leu Asp Val Cys Cys Cys Val Lys Pro Arg
                805                 810                 815
Glu Leu Pro Pro Pro Gly Gln Gly Glu Gly Leu Leu Leu Gly Phe Phe
            820                 825                 830
Gln Lys Ala Tyr Ala Pro Phe Leu Leu His Trp Ile Thr Arg Gly Val
        835                 840                 845
Val Leu Leu Leu Phe Leu Ala Leu Phe Gly Val Ser Leu Tyr Ser Met
    850                 855                 860
Cys His Ile Ser Val Gly Leu Asp Gln Glu Leu Ala Leu Pro Lys Asp
865                 870                 875                 880
Ser Tyr Leu Leu Asp Tyr Phe Leu Phe Leu Asn Arg Tyr Phe Glu Val
                885                 890                 895
Gly Ala Pro Val Tyr Phe Val Thr Thr Leu Gly Tyr Asn Phe Ser Ser
            900                 905                 910
Glu Ala Gly Met Asn Ala Ile Cys Ser Ser Ala Gly Cys Asn Asn Phe
        915                 920                 925
Ser Phe Thr Gln Lys Ile Gln Tyr Ala Thr Glu Phe Pro Glu Gln Ser
    930                 935                 940
Tyr Leu Ala Ile Pro Ala Ser Ser Trp Val Asp Asp Phe Ile Asp Trp
945                 950                 955                 960
Leu Thr Pro Ser Ser Cys Cys Arg Leu Tyr Ile Ser Gly Pro Asn Lys
                965                 970                 975
Asp Lys Phe Cys Pro Ser Thr Val Asn Ser Leu Asn Cys Leu Lys Asn
            980                 985                 990
Cys Met Ser Ile Thr Met Gly Ser  Val Arg Pro Ser Val  Glu Gln Phe
```

-continued

```
                995                1000               1005
His Lys Tyr Leu Pro Trp Phe Leu Asn Asp Arg Pro Asn Ile Lys
    1010               1015               1020

Cys Pro Lys Gly Gly Leu Ala Ala Tyr Ser Thr Ser Val Asn Leu
    1025               1030               1035

Thr Ser Asp Gly Gln Val Leu Ala Ser Arg Phe Met Ala Tyr His
    1040               1045               1050

Lys Pro Leu Lys Asn Ser Gln Asp Tyr Thr Glu Ala Leu Arg Ala
    1055               1060               1065

Ala Arg Glu Leu Ala Ala Asn Ile Thr Ala Asp Leu Arg Lys Val
    1070               1075               1080

Pro Gly Thr Asp Pro Ala Phe Glu Val Phe Pro Tyr Thr Ile Thr
    1085               1090               1095

Asn Val Phe Tyr Glu Gln Tyr Leu Thr Ile Leu Pro Glu Gly Leu
    1100               1105               1110

Phe Met Leu Ser Leu Cys Leu Val Pro Thr Phe Ala Val Ser Cys
    1115               1120               1125

Leu Leu Leu Gly Leu Asp Leu Arg Ser Gly Leu Leu Asn Leu Leu
    1130               1135               1140

Ser Ile Val Met Ile Leu Val Asp Thr Val Gly Phe Met Ala Leu
    1145               1150               1155

Trp Gly Ile Ser Tyr Asn Ala Val Ser Leu Ile Asn Leu Val Ser
    1160               1165               1170

Ala Val Gly Met Ser Val Glu Phe Val Ser His Ile Thr Cys Ser
    1175               1180               1185

Phe Ala Ile Ser Thr Lys Pro Thr Trp Leu Glu Arg Ala Lys Glu
    1190               1195               1200

Ala Thr Ile Ser Met Gly Ser Ala Val Phe Ala Gly Val Ala Met
    1205               1210               1215

Thr Asn Leu Pro Gly Ile Leu Val Leu Gly Leu Ala Lys Ala Gln
    1220               1225               1230

Leu Ile Gln Ile Phe Phe Phe Arg Leu Asn Leu Leu Ile Thr Leu
    1235               1240               1245

Leu Gly Leu Leu His Gly Leu Val Phe Leu Pro Val Ile Leu Ser
    1250               1255               1260

Tyr Val Gly Pro Asp Val Asn Pro Ala Leu Ala Leu Glu Gln Lys
    1265               1270               1275

Arg Ala Glu Glu Ala Val Ala Ala Val Met Val Ala Ser Cys Pro
    1280               1285               1290

Asn His Pro Ser Arg Val Ser Thr Ala Asp Asn Ile Tyr Val Asn
    1295               1300               1305

His Ser Phe Glu Gly Ser Ile Lys Gly Ala Gly Ala Ile Ser Asn
    1310               1315               1320

Phe Leu Pro Asn Asn Gly Arg Gln Phe
    1325               1330

<210> SEQ ID NO 27
<211> LENGTH: 1333
<212> TYPE: PRT
<213> ORGANISM: Mus

<400> SEQUENCE: 27

Met Ala Ala Ala Trp Gln Gly Trp Leu Leu Trp Ala Leu Leu Leu Asn
1               5                   10                  15

Ser Ala Gln Gly Glu Leu Tyr Thr Pro Thr His Lys Ala Gly Phe Cys
```

```
                  20                  25                  30
Thr Phe Tyr Glu Glu Cys Gly Lys Asn Pro Glu Leu Ser Gly Gly Leu
            35                  40                  45

Thr Ser Leu Ser Asn Ile Ser Cys Leu Ser Asn Thr Pro Ala Arg His
50                  55                  60

Val Thr Gly Asp His Leu Ala Leu Leu Gln Arg Val Cys Pro Arg Leu
65                  70                  75                  80

Tyr Asn Gly Pro Asn Asp Thr Tyr Ala Cys Cys Ser Thr Lys Gln Leu
            85                  90                  95

Val Ser Leu Asp Ser Ser Leu Ser Ile Thr Lys Ala Leu Leu Thr Arg
            100                 105                 110

Cys Pro Ala Cys Ser Glu Asn Phe Val Ser Ile His Cys His Asn Thr
            115                 120                 125

Cys Ser Pro Asp Gln Ser Leu Phe Ile Asn Val Thr Arg Val Val Gln
            130                 135                 140

Arg Asp Pro Gly Gln Leu Pro Ala Val Val Ala Tyr Glu Ala Phe Tyr
145                 150                 155                 160

Gln Arg Ser Phe Ala Glu Lys Ala Tyr Glu Ser Cys Ser Arg Val Arg
            165                 170                 175

Ile Pro Ala Ala Ala Ser Leu Ala Val Gly Ser Met Cys Gly Val Tyr
            180                 185                 190

Gly Ser Ala Leu Cys Asn Ala Gln Arg Trp Leu Asn Phe Gln Gly Asp
            195                 200                 205

Thr Gly Asn Gly Leu Ala Pro Leu Asp Ile Thr Phe His Leu Leu Glu
            210                 215                 220

Pro Gly Gln Ala Leu Ala Asp Gly Met Lys Pro Leu Asp Gly Lys Ile
225                 230                 235                 240

Thr Pro Cys Asn Glu Ser Gln Gly Glu Asp Ser Ala Ala Cys Ser Cys
            245                 250                 255

Gln Asp Cys Ala Ala Ser Cys Pro Val Ile Pro Pro Pro Ala Leu
            260                 265                 270

Arg Pro Ser Phe Tyr Met Gly Arg Met Pro Gly Trp Leu Ala Leu Ile
            275                 280                 285

Ile Ile Phe Thr Ala Val Phe Val Leu Leu Ser Val Val Leu Val Tyr
            290                 295                 300

Leu Arg Val Ala Ser Asn Arg Asn Lys Asn Thr Ala Gly Ser Gln
305                 310                 315                 320

Glu Ala Pro Asn Leu Pro Arg Lys Arg Phe Ser Pro His Thr Val
            325                 330                 335

Leu Gly Arg Phe Phe Glu Ser Trp Gly Thr Arg Val Ala Ser Trp Pro
            340                 345                 350

Leu Thr Val Leu Ala Leu Ser Phe Ile Val Val Ile Ala Leu Ser Val
            355                 360                 365

Gly Leu Thr Phe Ile Glu Leu Thr Thr Asp Pro Val Glu Leu Trp Ser
            370                 375                 380

Ala Pro Lys Ser Gln Ala Arg Lys Glu Lys Ala Phe His Asp Glu His
385                 390                 395                 400

Phe Gly Pro Phe Phe Arg Thr Asn Gln Ile Phe Val Thr Ala Lys Asn
            405                 410                 415

Arg Ser Ser Tyr Lys Tyr Asp Ser Leu Leu Leu Gly Pro Lys Asn Phe
            420                 425                 430

Ser Gly Ile Leu Ser Leu Asp Leu Leu Gln Glu Leu Leu Glu Leu Gln
            435                 440                 445
```

-continued

```
Glu Arg Leu Arg His Leu Gln Val Trp Ser His Glu Ala Gln Arg Asn
450                 455                 460

Ile Ser Leu Gln Asp Ile Cys Tyr Ala Pro Leu Lys Pro His Asn Thr
465                 470                 475                 480

Ser Leu Thr Asp Cys Cys Val Asn Ser Leu Leu Gln Tyr Phe Gln Asn
                485                 490                 495

Asn His Thr Leu Leu Leu Thr Ala Asn Gln Thr Leu Asn Gly Gln
            500                 505                 510

Thr Ser Leu Val Asp Trp Lys Asp His Phe Leu Tyr Cys Ala Asn Ala
        515                 520                 525

Pro Leu Thr Tyr Lys Asp Gly Thr Ala Leu Ala Leu Ser Cys Ile Ala
530                 535                 540

Asp Tyr Gly Ala Pro Val Phe Pro Phe Leu Ala Val Gly Gly Tyr Gln
545                 550                 555                 560

Gly Thr Asp Tyr Ser Glu Ala Glu Ala Leu Ile Ile Thr Phe Ser Ile
                565                 570                 575

Asn Asn Tyr Pro Ala Asp Asp Pro Arg Met Ala His Ala Lys Leu Trp
            580                 585                 590

Glu Glu Ala Phe Leu Lys Glu Met Gln Ser Phe Gln Arg Ser Thr Ala
        595                 600                 605

Asp Lys Phe Gln Ile Ala Phe Ser Ala Glu Arg Ser Leu Glu Asp Glu
610                 615                 620

Ile Asn Arg Thr Thr Ile Gln Asp Leu Pro Val Phe Ala Ile Ser Tyr
625                 630                 635                 640

Leu Ile Val Phe Leu Tyr Ile Ser Leu Ala Leu Gly Ser Tyr Ser Arg
                645                 650                 655

Trp Ser Arg Val Ala Val Asp Ser Lys Ala Thr Leu Gly Leu Gly Gly
            660                 665                 670

Val Ala Val Leu Gly Ala Val Ala Ala Met Gly Phe Tyr Ser
        675                 680                 685

Tyr Leu Gly Val Pro Ser Ser Leu Val Ile Ile Gln Val Val Pro Phe
690                 695                 700

Leu Val Leu Ala Val Gly Ala Asp Asn Ile Phe Ile Phe Val Leu Glu
705                 710                 715                 720

Tyr Gln Arg Leu Pro Arg Met Pro Gly Glu Gln Arg Glu Ala His Ile
                725                 730                 735

Gly Arg Thr Leu Gly Ser Val Ala Pro Ser Met Leu Leu Cys Ser Leu
            740                 745                 750

Ser Glu Ala Ile Cys Phe Phe Leu Gly Ala Leu Thr Ser Met Pro Ala
        755                 760                 765

Val Arg Thr Phe Ala Leu Thr Ser Gly Leu Ala Ile Ile Phe Asp Phe
770                 775                 780

Leu Leu Gln Met Thr Ala Phe Val Ala Leu Leu Ser Leu Asp Ser Lys
785                 790                 795                 800

Arg Gln Glu Ala Ser Arg Pro Asp Val Val Cys Cys Phe Ser Ser Arg
                805                 810                 815

Asn Leu Pro Pro Pro Lys Gln Lys Glu Gly Leu Leu Leu Cys Phe Phe
            820                 825                 830

Arg Lys Ile Tyr Thr Pro Phe Leu Leu His Arg Phe Ile Arg Pro Val
        835                 840                 845

Val Leu Leu Leu Phe Leu Val Leu Phe Gly Ala Asn Leu Tyr Leu Met
850                 855                 860

Cys Asn Ile Ser Val Gly Leu Asp Gln Asp Leu Ala Leu Pro Lys Asp
865                 870                 875                 880
```

-continued

Ser Tyr Leu Ile Asp Tyr Phe Leu Phe Leu Asn Arg Tyr Leu Glu Val
            885                 890                 895

Gly Pro Pro Val Tyr Phe Asp Thr Thr Ser Gly Tyr Asn Phe Ser Thr
            900                 905                 910

Glu Ala Gly Met Asn Ala Ile Cys Ser Ser Ala Gly Cys Glu Ser Phe
            915                 920                 925

Ser Leu Thr Gln Lys Ile Gln Tyr Ala Ser Glu Phe Pro Asn Gln Ser
    930                 935                 940

Tyr Val Ala Ile Ala Ala Ser Ser Trp Val Asp Phe Ile Asp Trp
945                 950                 955                 960

Leu Thr Pro Ser Ser Ser Cys Cys Arg Ile Tyr Thr Arg Gly Pro His
                965                 970                 975

Lys Asp Glu Phe Cys Pro Ser Thr Asp Thr Ser Phe Asn Cys Leu Lys
            980                 985                 990

Asn Cys Met Asn Arg Thr Leu Gly Pro Val Arg Pro Thr Thr Glu Gln
        995                 1000                1005

Phe His Lys Tyr Leu Pro Trp Phe Leu Asn Asp Thr Pro Asn Ile
    1010                1015                1020

Arg Cys Pro Lys Gly Gly Leu Ala Ala Tyr Arg Thr Ser Val Asn
    1025                1030                1035

Leu Ser Ser Asp Gly Gln Ile Ile Ala Ser Gln Phe Met Ala Tyr
    1040                1045                1050

His Lys Pro Leu Arg Asn Ser Gln Asp Phe Thr Glu Ala Leu Arg
    1055                1060                1065

Ala Ser Arg Leu Leu Ala Ala Asn Ile Thr Ala Glu Leu Arg Lys
    1070                1075                1080

Val Pro Gly Thr Asp Pro Asn Phe Glu Val Phe Pro Tyr Thr Ile
    1085                1090                1095

Ser Asn Val Phe Tyr Gln Gln Tyr Leu Thr Val Leu Pro Glu Gly
    1100                1105                1110

Ile Phe Thr Leu Ala Leu Cys Phe Val Pro Thr Phe Val Val Cys
    1115                1120                1125

Tyr Leu Leu Leu Gly Leu Asp Ile Arg Ser Gly Ile Leu Asn Leu
    1130                1135                1140

Leu Ser Ile Ile Met Ile Leu Val Asp Thr Ile Gly Leu Met Ala
    1145                1150                1155

Val Trp Gly Ile Ser Tyr Asn Ala Val Ser Leu Ile Asn Leu Val
    1160                1165                1170

Thr Ala Val Gly Met Ser Val Glu Phe Val Ser His Ile Thr Arg
    1175                1180                1185

Ser Phe Ala Val Ser Thr Lys Pro Thr Arg Leu Glu Arg Ala Lys
    1190                1195                1200

Asp Ala Thr Ile Phe Met Gly Ser Ala Val Phe Ala Gly Val Ala
    1205                1210                1215

Met Thr Asn Phe Pro Gly Ile Leu Ile Leu Gly Phe Ala Gln Ala
    1220                1225                1230

Gln Leu Ile Gln Ile Phe Phe Phe Arg Leu Asn Leu Leu Ile Thr
    1235                1240                1245

Leu Leu Gly Leu Leu His Gly Leu Val Phe Leu Pro Val Val Leu
    1250                1255                1260

Ser Tyr Leu Gly Pro Asp Val Asn Gln Ala Leu Val Leu Glu Glu
    1265                1270                1275

Lys Leu Ala Thr Glu Ala Ala Met Val Ser Glu Pro Ser Cys Pro

-continued

```
                1280                1285                1290

Gln Tyr  Pro Phe Pro Ala  Asp Ala Asn Thr Ser  Asp Tyr Val Asn
        1295            1300                1305

Tyr Gly  Phe Asn Pro Glu  Phe Ile Pro Glu Ile  Asn Ala Ala Ser
        1310            1315                1320

Ser Ser  Leu Pro Lys Ser  Asp Gln Lys Phe
        1325            1330

<210> SEQ ID NO 28
<211> LENGTH: 1331
<212> TYPE: PRT
<213> ORGANISM: Rattus

<400> SEQUENCE: 28

Met Ala Ala Ala Trp Leu Gly Trp Leu Leu Trp Ala Leu Leu Leu Ser
1               5                   10                  15

Ala Ala Gln Gly Glu Leu Tyr Thr Pro Lys His Glu Ala Gly Val Cys
            20                  25                  30

Thr Phe Tyr Glu Glu Cys Gly Lys Asn Pro Glu Leu Ser Gly Gly Leu
        35                  40                  45

Thr Ser Leu Ser Asn Val Ser Cys Leu Ser Asn Thr Pro Ala Arg His
    50                  55                  60

Val Thr Gly Glu His Leu Ala Leu Leu Gln Arg Ile Cys Pro Arg Leu
65                  70                  75                  80

Tyr Asn Gly Pro Asn Thr Thr Phe Ala Cys Cys Ser Thr Lys Gln Leu
                85                  90                  95

Leu Ser Leu Glu Ser Ser Met Ser Ile Thr Lys Ala Leu Leu Thr Arg
            100                 105                 110

Cys Pro Ala Cys Ser Asp Asn Phe Val Ser Leu His Cys His Asn Thr
        115                 120                 125

Cys Ser Pro Asp Gln Ser Leu Phe Ile Asn Val Thr Arg Val Val Glu
    130                 135                 140

Arg Gly Ala Gly Glu Pro Pro Ala Val Val Ala Tyr Glu Ala Phe Tyr
145                 150                 155                 160

Gln Arg Ser Phe Ala Glu Lys Ala Tyr Glu Ser Cys Ser Gln Val Arg
                165                 170                 175

Ile Pro Ala Ala Ala Ser Leu Ala Val Gly Ser Met Cys Gly Val Tyr
            180                 185                 190

Gly Ser Ala Leu Cys Asn Ala Gln Arg Trp Leu Asn Phe Gln Gly Asp
        195                 200                 205

Thr Gly Asn Gly Leu Ala Pro Leu Asp Ile Thr Phe His Leu Leu Glu
    210                 215                 220

Pro Gly Gln Ala Leu Pro Asp Gly Ile Gln Pro Leu Asn Gly Lys Ile
225                 230                 235                 240

Ala Pro Cys Asn Glu Ser Gln Gly Asp Asp Ser Ala Val Cys Ser Cys
                245                 250                 255

Gln Asp Cys Ala Ala Ser Cys Pro Val Ile Pro Pro Glu Ala Leu
            260                 265                 270

Arg Pro Ser Phe Tyr Met Gly Arg Met Pro Gly Trp Leu Ala Leu Ile
        275                 280                 285

Ile Ile Phe Thr Ala Val Phe Val Ser Leu Ser Ala Val Leu Val Arg
    290                 295                 300

Leu Arg Val Val Ser Asn Arg Asn Lys Asn Lys Ala Pro Glu Pro Gln
305                 310                 315                 320

Glu Ala Pro Asn Leu Pro His Lys His Lys Leu Ser Pro His Thr Ile
```

```
                    325                 330                 335
Leu Gly Arg Phe Phe Gln Asn Trp Gly Thr Arg Val Val Ser Trp Pro
                340                 345                 350

Leu Thr Val Leu Ala Leu Ser Phe Ile Val Val Ile Ala Leu Ala Ala
                355                 360                 365

Gly Leu Thr Phe Ile Glu Leu Thr Thr Asp Pro Val Glu Leu Trp Ser
                370                 375                 380

Ala Pro Lys Ser Gln Ala Arg Lys Glu Lys Ser Phe His Asp Glu His
385                 390                 395                 400

Phe Gly Pro Phe Phe Arg Thr Asn Gln Ile Phe Val Thr Ala Arg Asn
                405                 410                 415

Arg Ser Ser Tyr Lys Tyr Asp Ser Leu Leu Gly Ser Lys Asn Phe
                420                 425                 430

Ser Gly Ile Leu Ser Leu Asp Phe Leu Leu Glu Leu Leu Glu Leu Gln
                435                 440                 445

Glu Arg Leu Arg His Leu Gln Val Trp Ser Pro Glu Ala Glu Arg Asn
450                 455                 460

Ile Ser Leu Gln Asp Ile Cys Tyr Ala Pro Leu Asn Pro Tyr Asn Thr
465                 470                 475                 480

Ser Leu Ser Asp Cys Cys Val Asn Ser Leu Leu Gln Tyr Phe Gln Asn
                485                 490                 495

Asn Arg Thr Leu Leu Met Leu Thr Ala Asn Gln Thr Leu Asn Gly Gln
                500                 505                 510

Thr Ser Leu Val Asp Trp Lys Asp His Phe Leu Tyr Cys Ala Asn Ala
                515                 520                 525

Pro Leu Thr Phe Lys Asp Gly Thr Ser Leu Ala Leu Ser Cys Met Ala
                530                 535                 540

Asp Tyr Gly Ala Pro Val Phe Pro Phe Leu Ala Val Gly Gly Tyr Gln
545                 550                 555                 560

Gly Thr Asp Tyr Ser Glu Ala Glu Ala Leu Ile Ile Thr Phe Ser Leu
                565                 570                 575

Asn Asn Tyr Pro Ala Asp Asp Pro Arg Met Ala Gln Ala Lys Leu Trp
                580                 585                 590

Glu Glu Ala Phe Leu Lys Glu Met Glu Ser Phe Gln Arg Asn Thr Ser
                595                 600                 605

Asp Lys Phe Gln Val Ala Phe Ser Ala Glu Arg Ser Leu Glu Asp Glu
                610                 615                 620

Ile Asn Arg Thr Thr Ile Gln Asp Leu Pro Val Phe Ala Val Ser Tyr
625                 630                 635                 640

Ile Ile Val Phe Leu Tyr Ile Ser Leu Ala Leu Gly Ser Tyr Ser Arg
                645                 650                 655

Cys Ser Arg Val Ala Val Glu Ser Lys Ala Thr Leu Gly Leu Gly Gly
                660                 665                 670

Val Ile Val Val Leu Gly Ala Val Leu Ala Ala Met Gly Phe Tyr Ser
                675                 680                 685

Tyr Leu Gly Val Pro Ser Ser Leu Val Ile Ile Gln Val Val Pro Phe
                690                 695                 700

Leu Val Leu Ala Val Gly Ala Asp Asn Ile Phe Ile Phe Val Leu Glu
705                 710                 715                 720

Tyr Gln Arg Leu Pro Arg Met Pro Gly Glu Gln Arg Glu Ala His Ile
                725                 730                 735

Gly Arg Thr Leu Gly Ser Val Ala Pro Ser Met Leu Leu Cys Ser Leu
                740                 745                 750
```

-continued

Ser Glu Ala Ile Cys Phe Phe Leu Gly Ala Leu Thr Pro Met Pro Ala
            755                 760                 765

Val Arg Thr Phe Ala Leu Thr Ser Gly Leu Ala Ile Ile Leu Asp Phe
    770                 775                 780

Leu Leu Gln Met Thr Ala Phe Val Ala Leu Leu Ser Leu Asp Ser Lys
785                 790                 795                 800

Arg Gln Glu Ala Ser Arg Pro Asp Val Leu Cys Cys Phe Ser Thr Arg
                805                 810                 815

Lys Leu Pro Pro Lys Glu Lys Glu Gly Leu Leu Leu Arg Phe Phe
            820                 825                 830

Arg Lys Ile Tyr Ala Pro Phe Leu Leu His Arg Phe Ile Arg Pro Val
            835                 840                 845

Val Met Leu Leu Phe Leu Thr Leu Phe Gly Ala Asn Leu Tyr Leu Met
    850                 855                 860

Cys Asn Ile Asn Val Gly Leu Asp Gln Glu Leu Ala Leu Pro Lys Asp
865                 870                 875                 880

Ser Tyr Leu Ile Asp Tyr Phe Leu Phe Leu Asn Arg Tyr Leu Glu Val
                885                 890                 895

Gly Pro Pro Val Tyr Phe Val Thr Thr Ser Gly Phe Asn Phe Ser Ser
            900                 905                 910

Glu Ala Gly Met Asn Ala Thr Cys Ser Ser Ala Gly Cys Lys Ser Phe
            915                 920                 925

Ser Leu Thr Gln Lys Ile Gln Tyr Ala Ser Glu Phe Pro Asp Gln Ser
930                 935                 940

Tyr Val Ala Ile Ala Ala Ser Ser Trp Val Asp Asp Phe Ile Asp Trp
945                 950                 955                 960

Leu Thr Pro Ser Ser Ser Cys Cys Arg Leu Tyr Ile Arg Gly Pro His
                965                 970                 975

Lys Asp Glu Phe Cys Pro Ser Thr Asp Thr Ser Phe Asn Cys Leu Lys
            980                 985                 990

Asn Cys Met Asn Arg Thr Leu Gly Pro Val Arg Pro Thr Ala Glu Gln
        995                 1000                1005

Phe His Lys Tyr Leu Pro Trp Phe Leu Asn Asp Pro Pro Asn Ile
    1010                1015                1020

Arg Cys Pro Lys Gly Gly Leu Ala Ala Tyr Arg Thr Ser Val Asn
    1025                1030                1035

Leu Ser Ser Asp Gly Gln Val Ile Ala Ser Gln Phe Met Ala Tyr
    1040                1045                1050

His Lys Pro Leu Arg Asn Ser Gln Asp Phe Thr Glu Ala Leu Arg
    1055                1060                1065

Ala Ser Arg Leu Leu Ala Ala Asn Ile Thr Ala Asp Leu Arg Lys
    1070                1075                1080

Val Pro Gly Thr Asp Pro Asn Phe Glu Val Phe Pro Tyr Thr Ile
    1085                1090                1095

Ser Asn Val Phe Tyr Gln Gln Tyr Leu Thr Val Leu Pro Glu Gly
    1100                1105                1110

Ile Phe Thr Leu Ala Leu Cys Phe Val Pro Thr Phe Val Val Cys
    1115                1120                1125

Tyr Leu Leu Leu Gly Leu Asp Met Cys Ser Gly Ile Leu Asn Leu
    1130                1135                1140

Leu Ser Ile Ile Met Ile Leu Val Asp Thr Ile Gly Leu Met Ala
    1145                1150                1155

Val Trp Gly Ile Ser Tyr Asn Ala Val Ser Leu Ile Asn Leu Val
    1160                1165                1170

```
Thr Ala Val Gly Met Ser Val Glu Phe Val Ser His Ile Thr Arg
    1175                1180                1185

Ser Phe Ala Val Ser Thr Lys Pro Thr Arg Leu Glu Arg Ala Lys
    1190                1195                1200

Asp Ala Thr Val Phe Met Gly Ser Ala Val Phe Ala Gly Val Ala
    1205                1210                1215

Met Thr Asn Phe Pro Gly Ile Leu Ile Leu Gly Phe Ala Gln Ala
    1220                1225                1230

Gln Leu Ile Gln Ile Phe Phe Arg Leu Asn Leu Leu Ile Thr
    1235                1240                1245

Leu Leu Gly Leu Leu His Gly Leu Val Phe Leu Pro Val Val Leu
    1250                1255                1260

Ser Tyr Leu Gly Pro Asp Val Asn Gln Ala Leu Val Gln Glu Glu
    1265                1270                1275

Lys Leu Ala Ser Glu Ala Ala Val Ala Pro Glu Pro Ser Cys Pro
    1280                1285                1290

Gln Tyr Pro Ser Pro Ala Asp Ala Asp Ala Asn Val Asn Tyr Gly
    1295                1300                1305

Phe Ala Pro Glu Leu Ala His Gly Ala Asn Ala Ala Arg Ser Ser
    1310                1315                1320

Leu Pro Lys Ser Asp Gln Lys Phe
    1325                1330

<210> SEQ ID NO 29
<211> LENGTH: 1333
<212> TYPE: PRT
<213> ORGANISM: Bos taurus

<400> SEQUENCE: 29

Met Val Glu Thr Gly Leu Lys Gly Trp Leu Leu Trp Ala Leu Leu Leu
1               5                   10                  15

His Ser Ala Gln Ser Glu Val Tyr Thr Pro Ile His Gln Pro Gly Tyr
                20                  25                  30

Cys Ala Phe Tyr Asp Glu Cys Gly Lys Asn Pro Glu Leu Ser Gly Ser
            35                  40                  45

Leu Ala Ser Leu Ser Asn Val Ser Cys Leu Asp Asn Ser Pro Ala Arg
        50                  55                  60

His Ile Thr Gly Asp His Leu Ala Leu Leu Gln Ser Ile Cys Pro Arg
65                  70                  75                  80

Leu Tyr Thr Gly Ala Ser Thr Thr Tyr Ala Cys Cys Ser Ser Lys Gln
                85                  90                  95

Leu Val Ala Leu Asp Met Ser Leu Arg Ile Thr Lys Ala Leu Leu Thr
            100                 105                 110

Arg Cys Pro Ala Cys Ser Asp Asn Phe Val Ser Leu His Cys His Asn
        115                 120                 125

Thr Cys Ser Pro Asn Gln Ser Leu Phe Ile Asn Val Thr Arg Val Val
    130                 135                 140

Thr Gln Gly Asp Ser Gln Ser Gln Ala Val Val Ala Tyr Glu Ala Phe
145                 150                 155                 160

Tyr Gln Arg Ser Phe Ala Glu Gln Thr Tyr Asn Ser Cys Ser Arg Val
                165                 170                 175

Arg Ile Pro Ala Ala Ala Thr Leu Ala Val Gly Ser Met Cys Gly Val
            180                 185                 190

Tyr Gly Ser Ala Leu Cys Asn Ala Gln Arg Trp Leu Asn Phe Gln Gly
        195                 200                 205
```

```
Asp Thr Ser Asn Gly Leu Ala Pro Leu Asp Ile Thr Phe His Leu Trp
        210                 215                 220

Glu Pro Ser Gln Ala Glu Gly Ser Thr Ile Gln Pro Leu Asn Asp Glu
225                 230                 235                 240

Val Val Pro Cys Asn Gln Ser Gln Gly Asp Gly Ala Ala Ala Cys Ser
                245                 250                 255

Cys Gln Asp Cys Ala Ala Ser Cys Pro Val Ile Ala Gln Pro Arg Ala
            260                 265                 270

Leu Asp Pro Thr Phe Arg Leu Gly Arg Met Glu Gly Ser Leu Val Leu
        275                 280                 285

Ile Ile Ile Leu Cys Ser Leu Phe Val Leu Leu Thr Ala Phe Leu Leu
        290                 295                 300

Arg Ser Arg Leu Ala Glu Trp Cys Arg Gly Lys Arg Lys Thr Pro Lys
305                 310                 315                 320

Pro Lys Ala Ser Ile Asn Leu Ala His Arg Leu Ser Leu Ser Thr His
                325                 330                 335

Thr Leu Leu Ser Arg Cys Phe Gln Cys Trp Gly Thr Trp Val Ala Ser
            340                 345                 350

Trp Pro Leu Thr Ile Leu Ala Val Ser Val Ile Val Val Ala Leu
        355                 360                 365

Ala Gly Gly Leu Ala Phe Ile Glu Leu Thr Thr Asp Pro Val Glu Leu
        370                 375                 380

Trp Ser Ala Pro Asn Ser Leu Ala Arg Arg Glu Lys Ala Phe His Asp
385                 390                 395                 400

Lys Tyr Phe Gly Pro Phe Phe Arg Thr Ser Gln Val Phe Met Thr Ala
                405                 410                 415

Pro His Arg Pro Ser Tyr Arg Tyr Asp Ser Leu Leu Leu Gly Pro Lys
            420                 425                 430

Asn Phe Ser Gly Ile Leu Ser Ser Asp Leu Leu Leu Glu Val Leu Glu
        435                 440                 445

Leu Gln Glu Arg Leu Arg His Leu Gln Val Trp Ser Pro Glu Glu Gln
        450                 455                 460

Arg Asn Val Ser Leu Arg Asp Thr Cys Tyr Ala Pro Leu Asn Pro His
465                 470                 475                 480

Asn Ala Ser Leu Ser Asp Cys Cys Val Asn Ser Leu Leu Gln Tyr Phe
                485                 490                 495

Gln Asn Asn Arg Thr Gln Leu Leu Leu Thr Ala Asn Gln Thr Leu Ser
            500                 505                 510

Gly Gln Thr Ala Gln Val Asp Trp Arg Asp His Phe Leu Tyr Cys Ala
        515                 520                 525

Asn Ala Pro Leu Thr Tyr Lys Asp Gly Thr Ala Leu Ala Leu Ser Cys
        530                 535                 540

Met Ala Asp Tyr Gly Ala Pro Ile Phe Pro Phe Leu Ala Val Gly Gly
545                 550                 555                 560

Tyr Lys Gly Lys Asp Tyr Ser Glu Ala Glu Ala Leu Ile Met Thr Phe
                565                 570                 575

Ser Leu Asn Asn Tyr Pro Pro Gly Asp Pro Lys Leu Ala Gln Ala Lys
            580                 585                 590

Leu Trp Glu Ala Ala Phe Leu Glu Glu Met Arg Ala Phe Gln Arg Arg
        595                 600                 605

Thr Ala Gly Val Phe Gln Val Thr Phe Met Ala Glu Arg Ser Leu Glu
        610                 615                 620

Asp Glu Ile Asn Ser Thr Thr Ala Glu Asp Leu Pro Val Phe Ala Val
```

-continued

```
               625                 630                 635                 640
Ser Tyr Leu Val Ile Phe Leu Tyr Ile Ser Leu Ala Leu Gly Ser Tyr
                645                 650                 655

Ser Ser Trp Arg Arg Val Pro Val Asp Ser Lys Ala Thr Leu Gly Leu
                660                 665                 670

Gly Val Ala Val Val Leu Gly Ala Val Ala Ser Met Gly Phe
        675                 680                 685

Phe Ser Tyr Leu Gly Val Pro Ser Ser Leu Val Ile Leu Gln Val Val
        690                 695                 700

Pro Phe Leu Val Leu Ala Val Gly Ala Asp Asn Ile Phe Ile Phe Val
705                 710                 715                 720

Leu Glu Tyr Gln Arg Leu Pro Arg Arg Pro Gly Glu Arg Glu Ala
                725                 730                 735

His Ile Gly Arg Ala Leu Gly Arg Val Ala Pro Ser Met Leu Leu Cys
                740                 745                 750

Ser Leu Ser Glu Ala Ile Cys Phe Phe Leu Gly Ala Leu Thr Pro Met
                755                 760                 765

Pro Ala Val Arg Thr Phe Ala Leu Thr Ser Gly Phe Ala Val Leu Leu
770                 775                 780

Asp Phe Leu Leu Gln Met Ser Ala Phe Val Ala Leu Leu Ser Leu Asp
785                 790                 795                 800

Ser Arg Arg Gln Glu Ala Ser Arg Met Asp Ile Cys Cys Cys Lys Thr
                805                 810                 815

Ala Gln Lys Leu Pro Pro Ser Gln Asp Glu Gly Leu Leu Leu Arg
                820                 825                 830

Phe Phe Arg Lys Phe Tyr Val Pro Phe Leu Leu His Trp Leu Thr Arg
                835                 840                 845

Val Val Val Leu Leu Phe Leu Ala Leu Phe Ala Ala Ser Leu Tyr
        850                 855                 860

Phe Met Cys Tyr Ile Asn Val Gly Leu Asp Gln Gln Leu Ala Leu Pro
865                 870                 875                 880

Lys Asp Ser Tyr Leu Ile Asp Tyr Phe Leu Phe Met Asn Arg Tyr Phe
                885                 890                 895

Glu Val Gly Ala Pro Val Tyr Phe Val Thr Thr Gly Gly Tyr Asn Phe
                900                 905                 910

Ser Ser Glu Glu Gly Met Asn Ala Ile Cys Ser Ser Ala Gly Cys Asn
                915                 920                 925

Asn Phe Ser Leu Thr Gln Lys Ile Gln Tyr Ala Thr Asp Phe Pro Asp
        930                 935                 940

Met Ser Tyr Leu Ala Ile Pro Ala Ser Ser Trp Val Asp Asp Phe Ile
945                 950                 955                 960

Asp Trp Leu Thr Ser Ser Ser Cys Cys Arg Leu Tyr Ile Ser Gly Pro
                965                 970                 975

Asn Lys Asp Glu Phe Cys Pro Ser Thr Val Asn Ser Leu Ala Cys Leu
                980                 985                 990

Lys Thr Cys Val Ser Pro Thr Ala Gly Ser Ala Arg Pro Ser Val Glu
                995                1000                1005

Gln Phe His Lys Tyr Leu Pro Trp Phe Leu Ser Asp Glu Pro Asn
                1010                1015                1020

Ile Lys Cys Pro Lys Gly Gly Leu Ala Ala Tyr Ser Thr Ser Val
        1025                1030                1035

Asn Met Ser Ser Asp Gly Gln Ile Leu Ala Ser Arg Phe Met Ala
        1040                1045                1050
```

```
Tyr Asn Lys Pro Leu Lys Asn Ser Arg Asp Phe Thr Glu Ala Leu
    1055            1060                1065

Arg Ala Thr Arg Ala Leu Ala Ala Asn Ile Thr Ala Asp Leu Arg
    1070            1075                1080

Lys Val Pro Gly Thr Asp Pro Asp Phe Glu Val Phe Pro Tyr Ser
    1085            1090                1095

Val Thr Asn Val Phe Tyr Glu Gln Tyr Leu Thr Ile Val Pro Glu
    1100            1105                1110

Gly Leu Phe Met Leu Thr Ile Cys Leu Val Pro Thr Phe Val Val
    1115            1120                1125

Cys Cys Phe Leu Leu Gly Met Asp Val Arg Ser Gly Leu Leu Asn
    1130            1135                1140

Leu Phe Ser Ile Ile Met Ile Leu Val Asp Thr Val Gly Phe Met
    1145            1150                1155

Met Leu Trp Asp Ile Ser Tyr Asn Ala Val Ser Leu Ile Asn Leu
    1160            1165                1170

Val Thr Ala Val Gly Ile Ser Val Glu Phe Val Ser His Ile Thr
    1175            1180                1185

Arg Ser Phe Ala Ile Ser Thr Lys Pro Thr Arg Leu Glu Arg Ala
    1190            1195                1200

Lys Glu Ala Thr Ile Ser Met Gly Ser Ala Val Phe Ala Gly Val
    1205            1210                1215

Ala Met Thr Asn Leu Pro Gly Ile Leu Val Leu Gly Leu Ala Lys
    1220            1225                1230

Ala Gln Leu Ile Gln Ile Phe Phe Phe Arg Leu Asn Leu Leu Ile
    1235            1240                1245

Thr Val Leu Gly Leu Leu His Gly Leu Val Phe Leu Pro Val Ile
    1250            1255                1260

Leu Ser Tyr Leu Gly Pro Asp Val Asn Pro Ala Leu Val Gln Gln
    1265            1270                1275

Gln Lys Gln Gln Glu Glu Ala Ala Ala Ala Lys Glu Thr Ser Cys
    1280            1285                1290

Ser Lys His Pro Ala Gln Met Ser Thr Asp Tyr Gly Val Tyr Val
    1295            1300                1305

Asn Cys Ser Phe Glu His His Pro Ala Lys Ser Val Gly Gly Leu Glu
    1310            1315                1320

Ser Ser Pro Ser Glu Asn Arg Gln Lys Phe
    1325            1330
```